US007982036B2

(12) United States Patent  
Singh et al.

(10) Patent No.: US 7,982,036 B2
(45) Date of Patent: Jul. 19, 2011

(54) 4,6-DISUBSTITUED PYRIMIDINES USEFUL AS KINASE INHIBITORS

(75) Inventors: Juswinder Singh, Ashland, MA (US); Shomir Ghosh, Brookline, MA (US); Arthur F. Kluge, Lincoln, MA (US); Russell C. Petter, Stowe, MA (US); Richland W. Tester, Marlborough, MA (US)

(73) Assignee: Avila Therapeutics, Inc., Waltham, MA (US)

( * ) Notice: Subject to any disclaimer, the term of this patent is extended or adjusted under 35 U.S.C. 154(b) by 0 days.

(21) Appl. No.: 12/253,424

(22) Filed: Oct. 17, 2008

(65) Prior Publication Data

US 2009/0137588 A1 May 28, 2009

Related U.S. Application Data

(60) Provisional application No. 60/981,432, filed on Oct. 19, 2007, provisional application No. 61/052,002, filed on May 9, 2008.

(51) Int. Cl.
C07D 239/02 (2006.01)
(52) U.S. Cl. ........ 544/326; 544/111; 544/359; 546/119; 546/121; 546/210; 546/290; 548/165; 548/205; 548/217; 548/518; 549/408; 549/548
(58) Field of Classification Search .......... 544/111, 544/326, 359; 546/119, 121, 210, 290; 548/165, 548/205, 217, 518; 549/408, 548
See application file for complete search history.

(56) References Cited

U.S. PATENT DOCUMENTS

| 5,977,117 A | 11/1999 | Chan et al. |
| 5,994,375 A | 11/1999 | Kochanny et al. |
| 6,160,010 A | 12/2000 | Uckun et al. |
| 6,197,779 B1 | 3/2001 | Andries et al. |
| 6,686,367 B2 | 2/2004 | Phillips |
| 6,740,655 B2 | 5/2004 | Magee et al. |
| 7,241,458 B1 | 7/2007 | Verreck et al. |
| 7,514,444 B2 | 4/2009 | Honigberg et al. |
| 2004/0019067 A1 | 1/2004 | Armistead et al. |
| 2004/0023895 A1 | 2/2004 | Wang et al. |
| 2004/0077661 A1 | 4/2004 | Arbiser et al. |
| 2004/0265917 A1 | 12/2004 | Benjamin et al. |
| 2005/0004125 A1 | 1/2005 | Freyne et al. |
| 2005/0014753 A1 | 1/2005 | Ding et al. |
| 2006/0030018 A1 | 2/2006 | Zuccola et al. |
| 2006/0063789 A1 | 3/2006 | Freyne et al. |
| 2006/0166943 A1 | 7/2006 | Van Roey et al. |
| 2007/0032493 A1 | 2/2007 | Foley et al. |
| 2007/0043049 A1 | 2/2007 | Bakthavatchalam et al. |
| 2007/0099938 A1 | 5/2007 | Ohmoto et al. |
| 2008/0076921 A1 | 3/2008 | Honigberg et al. |
| 2008/0139582 A1 | 6/2008 | Honigberg et al. |
| 2008/0207613 A1 | 8/2008 | Styles et al. |
| 2008/0214501 A1 | 9/2008 | Pan et al. |
| 2009/0181987 A1 | 7/2009 | Honigberg et al. |
| 2010/0004270 A1 | 1/2010 | Honigberg et al. |
| 2010/0022561 A1 | 1/2010 | Honigberg et al. |
| 2010/0029610 A1 | 2/2010 | Singh et al. |

FOREIGN PATENT DOCUMENTS

| JP | 07041461 | 2/1995 |
| WO | WO-95/15952 | 6/1995 |
| WO | WO-99/50250 | 10/1999 |
| WO | WO-00/71536 | 11/2000 |
| WO | WO-02/083653 | 10/2002 |
| WO | WO-2004/031232 | 4/2004 |
| WO | WO-2006/045066 | 4/2006 |
| WO | WO-2006/061415 | 6/2006 |
| WO | WO-2006/108487 | 10/2006 |
| WO | WO-2006/128129 | 11/2006 |
| WO | WO-2007/056151 | 5/2007 |
| WO | WO-2007/081630 | 7/2007 |
| WO | WO-2008/092199 | 8/2008 |

OTHER PUBLICATIONS

U.S. Appl. No. 12/426,495, Singh et al.
U.S. Appl. No. 12/648,693, Singh et al.
International Search Report, PCT/US2008/11911, date of mailing Dec. 23, 2008.
Written Opinion, PCT/US2008/11911, date of mailing Dec. 23, 2008.
Okoh et al., "Pleckstrin Homology Domains of Tec Family Protein Kinases," *Biochemical and Biophysical Research Communications* 265:151-157 (1999).
Declue et al., "Epidermal growth factor receptor expression in neurofibromatosis type 1 related tumors and NF1 animal model," *Journal of Clinical Investigation* 105:1233-1241 (2000).
Zhang et al., "Targeting Cancer with Small Molecule Kinase Inhibitors," *Nature Rev. Cancer* 9:28-39 (2009).
Cohen et al., "Structural bioinformatics-based design of selective, irreversible inhibitors," *Science* 308:1318-1321 (2005).
Kwak et al., "Irreversible inhibitors of the EGF receptor may circumvent acquired resistance to gefitinib," *Proc. Natl. Acad. Sci. USA* 102:7665-7670 (2005).
Zhang et al., "Antitumor Activity of Epidermal Growth Factor Receptor—Related Protein Is Mediated by Inactivation of ErbB Receptors and Nuclear Factor-kB in Pancreatic Cancer," *Cancer Res* 66:1025-1032 (2006).

(Continued)

*Primary Examiner* — James O Wilson
*Assistant Examiner* — Douglas M Willis
(74) *Attorney, Agent, or Firm* — Choate, Hall & Stewart LLP; Andrea L. C. Robidoux; Emilie Porter Huck

(57) ABSTRACT

The present invention provides compounds of formula I

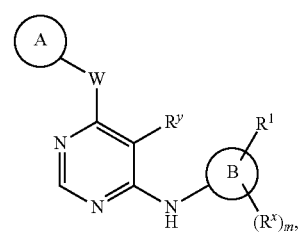

wherein Ring A, Ring B, m, $R^x$, $R^y$, W and $R^1$ are as defined herein, pharmaceutically acceptable salts and compositions thereof, and methods of using the same.

12 Claims, 19 Drawing Sheets

OTHER PUBLICATIONS

Lin et al., "New targets for therapy in breast cancer: Small molecule tyrosine kinase inhibitors," *Breast Cancer Res* 6:204-210 (2004).

Andrulis et al., "Neu/ErbB-2 amplification identifies a poor-prognosis group of women with node-negative breast cancer," *J Clin Oncol* 16:1340-9 (1998).

Fallon et al., "Constitutive activation of the neuregulin-1/erbB signaling pathway promotes the proliferation of a human peripheral neuroepithelioma cell line," *J Neuro Oncol* 66:273-84 (2004).

Stonecypher et al., "Activation of the neuregulin-1/ErbB signaling pathway promotes the proliferation of neoplastic Schwann cells in human malignant peripheral nerve sheath tumors," *Oncogene* 24:5589-5605 (2005).

Pelton et al., "Ruffling membrane, stress fiber, cell spreading and proliferation abnormalities in human Schwann cells," *Oncogene* 17:2195-2209 (1998).

Lajeunesse et al., "A systematic screen for dominant second-site modifiers of Merlin/NF2 phenotypes reveals an interaction with blistered/DSRF and scribbler," *Genetics* 158:667-79 (2001).

McClatchey et al., "Membrane organization and tumorigenesis—the NF2 tumor suppressor, Merlin," *Genes Dev* 19:2265-77 (2005).

Curto et al., "Contact-dependent inhibition of EGFR signaling by Nf2/Merlin," *J Cell Biol* 177:893-903 (2007).

Readinger et al., "Selective Targeting of ITK Blocks Multiple Steps of HIV Replication," *Proc. Natl. Acad. Sci. USA* 105: 6684-6689 (2008).

Frank, "STAT signaling in the pathogenesis and treatment of cancer," *Mol. Med.* 5 :432-456 (1999).

Seidel et al., "Pharmaceutical intervention in the JAK/STAT signaling pathway," *Oncogene* 19 :2645-2656 (2000).

Malaviya et al., "Targeting Janus Kinase 3 in Mast Cells Prevents Immediate Hypersensitivity Reactions and Anaphylaxis," *J. Biol. Chem.* 274 :27028-27038 (1999).

Kirken, "Targeting Jak3 for immune suppression and allograft acceptance," *Transplant. Proc.* 33 :3268-3270 (2001).

Trieu et al., "A specific inhibitor of janus kinase-3 increases survival in a transgenic mouse model of amyotrophic lateral sclerosis," *Biochem. Biophys. Res. Commun.* 267 :22-25 (2000).

Sudbeck et al., "Structure-based Design of Specific Inhibitors of Janus Kinase 3 as Apoptosis-inducing Antileukemic Agents," *Clin. Cancer Res.* 5: 1569-1582 (1999).

Fry et al., "Specific, irreversible inactivation of the epidermal growth factor receptor and erbB2, by a new class of tyrosine kinase inhibitor," *Proc. Natl. Acad. Sci. USA* 95:12022-12027 (1998).

Zhang et al., "Discovery of EGFR selective 4,6-disubstituted pyrimidines from a combinatorial kinase-directed heterocycle library," *J. Am. Chem. Soc.* 128:2182-2183 (2006).

Zhou et al., "Novel mutant-selective EGFR kinase inhibitors against EGFR T790M," *Nature* 462:1070-1074 (Dec. 2009).

Showalter et al, "Tyrosine kinase inhibitors. 16. 6,5,6-Tricyclic benzothieno[3,2-d]pyrimidines and Pyrimido[5,4-b] and —[4,5-b]indoles as potent inhibitors of the epidermal growth factor receptor tyrosine kinase," *J. Med. Chem.* 42:5464-5474 (1999).

Singh et al, "Structure-based design of a potent, selective, and irreversible inhibitor of the catalytic domain of the erbB receptor subfamily of protein tyrosine kinases," *J. Med. Chem.* 40:1130-1135 (1997).

International Search Report, PCT/US2010/31714, date of mailing Aug. 13, 2010.

Written Opinion, PCT/US2010/31714, date of mailing Aug. 13, 2010.

Li et al., "BIBW2992, an irreversible EGFR/HER2 inhibitor highly effective in preclinical lung cancer models," *Oncogene* 27:4702-4711 (2008).

Hur et al., "Clinical stage EGFR inhibitors irreversibly alkylate Bmx kinase," *Bioorg. Med. Chem. Lett.* 18:5916-5919 (2008).

Dose Response with I-16 and I-17 in A431 cells

Dose Response with I-19 in A431 cells

SEQ_ID_1: FULL LENGTH BTK PROTEIN:

MAAVILESIFLKRSQQKKKTSPLNFKKRLFLLTVHKLSYYEYDFERGRRGSKKGSIDVEK
ITCVETVVPEKNPPPERQIPRRGEESSEMEQISIIERFPYPFQVVYDEGPLYVFSPTEEL
RKRWIHQLKNVIRYNSDLVQKYHPCFWIDGQYLCCSQTAKNAMGCQILENRNGSLKPG
SSHRKTKKPLPPTPEEDQILKKPLPPEPAAAPVSTSELKKVVALYDYMPMNANDLQLRK
GDEYFILEESNLPWWRARDKNGQEGYIPSNYVTEAEDSIEMYEWYSKHMTRSQAEQLL
KQEGKEGGFIVRDSSKAGKYTVSVFAKSTGDPQGVIRHYVVCSTPQSQYYLAEKHLFST
IPELINYHQHNSAGLISRLKYPVSQQNKNAPSTAGLGYGSWEIDPKDLTFLKELGTGQFG
VVKYGKWRGQYDVAIKMIKEGSMSEDEFIEEAKVMMNLSHEKLVQLYGVCTKQRPIFII
TEYMANGCLLNYLREMRHRFQTQQLLEMCKDVCEAMEYLESKQFLHRDLAARNCLVN
DQGVVKVSDF

Cys=481

Figure 14

SEQ ID 2: FULL LENGTH TEC PROTEIN_NP_003206_631 aa

MNFNTILEEILIKRSQQKKKTSPLNYKERLFVLTKSMLTYYEGRAEKKYRKGFIDVSKIK
CVEIVKNDDGVIPCQNKYPFQVVHDANTLYIFAPSPQSRDLWVKKLKEEIKNNNNIMIK
YHPKFWTDGSYQCCRQTEKLAPGCEKYNLFESSIRKALPPAPETKKRRPPPPIPLEEEDNS
EEIVVAMYDFQAAEGHDLRLERGQEYLILEKNDVHWWRARDKYGNEGYIPSNYVTGK
KSNNLDQYEWYCRNMNRSKAEQLLRSEDKEGGFMVRDSSQPGLYTVSLYTKFGGEGS
SGFRHYHIKETTTSPKKYYLAEKHAFGSIPEIIEYHKHNAAGLVTRLRYPVSVKGK
NAPTTAGFSYEKWEINPSELTFMRELGSGLFGVVRLGKWRAQYKVAIKAIREGAMCEE
DFIEEAKVMMKLTHPKLVQLYGVCTQQKPIYIVTEFMERGCLLNFLRQRQGHFSRDVLL
SMCQDVCEGMEYLERNSFIHRDLAARNCLVSEAGVVKVSDFGMARYVLDDQYTSSSG
AKFPVKWCPPEVFNYSRFSSKSDVWSFGVLMWEVFTEGRMPFEKYTNYEVVTMVTRG
HRLYQPKLASNYVYEVMLRCWQEKPEGRPSFEDLLRTIDELVECEETFGR

Cys=449

Figure 15

SEQ ID 3: FULL LENGTH ITK PROTEIN NP_005537 620aa

MNNFILLEEQLIKKSQQKRRTSPSNFKVRFFVLTKASLAYFEDRHGKKRTLKGSIELSRIKCVE
IVKSDISIPCHYKYPFQVVHDNYLLYVFAPDRESRQRWVLALKEETRNNNSLVPKYHPNFWMDG
KWRCCSQLEKLATGCAQYDPTKNASKKPLPPTPEDNRRPLWEPEETVVIALYDYQTNDPQELAL
RRNEEYCLLDSSEIHWWRVQDRNGHEGYVPSSYLVEKSPNNLETYEWYNKSISRDKAEKLLLDT
GKEGAFMVRDSRTAGTYTVSVFTKAVVSENNPCIKHYHIKETNDNPKRYYVAEKYVFDSIPLLI
NYHQHNGGGLVTRLRYPVCFGRQKAPVTAGLRYGKWVIDPSELTFVQEIGSGQFGLVHLGYWLN
KDKVAIKTIREGAMSEEDFIEEAEVMMKLSHPKLVQLYGVCLEQAPICLVFEFMEHGCLSDYLR
TQRGLFAAETLLGMCLDVCEGMAYLEEACVIHRDLAARNCLVGENQVIKVSDFGMTRFVLDDQY
TSSTGTKFPVKWASPEVFSFSRYSSKSDVWSFGVLMWEVFSEGKIPYENRSNSEVVEDISTGFR
LYKPRLASTHVYQIMNHCWKERPEDRPAFSRLLRQLAEIAESGL

Cys=442

Figure 16

SEQ ID 4: FULL LENGTH BMX PROTEIN NP_001712 675aa

MDTKSILEELLLKRSQQKKKMSPNNYKERLFVLTKTNLSYYEYDKMKRGSRKGSIEIKK
IRCVEKVNLEEQTPVERQYPFQIVYKDGLLYVYASNEESRSQWLKALQKEIRGNPHLLV
KYHSGFFVDGKFLCCQQSCKAAPGCTLWEAYANLHTAVNEEKHRVPTFPDRVLKIPRA
VPVLKMDAPSSSTTLAQYDNESKKNYGSQPPSSSTSLAQYDSNSKKIYGSQPNFNMQYIP
REDFPDWWQVRKLKSSSSSEDVASSNQKERNVNHTTSKISWEFPESSSSEEEENLDDYD
WFAGNISRSQSEQLLRQKGKEGAFMVRNSSQVGMYTVSLFSKAVNDKKGTVKHYH
VHTNAENKLYLAENYCFDSIPKLIHYHQHNSAGMITRLRHPVSTKANKVPDSVSLGNGI
WELKREEITLLKELGSGQFGVVQLGKWKGQYDVAVKMIKEGSMSEDEFFQEAQTMMK
LSHPKLVKFYGVCSKEYPIYIVTEYISNGCLLNYLRSHGKGLEPSQLLEMCYDVCEGMA
FLESHQFIHRDLAARNCLVDRDLCVKVSDFGMTRYVLDDQYVSSVGTKFPVKWSAPEV
FHYFKYSSKSDVWAFGILMWEVFSLGKQPYDLYDNSQVVLKVSQGHRLYRPHLASDTI
YQIMYSCWHELPEKRPTFQQLLSSIEPLREKDKH

Cys=496

Figure 17

SEQ ID 5: FULL LENGTH JAK3 PROTEIN NP_000206 1124 aa

```
MAPPSEETPLIPQRSCSLLSTEAGALHVLLPARGPGPPQRLSFSFGDHLAEDLCVQAAKASGIL
PVYHSLFALATEDLSCWFPPSHIFSVEDASTQVLLYRIRFYFPNWFGLEKCHRFGLRKDLASAI
LDLPVLEHLFAQHRSDLVSGRLPVGLSLKEQGECLSLAVLDLARMAREQAQRPGELLKTVSYKA
CLPPSLRDLIQGLSFVTRRRIRRTVRRALRRVAACQADRHSLMAKYIMDLERLDPAGAAETFHV
GLPGALGGHDGLGLLRVAGDGGIAWTQGEQEVLQPFCDFPEIVDISIKQAPRVGPAGEHRLVTV
TRTDNQILEAEFPGLPEALSFVALVDGYFRLTTDSQHFFCKEVAPPRLLEEVAEQCHGPITLDF
AINKLKTGGSRPGSYVLRRSPQDFDSFLLTVCVQNPLGPDYKGCLIRRSPTGTFLLVGLSRPHS
SLRELLATCWDGGLHVDGVAVTLTSCCIPRPKEKSNLIVVQRGHSPPTSSLVQPQSQYQLSQMT
FHKIPADSLEWHENLGHGSFTKIYRGCRHEVVDGEARKTEVLLKVMDAKHKNCMESFLEAASLM
SQVSYRHLVLLHGVCMAGDSTMVQEFVHLGAIDMYLRKRGHLVPASWKLQVVKQLAYALNYLED
KGLPHGNVSARKVLLAREGADGSPPFIKLSDPGVSPAVLSLEMLTDRIPWVAPECLREAQTLSL
EADKWGFGATVWEVFSGVTMPISALDPAKKLQFYEDRQQLPAPKWTELALLIQQCMAYEPVQRP
SFRAVIRDLNSLISSDYELLSDPTPGALAPRDGLWNGAQLYACQDPTIFEERHLKYISQLGKGN
FGSVELCRYDPLGDNTGALVAVKQLQHSGPDQQRDFQREIQILKALHSDFIVKYRGVSYGPGRQ
SLRLVMEYLPSGCLRDFLQRHRARLDASRLLLYSSQICKGMEYLGSRRCVHRDLAARNILVESE
AHVKIADFGLAKLLPLDKDYYVVREPGQSPIFWYAPESLSDNIFSRQSDVWSFGVVLYELFTYC
DKSCSPSAEFLRMMGCERDVPALCRLLELLEEGQRLPAPPACPAEVHELMKLCWAPSPQDRPSF
SALGPQLDMLWSGSRGCETHAFTAHPEGKHHSLSFS
```

Cys=909

Figure 18

SEQ ID 6: FULL LENGTH TXK PROTEIN_NP_003319 527 aa

MILSSYNTIQSVFCCCCCCSVQKRQMRTQISLSTDEELPEKYTQRRRPWLSQLSNKKQSN
TGRVQPSKRKPLPPLPPSEVAEEKIQVKALYDFLPREPCNLALRRAEEYLILEKYNPHWW
KARDRLGNEGLIPSNYVTENKITNLEIYEWYHRNITRNQAEHLLRQESKEGAFIVRDSRH
LGSYTISVFMGARRSTEAAIKHYQIKKNDSGQWYVAERHAFQSIPELIWYHQHNAAGL
MTRLRYPVGLMGSCLPATAGFSYEKWEIDPSELAFIKEIGSGQFGVVHLGEWRSHIQVAI
KAINEGSMSEEDFIEEAKVMMKLSHSKLVQLYGVCIQRKPLYIVTEFMENG<u>C</u>LLNYLRE
NKGKLRKEMLLSVCQDICEGMEYLERNGYIHRDLAARNCLVSSTCIVKISDFGMTRYVL
DDEYVSSFGAKFPIKWSPPEVFLFNKYSSKSDVWSFGVLMWEVFTEGKMPFENKSNLQ
VVEAISEGFRLYRPHLAPMSIYEVMYSCWHEKPEGRPTFAELLRAVTEIAETW

Cys 350

Figure 19

4,6-DISUBSTITUED PYRIMIDINES USEFUL AS KINASE INHIBITORS

CROSS-REFERENCE TO RELATED APPLICATIONS

The present invention claims priority to U.S. provisional application Ser. No. 60/981,432, filed Oct. 19, 2007, and U.S. provisional application Ser. No. 61/052,002, filed May 9, 2008, the entirety of each of which is hereby incorporated herein by reference.

TECHNICAL FIELD OF THE INVENTION

The present invention relates to compounds useful as inhibitors of protein kinases. The invention also provides pharmaceutically acceptable compositions comprising compounds of the present invention and methods of using said compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there remains a need to find protein kinase inhibitors useful as therapeutic agents.

SUMMARY OF THE INVENTION

It has now been found that compounds of this invention, and pharmaceutically acceptable compositions thereof, are effective as inhibitors of one or more protein kinases. Such compounds have the general formula I:

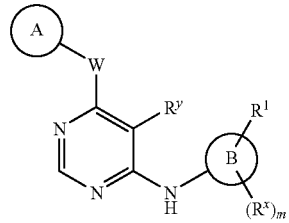

I or a pharmaceutically acceptable salt thereof, wherein Ring A, Ring B, m, $R^x$, $R^y$, W, and $R^1$ are as defined herein.

Compounds of the present invention, and pharmaceutically acceptable compositions thereof, are useful for treating a variety of diseases, disorders or conditions, associated with abnormal cellular responses triggered by protein kinase-mediated events. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

BRIEF DESCRIPTION OF THE DRAWINGS

FIG. 14 depicts an amino acid sequence for BTK (SEQ ID 1).

FIG. 15 depicts an amino acid sequence for TEC (SEQ ID 2).

FIG. 16 depicts an amino acid sequence for ITK (SEQ ID 3).

FIG. 17 depicts an amino acid sequence for BMX (SEQ ID 4).

FIG. 18 depicts an amino acid sequence for JAK3 (SEQ ID 5).

FIG. 19 depicts an amino acid sequence for TXK (SEQ ID 6).

DETAILED DESCRIPTION OF CERTAIN EMBODIMENTS

Figure 1:
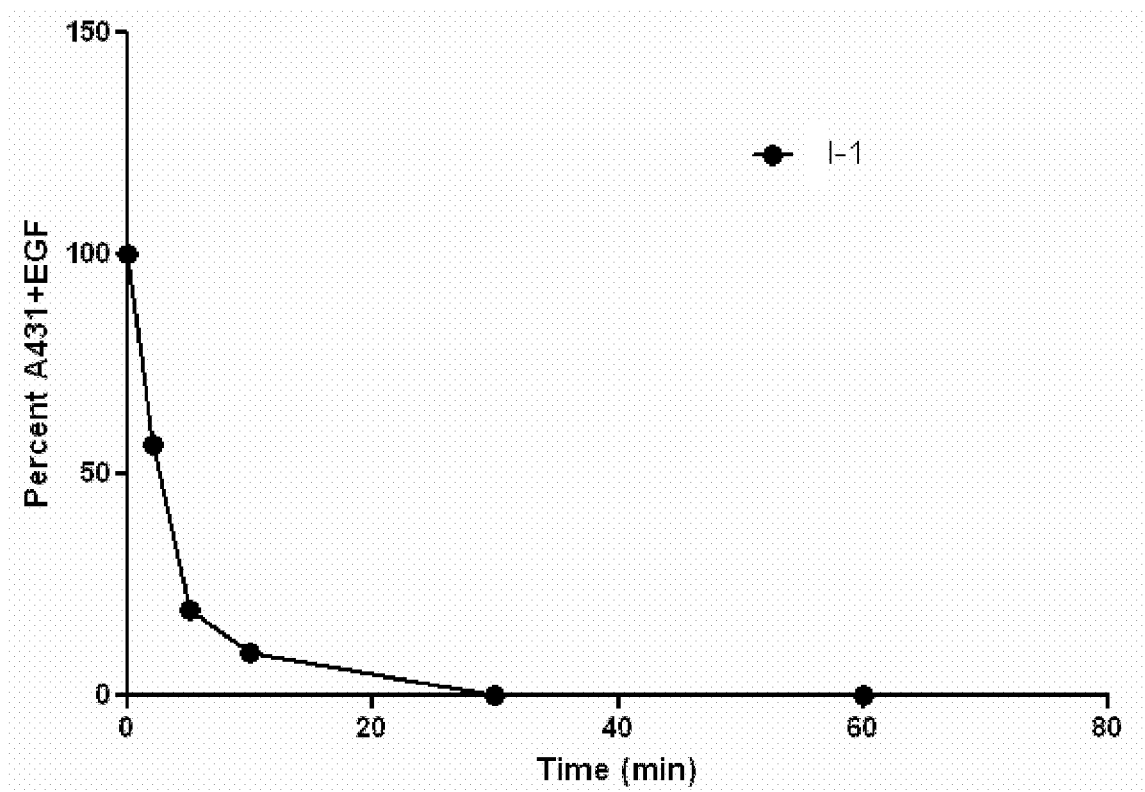
FIG. 1 depicts the EGF inhibiting activity of compound I-1.

1. General Description of Compounds of the Invention

In certain embodiments, the present invention provides a compound of formula I:

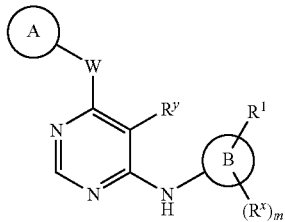

I or a pharmaceutically acceptable salt thereof, wherein:

Ring A is an optionally substituted group selected from phenyl, an 8-10 membered bicyclic partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is phenyl, a 5-6 membered heteroaryl ring having 1-3 heteroatoms independently selected from N, O or S, a 5-6 membered saturated heterocyclic ring having 1-2 heteroatoms independently selected from N, O or S, or an 8-10 membered bicyclic partially unsaturated or aryl ring having 1-3 heteroatoms independently selected from N, O or S;

$R^1$ is a warhead group;

$R^y$ is hydrogen, halogen, CN, lower alkyl, or lower haloalkyl;

W is a bivalent $C_{1-3}$ alkylene chain wherein one methylene unit of W is optionally replaced by —NR$^2$—, —N(R$^2$)C(O)—, —C(O)N(R$^2$)—, —N(R$^2$)SO$_2$—, —SO$_2$N(R$^2$)—, —O—, —C(O)—, —OC(O)—, —C(O)O—, —S—, —SO— or —SO$_2$—;

$R^2$ is hydrogen or optionally substituted $C_{1-6}$ aliphatic, or:
  $R^2$ and a substituent on Ring A are taken together with their intervening atoms to form a 4-6 membered saturated ring, or:
  $R^2$ and $R^y$ are taken together with their intervening atoms to form a 4-7 membered carbocyclic ring;

m is 0-4;

each $R^x$ is independently selected from —R, halogen, —OR, —CN, —NO$_2$, —SO$_2$R, —SOR, —C(O)R, —CO$_2$R, —C(O)N(R)$_2$, —NRC(O)R, —NRC(O)NR$_2$, —NRSO$_2$R, or —N(R)$_2$; or:
  $R^x$ and $R^1$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or $C_{1-6}$ aliphatic; and each R group is independently hydrogen or an optionally substituted group selected from $C_{1-6}$ aliphatic, phenyl, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, the present invention provides a compound of formula II:

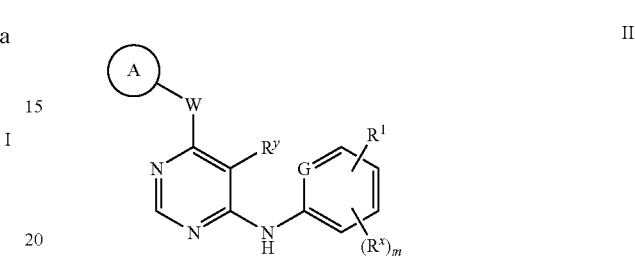

II or a pharmaceutically acceptable salt thereof, wherein:

Ring A is an optionally substituted group selected from phenyl, an 8-10 membered bicyclic partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

$R^1$ is a warhead group;

$R^y$ is hydrogen, halogen, CN, lower alkyl, or lower haloalkyl;

G is CH, or N;

W is —NR$^2$—, —S—, or —O—;

$R^2$ is hydrogen or optionally substituted $C_{1-6}$ aliphatic, or:
  $R^2$ and a substituent on Ring A are taken together with their intervening atoms to form a 4-6 membered saturated ring;

m is 0-4;

each $R^x$ is independently selected from —R, halogen, —OR, —CN, —NO$_2$, —SO$_2$R, —SOR, —C(O)R, —CO$_2$R, —C(O)N(R)$_2$, —NRC(O)R, —NRC(O)NR$_2$, —NRSO$_2$R, or —N(R)$_2$; or:
  $R^x$ and $R^1$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or $C_{1-6}$ aliphatic; and each R group is independently hydrogen or an optionally substituted group selected from $C_{1-6}$ aliphatic, phenyl, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

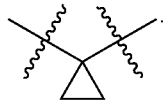

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —$O$—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH=CHPh$, which may be substituted with $R^\circ$; —$(CH_2)_{0-4}O(CH_2)_{0-1}$-pyridyl which may be substituted with $R^\circ$; —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)$O$—$N(R^\circ)_2$; or —$(C_{1-4}$ straight or branched alkylene)$C(O)O$—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —$CN$, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(haloR$^\bullet$), —$OH$, —$OR^\bullet$, —$O(haloR^\bullet)$, —$CN$, —$C(O)OH$, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —$OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}$-alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$— or $^{14}C$-enriched carbon are within the scope of this invention. Such compounds are useful, for example, as analytical tools, as probes in biological assays, or as therapeutic agents in accordance with the present invention. In some embodiments, the $R^1$ group of formula I comprises one or more deuterium atoms. Such compounds include compound I-61 as depicted in Table 5.

As used herein, the term "irreversible" or "irreversible inhibitor" refers to an inhibitor (i.e. a compound) that is able to be covalently bonded to a target protein kinase in a substantially non-reversible manner. That is, whereas a reversible inhibitor is able to bind to (but is generally unable to form a covalent bond) the target protein kinase, and therefore can become dissociated from the target protein kinase, an irreversible inhibitor will remain substantially bound to the target protein kinase once covalent bond formation has occurred. Irreversible inhibitors usually display time dependency, whereby the degree of inhibition increases with the time with which the inhibitor is in contact with the enzyme. Methods for identifying if a compound is acting as an irreversible inhibitor are known to one of ordinary skill in the art. Such methods include, but are not limited to, enzyme kinetic analysis of the inhibition profile of the compound with the protein kinase target, the use of mass spectrometry of the protein drug target modified in the presence of the inhibitor compound, discontinuous exposure, also known as "washout," experiments, and the use of labeling, such as radiolabelled inhibitor, to show covalent modification of the enzyme, as well as other methods known to one of skill in the art.

One of ordinary skill in the art will recognize that certain reactive functional groups can act as "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. It will be appreciated that the -L-Y group, as defined and described herein, provides such warhead groups for covalently, and irreversibly, inhibiting the protein.

As used herein, the term "inhibitor" is defined as a compound that binds to and/or inhibits the target protein kinase with measurable affinity. In certain embodiments, an inhibitor has an IC$_{50}$ and/or binding constant of less about 50 µM, less than about 1 µM, less than about 500 nM, less than about 100 nM, or less than about 10 nM.

A compound of the present invention may be tethered to a detectable moiety. One of ordinary skill in the art will recognize that a detectable moiety may be attached to a provided compound via a suitable substituent on Ring A or a suitable $R^x$ substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound (i.e. directly attached to Ring A or the aniline ring) or via a tethering group, such as a bivalent saturated or unsaturated hydrocarbon chain.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in at least one of ErbB1, ErbB2, ErbB3, ErbB4, a TEC-kinase, and/or JAK3 activity between a sample comprising a compound of the present invention, or composition thereof, and at least one of ErbB1, ErbB2, ErbB4, a TEC-kinase, and/or JAK3, and an equivalent sample comprising at least one of ErbB1, ErbB2, ErbB3, ErbB4, a TEC-kinase, and/or JAK3, in the absence of said compound, or composition thereof.

3. Description of Exemplary Compounds

According to one aspect, the present invention provides a compound of formula I,

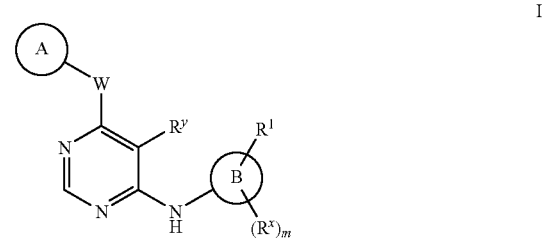

I or a pharmaceutically acceptable salt thereof, wherein:

Ring A is an optionally substituted group selected from phenyl, an 8-10 membered bicyclic partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is phenyl, a 5-6 membered heteroaryl ring having 1-3 heteratoms independently selected from N, O or S, a 5-6 membered saturated heterocyclic ring having 1-2 heteroatoms independently selected from N, O or S, or an 8-10 membered bicyclic partially unsaturated or aryl ring having 1-3 heteroatoms independently selected from N, O or S;

$R^1$ is -L-Y, wherein:

L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;

Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:

Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, NO$_2$, or CN;

$R^y$ is hydrogen, halogen, CN, lower alkyl, or lower haloalkyl;

W is a bivalent $C_{1-3}$ alkylene chain wherein one methylene unit of W is optionally replaced by —NR$^2$—, —N(R$^2$)C(O)—, —C(O)N(R$^2$)—, —N(R$^2$)SO$_2$—, —SO$_2$N(R$^2$)—, —O—, —C(O)—, —OC(O)—, —C(O)O—, S—, —SO— or —SO$_2$—;

R² is hydrogen or optionally substituted C₁₋₆ aliphatic, or:
  R² and a substituent on Ring A are taken together with their intervening atoms to form a 4-6 membered saturated ring, or:
  R² and R^y are taken together with their intervening atoms to form a 4-7 membered carbocyclic ring;
m is 0-4;
each R^x is independently selected from —R, halogen, —OR, —CN, —NO₂, —SO₂R, —SOR, —C(O)R, —CO₂R, —C(O)N(R)₂, —NRC(O)R, —NRC(O)NR₂, —NRSO₂R, or —N(R)₂; or:
  R^x and R¹ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or C₁₋₆ aliphatic; and
each R group is independently hydrogen or an optionally substituted group selected from C₁₋₆ aliphatic, phenyl, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

In certain embodiments, the present invention provides a compound of formula II:

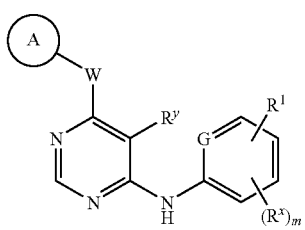

II or a pharmaceutically acceptable salt thereof, wherein:
Ring A is an optionally substituted group selected from phenyl, an 8-10 membered bicyclic partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;
R¹ is -L-Y, wherein:
  L is a covalent bond or a bivalent C₁₋₈ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO₂—, —SO₂N(R)—, —O—, —C(O)—, —OC(O)—, —C(O)O—, —S—, —SO—, —SO₂—, —C(=S)—, —C(=NR)—, —N=N—, or —C(=N₂)—;
  Y is hydrogen, C₁₋₆ aliphatic optionally substituted with oxo, halogen, NO₂, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R^e groups; and each R^e is independently selected from -Q-Z, oxo, NO₂, halogen, CN, a suitable leaving group, or a C₁₋₆ aliphatic optionally substituted with oxo, halogen, NO₂, or CN, wherein:
  Q is a covalent bond or a bivalent C₁₋₆ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO₂—, —N(R)C(O)—, —C(O)N(R)—, —N(R)SO₂—, or —SO₂N(R)—; and
  Z is hydrogen or C₁₋₆ aliphatic optionally substituted with oxo, halogen, NO₂, or CN;
R^y is hydrogen, halogen, CN, lower alkyl, or lower haloalkyl;
G is CH, or N;
W is —NR²—, —S—, or —O—;
R² is hydrogen or optionally substituted C₁₋₆ aliphatic, or:
  R² and a substituent on Ring A are taken together with their intervening atoms to form a 4-6 membered saturated ring;
m is 0-4;
each R^x is independently selected from —R, halogen, —OR, —CN, —NO₂, —SO₂R, —SOR, —C(O)R, —CO₂R, —C(O)N(R)₂, —NRC(O)R, —NRC(O)NR₂, —NRSO₂R, or —N(R)₂; or:
  R^x and R¹ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or C₁₋₆ aliphatic; and
each R group is independently hydrogen or an optionally substituted group selected from C₁₋₆ aliphatic, phenyl, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

According to one aspect, the present invention provides a compound of formula II-a or II-b:

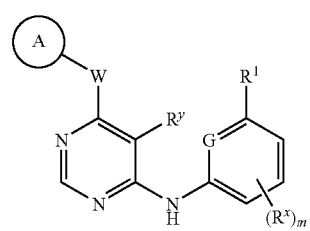

II-a

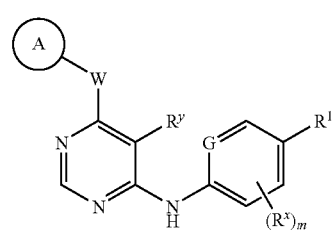

II-b or a pharmaceutically acceptable salt thereof, wherein each of Ring A, W, R¹, G, R^y, R^x and m are as defined above for formula II and as described herein.

In certain embodiments, the present invention provides a compound of formula II-b where in said compound is other than $N^6$-m-tolyl-$N^4$-p-tolylpyrimidine-4,6-diamine.

In certain embodiments, the present invention provides a compound of formula II-a wherein said compound is other than $N^4$-(3-aminophenyl)-$N^6$-(3-bromophenyl)pyrimidine-4,6-diamine, N-(3-(6-(3-(trifluoromethyl)phenylamino)pyrimidin-4-ylamino)phenyl)cyclopropane-carboxamide, N-(3-(6-(3-bromophenylamino)pyrimidin-4-ylamino)phenyl) propionamide, $N^4$-(3-aminophenyl)-$N^6$-m-tolylpyrimidine-4,6-diamine, or $N^4$-(3-aminophenyl) -$N^6$-methyl-N6-phenyl-pyrimidine-4,6-diamine.

As defined generally above, the Ring A group of formulae I and II is an optionally substituted group selected from phenyl, an 8-10 membered bicyclic partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In certain embodiments, Ring A is an optionally substituted phenyl group. In some embodiments, Ring A is an optionally substituted naphthyl ring or a bicyclic 8-10 membered heteraryl ring having 1-4 heteroatoms independently selected from nitrogen, oxygen, or sulfur. In some embodiments, Ring A is an optionally substituted diphenyl ether. In some embodiments, Ring A is an optionally substituted phenyl benzyl ether. In other embodiments, Ring A is an optionally substituted pyridine methoxy phenyl group.

In certain embodiments, the Ring A group of formulae I and II is substituted as defined herein. In some embodiments, Ring A is substituted with one, two, or three groups independently selected from halogen, $R^\circ$, or —$(CH_2)_{0-4}OR^\circ$, or —$O(CH_2)_{0-4}R^\circ$, wherein each $R^\circ$ is as defined herein. Exemplary substituents on Ring A include Br, I, Cl, methyl, —$CF_3$, —C≡CH, —$OCH_2$-phenyl, —$OCH_2$(fluorophenyl), or —$OCH_2$pyridyl.

Exemplary Ring A groups of formulae I and II are set forth in Table 1.

TABLE 1

| Exemplary Ring A Groups | |
|---|---|
| 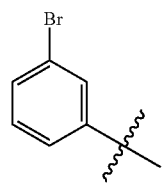 | i |
| 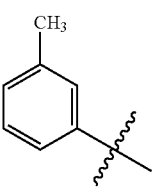 | ii |

TABLE 1-continued

| Exemplary Ring A Groups | |
|---|---|
| 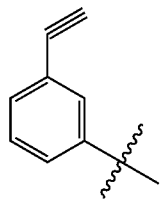 | iii |
| 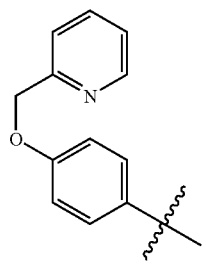 | iv |
| 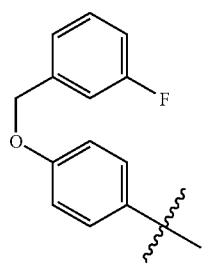 | v |
| 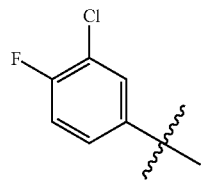 | vi |
| 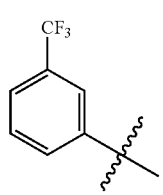 | vii |
| 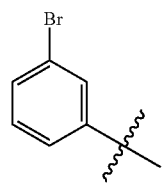 | viii |

TABLE 1-continued
Exemplary Ring A Groups
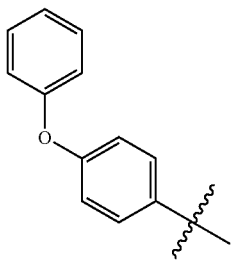 ix
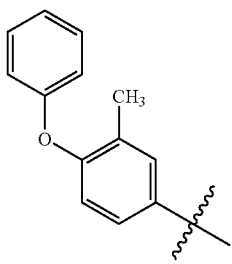 x
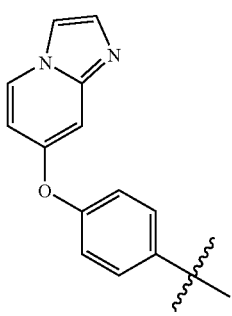 xi
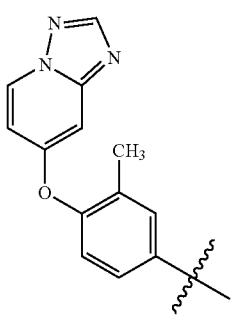 xii
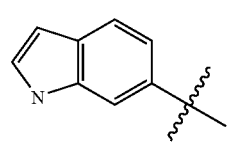 xiii
TABLE 1-continued
Exemplary Ring A Groups
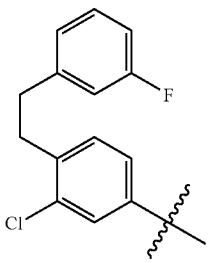 xiv
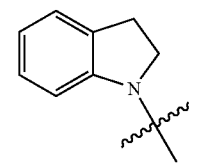 xv
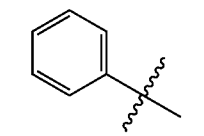 xvi
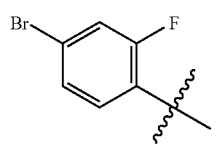 xvii
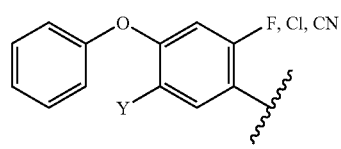 xviii
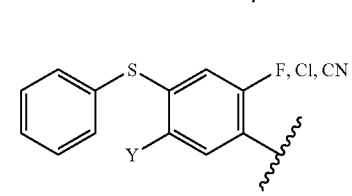 xix
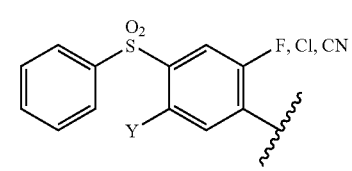 xx
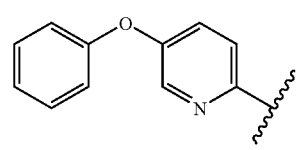 xxi TABLE 1-continued
Exemplary Ring A Groups
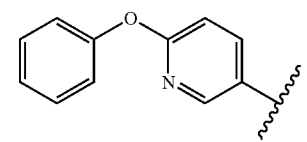 xxii
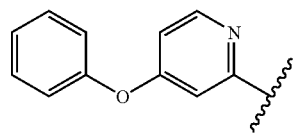 xxiii
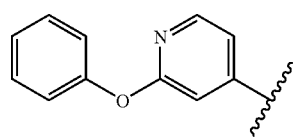 xxiv
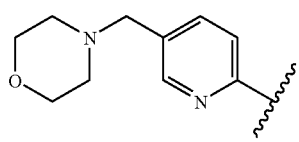 xxv
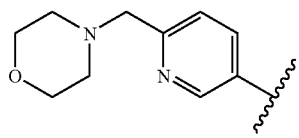 xxvi
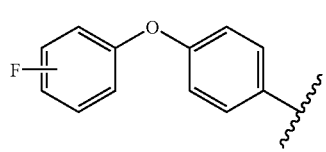 xxvii
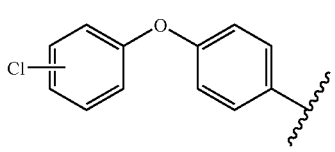 xxviii
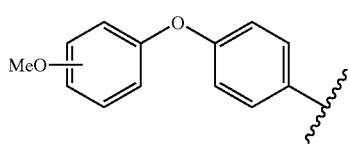 xxix
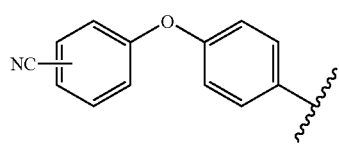 xxx
TABLE 1-continued
Exemplary Ring A Groups
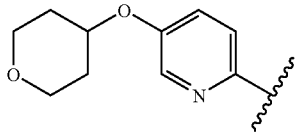 xxxi
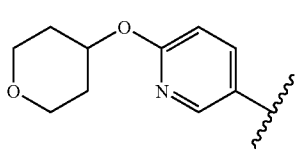 xxxii
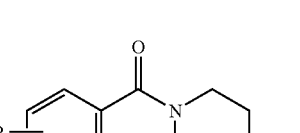 xxxiii
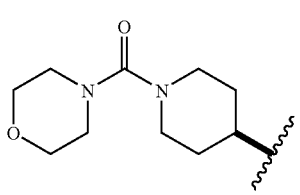 xxxiv
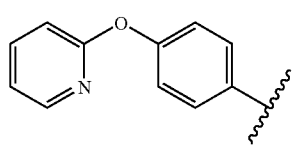 xxxv
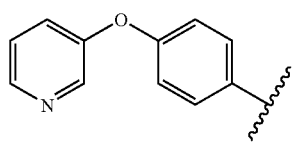 xxxvi
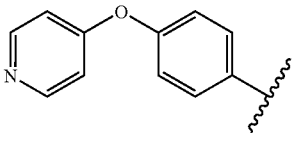 xxxvii
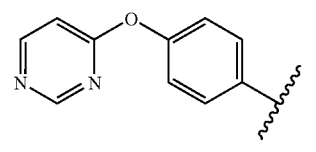 xxxviii TABLE 1-continued
Exemplary Ring A Groups
xxxix
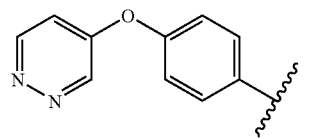
xl
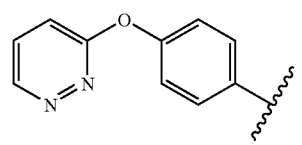
xli
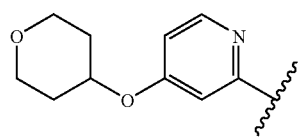
xlii
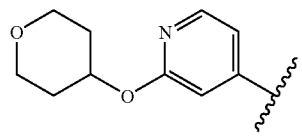
xliii
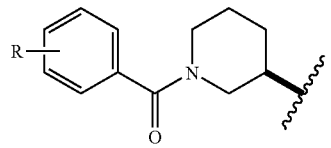
xliv
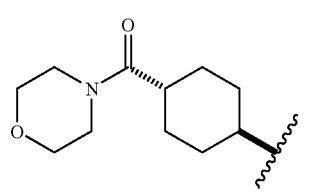
xlv
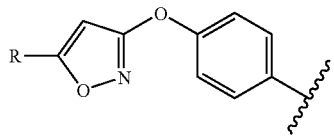
xlvi
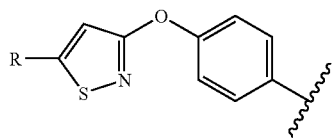
xlvii
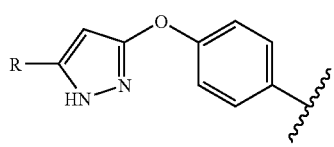
TABLE 1-continued
Exemplary Ring A Groups
xlviii
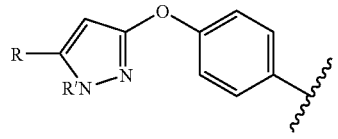
xlix
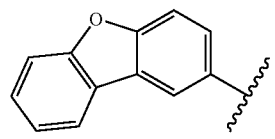
l
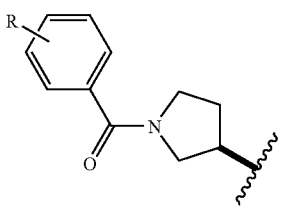
li
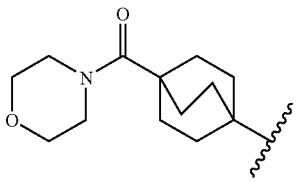
lii
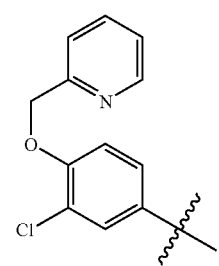
liii
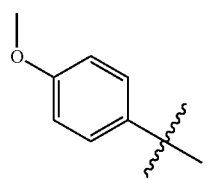
liv
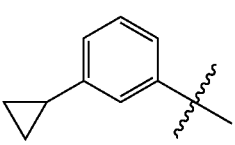

TABLE 1-continued

Exemplary Ring A Groups lv

[Chemical structure: 3-trifluoromethyl-4-chlorophenyl urea linked to phenyl]

lvi

[Chemical structure: 2,3-dihydro-1,4-benzodioxine]

As defined generally above, the Ring B group of formula I is phenyl, a 5-6 membered heteroaryl ring having 1-3 heteratoms independently selected from N, O or S, a 5-6 membered saturated heterocyclic ring having 1-2 heteroatoms independently selected from N, O or S, or an 8-10 membered bicyclic partially unsaturated or aryl ring having 1-3 heteroatoms independently selected from N, O or S.

In some embodiments, the Ring B group of formula I is phenyl. In some embodiments, Ring B is a 6-membered heteroaryl ring having 1-3 nitrogens. In some embodiments, Ring B is a 5-membered heteroaryl ring having 1 or 2 or 3 heteroatoms independently selected from N, O or S.

In some embodiments, the Ring B group of formula I is a 5-6 membered saturated heterocyclic ring having 1 nitrogen. In some embodiments, Ring B is a 9-10 membered bicyclic partially saturated heteroaryl ring having 1-3 nitrogens. In some embodiments, Ring B is a 9-10 membered bicyclic partially saturated heteroaryl ring having 1 nitrogen.

Exemplary Ring B groups are set forth in Table 2.

TABLE 2

Ring B Groups i

[Chemical structure: phenyl with $R^1$ and $R^x$ substituents]

ii

[Chemical structure: pyridine with $R^1$ and $R^x$ substituents]

TABLE 2-continued

Ring B Groups iii

[Chemical structure: pyrazine with $R^1$ and $R^x$ substituents]

iv

[Chemical structure: pyrimidine with $R^1$ and $R^x$ substituents]

v

[Chemical structure: phenyl with $R^1$ and $R^x$ substituents]

vi

[Chemical structure: imidazole with $R^1$ and $R^x$ substituents]

vii

[Chemical structure: piperidine with $R^1$ substituent]

viii

[Chemical structure: pyrrolidine with $R^1$ substituent]

ix

[Chemical structure: indoline with $R^1$ and $R^x$ substituents]

TABLE 2-continued

Ring B Groups x xi xii xiii xiv

In some embodiments, the m moiety of formula I, II, IIa, or IIb is 1, 2, 3 or 4. In some embodiments, m is 1. In other embodiments, m is 0.

As defined generally above, each $R^x$ group of formula I or II is independently selected from —R, halogen, —OR, —CN, —NO$_2$, —SO$_2$R, —SOR, —C(O)R, —CO$_2$R, —C(O)N(R)$_2$, —NRC(O)R, —NRC(O)NR$_2$, —NRSO$_2$R, or —N(R)$_2$, or $R^x$ and $R^1$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group, wherein the warhead group is -Q-Z, and said ring is further substituted with 0-3 groups independently selected from oxo, halogen, CN, or $C_{1-6}$ aliphatic.

In some embodiments, each instance of $R^x$ is independently selected from —R, —OR or halogen. In certain embodiments, $R^x$ is lower alkyl, lower alkoxy, or halogen. Exemplary $R^x$ groups include methyl, methoxy, and chloro. In some embodiments, $R^x$ is hydrogen.

In some embodiments, the G group of any of formula II, II-a, or II-b is CH. In other embodiments, the G group of any of formula II, II-a, or II-b is N.

As defined generally above, the W group of formula I is a bivalent $C_{1-3}$ alkylene chain wherein one methylene unit of W is optionally replaced by —NR$^2$—, —N(R$^2$)C(O)—, —C(O)N(R$^2$)—, —N(R$^2$)SO$_2$—, —SO$_2$N(R$^2$)—, —O—, —C(O)—, —OC(O)—, —C(O)O—, —S—, —SO— or —SO$_2$—.

In certain embodiments, the W group of formula I is —NH—, —S—, or —O—. In some embodiments, the W group of formula I is —CH$_2$O—, —CH$_2$S—, or —CH$_2$NH—. In some aspects, W is —OCH$_2$—, —SCH$_2$—, —NHCH$_2$—, or —CH$_2$CH$_2$—.

In some embodiments, the W group of formula I is —O— thus forming a compound of formula I-i:

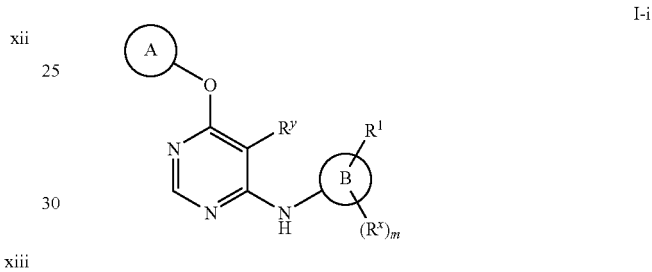

I-i or a pharmaceutically acceptable salt thereof, wherein each of Ring A, $R^1$, $R^x$, $R^y$, and m are as defined above and described in classes and subclasses above and herein.

In some embodiments, W is —NR$^2$— thus forming a compound of formula I-ii:

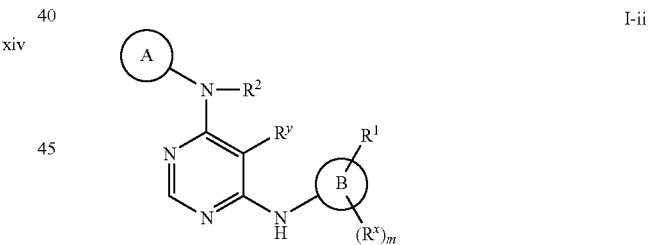

I-ii or a pharmaceutically acceptable salt thereof, wherein each of Ring A, $R^1$, $R^2$, $R^x$, $R^y$, and m are as defined above and described in classes and subclasses above and herein.

In some embodiments, W is —S— thus forming a compound of formula I-iii:

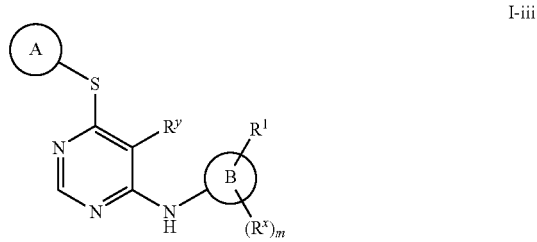

I-iii or a pharmaceutically acceptable salt thereof, wherein each of Ring A, $R^1$, $R^x$, $R^y$, and m are as defined above and described in classes and subclasses above and herein.

In some embodiments, the W group of formula II is —O— thus forming a compound of formula II-i:

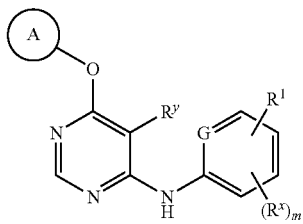

II-i or a pharmaceutically acceptable salt thereof, wherein each of Ring A, $R^1$, $R^x$, $R^y$, and m are as defined above and described in classes and subclasses above and herein.

In some embodiments, the W group of formula II is —$NR^2$— thus forming a compound of formula II-ii:

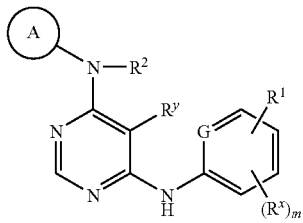

II-ii or a pharmaceutically acceptable salt thereof, wherein each of Ring A, $R^1$, $R^2$, $R^x$, $R^y$, and m are as defined above and described in classes and subclasses above and herein.

In certain embodiments, $R^2$ is hydrogen. In some embodiments, $R^2$ is methyl. In still other embodiments, $R^2$ is lower alkyl.

In some embodiments, the W group of formula II is —S— thus forming a compound of formula II-iii:

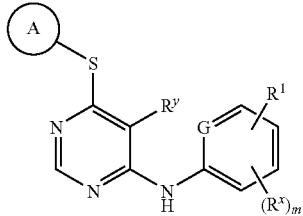

II-iii or a pharmaceutically acceptable salt thereof, wherein each of Ring A, $R^1$, $R^x$, $R^y$, and m are as defined above and described In certain embodiments, the G group of formula II is CH, thus forming a compound of formula III:

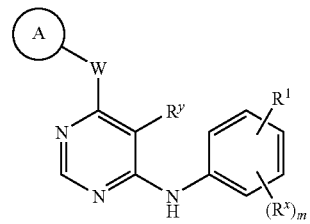

III or a pharmaceutically acceptable salt thereof, wherein each of Ring A, W, $R^1$, $R^x$, $R^y$, and m are as defined above and described in classes and subclasses above and herein.

In certain embodiments, the compound of formula III is of formula III-a-i, III-b-i, III-a-ii, III-b-ii, III-a-iii, or III-b-iii:

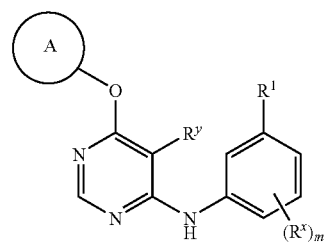

III-a-i

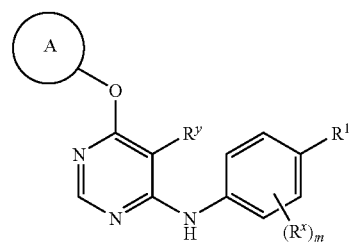

III-b-i

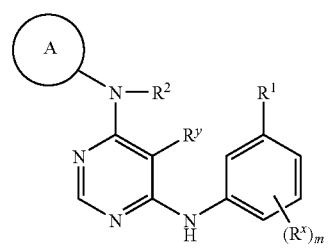

III-a-ii

III-b-ii

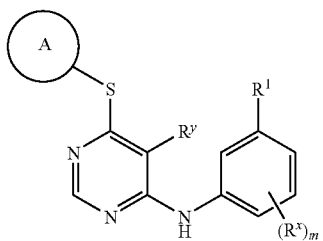
III-a-iii

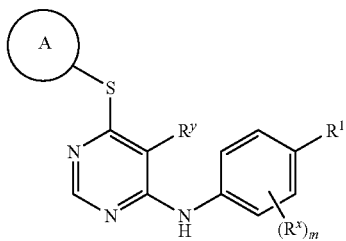
III-b-iii or a pharmaceutically acceptable salt thereof, wherein each of Ring A, $R^1$, $R^2$, $R^x$, $R^y$, and m are as defined above and described in classes and subclasses above and herein.

In certain embodiments, the G group of formula II is N, thus forming a compound of formula IV:

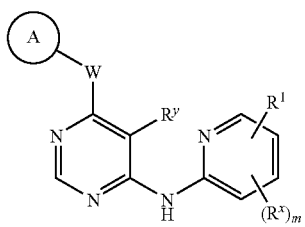
IV or a pharmaceutically acceptable salt thereof, wherein each of Ring A, W, $R^1$, $R^x$, $R^y$, and m are as defined above and described in classes and subclasses above and herein.

In certain embodiments, the compound of formula IV is of formula IV-a-i, IV-b-i, IV-a-ii, IV-b-ii, IV-a-iii, or IV-b-iii:

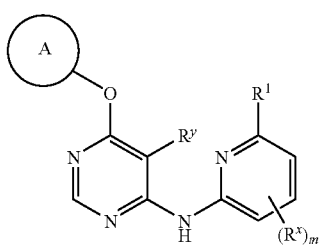
IV-a-i

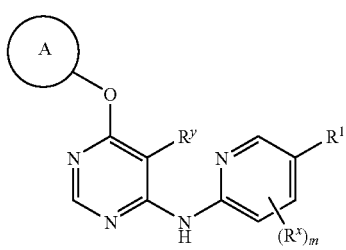
IV-b-i

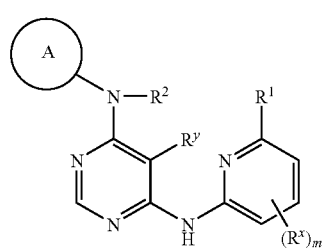
IV-a-ii

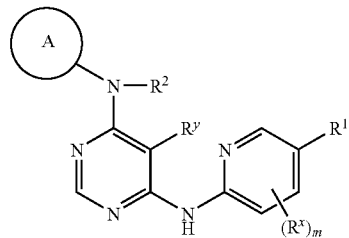
IV-b-ii

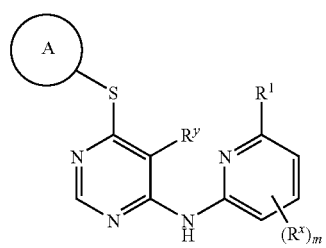
IV-a-iii

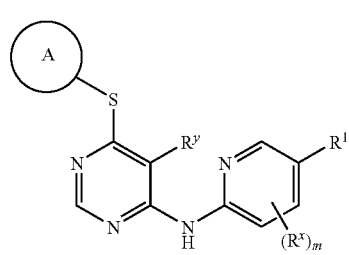
IV-b-iii or a pharmaceutically acceptable salt thereof, wherein each of Ring A, $R^1$, $R^2$, $R^x$, $R^y$, and m are as defined above and described in classes and subclasses above and herein.

According to some aspects, $R^2$ and a substituent on Ring A are taken together with their intervening atoms to form a 4-7 membered saturated or partially unsaturated ring, thus forming a compound of formula II-a-iv or II-b-iv:

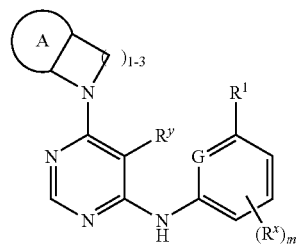
II-a-iv

-continued

II-b-iv

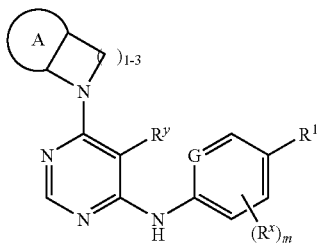

or a pharmaceutically acceptable salt thereof, wherein each of Ring A, R¹, R$^x$, and m are as defined above and described in classes and subclasses above and herein.

In certain embodiments, the present invention provides a compound of formula II-a-v or II-b-v wherein Ring A is phenyl and said compound is of formula II-a-v or II-b-v:

II-a-v

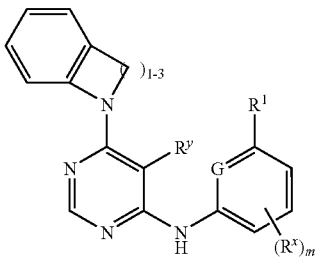

II-b-v

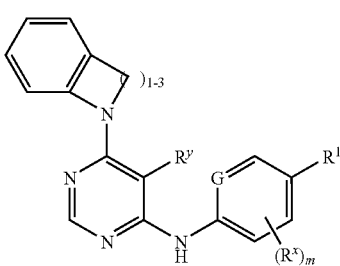

or a pharmaceutically acceptable salt thereof, wherein the Ring A phenyl moiety is optionally substituted and each of R¹, R$^x$, R$^y$, and m are as defined above and described in classes and subclasses above and herein.

In some embodiments, R² is hydrogen. In other embodiments, R² and R$^y$ are taken together thereby forming a compound of formula II-a-vi or II-b-vi:

II-a-vi

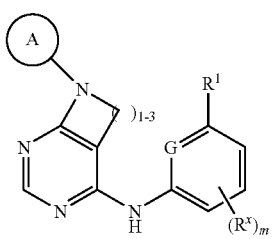

-continued

II-b-vi

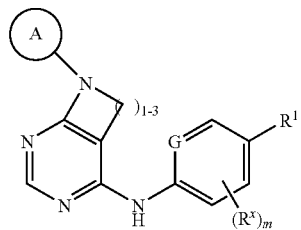

As defined generally above, the R¹ group of formulae I and II is -L-Y, wherein:
L is a covalent bond or a bivalent $C_{1-8}$ saturated or unsaturated, straight or branched, hydrocarbon chain, wherein one, two, or three methylene units of L are optionally and independently replaced by cyclopropylene, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—;
Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; and
each R$^e$ is independently selected from -Q-Z, oxo, NO$_2$, halogen, CN, a suitable leaving group, or a $C_{1-6}$ aliphatic optionally substituted with oxo, halogen, NO$_2$, or CN, wherein:
Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and
Z is hydrogen or $C_{1-6}$ aliphatic optionally substituted with oxo, halogen, NO$_2$, or CN.

In certain embodiments, L is a covalent bond.
In certain embodiments, L is a bivalent $C_{1-8}$ saturated or unsaturated, straight or branched, hydrocarbon chain. In certain embodiments, L is —CH$_2$—.
In certain embodiments, L is a covalent bond, —CH$_2$—, —NH—, —CH$_2$NH—, —NHCH$_2$—, —NHC(O)—, —NHC(O)CH$_2$OC(O)—, —CH$_2$NHC(O)—, —NHSO$_2$—, —NHSO$_2$CH$_2$—, —NHC(O)CH$_2$OC(O)—, or —SO$_2$NH—.
In some embodiments, L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—.
In certain embodiments, L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—.
In some embodiments, L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

As described above, in certain embodiments, L is a bivalent $C_{2-8}$ straight or branched, hydrocarbon chain wherein L has at least one double bond. One of ordinary skill in the art will recognize that such a double bond may exist within the hydrocarbon chain backbone or may be "exo" to the backbone chain and thus forming an alkylidene group. By way of example, such an L group having an alkylidene branched chain includes —CH$_2$C(=CH$_2$)CH$_2$—. Thus, in some embodiments, L is a bivalent $C_{2-8}$ straight or branched, hydrocarbon chain wherein L has at least one alkylidenyl double bond. Exemplary L groups include —NHC(O)C(=CH$_2$)CH$_2$—.

In certain embodiments, L is a bivalent $C_{2-8}$ straight or branched, hydrocarbon chain wherein L has at least one double bond and at least one methylene unit of L is replaced by —C(O)—. In certain embodiments, L is —C(O)CH=CH(CH$_3$)—, —C(O)CH=CHCH$_2$NH(CH$_3$)—, —C(O)CH=CH(CH$_3$)—, —C(O)CH=CH—, —CH$_2$C(O)CH=CH—, —CH$_2$C(O)CH=CH(CH$_3$)—, —CH$_2$CH$_2$C(O)CH=CH—, —CH$_2$CH$_2$C(O)CH=CHCH$_2$—, —CH$_2$CH$_2$C(O)CH=CHCH$_2$NH(CH$_3$)—, or —CH$_2$CH$_2$C(O)CH=CH(CH$_3$)—, or —CH(CH$_3$)OC(O)CH=CH—.

In certain embodiments, L is a bivalent $C_{2-8}$ straight or branched, hydrocarbon chain wherein L has at least one double bond and at least one methylene unit of L is replaced by —OC(O)—.

In some embodiments, L is a bivalent $C_{2-8}$ straight or branched, hydrocarbon chain wherein L has at least one double bond and at least one methylene unit of L is replaced by —NRC(O)—, —C(O)NR—, —N(R)SO$_2$—, —SO$_2$N(R)—, —S—, —S(O)—, —SO$_2$—, —OC(O)—, or —C(O)O—, and one or two additional methylene units of L are optionally and independently replaced by cyclopropylene, —O—, —N(R)—, or —C(O)—. In some embodiments, L is —CH$_2$OC(O)CH=CHCH$_2$—, —CH$_2$—OC(O)CH=CH—, or —CH(CH=CH$_2$)OC(O)CH=CH—.

In certain embodiments, L is —NRC(O)CH=CH—, —NRC(O)CH=CHCH$_2$N(CH$_3$)—, —NRC(O)CH=CHCH$_2$O—, —CH$_2$NRC(O)CH=CH—, —NRSO$_2$CH=CH—, —NRSO$_2$CH=CHCH$_2$—, —NRC(O)(C=N$_2$)C(O)—, —NRC(O)CH=CHCH$_2$N(CH$_3$)—, —NRSO$_2$CH=CH—, —NRSO$_2$CH=CHCH$_2$—, —NRC(O)CH=CHCH$_2$O—, —NRC(O)C(=CH$_2$)CH$_2$—, —CH$_2$NRC(O)—, —CH$_2$NRC(O)CH=CH—, —CH$_2$CH$_2$NRC(O)—, or —CH$_2$NRC(O)cyclopropylene-, wherein each R is independently hydrogen or optionally substituted $C_{1-6}$ aliphatic.

In certain embodiments, L is —NHC(O)CH=CH—, —NHC(O)CH=CHCH$_2$N(CH$_3$)—, —NHC(O)CH=CHCH$_2$O—, —CH$_2$NHC(O)CH=CH—, —NHSO$_2$CH=CH—, —NHSO$_2$CH=CHCH$_2$—, —NHC(O)(C=N$_2$)C(O)—, —NHC(O)CH=CHCH$_2$N(CH$_3$)—, —NHSO$_2$CH=CH—, —NHSO$_2$CH=CHCH$_2$—, —NHC(O)CH=CHCH$_2$O—, —NHC(O)C(=CH$_2$)CH$_2$—, —CH$_2$NHC(O)—, —CH$_2$NHC(O)CH=CH—, —CH$_2$CH$_2$NHC(O)—, or —CH$_2$NHC(O)cyclopropylene-.

In some embodiments, L is a bivalent $C_{2-8}$ straight or branched, hydrocarbon chain wherein L has at least one triple bond. In certain embodiments, L is a bivalent $C_{2-8}$ straight or branched, hydrocarbon chain wherein L has at least one triple bond and one or two additional methylene units of L are optionally and independently replaced by —NRC(O)—, —C(O)NR—, —S—, —S(O)—, —SO$_2$—, —C(=S)—, —C(=NR)—, —O—, —N(R)—, or —C(O)—. In some embodiments, L has at least one triple bond and at least one methylene unit of L is replaced by —N(R)—, —N(R)C(O)—, —C(O)—, —C(O)O—, or —OC(O)—, or —O—.

Exemplary L groups include —C≡C—, —C≡CCH$_2$N(isopropyl)-, —NHC(O)C≡CCH$_2$CH$_2$—, —CH$_2$—C≡C—CH$_2$—, —C≡CCH$_2$O—, —CH$_2$C(O)C≡C—, —C(O)C≡C—, or —CH$_2$C(=O)C≡C—.

In certain embodiments, L is a bivalent $C_{2-8}$ straight or branched, hydrocarbon chain wherein one methylene unit of L is replaced by cyclopropylene and one or two additional methylene units of L are independently replaced by —C(O)—, —NRC(O)—, —C(O)NR—, —N(R)SO$_2$—, or —SO$_2$N(R)—. Exemplary L groups include —NHC(O)-cyclopropylene-SO$_2$— and —NHC(O)-cyclopropylene-.

As defined generally above, Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with at 1-4 $R^e$ groups, each $R^e$ is independently selected from -Q-Z, oxo, NO$_2$, halogen, CN, a suitable leaving group, or $C_{1-6}$ aliphatic, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and, Z is hydrogen or $C_{1-6}$ aliphatic optionally substituted with oxo, halogen, NO$_2$, or CN.

In certain embodiments, Y is hydrogen.

In certain embodiments, Y is $C_{1-6}$ aliphatic optionally substituted with oxo, halogen, NO$_2$, or CN. In some embodiments, Y is $C_{2-6}$ alkenyl optionally substituted with oxo, halogen, NO$_2$, or CN. In other embodiments, Y is $C_{2-6}$ alkynyl optionally substituted with oxo, halogen, NO$_2$, or CN. In some embodiments, Y is $C_{2-6}$ alkenyl. In other embodiments, Y is $C_{2-4}$ alkynyl.

In other embodiments, Y is $C_{1-6}$ alkyl substituted with oxo, halogen, NO$_2$, or CN. Such Y groups include —CH$_2$F, —CH$_2$Cl, —CH$_2$CN, and —CH$_2$NO$_2$.

In certain embodiments, Y is a saturated 3-6 membered monocyclic ring having 0-3 heteroatoms independently selected from nitrogen, oxygen, or sulfur, wherein Y is substituted with 1-4 $R^e$ groups, wherein each $R^e$ is as defined above and described herein.

In some embodiments, Y is a saturated 3-4 membered heterocyclic ring having 1 heteroatom selected from oxygen or nitrogen wherein said ring is substituted with 1-2 $R^e$ groups, wherein each $R^e$ is as defined above and described herein. Exemplary such rings are epoxide and oxetane rings, wherein each ring is substituted with 1-2 $R^e$ groups, wherein each $R^e$ is as defined above and described herein.

In other embodiments, Y is a saturated 5-6 membered heterocyclic ring having 1-2 heteroatom selected from oxygen or nitrogen wherein said ring is substituted with 1-4 $R^e$ groups, wherein each $R^e$ is as defined above and described herein. Such rings include piperidine and pyrrolidine, wherein each ring is substituted with 1-4 $R^e$ groups, wherein each $R^e$ is as defined above and described herein. In certain embodiments, Y is

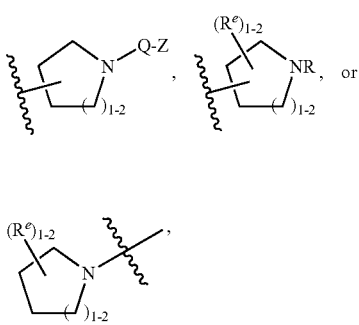

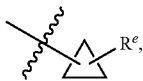

wherein each R, Q, Z, and $R^e$ is as defined above and described herein.

In some embodiments, Y is a saturated 3-6 membered carbocyclic ring, wherein said ring is substituted with 1-4 $R^e$ groups, wherein each $R^e$ is as defined above and described herein. In certain embodiments, Y is cyclopropyl, cyclobutyl, cyclopentyl, or cyclohexyl, wherein each ring is substituted with 1-4 $R^e$ groups, wherein each $R^e$ is as defined above and described herein. In certain embodiments, Y is

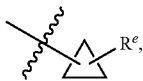

wherein $R^e$ is as defined above and described herein. In certain embodiments, Y is cyclopropyl optionally substituted with halogen, CN or $NO_2$.

In certain embodiments, Y is a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein.

In some embodiments, Y is a partially unsaturated 3-6 membered carbocyclic ring, wherein said ring is substituted with 1-4 $R^e$ groups, wherein each $R^e$ is as defined above and described herein. In some embodiments, Y is cyclopropenyl, cyclobutenyl, cyclopentenyl, or cyclohexenyl wherein each ring is substituted with 1-4 $R^e$ groups, wherein each $R^e$ is as defined above and described herein. In certain embodiments, Y is

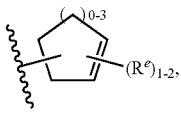

wherein each $R^e$ is as defined above and described herein.

In certain embodiments, Y is a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein. In certain embodiments, Y is selected from:

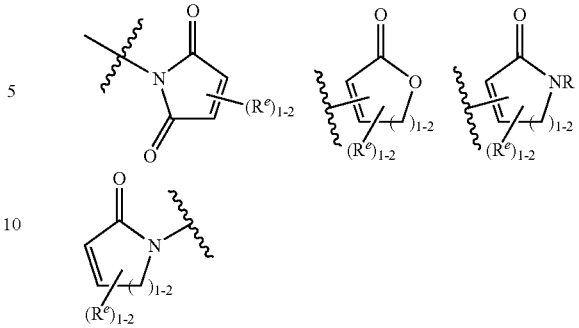

wherein each R and $R^e$ is as defined above and described herein.

In certain embodiments, Y is a 6-membered aromatic ring having 0-2 nitrogens wherein said ring is substituted with 1-4 $R^e$ groups, wherein each $R^e$ group is as defined above and described herein. In certain embodiments, Y is phenyl, pyridyl, or pyrimidinyl, wherein each ring is substituted with 1-4 $R^e$ groups, wherein each $R^e$ is as defined above and described herein.

In some embodiments, Y is selected from:

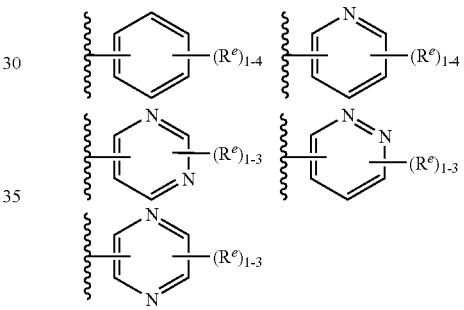

wherein each $R^e$ is as defined above and described herein.

In other embodiments, Y is a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein. In some embodiments, Y is a 5 membered partially unsaturated or aryl ring having 1-3 heteroatoms independently selected from nitrogen, oxygen, and sulfur, wherein said ring is substituted with 1-4 $R^e$ groups, wherein each $R^e$ group is as defined above and described herein. Exemplary such rings are isoxazolyl, oxazolyl, thiazolyl, imidazolyl, pyrazolyl, pyrrolyl, furanyl, thienyl, triazole, thiadiazole, and oxadiazole, wherein each ring is substituted with 1-3 $R^e$ groups, wherein each $R^e$ group is as defined above and described herein. In certain embodiments, Y is selected from:

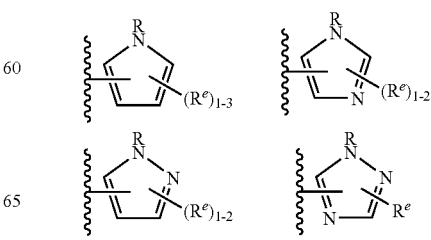

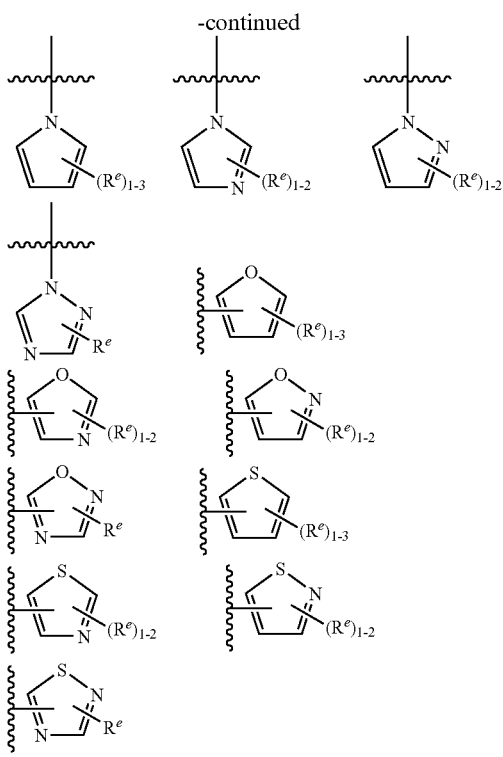

wherein each R and $R^e$ is as defined above and described herein.

In certain embodiments, Y is an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein. According to another aspect, Y is a 9-10 membered bicyclic, partially unsaturated, or aryl ring having 1-3 heteroatoms independently selected from nitrogen, oxygen, or sulfur, wherein said ring is substituted with 1-4 $R^e$ groups, wherein $R^e$ is as defined above and described herein. Exemplary such bicyclic rings include 2,3-dihydrobenzo[d]isothiazole, wherein said ring is substituted with 1-4 $R^e$ groups, wherein $R^e$ is as defined above and described herein.

As defined generally above, each $R^e$ group is independently selected from -Q-Z, oxo, $NO_2$, halogen, CN, a suitable leaving group, or $C_{1-6}$ aliphatic optionally substituted with oxo, halogen, $NO_2$, or CN, wherein Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —$SO_2$—, —N(R)C(O)—, —C(O)N(R)—, —N(R)$SO_2$—, or —$SO_2$N(R)—; and Z is hydrogen or $C_{1-6}$ aliphatic optionally substituted with oxo, halogen, $NO_2$, or CN.

In certain embodiments, $R^e$ is $C_{1-6}$ aliphatic optionally substituted with oxo, halogen, $NO_2$, or CN. In other embodiments, $R^e$ is oxo, $NO_2$, halogen, or CN.

In some embodiments, $R^e$ is -Q-Z, wherein Q is a covalent bond and Z is hydrogen (i.e., $R^e$ is hydrogen). In other embodiments, $R^e$ is -Q-Z, wherein Q is a bivalent $C_{1-6}$ saturated or unsaturated, straight or branched, hydrocarbon chain, wherein one or two methylene units of Q are optionally and independently replaced by —NR—, —NRC(O)—, —C(O)NR—, —S—, —O—, —C(O)—, —SO—, or —$SO_2$—. In other embodiments, Q is a bivalent $C_{2-6}$ straight or branched, hydrocarbon chain having at least one double bond, wherein one or two methylene units of Q are optionally and independently replaced by —NR—, —NRC(O)—, —C(O)NR—, —S—, —O—, —C(O)—, —SO—, or —$SO_2$—. In certain embodiments, the Z moiety of the $R^e$ group is hydrogen. In some embodiments, -Q-Z is —NHC(O)CH=$CH_2$ or —C(O)CH=$CH_2$.

In certain embodiments, each $R^e$ is independently selected from oxo, $NO_2$, CN, fluoro, chloro, —NHC(O)CH=$CH_2$, —C(O)CH=$CH_2$, —$CH_2$CH=$CH_2$, —C≡CH, —C(O)OCH_2Cl, —C(O)OCH_2F, —C(O)OCH_2CN, —C(O)CH_2Cl, —C(O)CH_2F, —C(O)CH_2CN, or —$CH_2$C(O)$CH_3$.

In certain embodiments, $R^e$ is a suitable leaving group, ie a group that is subject to nucleophilic displacement. A "suitable leaving" is a chemical group that is readily displaced by a desired incoming chemical moiety such as the thiol moiety of a cysteine of interest. Suitable leaving groups are well known in the art, e.g., see, "Advanced Organic Chemistry," Jerry March, 5th Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methanesulfonyloxy (mesyloxy), tosyloxy, triflyloxy, nitro-phenylsulfonyloxy (nosyloxy), and bromo-phenylsulfonyloxy (brosyloxy).

In certain embodiments, the following embodiments and combinations of -L-Y apply:

(a) L is a bivalent $C_{2-8}$ straight or branched, hydrocarbon chain wherein L has at least one double bond and one or two additional methylene units of L are optionally and independently replaced by —NRC(O)—, —C(O)NR—, —N(R)$SO_2$—, —$SO_2$N(R)—, —S—, —S(O)—, —$SO_2$—, —OC(O)—, —C(O)O—, cyclopropylene, —O—, —N(R)—, or —C(O)—; and Y is hydrogen or $C_{1-6}$ aliphatic optionally substituted with oxo, halogen, $NO_2$, or CN; or (b) L is a bivalent $C_{2-8}$ straight or branched, hydrocarbon chain wherein L has at least one double bond and at least one methylene unit of L is replaced by —C(O)—, —NRC(O)—, —C(O)NR—, —N(R)$SO_2$—, —$SO_2$N(R)—, —S—, —S(O)—, —$SO_2$—, —OC(O)—, or —C(O)O—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (c) L is a bivalent $C_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—; and Y is hydrogen or $C_{1-6}$ aliphatic optionally substituted with oxo, halogen, $NO_2$, or CN; or (d) L is a bivalent $C_{2-8}$ straight or branched, hydrocarbon chain wherein L has at least one double bond and at least one methylene unit of L is replaced by —C(O)—; and Y is hydrogen or $C_{1-6}$ aliphatic optionally substituted with oxo, halogen, $NO_2$, or CN; or (e) L is a bivalent $C_{2-8}$ straight or branched, hydrocarbon chain wherein L has at least one double bond and at least one methylene unit of L is replaced by —OC(O)—; and Y is hydrogen or $C_{1-6}$ aliphatic optionally substituted with oxo, halogen, $NO_2$, or CN; or (f) L is —NRC(O)CH=CH—, —NRC(O)CH=CHCH₂N(CH₃)—, —NRC(O)CH=CHCH₂O—, —CH₂NRC(O)CH=CH—, —NRSO₂CH=CH—, —NRSO₂CH=CHCH₂—, —NRC(O)(C=N₂)—, —NRC(O)(C=N₂)C(O)—, —NRC(O)CH=CHCH₂N(CH₃)—, —NRSO₂CH=CH—, —NRSO₂CH=CHCH₂—, —NRC(O)CH=CHCH₂O—, —NRC(O)C(=CH₂)CH₂—, —CH₂NRC(O)—, —CH₂NRC(O)CH=CH—, —CH₂CH₂NRC(O)—, or —CH₂NRC(O)cyclopropylene-; wherein R is H or optionally substituted C₁₋₆ aliphatic; and Y is hydrogen or C₁₋₆ aliphatic optionally substituted with oxo, halogen, NO₂, or CN; or (g) L is —NHC(O)CH=CH—, —NHC(O)CH=CHCH₂N(CH₃)—, —NHC(O)CH=CHCH₂O—, —CH₂NHC(O)CH=CH—, —NHSO₂CH=CH—, —NHSO₂CH=CHCH₂—, —NHC(O)(C=N₂)—, —NHC(O)(C=N₂)C(O)—, —NHC(O)CH=CHCH₂N(CH₃)—, —NHSO₂CH=CH—, —NHSO₂CH=CHCH₂—, —NHC(O)CH=CHCH₂O—, —NHC(O)C(=CH₂)CH₂—, —CH₂NHC(O)—, —CH₂NHC(O)CH=CH—, —CH₂CH₂NHC(O)—, or —CH₂NHC(O)cyclopropylene-; and Y is hydrogen or C₁₋₆ aliphatic optionally substituted with oxo, halogen, NO₂, or CN; or (h) L is a bivalent C₂₋₈ straight or branched, hydrocarbon chain wherein L has at least one alkylidenyl double bond and at least one methylene unit of L is replaced by —C(O)—, —NRC(O)—, —C(O)NR—, —N(R)SO₂—, —SO₂N(R)—, —S—, —S(O)—, —SO₂—, —OC(O)—, or —C(O)O—, and one or two additional methylene units of L are optionally and independently replaced by cyclopropylene, —O—, —N(R)—, or —C(O)—; and Y is hydrogen or C₁₋₆ aliphatic optionally substituted with oxo, halogen, NO₂, or CN; or (i) L is a bivalent C₂₋₈ straight or branched, hydrocarbon chain wherein L has at least one triple bond and one or two additional methylene units of L are optionally and independently replaced by —NRC(O)—, —C(O)NR—, —N(R)SO₂—, —SO₂N(R)—, —S—, —S(O)—, —SO₂—, —OC(O)—, or —C(O)O—, and Y is hydrogen or C₁₋₆ aliphatic optionally substituted with oxo, halogen, NO₂, or CN; or (j) L is —C≡C—, —C≡CCH₂N(isopropyl)-, —NHC(O)C≡CCH₂CH₂—, —CH₂—C≡C—CH₂—, —C≡CCH₂O—, —CH₂C(O)C≡C—, —C(O)C≡C—, or —CH₂OC(=O)C≡C—; and Y is hydrogen or C₁₋₆ aliphatic optionally substituted with oxo, halogen, NO₂, or CN; or (k) L is a bivalent C₂₋₈ straight or branched, hydrocarbon chain wherein one methylene unit of L is replaced by cyclopropylene and one or two additional methylene units of L are independently replaced by —NRC(O)—, —C(O)NR—, —N(R)SO₂—, —SO₂N(R)—, —S—, —S(O)—, —SO₂—, —OC(O)—, or —C(O)O—; and Y is hydrogen or C₁₋₆ aliphatic optionally substituted with oxo, halogen, NO₂, or CN; or (l) L is a covalent bond and Y is selected from:
 (i) C₁₋₆ alkyl substituted with oxo, halogen, NO₂, or CN;
 (ii) C₂₋₆ alkenyl optionally substituted with oxo, halogen, NO₂, or CN; or
 (iii) C₂₋₆ alkynyl optionally substituted with oxo, halogen, NO₂, or CN; or
 (iv) a saturated 3-4 membered heterocyclic ring having 1 heteroatom selected from oxygen or nitrogen wherein said ring is substituted with 1-2 R$^e$ groups, wherein each R$^e$ is as defined above and described herein; or
 (v) a saturated 5-6 membered heterocyclic ring having 1-2 heteroatom selected from oxygen or nitrogen wherein said ring is substituted with 1-4 R$^e$ groups, wherein each R$^e$ is as defined above and described herein; or
 (vi)

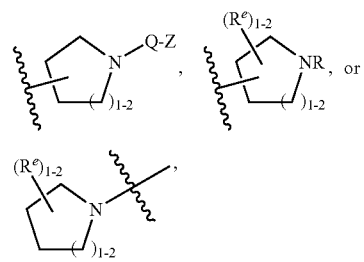

wherein each R, Q, Z, and R$^e$ is as defined above and described herein; or
 (vii) a saturated 3-6 membered carbocyclic ring, wherein said ring is substituted with 1-4 R$^e$ groups, wherein each R$^e$ is as defined above and described herein; or
 (viii) a partially unsaturated 3-6 membered monocyclic ring having 0-3 heteroatoms independently selected from nitrogen, oxygen, or sulfur, wherein said ring is substituted with 1-4 R$^e$ groups, wherein each R$^e$ is as defined above and described herein; or
 (ix) a partially unsaturated 3-6 membered carbocyclic ring, wherein said ring is substituted with 1-4 R$^e$ groups, wherein each R$^e$ is as defined above and described herein; or
 (x)

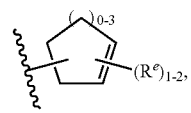

wherein each R$^e$ is as defined above and described herein; or
 (xi) a partially unsaturated 4-6 membered heterocyclic ring having 1-2 heteroatoms independently selected from nitrogen, oxygen, or sulfur, wherein said ring is substituted with 1-4 R$^e$ groups, wherein each R$^e$ is as defined above and described herein; or
 (xii)

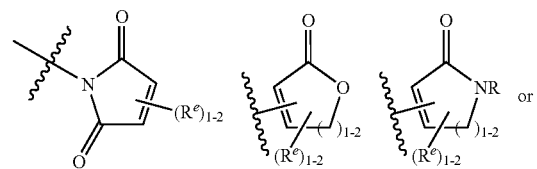

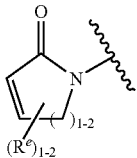

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

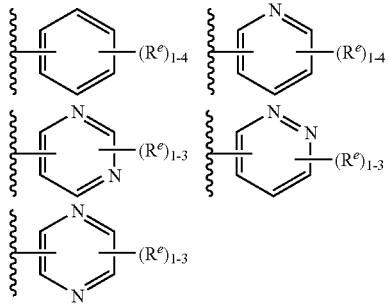

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

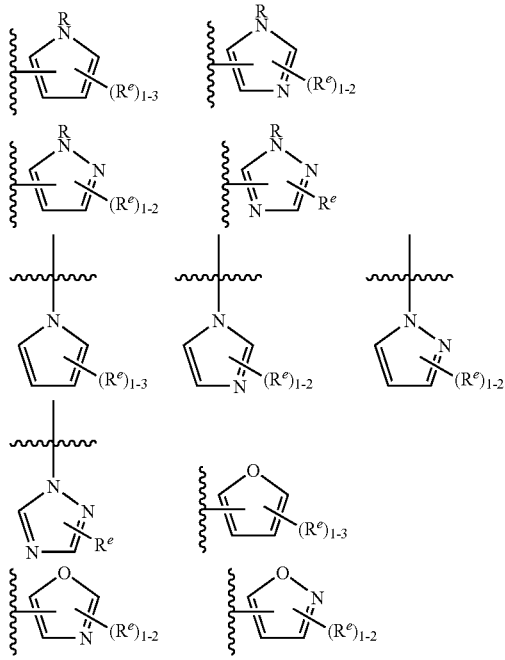

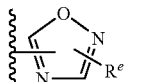
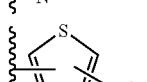
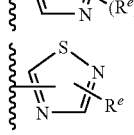

where in each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(m) L is —C(O)— and Y is selected from:
(i) $C_{1-6}$ alkyl substituted with oxo, halogen, $NO_2$, or CN; or
(ii) $C_{2-6}$ alkenyl optionally substituted with oxo, halogen, $NO_2$, or CN; or
(iii) $C_{2-6}$ alkynyl optionally substituted with oxo, halogen, $NO_2$, or CN; or
(iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or
(v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or
(vi)

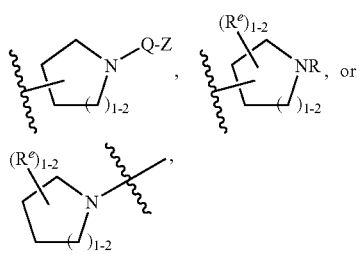

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or (x)

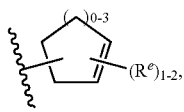

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

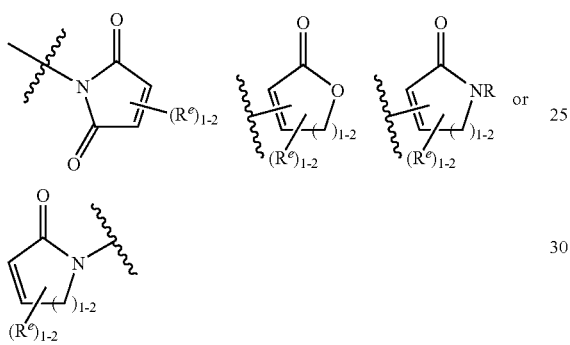

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

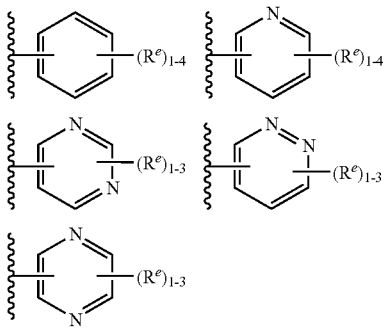

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

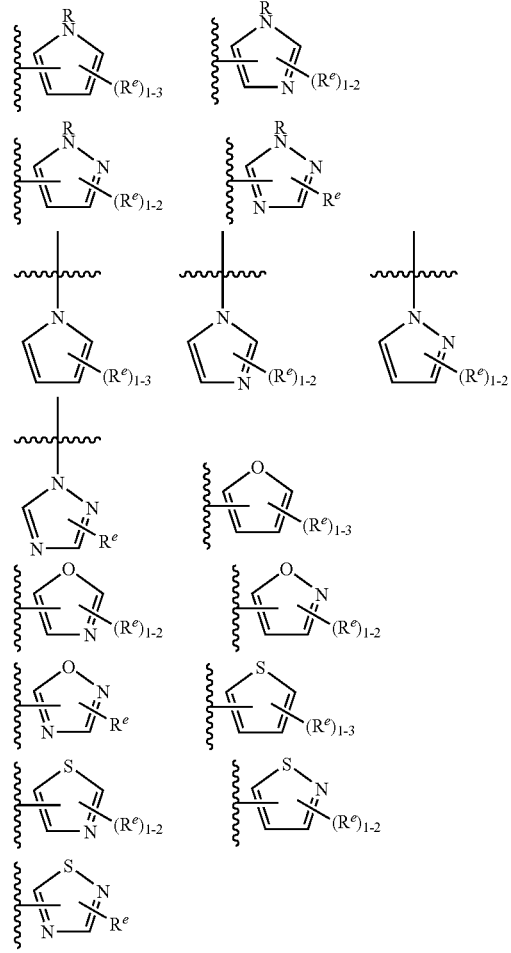

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(n) L is —N(R)C(O)— and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

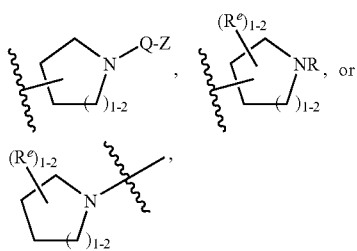

wherein each R, Q, Z, and $R^e$ is as defined above and described herein; or
(vii) a saturated 3-6 membered carbocyclic ring, wherein said ring is substituted with 1-4 $R^e$ groups, wherein each $R^e$ is as defined above and described herein; or
(viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or
(ix) a partially unsaturated 3-6 membered carbocyclic ring, wherein said ring is substituted with 1-4 $R^e$ groups, wherein each $R^e$ is as defined above and described herein; or
(x)

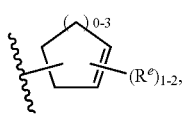

wherein each $R^e$ is as defined above and described herein; or
(xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or
(xii)

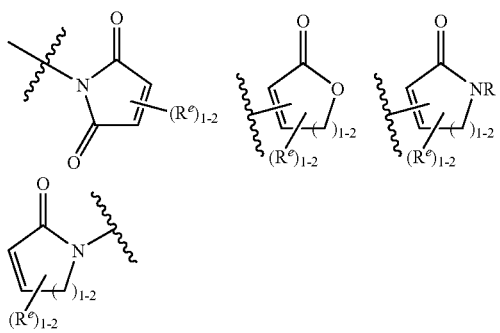

wherein each R and $R^e$ is as defined above and described herein; or
(xiii) a 6-membered aromatic ring having 0-2 nitrogens wherein said ring is substituted with 1-4 $R^e$ groups, wherein each $R^e$ group is as defined above and described herein; or (xiv)

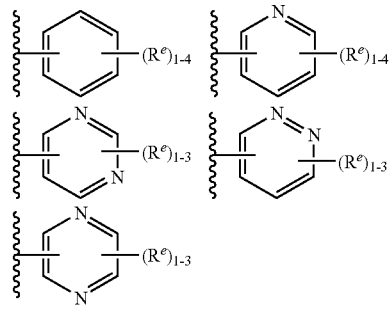

wherein each $R^e$ is as defined above and described herein; or
(xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or
(xvi)

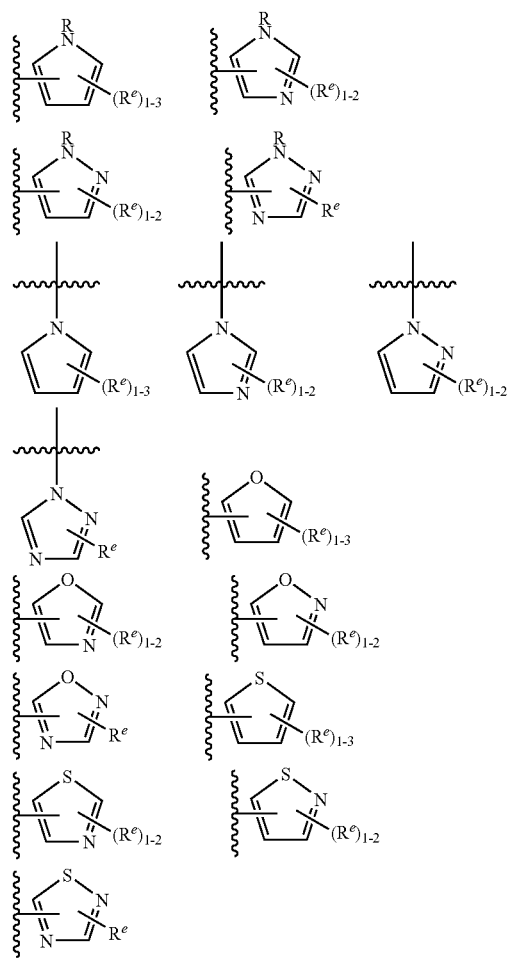

wherein each R and $R^e$ is as defined above and described herein; or
(xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(o) L is a bivalent $C_{1-8}$ saturated or unsaturated, straight or branched, hydrocarbon chain; and Y is selected from:

(i) $C_{1-6}$ alkyl substituted with oxo, halogen, $NO_2$, or CN;

(ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

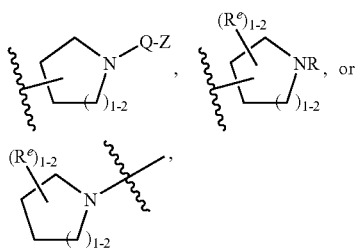

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

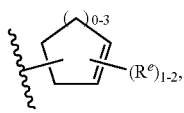

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

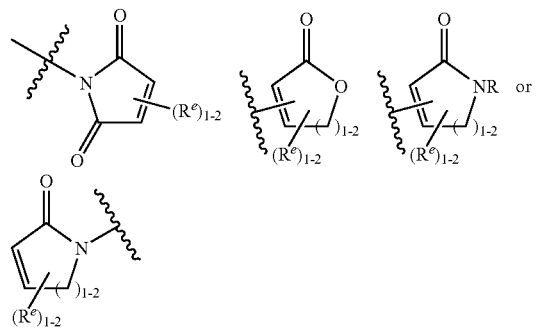

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

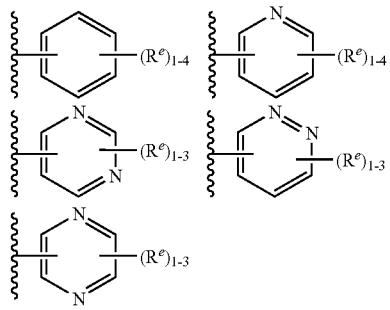

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

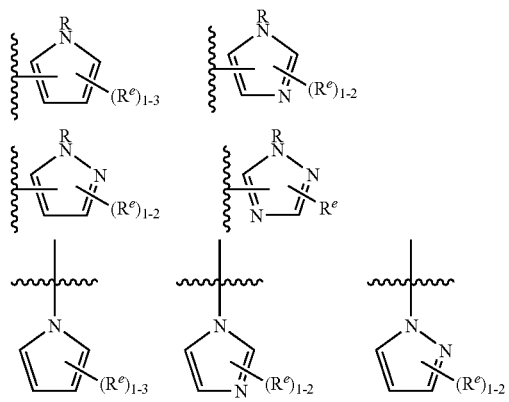

-continued

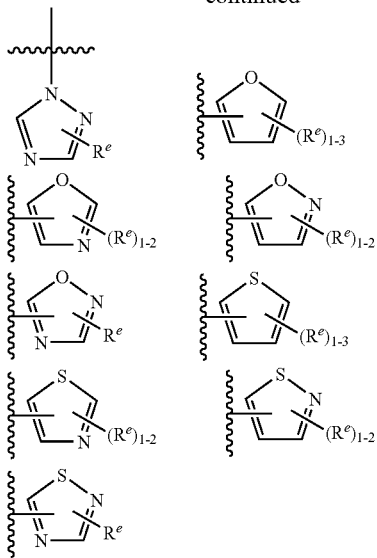

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein;

(p) L is a covalent bond, —$CH_2$—, —NH—, —C(O)—, —$CH_2$NH—, —NH$CH_2$—, —NHC(O)—, —NHC(O)$CH_2$OC(O)—, —$CH_2$NHC(O)—, —NH$SO_2$—, —NH$SO_2CH_2$—, —NHC(O)$CH_2$OC(O)—, or —$SO_2$NH—; and Y is selected from:

(i) $C_{1-6}$ alkyl substituted with oxo, halogen, $NO_2$, or CN; or (ii) $C_{2-6}$ alkenyl optionally substituted with oxo, halogen, $NO_2$, or CN; or (iii) $C_{2-6}$ alkynyl optionally substituted with oxo, halogen, $NO_2$, or CN; or (iv) a saturated 3-4 membered heterocyclic ring having 1 heteroatom selected from oxygen or nitrogen wherein said ring is substituted with 1-2 $R^e$ groups, wherein each $R^e$ is as defined above and described herein; or (v) a saturated 5-6 membered heterocyclic ring having 1-2 heteroatom selected from oxygen or nitrogen wherein said ring is substituted with 1-4 $R^e$ groups, wherein each $R^e$ is as defined above and described herein; or (vi)

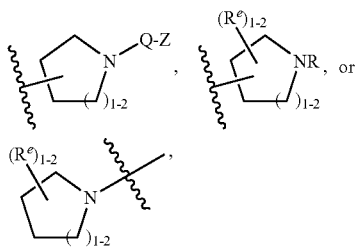

wherein each R, Q, Z, and $R^e$ is as defined above and described herein; or (vii) a saturated 3-6 membered carbocyclic ring, wherein said ring is substituted with 1-4 $R^e$ groups, wherein each $R^e$ is as defined above and described herein; or (viii) a partially unsaturated 3-6 membered monocyclic ring having 0-3 heteroatoms independently selected from nitrogen, oxygen, or sulfur, wherein said ring is substituted with 1-4 $R^e$ groups, wherein each $R^e$ is as defined above and described herein; or (ix) a partially unsaturated 3-6 membered carbocyclic ring, wherein said ring is substituted with 1-4 $R^e$ groups, wherein each $R^e$ is as defined above and described herein; or (x)

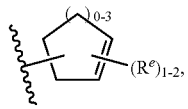

wherein each $R^e$ is as defined above and described herein; or (xi) a partially unsaturated 4-6 membered heterocyclic ring having 1-2 heteroatoms independently selected from nitrogen, oxygen, or sulfur, wherein said ring is substituted with 1-4 $R^e$ groups, wherein each $R^e$ is as defined above and described herein; or (xii)

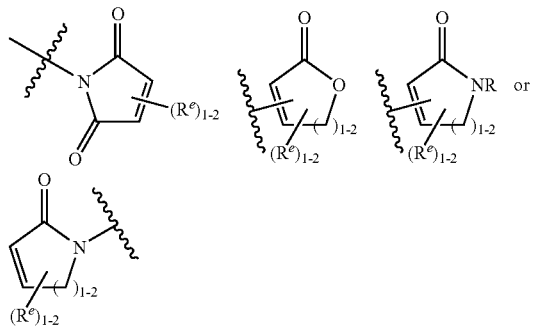

wherein each R and $R^e$ is as defined above and described herein; or (xiii) a 6-membered aromatic ring having 0-2 nitrogens wherein said ring is substituted with 1-4 $R^e$ groups, wherein each $R^e$ group is as defined above and described herein; or (xiv)

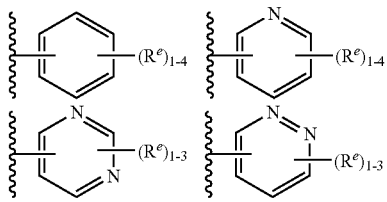

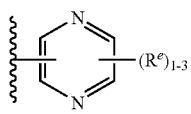

wherein each $R^e$ is as defined above and described herein; or (xv) a 5-membered heteroaryl ring having 1-3 heteroatoms independently selected from nitrogen, oxygen, or sulfur, wherein said ring is substituted with 1-3 $R^e$ groups, wherein each $R^e$ group is as defined above and described herein; or (xvi)

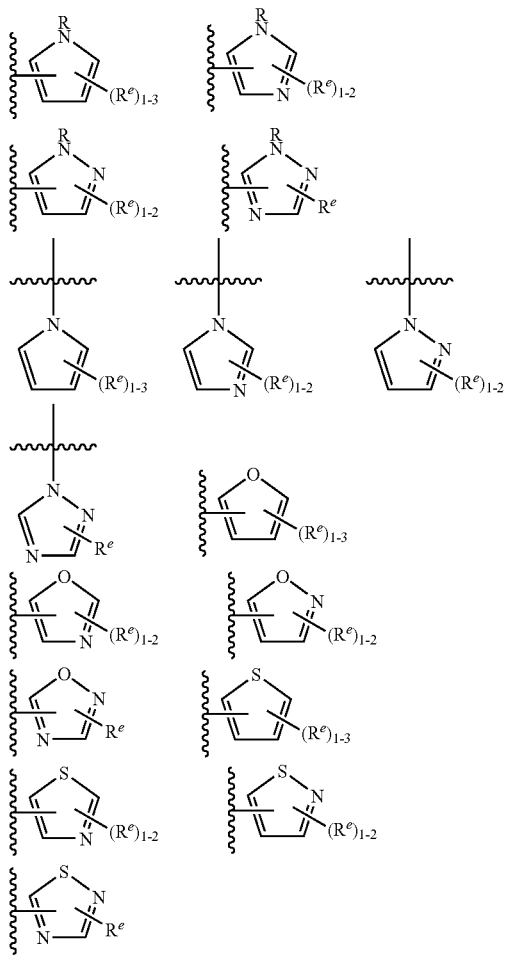

wherein each R and $R^e$ is as defined above and described herein; or (xvii) an 8-10 membered bicyclic, saturated, partially unsaturated, or aryl ring having 0-3 heteroatoms independently selected from nitrogen, oxygen, or sulfur, wherein said ring is substituted with 1-4 $R^e$ groups, wherein $R^e$ is as defined above and described herein.

In certain embodiments, the Y group of formula I is selected from those set forth in Table 3, below, wherein each wavy line indicates the point of attachment to the rest of the molecule.

TABLE 3

Exemplary Y groups:

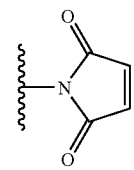 a

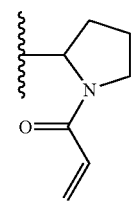 b

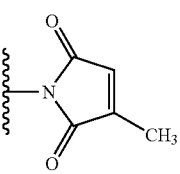 c

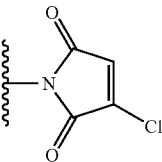 d

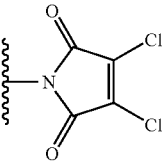 e

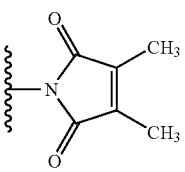 f

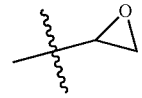 g

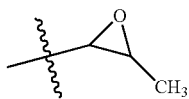 h

TABLE 3-continued
Exemplary Y groups:
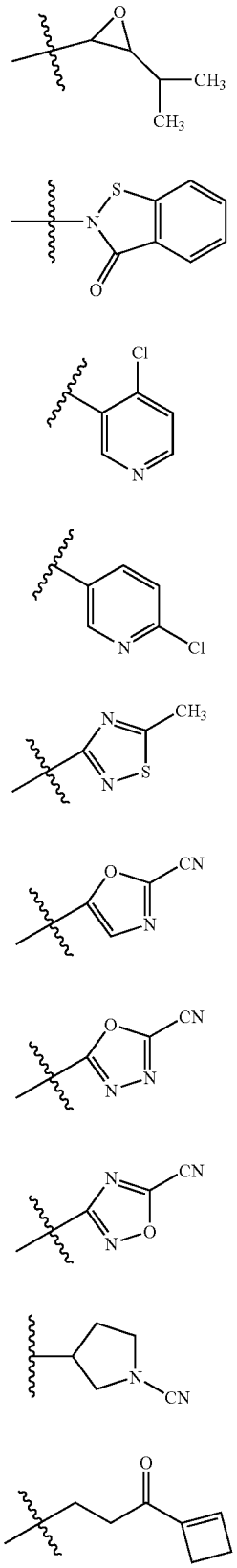
TABLE 3-continued
Exemplary Y groups:
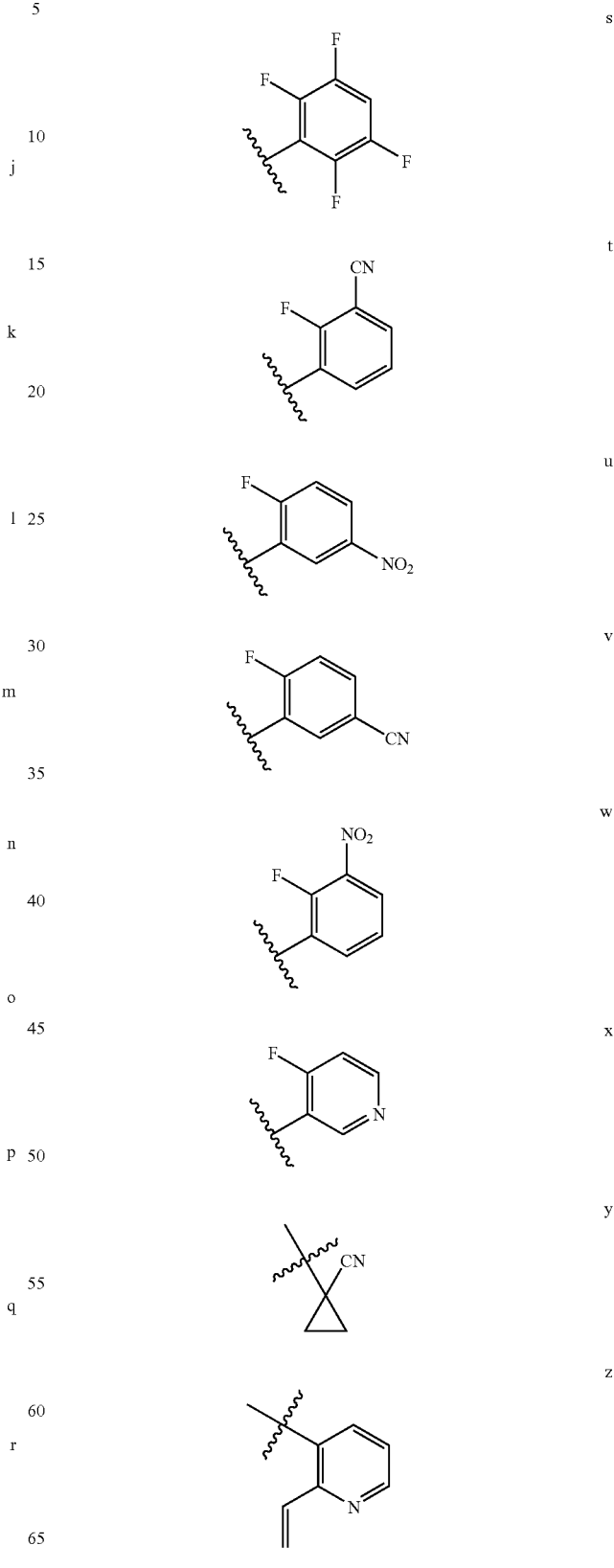

TABLE 3-continued
Exemplary Y groups:
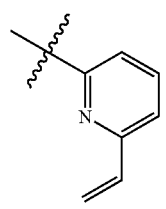 aa
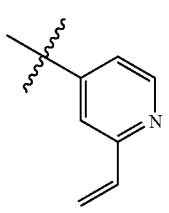 bb
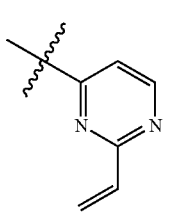 cc
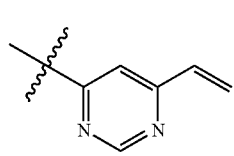 dd
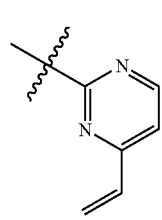 ee
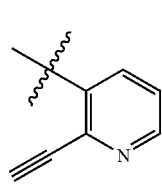 ff
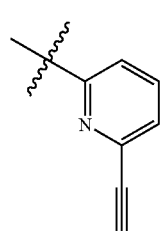 gg
TABLE 3-continued
Exemplary Y groups:
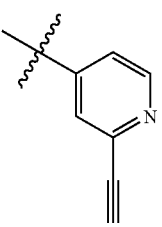 hh
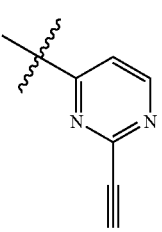 ii
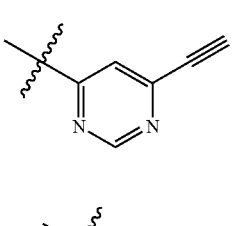 jj
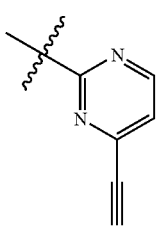 kk
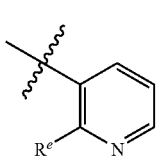 ll
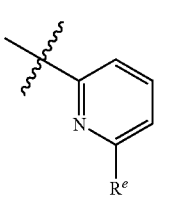 mm
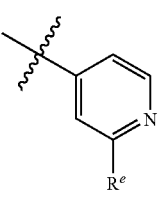 nn TABLE 3-continued
Exemplary Y groups:
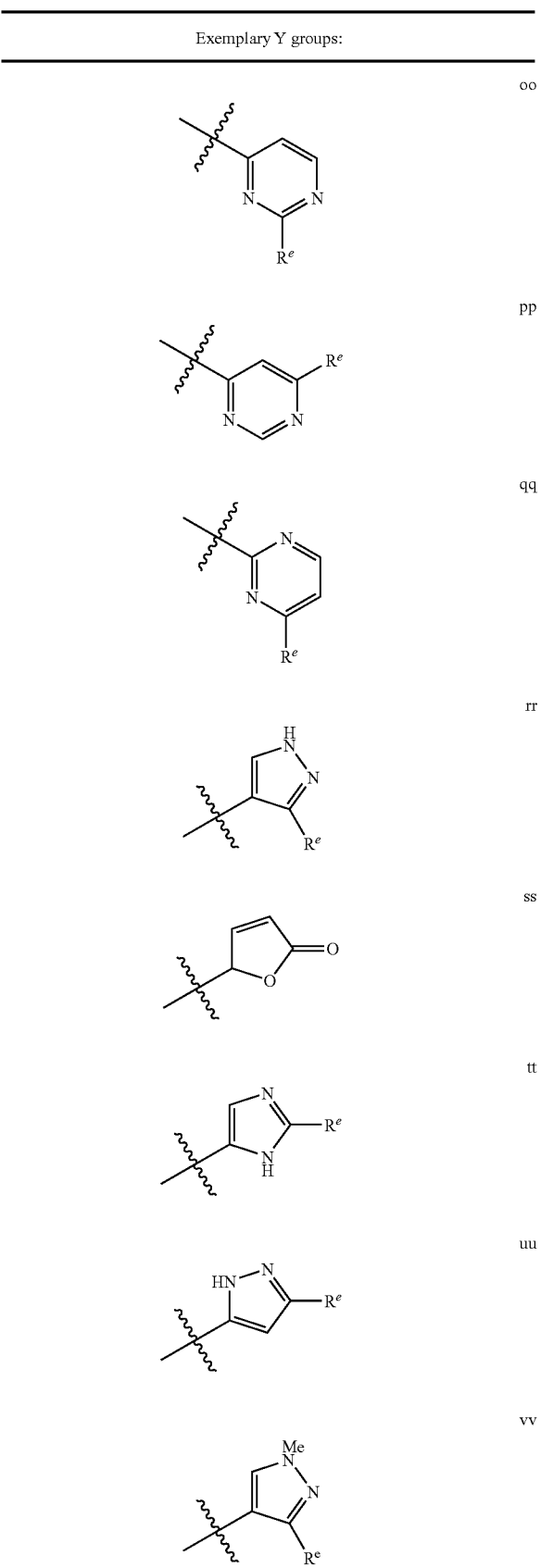
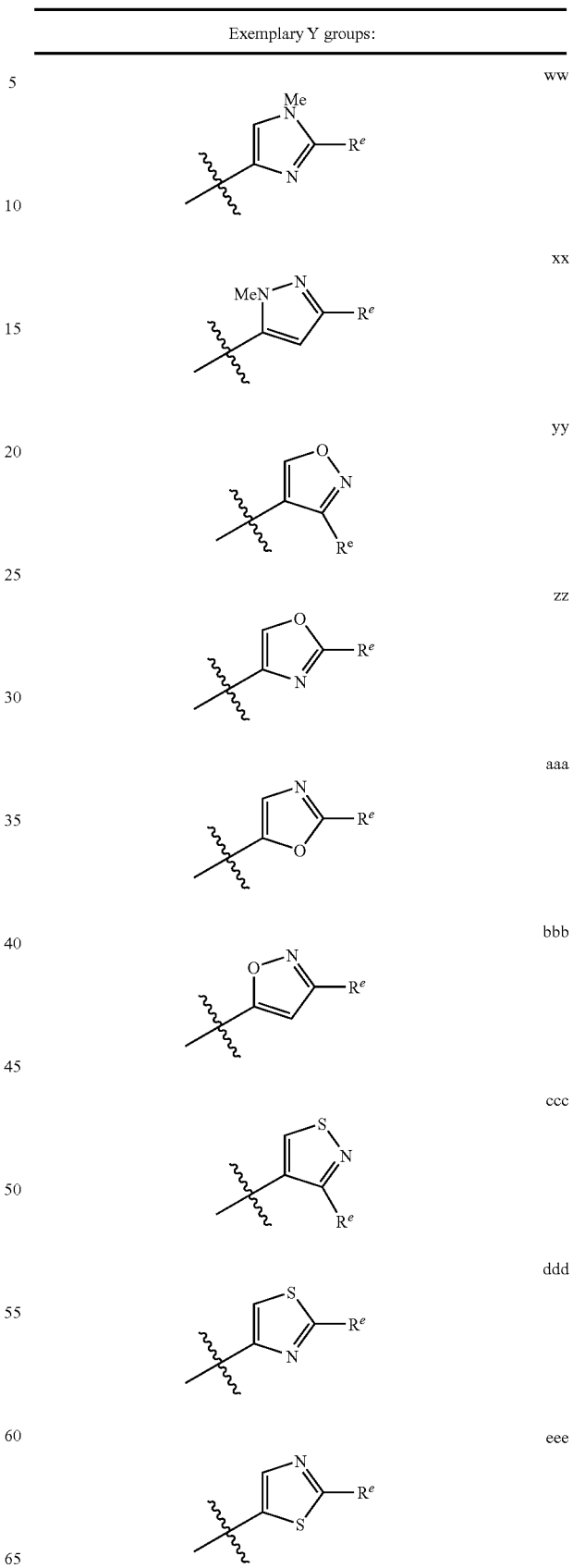

TABLE 3-continued

Exemplary Y groups:

| Label | |
|---|---|
| fff | 5-isothiazolyl with $R^e$ |
| ggg | 1H-pyrazol-4-yl with vinyl |
| hhh | 1H-imidazol-4-yl with vinyl |
| iii | 1H-pyrazol-3-yl with vinyl |
| jjj | 1-Me-pyrazol-4-yl with vinyl |
| kkk | 1-Me-imidazol-5-yl with vinyl |
| lll | 1-Me-imidazol-5-yl with vinyl |
| mmm | 1-Me-pyrazol-5-yl with vinyl |
| nnn | isoxazol-4-yl with vinyl |
| ooo | oxazol-4-yl with vinyl |
| ppp | oxazol-5-yl with vinyl |
| qqq | isothiazol-4-yl with vinyl |
| rrr | thiazol-4-yl with vinyl |
| sss | thiazol-5-yl with vinyl |
| ttt | isothiazol-5-yl with vinyl |
| uuu | isoxazol-5-yl with vinyl |
| vvv | 1H-pyrazol-4-yl with ethynyl |
| qqq | 5,6-dihydro-2H-pyran-2-one |

TABLE 3-continued
Exemplary Y groups:
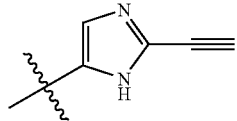 www
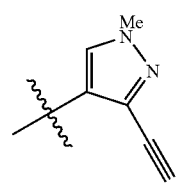 xxx
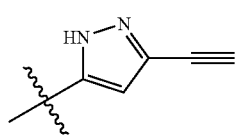 yyy
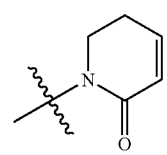 zzz
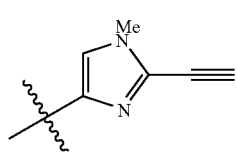 aaaa
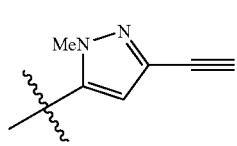 bbbb
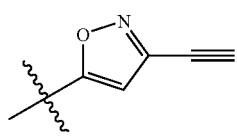 cccc
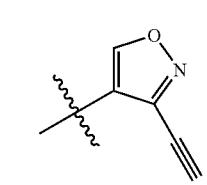 dddd
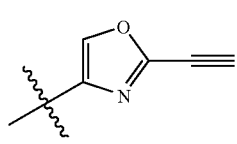 eeee
TABLE 3-continued
Exemplary Y groups:
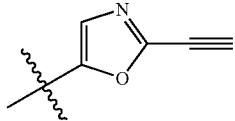 ffff
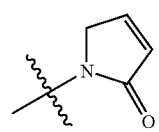 gggg
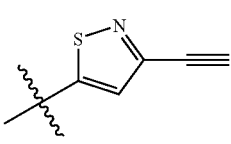 hhhh
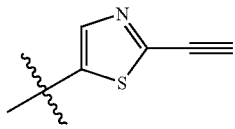 iiii
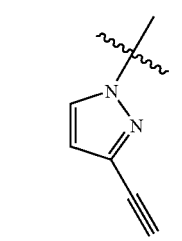 jjjj
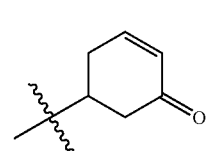 kkkk
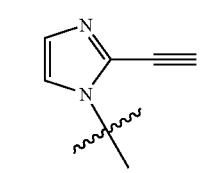 llll
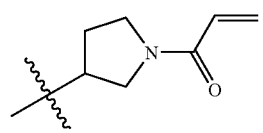 mmmm
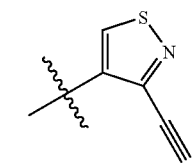 nnnn TABLE 3-continued Exemplary Y groups:

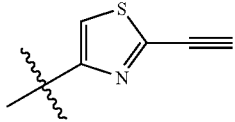 oooo

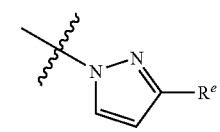 pppp

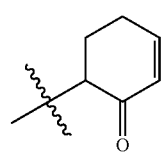 qqqq

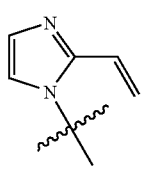 rrrr

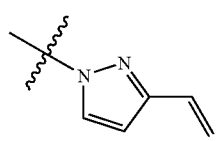 ssss

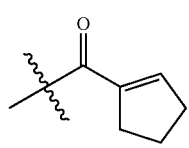 tttt

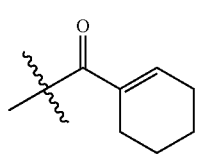 uuuu

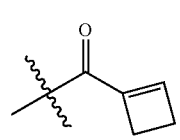 vvvv

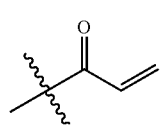 wwww

TABLE 3-continued

Exemplary Y groups:

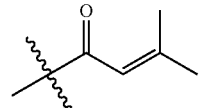 xxxx

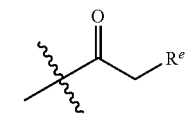 yyyy

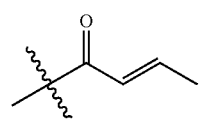 zzzz

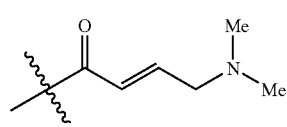 aaaaa

 bbbbb

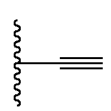 ccccc wherein each $R^e$ is independently a suitable leaving group, $NO_2$, CN, or oxo.

In certain embodiments, $R^1$ is —C≡CH, —C≡CCH₂NH (isopropyl), —NHC(O)C≡CCH₂CH₃, —CH₂—C≡C—CH₃, —C≡CCH₂OH, —CH₂C(O)C≡CH, —C(O)C≡CH, or —CH₂C(=O)C≡CH. In some embodiments, $R^1$ is selected from —NHC(O)CH=CH₂, —NHC(O)CH=CHCH₂N(CH₃)₂, or —CH₂NHC(O)CH=CH₂.

In certain embodiments, $R^1$ is selected from those set forth in Table 4, below, wherein each wavy line indicates the point of attachment to the rest of the molecule.

TABLE 4

Exemplary $R^1$ Groups

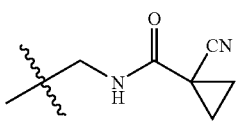 a

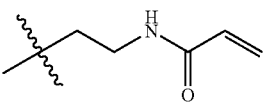 b

TABLE 4-continued
Exemplary R[1] Groups
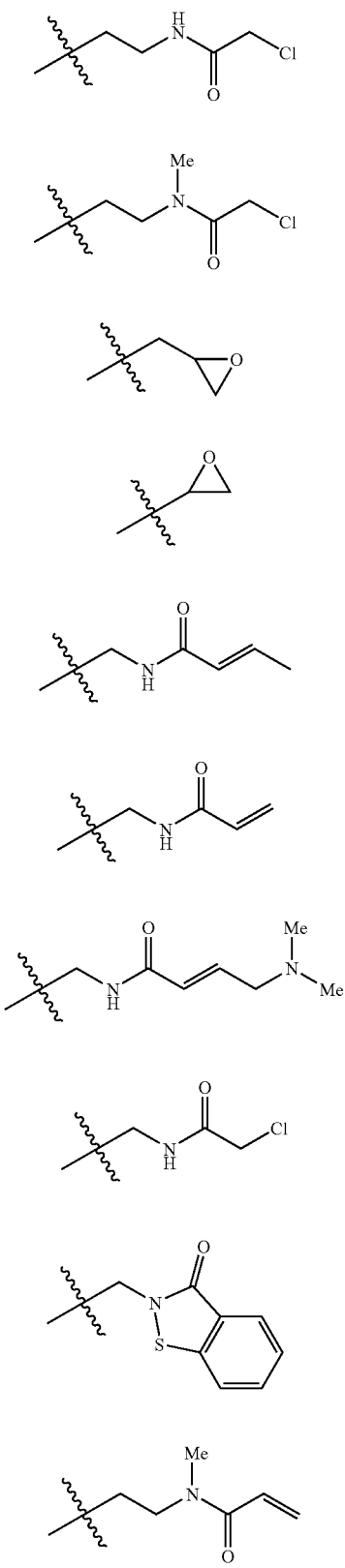
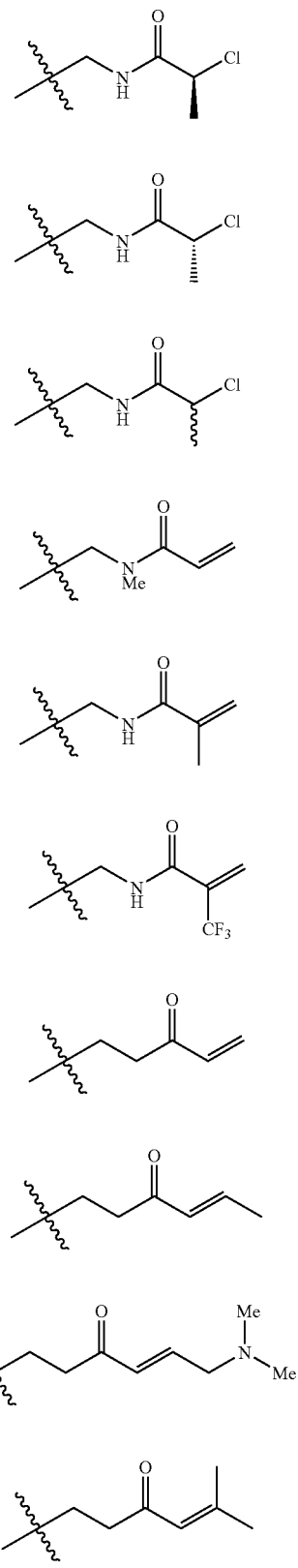

TABLE 4-continued
Exemplary R¹ Groups
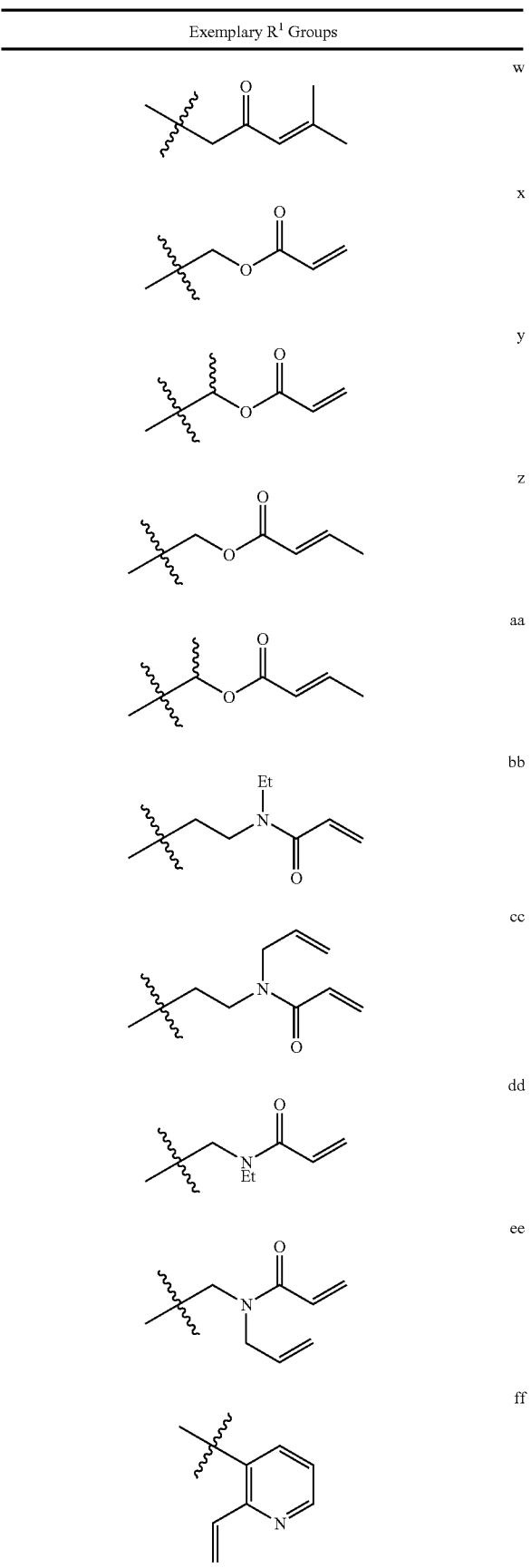
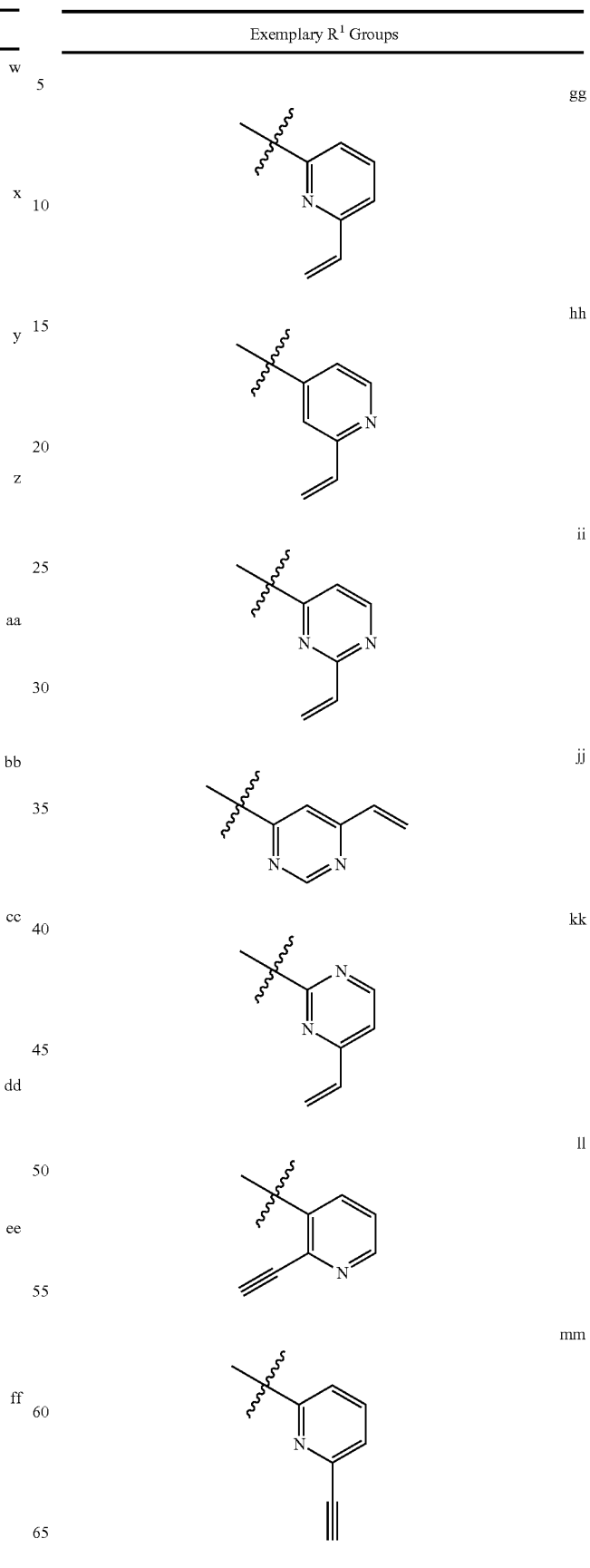

TABLE 4-continued
Exemplary R¹ Groups
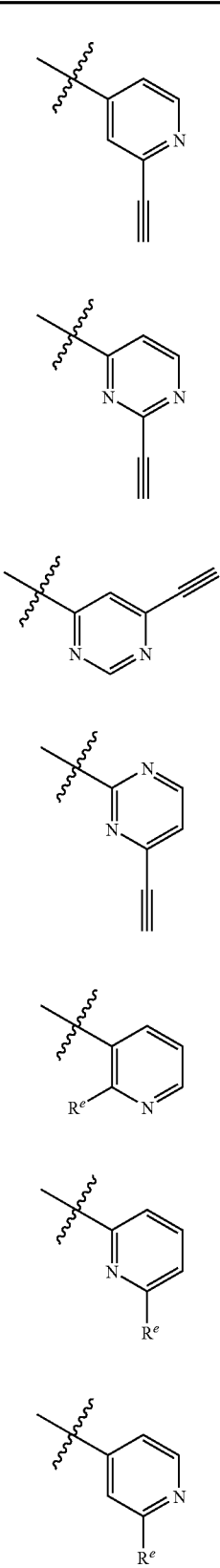
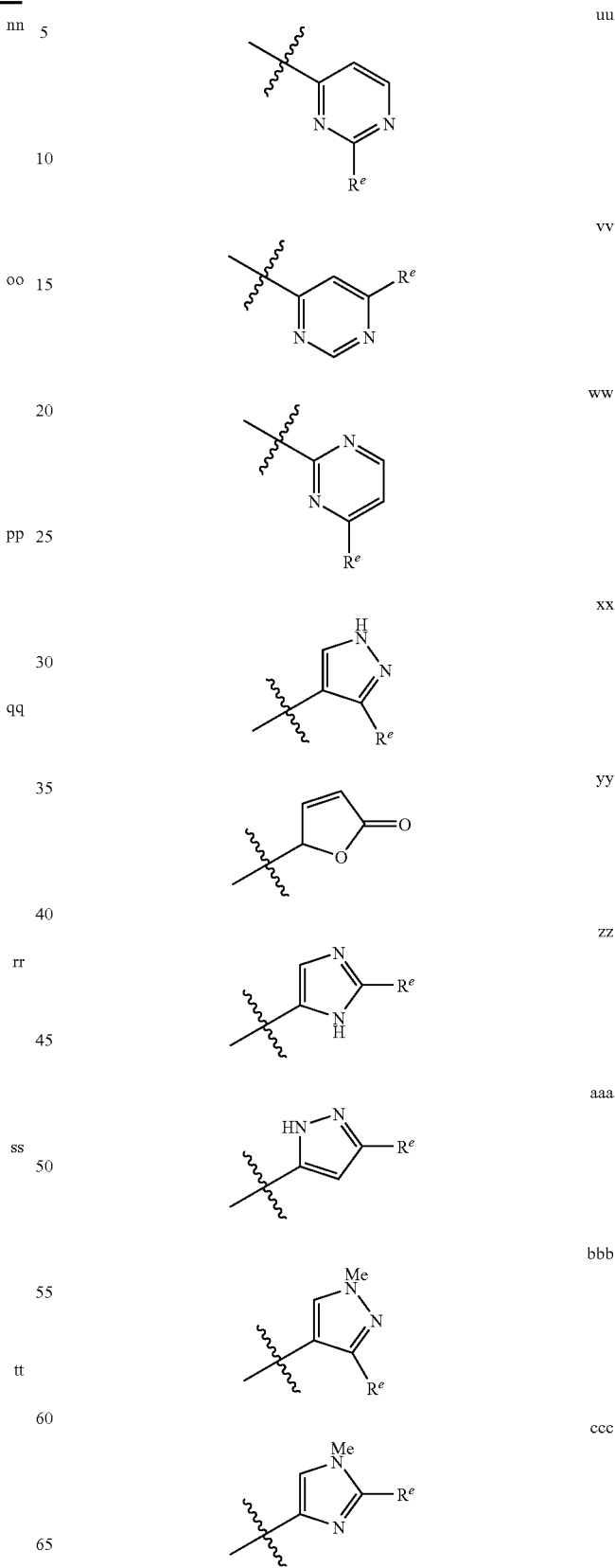

TABLE 4-continued

| Exemplary R¹ Groups | |
|---|---|
| ddd | (imidazole with Rᵉ, N-Me) |
| eee | (pyrazole, MeN, Rᵉ) |
| fff | (isoxazole with Rᵉ) |
| ggg | (oxazole with Rᵉ) |
| hhh | (oxazole with Rᵉ) |
| iii | (isoxazole with Rᵉ) |
| jjj | (isothiazole with Rᵉ) |
| kkk | (thiazole with Rᵉ) |
| lll | (thiazole with Rᵉ) |
| mmm | (isothiazole with Rᵉ) |
| nnn | (pyrazole NH, vinyl) |
| ooo | (imidazole NH, vinyl) |
| ppp | (pyrazole HN, vinyl; pyrazole MeN, vinyl) |
| qqq | (pyrazole N-Me, vinyl) |
| rrr | (isoxazole, vinyl) |
| sss | (oxazole, vinyl) |
| ttt | (oxazole, vinyl) |
| uuu | (isoxazole, vinyl) |

TABLE 4-continued
Exemplary R¹ Groups
vvv
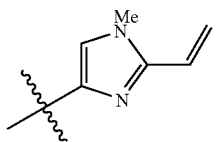
www
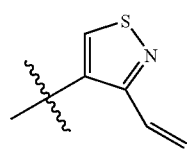
xxx
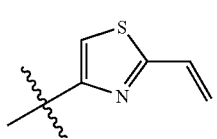
yyy
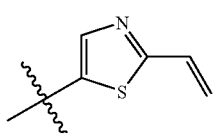
zzz
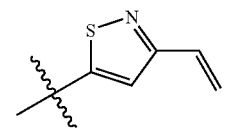
aaaa
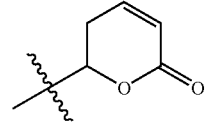
bbbb
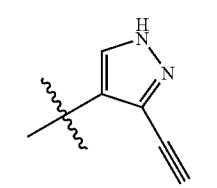
cccc
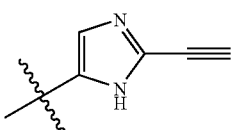
dddd
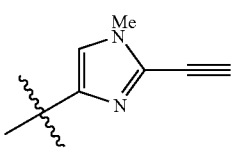
TABLE 4-continued
Exemplary R¹ Groups
eeee
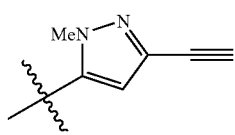
ffff
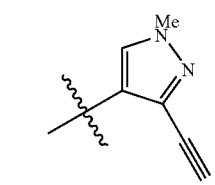
gggg
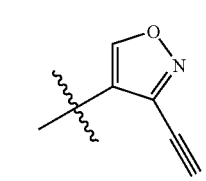
hhhh
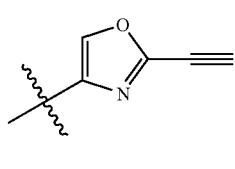
iiii
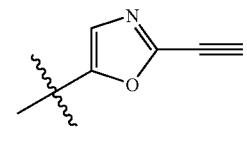
jjjj
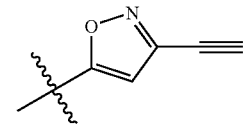
kkkk
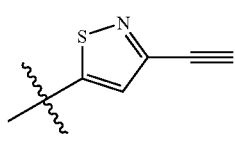
llll
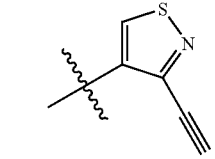
mmmm
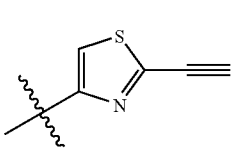

TABLE 4-continued
Exemplary R¹ Groups
nnnn 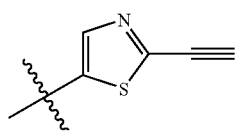
oooo 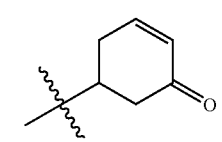
pppp 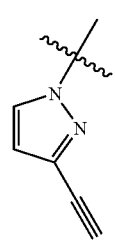
qqqq 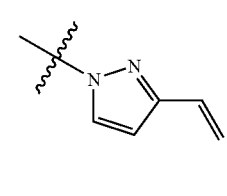
rrrr 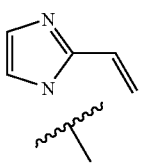
ssss 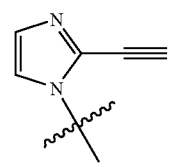
tttt 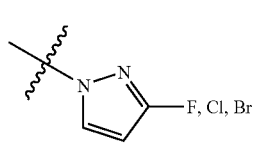
uuuu 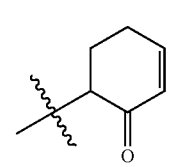
TABLE 4-continued
Exemplary R¹ Groups
vvvv 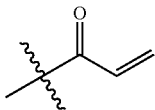
wwww 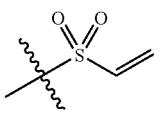
xxxx 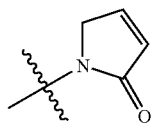
yyyy 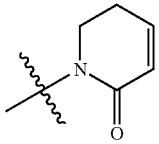
zzzz 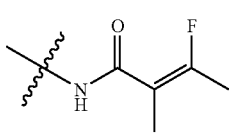
aaaaa 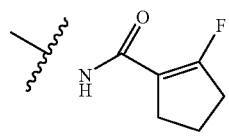
bbbbb 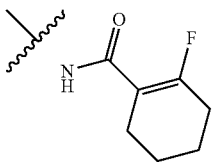
ccccc 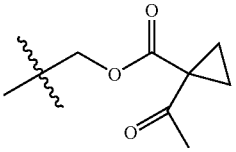
ddddd 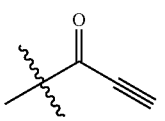

TABLE 4-continued
Exemplary R¹ Groups
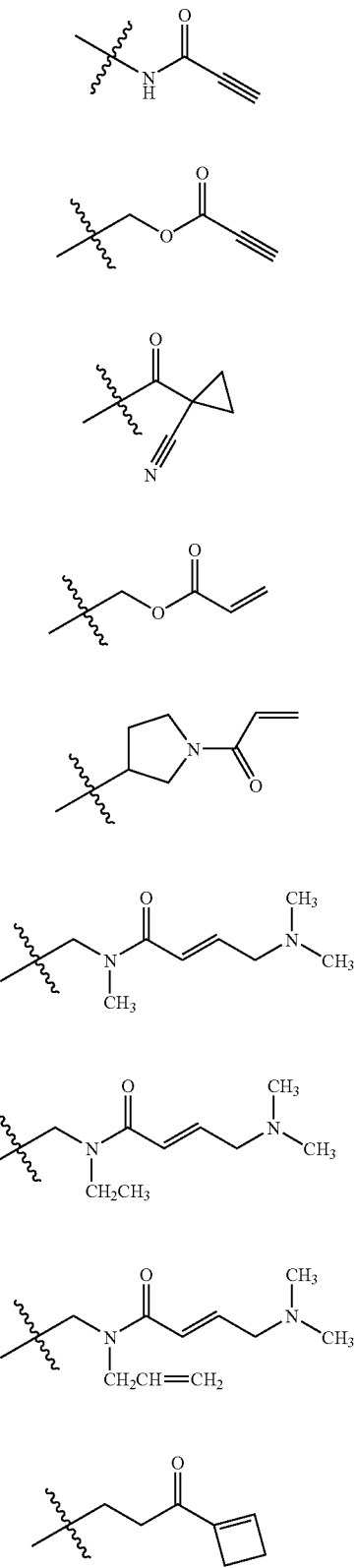
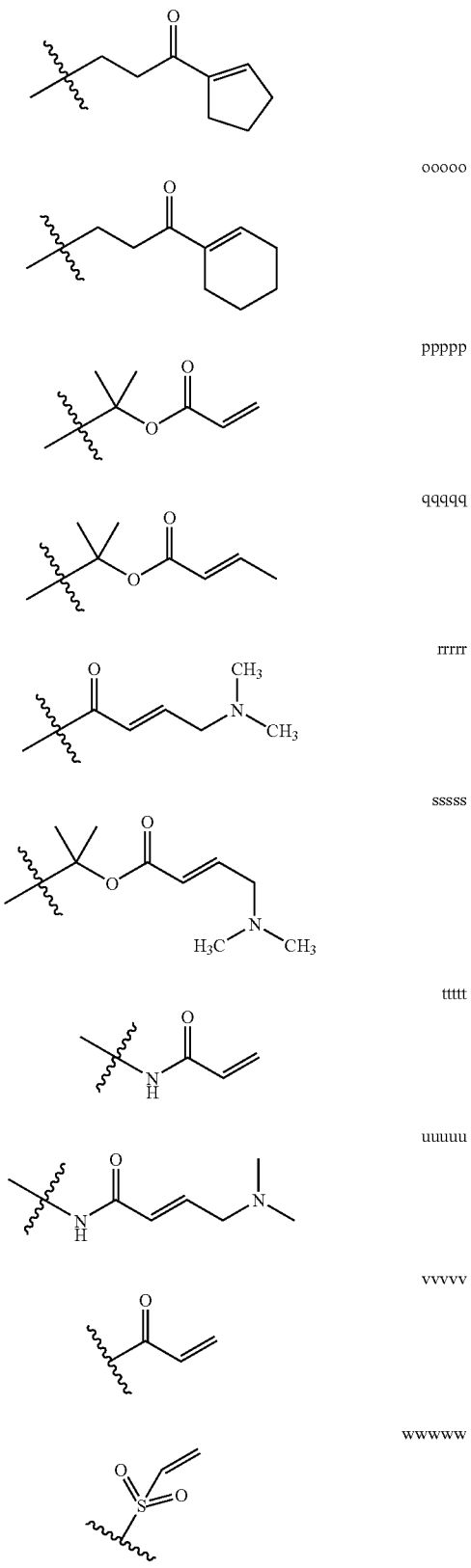

TABLE 4-continued
Exemplary R¹ Groups
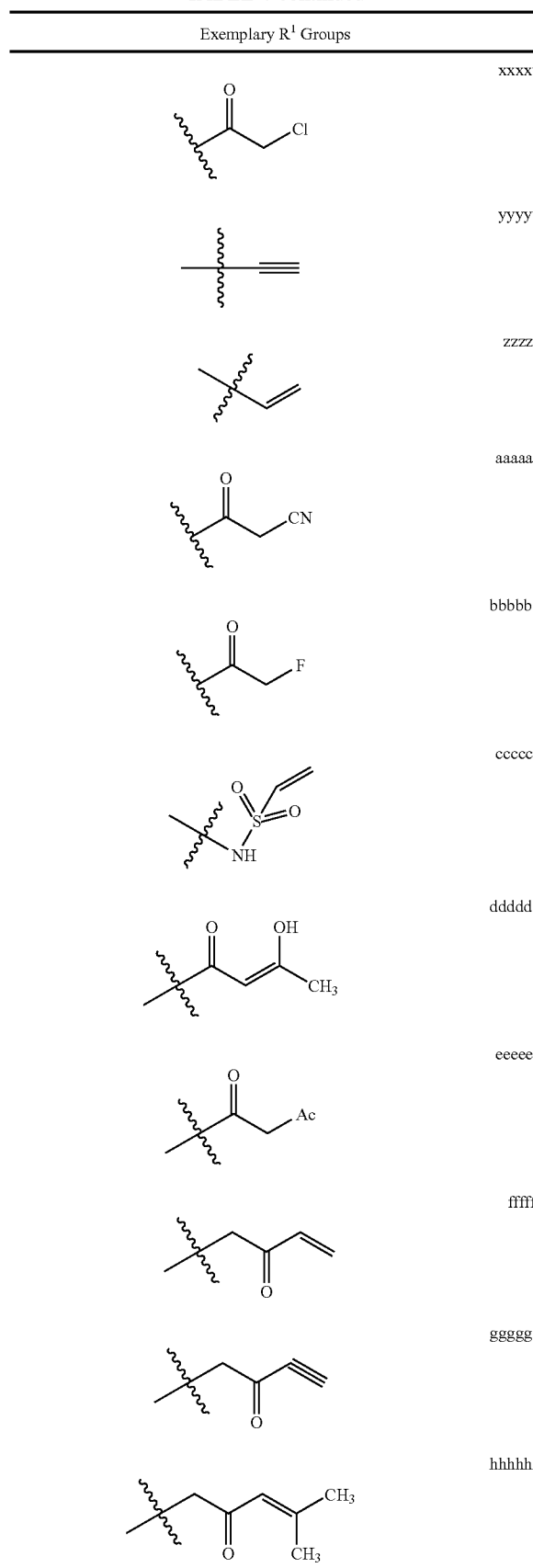
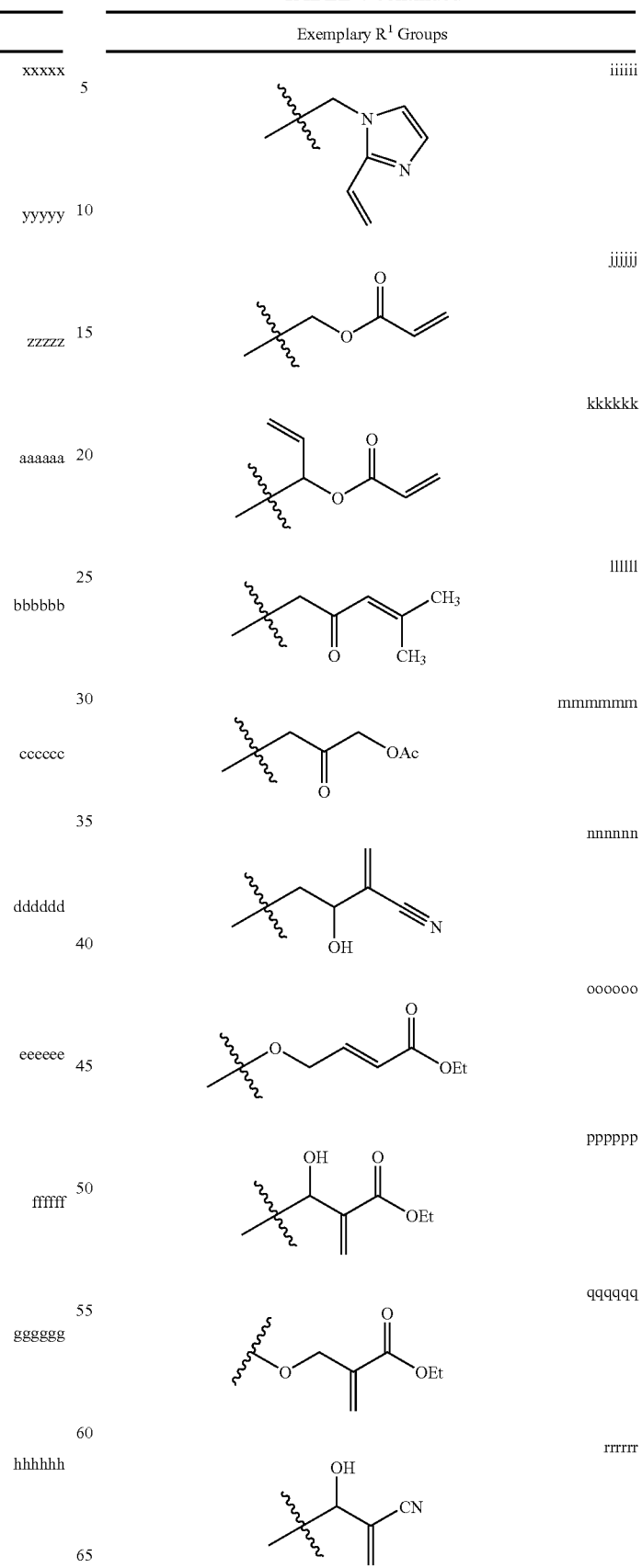

TABLE 4-continued

Exemplary $R^1$ Groups sssss ttttt uuuuuu vvvvvv wwwwww xxxxxx wherein each $R^e$ is independently a suitable leaving group, $NO_2$, CN, or oxo.

As defined generally above, $R^1$ is a warhead group, or, when $R^1$ and $R^x$ form a ring, then -Q-Z is a warhead group. Without wishing to be bound by any particular theory, it is believed that such $R^1$ groups, i.e. warhead groups, are particularly suitable for covalently binding to a key cysteine residue in the binding domain of certain protein kinases. Protein kinases having a cysteine residue in the binding domain are known to one of ordinary skill in the art and include ErbB1, ErbB2, and ErbB4, or a mutant thereof. In certain embodiments, compounds of the present invention have a warhead group characterized in that inventive compounds target one or more of the following cysteine residues:

```
ERBB1    SEQ ID 7:    ITQLMPFGCLLDYVREH

ERBB2    SEQ ID 8:    VTQLMPYGCLLDHVREN

ERBB4    SEQ ID 9:    VTQLMPHGCLLEYVHEH
```

Thus, in some embodiments, $R^1$ is characterized in that the -L-Y moiety is capable of covalently binding to a cysteine residue thereby irreversibly inhibiting the enzyme. In certain embodiments, the cysteine residue is Cys797 of ErbB1, Cys805 of ErbB2 and Cys803 of ErbB4, or a mutant thereof, where the provided residue numbering is in accordance with Uniprot (code POO533 for ErbB1; code PO4626 for ErbB2, and Q15303 for ErbB4). It will be understood that the Cys of ErbB1 (EGFR) is variably called 773 or 797 depending on whether the parent sequence contains the signal peptide or not. Thus, in accordance with the present invention, the relevant cysteine residue of ErbB1 may be described as Cys 773 or Cys 797 and these terms are used interchangeably.

One of ordinary skill in the art will recognize that a variety of warhead groups, as defined herein, are suitable for such covalent bonding. Such $R^1$ groups include, but are not limited to, those described herein and depicted in Table 4, infra. One of ordinary skill in the art will recognize that ErbB3 has no corresponding residue and, as recognized in the relevant art, is not catalytically active.

As depicted in Formula I supra, the $R^1$ warhead group can be in an ortho-, meta-, or para-position. In certain embodiments, the $R^1$ warhead group is in a meta-position of the phenyl ring relative to the rest of the molecule. Without wishing to be bound by any particular theory, it is believed that when $R^1$ is in such a meta-position, the warhead group is better positioned for covalent modification of the cysteine residue thus effecting irreversible inhibition of the enzyme. Indeed, it has been surprisingly found that a compound having a warhead group at a meta-position (compound I-1) irreversibly binds to ErbB1 whereas a compound having a warhead group at a para-position (compound I-93) reversibly binds to ErbB1. These compounds have the following structures:

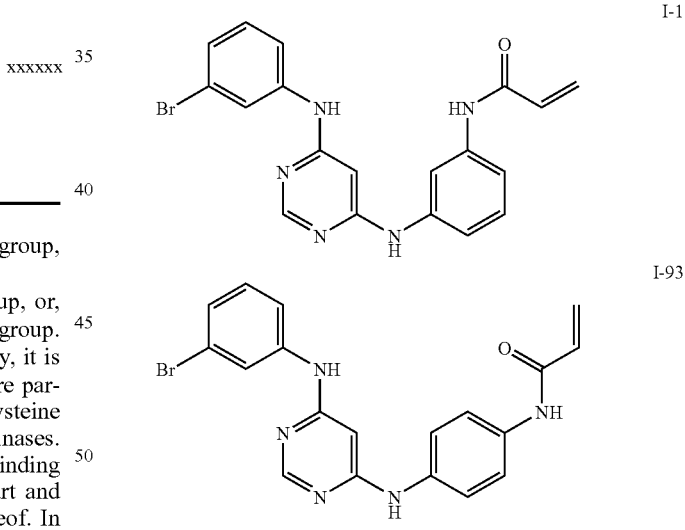

Figure 2:
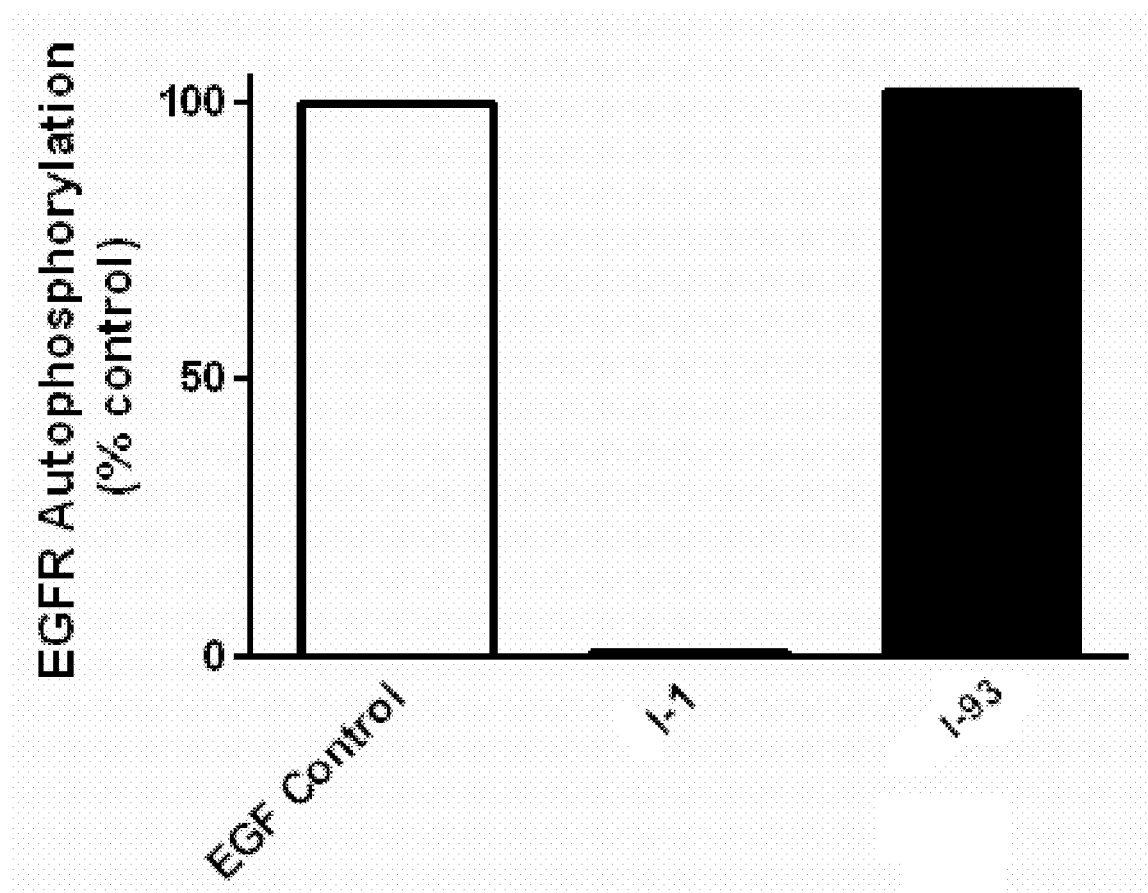
FIG. 2 depicts the results of compound I-1 in a "washout" experiment as compared with compound I-93.

This phenomenon was determined by performing a washout experiment using the protocol described in detail in Example 42, infra. The results of this experiment are depicted in FIG. 2 where it is shown that compound I-1 maintains enzyme inhibition after "washout" whereas compound I-93 was washed away in the experiment thereby resulting in reactivated enzyme activity.

In certain embodiments, $R^1$ is characterized in that the -L-Y moiety is capable of covalently binding to a cysteine residue of TEC, thereby irreversibly inhibiting the enzyme. In some embodiments, the cysteine residue is Cys 449.

In certain embodiments, $R^1$ is characterized in that the -L-Y moiety is capable of covalently binding to a cysteine residue of BTK, thereby irreversibly inhibiting the enzyme. In some embodiments, the cysteine residue is Cys 481.

In certain embodiments, R¹ is characterized in that the -L-Y moiety is capable of covalently binding to a cysteine residue of ITK, thereby irreversibly inhibiting the enzyme. In some embodiments, the cysteine residue is Cys 442.

In certain embodiments, R¹ is characterized in that the -L-Y moiety is capable of covalently binding to a cysteine residue of BMX, thereby irreversibly inhibiting the enzyme. In some embodiments, the cysteine residue is Cys 496.

In certain embodiments, R¹ is characterized in that the -L-Y moiety is capable of covalently binding to a cysteine residue of JAK3, thereby irreversibly inhibiting the enzyme. In some embodiments, the cysteine residue is Cys 909.

In certain embodiments, R¹ is characterized in that the -L-Y moiety is capable of covalently binding to a cysteine residue of TXK, thereby irreversibly inhibiting the enzyme. In some embodiments, the cysteine residue is Cys 350.

One of ordinary skill in the art will recognize that a variety of warhead groups, as defined herein, are suitable for such covalent bonding. Such R¹ groups include, but are not limited to, those described herein and depicted in Table 3, infra.

Exemplary compounds of formula I are set forth in Table 5 below.

TABLE 5

Exemplary Compounds of Formula I

I-1
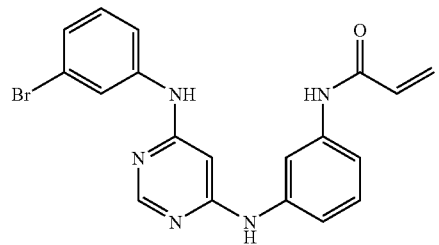

I-2
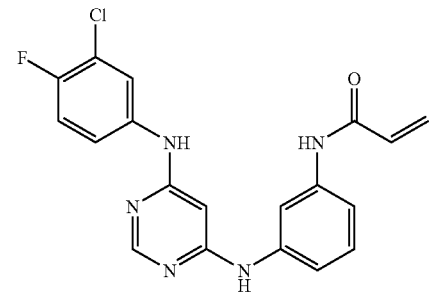

I-3
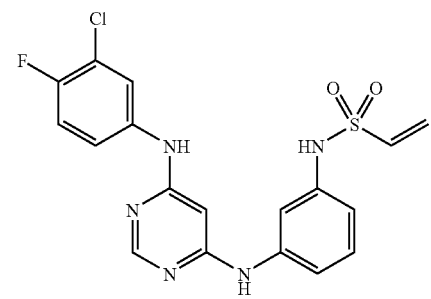

I-4
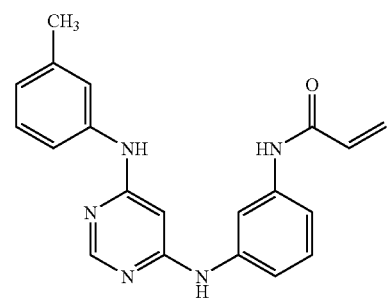

TABLE 5-continued
Exemplary Compounds of Formula I
I-5
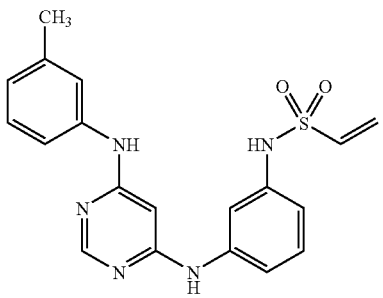
I-6
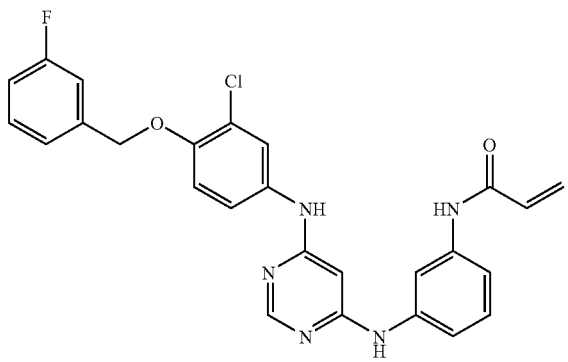
I-7
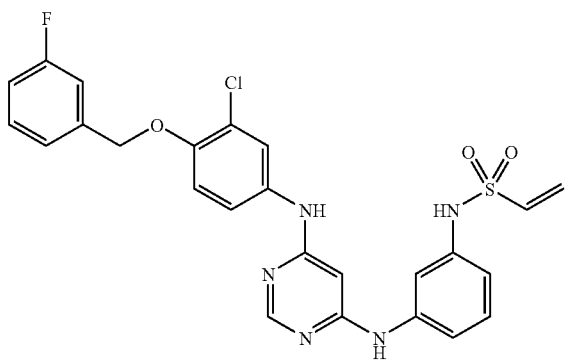
I-8
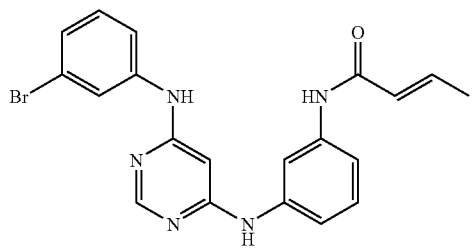

TABLE 5-continued
Exemplary Compounds of Formula I
I-9
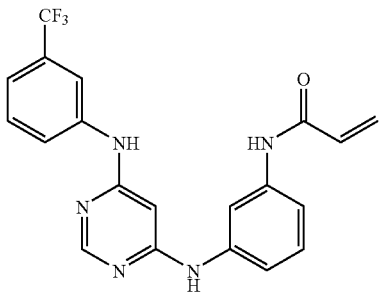
I-10
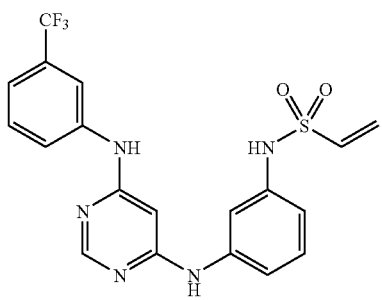
I-11
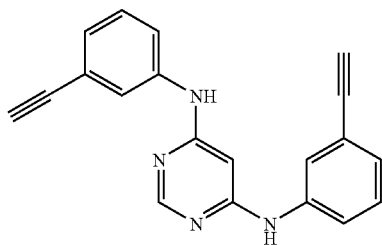
I-12
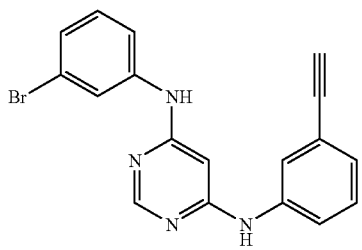
I-13
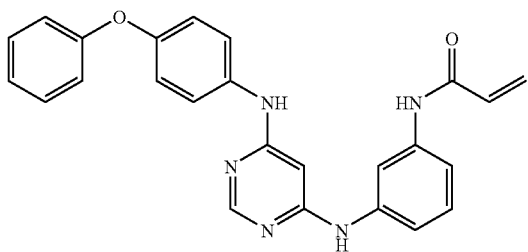

TABLE 5-continued
Exemplary Compounds of Formula I
I-14
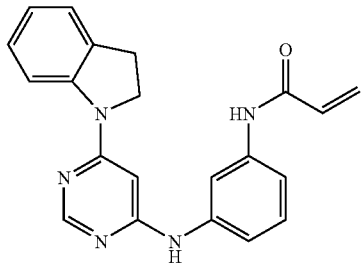
I-15
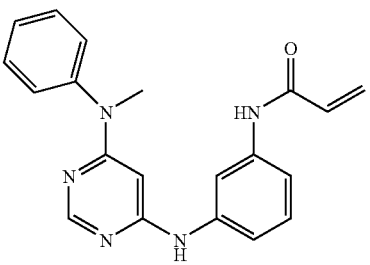
I-16
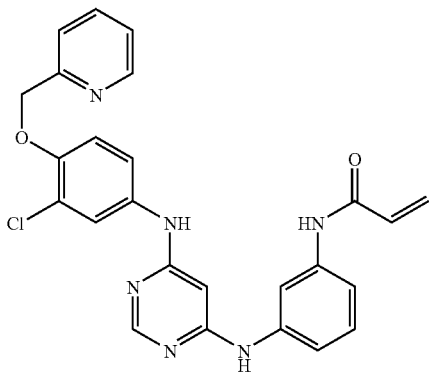
I-17
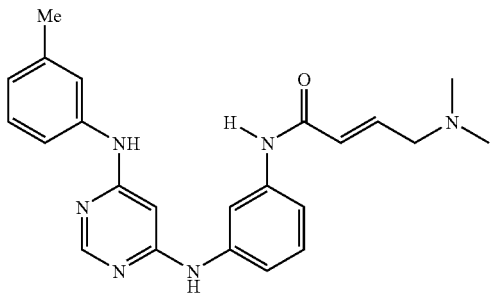
I-18
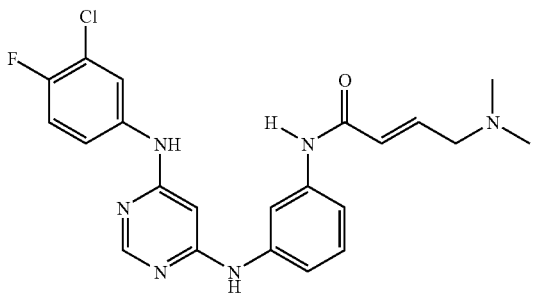

TABLE 5-continued
Exemplary Compounds of Formula I
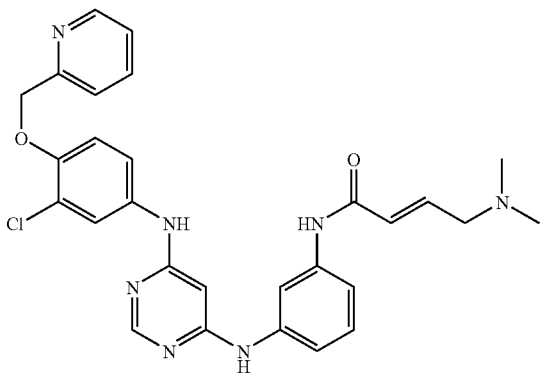
I-19
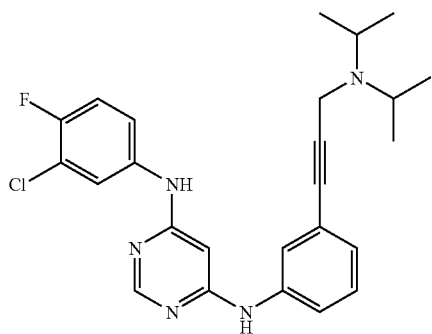
I-20
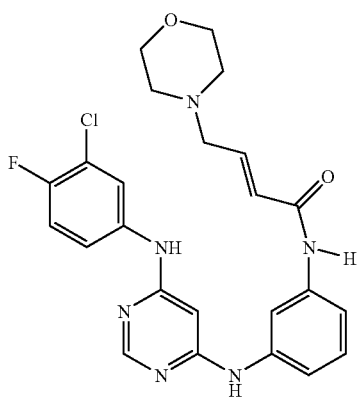
I-21

TABLE 5-continued
Exemplary Compounds of Formula I
I-22
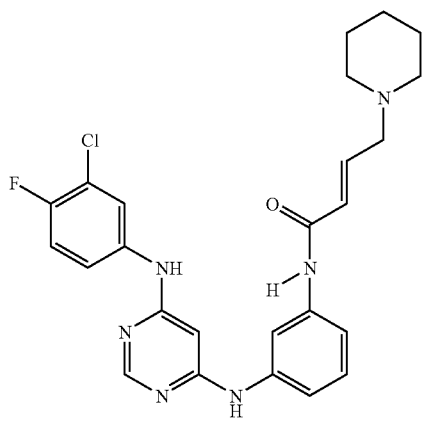
I-23
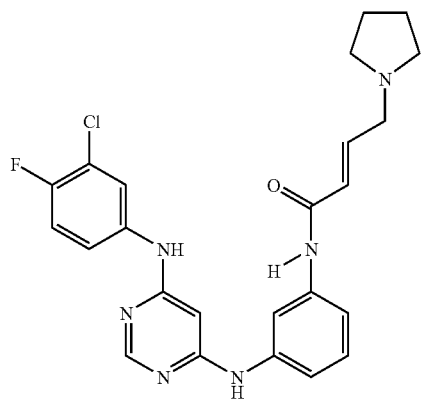
I-24
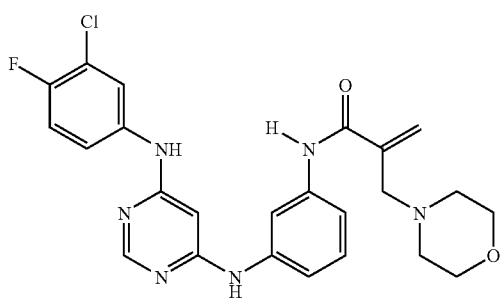
I-25
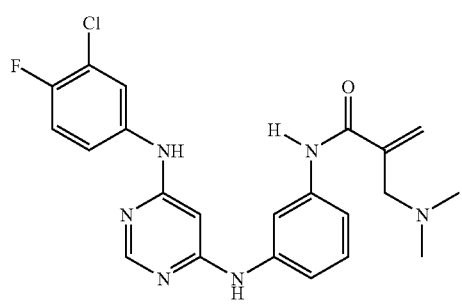

TABLE 5-continued
Exemplary Compounds of Formula I
I-26
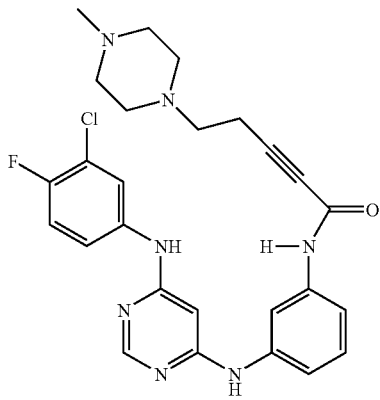
I-27
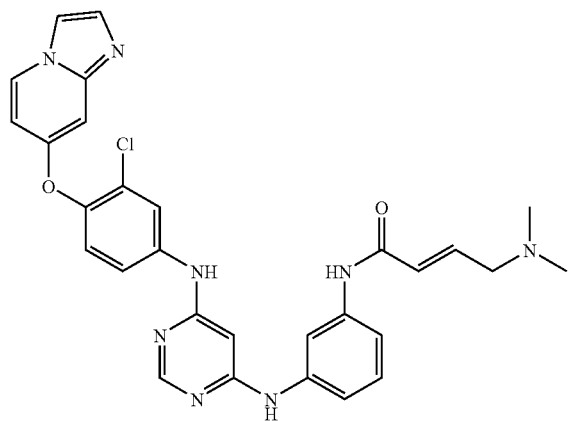
I-28
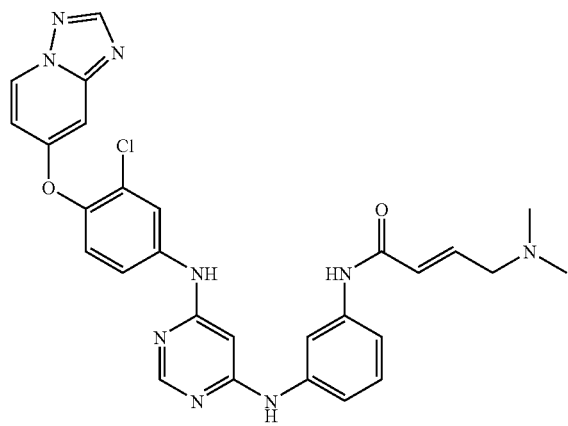

TABLE 5-continued
Exemplary Compounds of Formula I
I-29
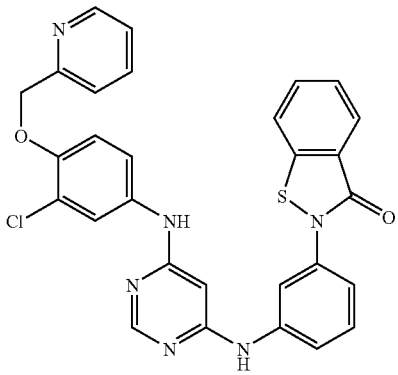
I-30
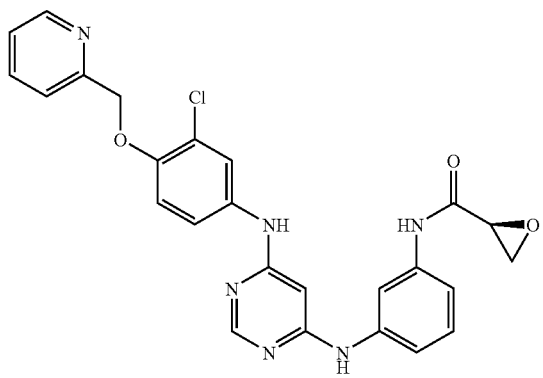
I-31
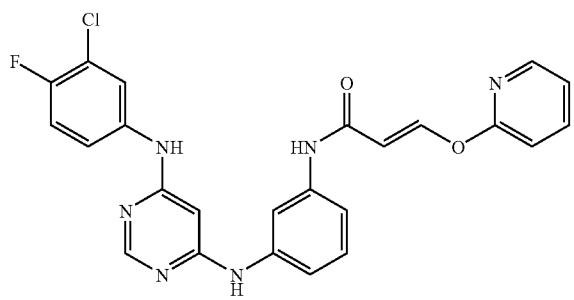
I-32
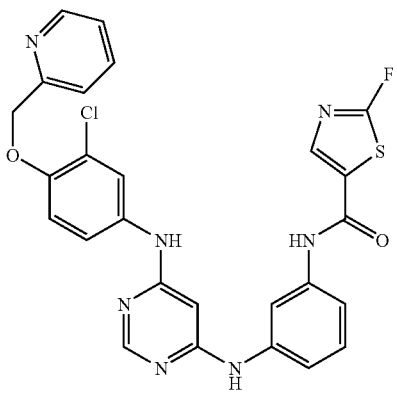

TABLE 5-continued
Exemplary Compounds of Formula I
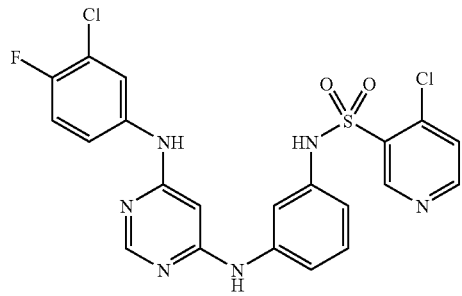
I-33
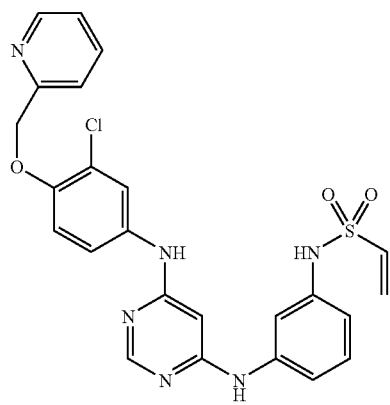
I-34
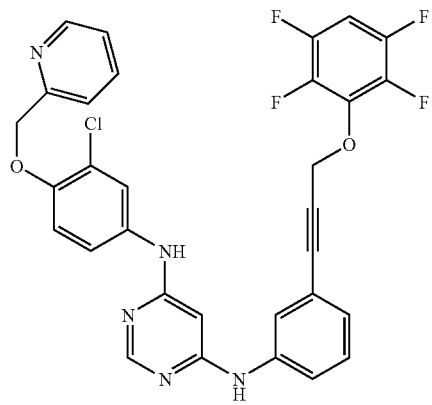
I-35
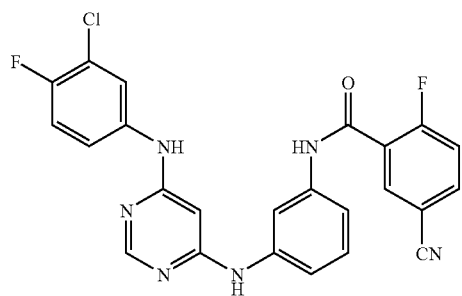
I-36

TABLE 5-continued
Exemplary Compounds of Formula I
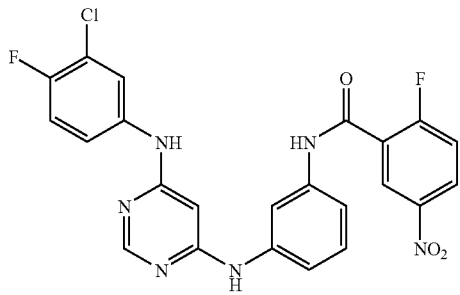
I-37
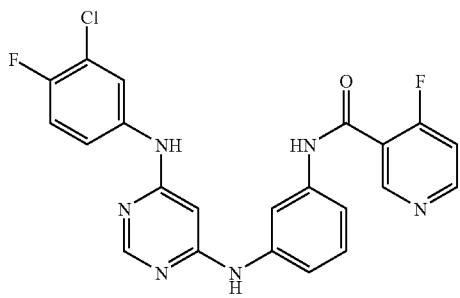
I-38
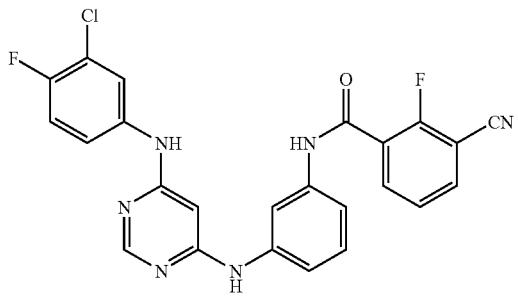
I-39
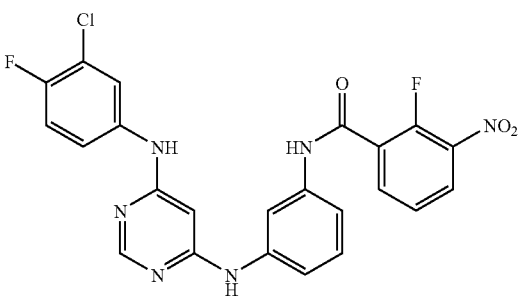
I-40
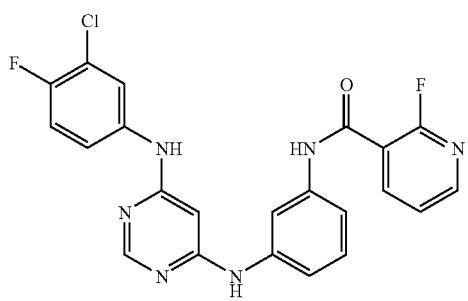
I-41

TABLE 5-continued
Exemplary Compounds of Formula I
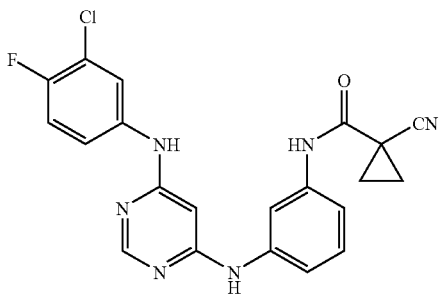
I-42
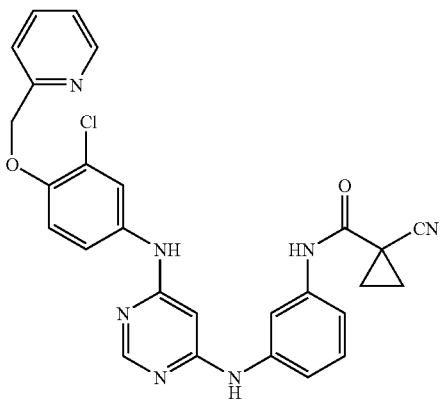
I-43
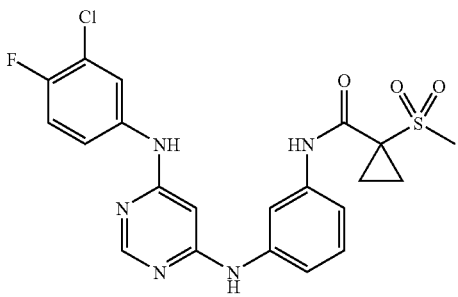
I-44
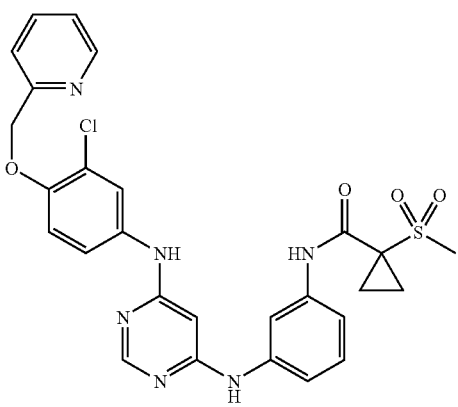
I-45

TABLE 5-continued
Exemplary Compounds of Formula I
I-46
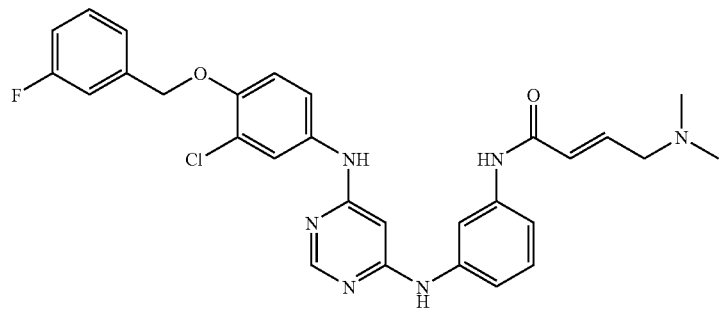
I-47
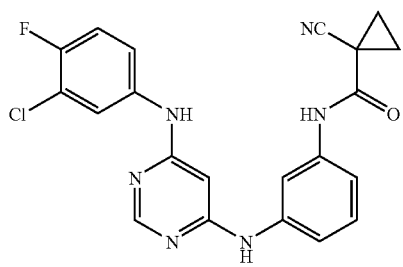
I-48
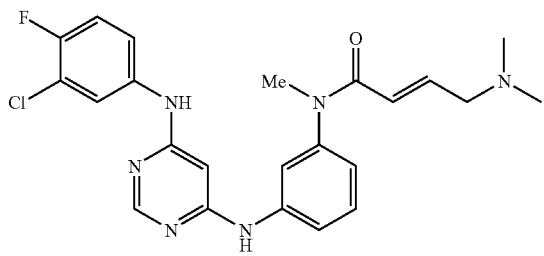
I-49
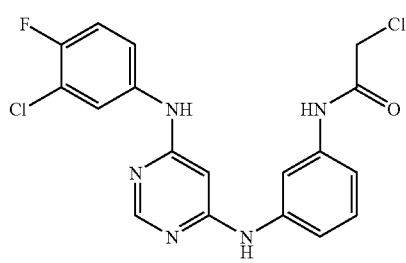
I-50
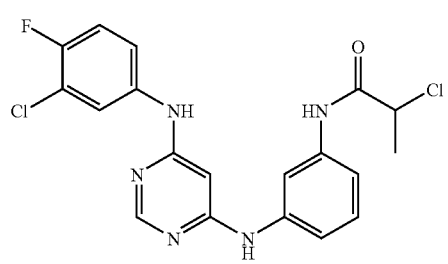

TABLE 5-continued
Exemplary Compounds of Formula I
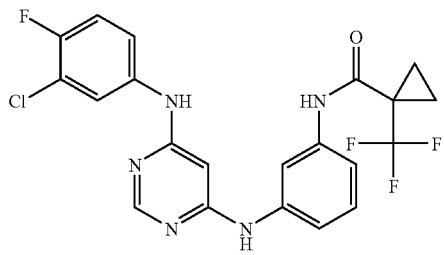
I-51
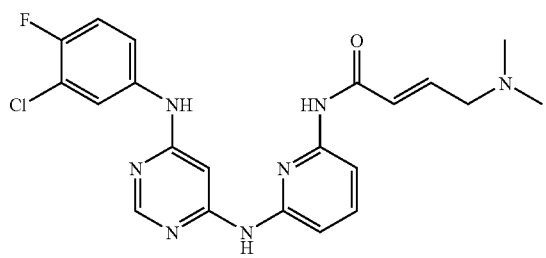
I-52
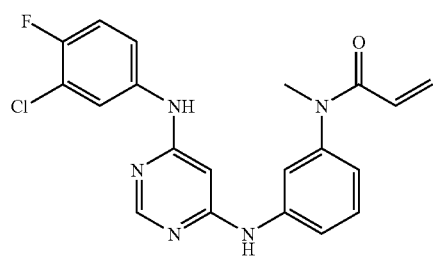
I-53
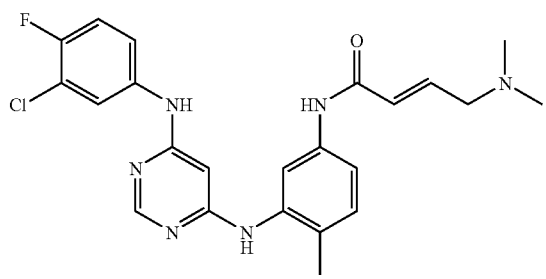
I-54
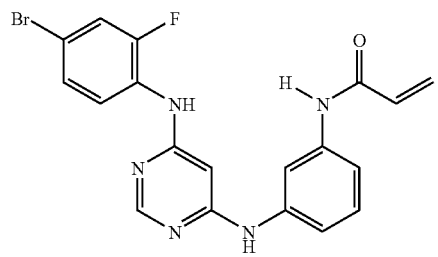
I-55

TABLE 5-continued
Exemplary Compounds of Formula I
I-56
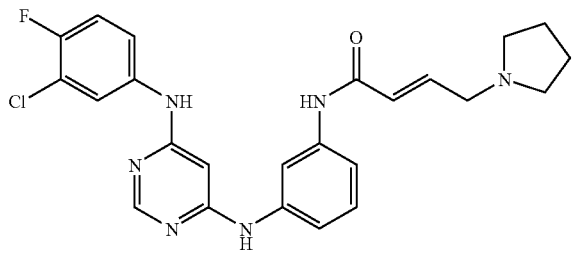
I-57
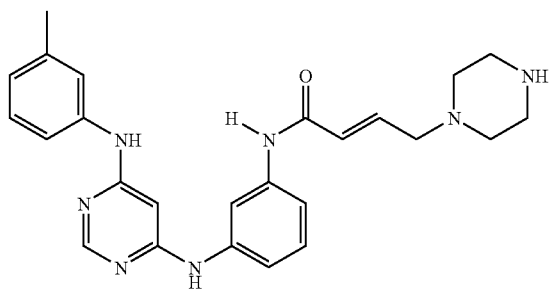
I-58
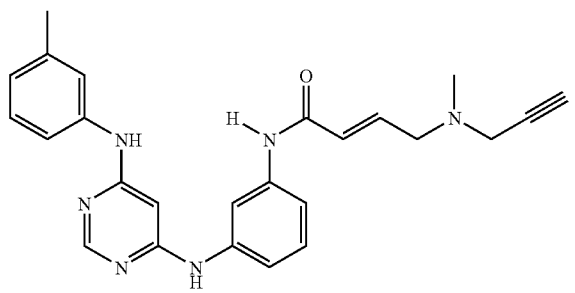
I-59
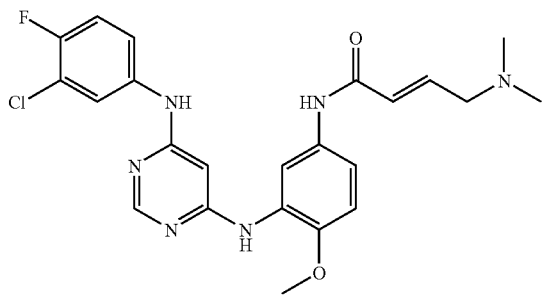
I-60
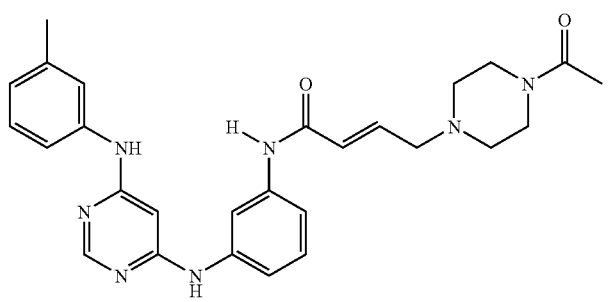

TABLE 5-continued
Exemplary Compounds of Formula I
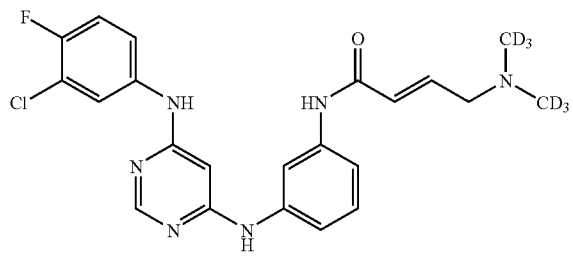
I-61
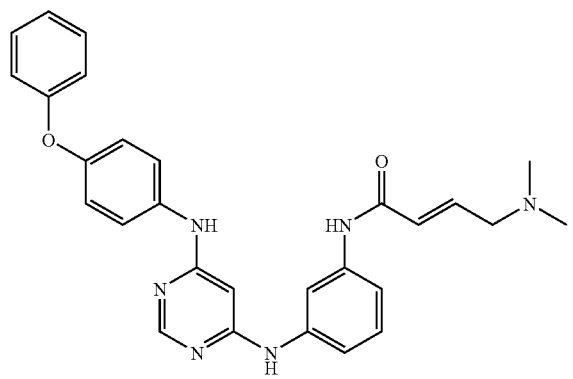
I-62
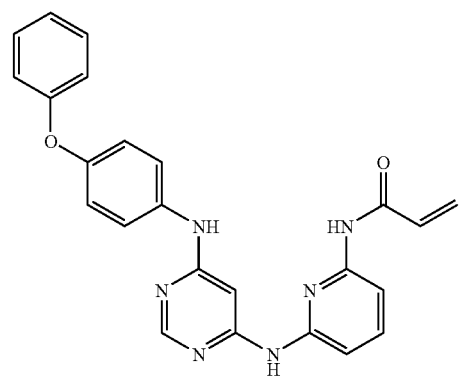
I-63
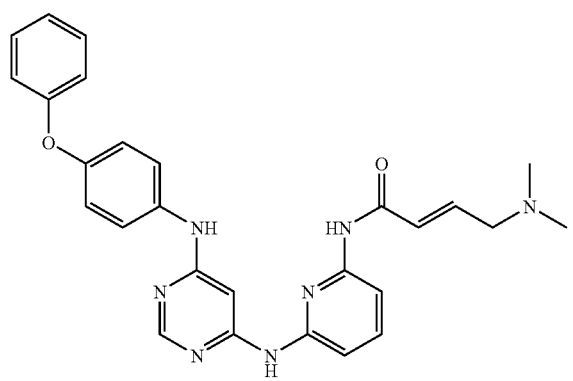
I-64

TABLE 5-continued
Exemplary Compounds of Formula I
I-65
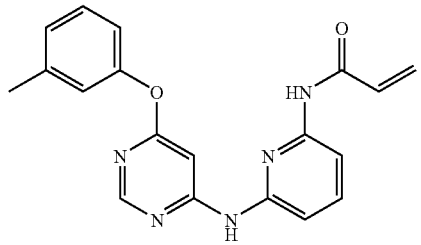
I-66
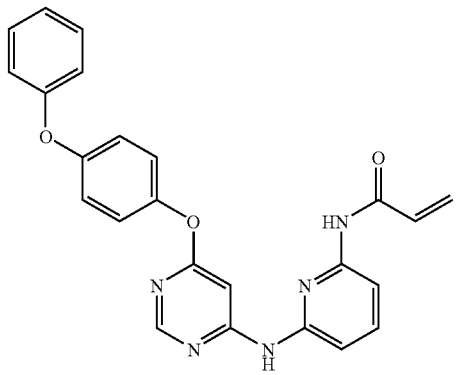
I-67
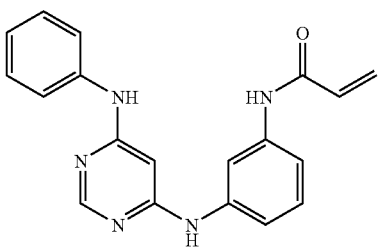
I-68
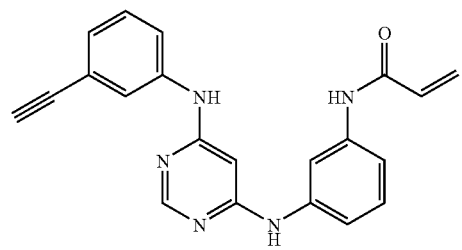
I-69
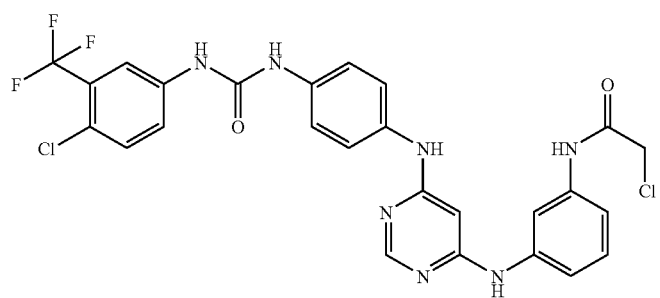

TABLE 5-continued
Exemplary Compounds of Formula I
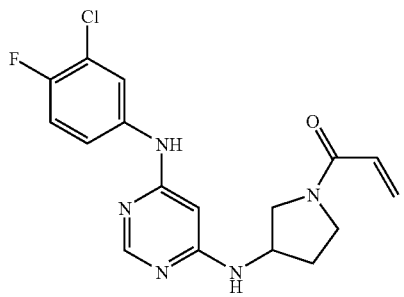
I-70
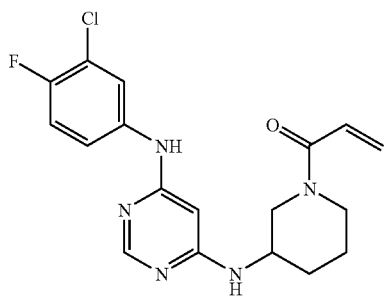
I-71
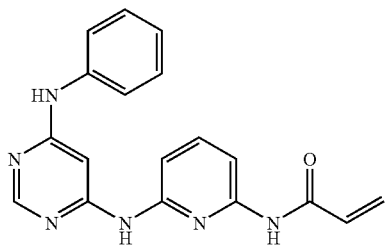
I-72
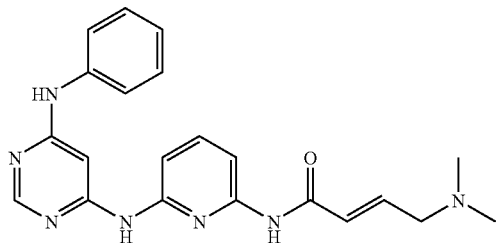
I-73
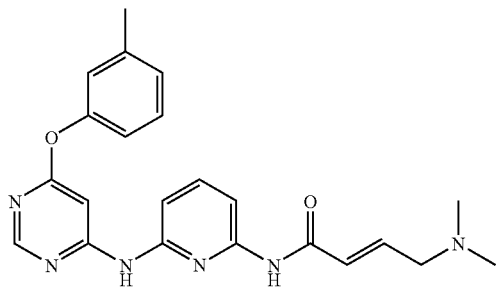
I-74

TABLE 5-continued
Exemplary Compounds of Formula I
I-75
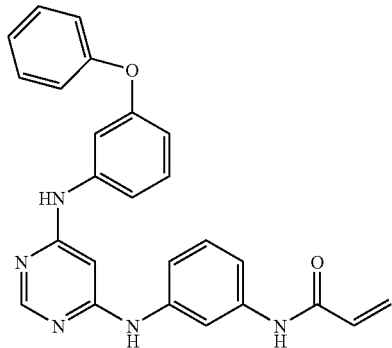
I-76
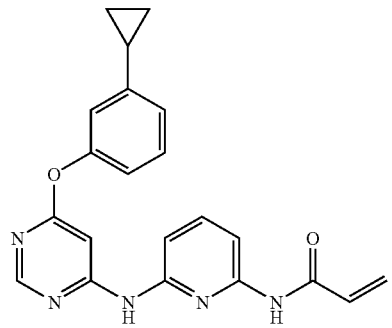
I-77
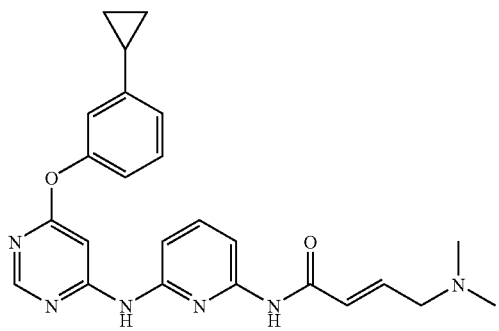
I-78
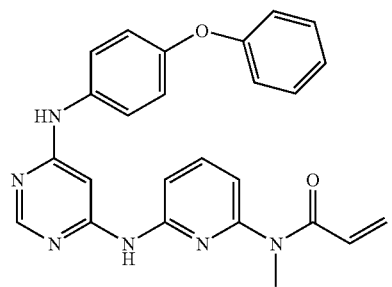

TABLE 5-continued
Exemplary Compounds of Formula I
I-79
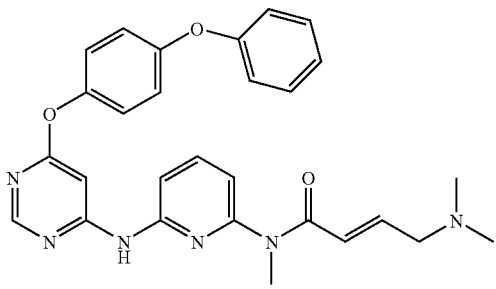
I-80
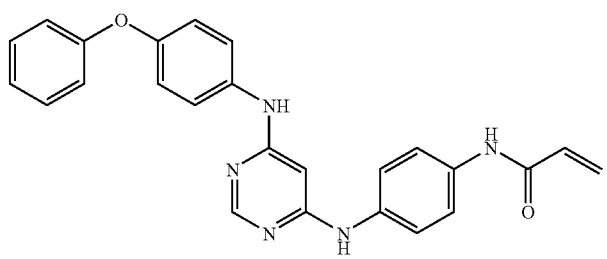
I-81
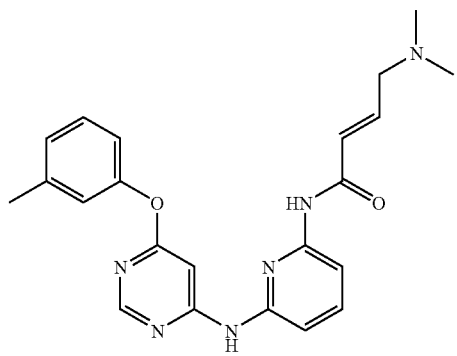
I-82
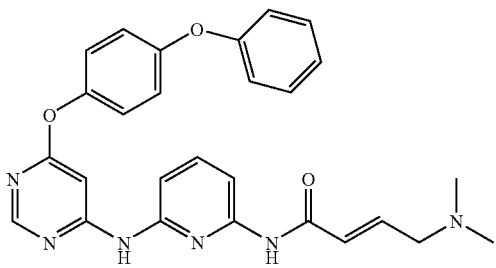
I-83
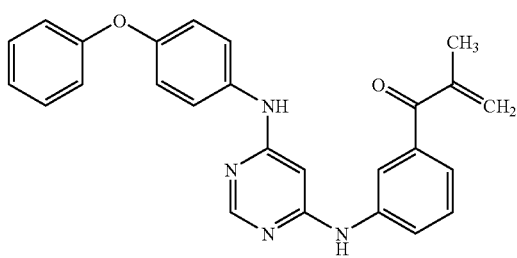

TABLE 5-continued
Exemplary Compounds of Formula I
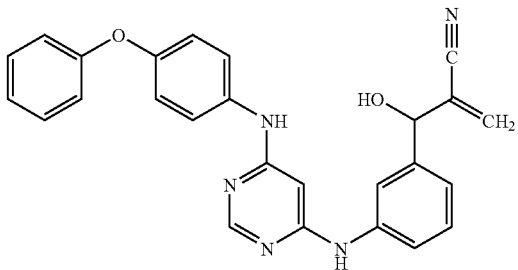
I-84
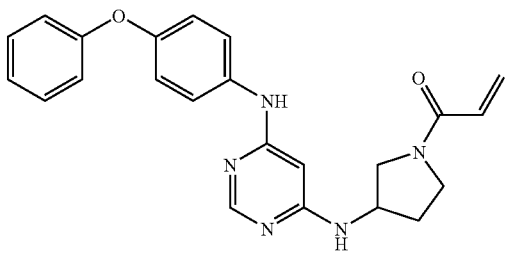
I-85
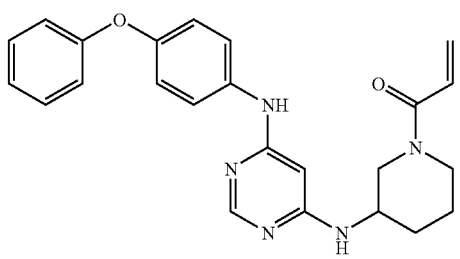
I-86
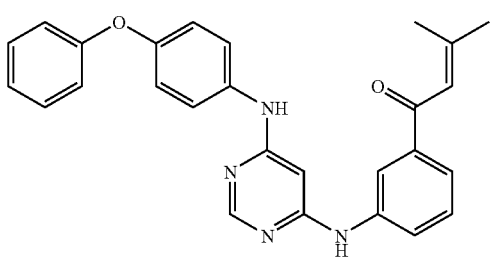
I-87
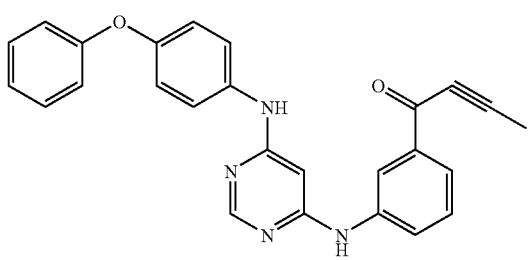
I-88

TABLE 5-continued
Exemplary Compounds of Formula I
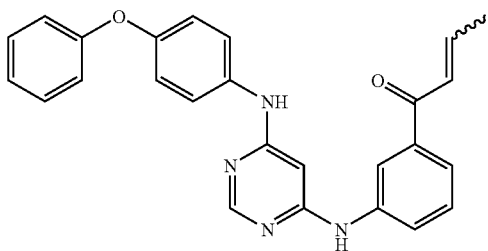
I-89
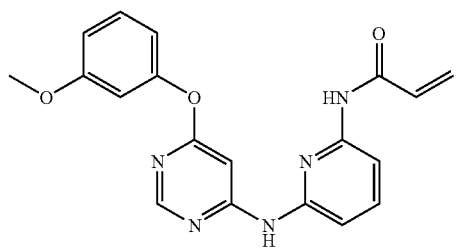
I-90
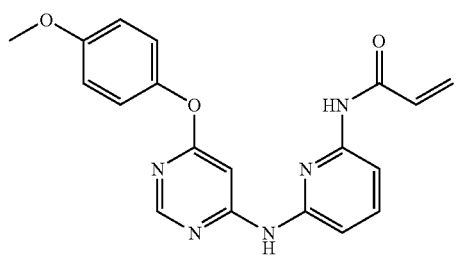
I-91
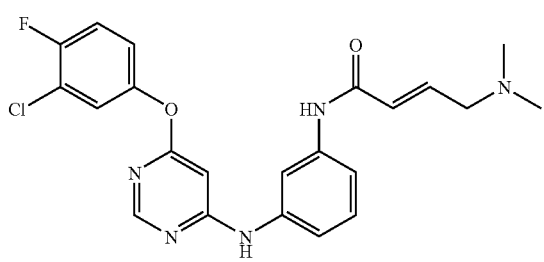
I-92
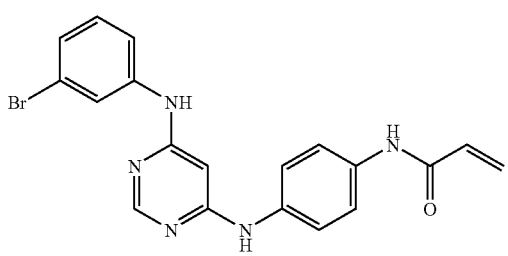
I-93

TABLE 5-continued
Exemplary Compounds of Formula I
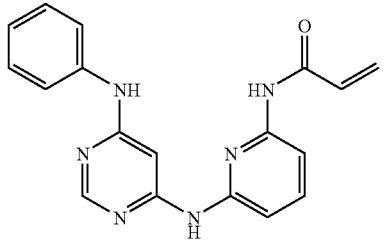
I-94
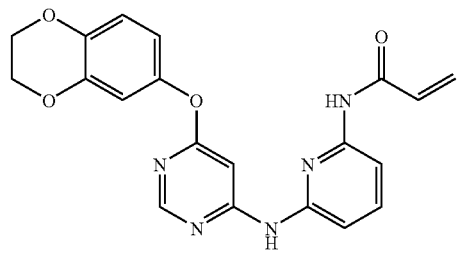
I-95
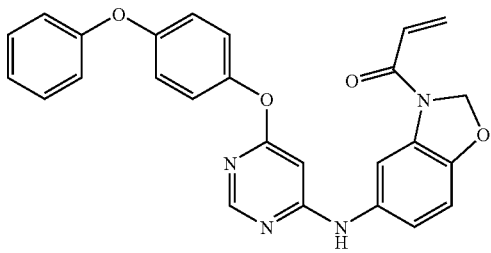
I-96
In certain embodiments, the present invention provides any compound depicted in Table 5, above, or a pharmaceutically acceptable salt thereof.
In certain embodiments, the present invention provides a compound selected from:
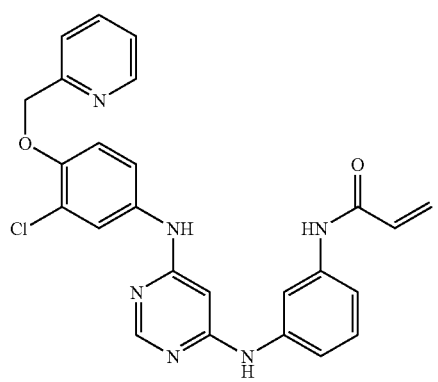
I-16
-continued
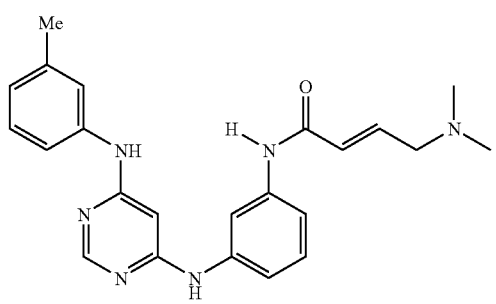
I-17
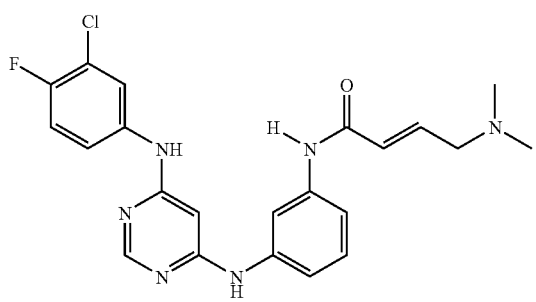
I-18

-continued

I-19
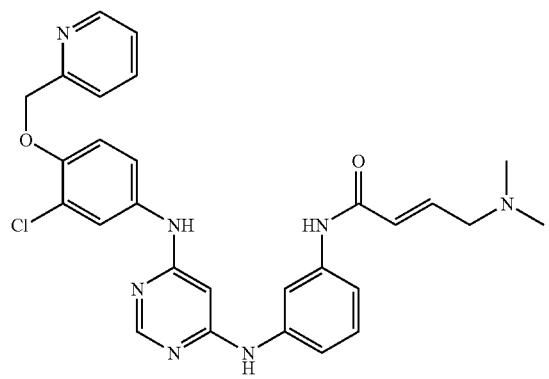

I-6
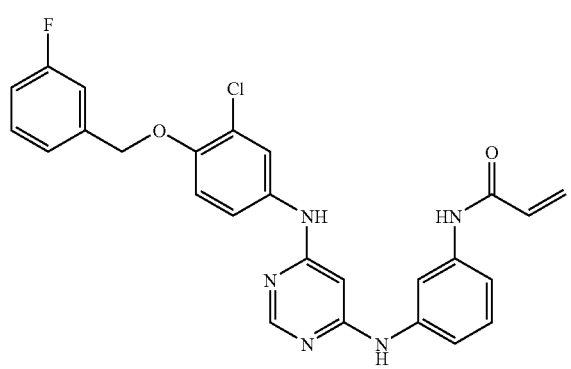

I-66
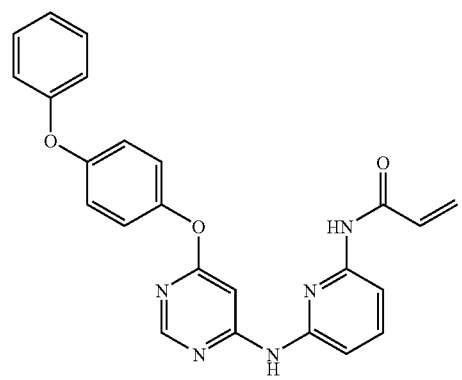

I-82
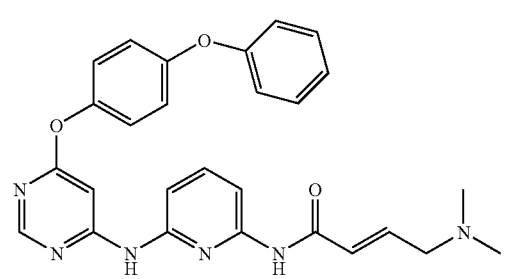

-continued

I-89
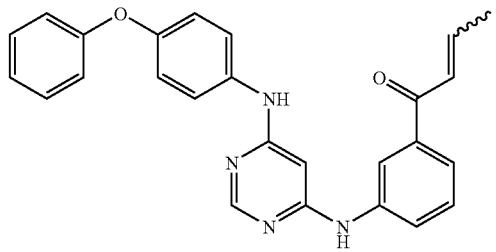

or a pharmaceutically acceptable salt thereof.

As described herein, compounds of the present invention are irreversible inhibitors of at least one of ErbB1, ErbB2, ErbB3 and ErbB4, or a mutant thereof. In some embodiments, provided compounds are irreversible inhibitors of a TEC-kinase (e.g. BTK) and JAK3. One of ordinary skill in the art will recognize that certain compounds of the present invention are reversible inhibitors. In certain embodiments, such compounds are useful as assay comparator compounds. In other embodiments, such reversible compounds are useful as inhibitors of ErbB1, ErbB2, ErbB3, ErbB4, a TEC-kinase, and/or JAK3, or a mutant thereof, and therefore useful for treating one or disorders as described herein. Exemplary reversible compounds of the present invention are set forth in Table 6, below.

TABLE 6

Reversible Inhibitors $I^R$-1
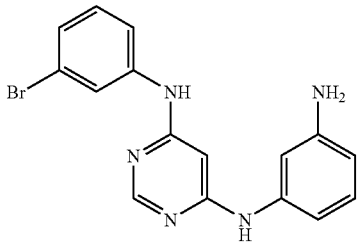

$I^R$-2
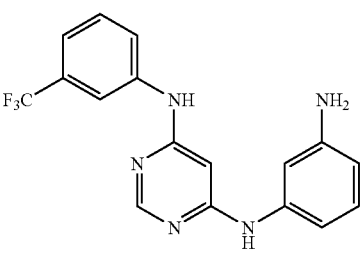

$I^R$-3
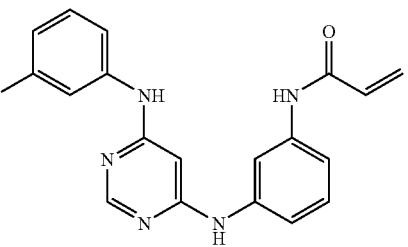

TABLE 6-continued

Reversible Inhibitors

TABLE 6-continued

Reversible Inhibitors

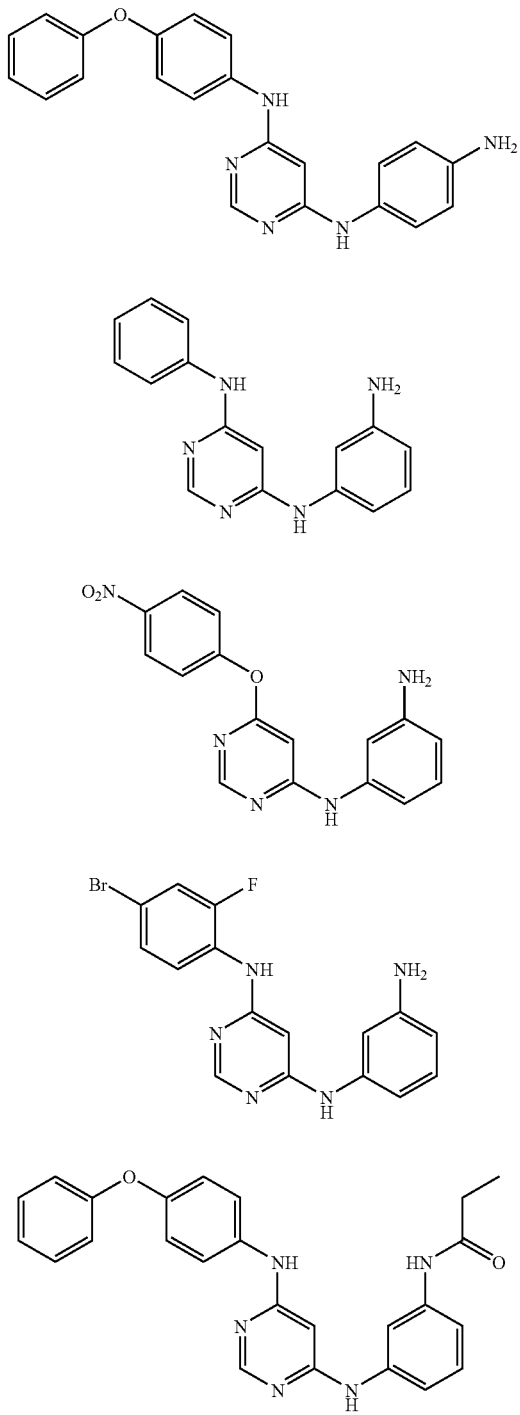

or a pharmaceutically acceptable salt thereof.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit a protein kinase, particularly at least one of ErbB1, ErbB2, ErbB3, ErbB4, a TEC-kinase, and/or JAK3, or a mutant thereof, in a biological sample or in a patient. In certain embodiments, the amount of compound in compositions of this invention is such that is effective to measurably inhibit at least one of ErbB1, ErbB2, ErbB3, ErbB4, a TEC-kinase, and/or JAK3, or a mutant thereof, in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of at least one of ErbB1, ErbB2, ErbB3, ErbB4, a TEC-kinase, and/or JAK3, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of protein kinase activity of one or more enzymes.

Drug resistance is emerging as a significant challenge for targeted therapies. For example, drug resistance has been reported for Gleevec® and Iressa®, as well as several other kinase inhibitors in development. In addition, drug resistance has been reported for the cKit and PDGFR receptors. It has been reported that irreversible inhibitors may be effective against drug resistant forms of protein kinases (Kwak, E. L., R. Sordella, et al. (2005). "Irreversible inhibitors of the EGF receptor may circumvent acquired resistance to gefitinib." PNAS 102(21): 7665-7670.) Without wishing to be bound by any particular theory, it is believed that compounds of the present invention may be effective inhibitors of drug resistant forms of protein kinases.

As used herein, the term "clinical drug resistance" refers to the loss of susceptibility of a drug target to drug treatment as a consequence of mutations in the drug target.

As used herein, the term "resistance" refers to changes in the wild-type nucleic acid sequence coding a target protein, and/or the protein sequence of the target, which change, decrease or abolish the inhibitory effect of the inhibitor on the target protein.

Examples of kinases that are inhibited by the compounds and compositions described herein and against which the methods described herein are useful include ErbB1, ErbB2, ErbB3, ErbB4, a TEC-kinase, and/or JAK3, or a mutant thereof.

The activity of a compound utilized in this invention as an inhibitor of ErbB1, ErbB2, ErbB3, ErbB4, a TEC-kinase, and/or JAK3, or a mutant thereof, may be assayed in vitro, in vivo or in a cell line. In vitro assays include assays that determine inhibition of either the phosphorylation activity and/or the subsequent functional consequences, or ATPase activity of activated ErbB1, ErbB2, ErbB3, ErbB4, a TEC-kinase, and/or JAK3, or a mutant thereof. Alternate in vitro assays quantitate the ability of the inhibitor to bind to ErbB1, ErbB2, ErbB3, ErbB4, a TEC-kinase, and/or JAK3. Inhibitor binding may be measured by radiolabelling the inhibitor prior to binding, isolating the inhibitor/ErbB1, inhibitor/ErbB2, inhibitor/ErbB3, inhibitor/ErbB4, inhibitor/TEC-kinase, or inhibitor/JAK3 complex and determining the amount of radiolabel bound. Alternatively, inhibitor binding may be determined by running a competition experiment where new inhibitors are incubated with ErbB1, ErbB2, ErbB3, ErbB4, a TEC-kinase, and/or JAK3 bound to known radioligands. Detailed conditions for assaying a compound utilized in this invention as an inhibitor of ErbB1, ErbB2, ErbB3, ErbB4, a TEC-kinase, and/or JAK3, or a mutant thereof, are set forth in the Examples below.

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

ErbB receptors, a major family of receptor tyrosine kinases, are composed of an extracellular ligand binding domain, a single transmembrane domain, and an intracellular domain with tyrosine kinase activity. The ErbB family comprises ErbB1 (commonly known as EGFR), ErbB2 (commonly known as HER2 or neu), ErbB3 (commonly known as HER3), and ErbB4 (commonly known as HER4). More than 10 ligands (including EGF, TGFα, AR, BTC, EPR, HB-EGF, NRG-1, NRG-2, NRG-3, NRG-4) have been identified for the various receptor family members. Upon ligand binding the extracellular domain undergoes conformational change, allowing the formation of homodimers or heterodimers with other members of the ErbB family. Dimerization induces tyrosine phosphorylation of specific residues in the intracellular domain that serve as docking sites for adaptor proteins and downstream effectors. In some contexts, activation of phosphatidyl-inositol 3-kinase (PI3K) and mitogen-activated protein kinase pathways occur, leading to cell proliferation and survival (Lin, N. U.; Winer, E. P., Breast Cancer Res 6: 204-210, 2004).

Interaction between family members is necessitated by deficiencies in ErbB2, which has no known ligand, and ErbB3, which is kinase dead. EGFR, ErbB3, and ErbB4 bind ligand to induce ErbB receptor homodimerization or heterodimerization, whereas ErbB2 functions as the preferred dimerization partner. The composition of the pairwise combinations is important for signal diversification, as dimer identity determines which downstream pathways are activated. Representative downstream gene products in the ErbB signal transduction pathway include Shc, Grb2, SOS1, Ras, Raf1, Mek, ERK1, ERK2, ERa, Akt, mTOR, FKHR, p27, Cyclin D1, FasL, GSK-3, Bad, and STAT3.

There is strong precedent for involvement of the EGFR and other members of the ErbB family in human cancer because over 60% of all solid tumors overexpress at least one of these proteins or their ligands. Constitutively active, tumorigenic EGFR vII, a mutant possessing a truncated extracellular domain, has been reported to be present in up to 78% of breast carcinomas and has also been found in glioblastomas. Overexpression of EGFR is commonly found in breast, lung, head and neck, bladder tumors, while ErbB2 expression is frequently elevated in human tumors of epithelial origin. Activating mutations in the tyrosine kinase domain have been identified in patients with non-small cell lung cancer (Lin, N. U.; Winer, E. P., Breast Cancer Res 6: 204-210, 2004). ErbB1 and/or ErbB2 amplification has also been implicated in squamous cell carcinomas, salivary gland carcinomas, ovarian carcinomas, and pancreatic cancers (Cooper, G. C. Oncogenes. $2^{nd}$ ed. Sudbury: Jones and Barlett, 1995; Zhang, Y., et al., Cancer Res 66: 1025-32, 2006). Overexpression of ErbB2 has potent transforming activity, likely due to its ability to cooperate with other ErbB receptors (Sherman, L., et al., Oncogene 18: 6692-99, 1999). In fact, some human cancers that overexpress both EGFR and ErbB2 have a poorer prognosis than cancers that overexpress either receptor alone.

The ErbB signaling network is often a key component in the pathogenesis of breast cancer. Amplification of ErbB2 is associated with an aggressive tumor phenotype that is characterized by relatively rapid tumor growth, metastatic spread to visceral sites, and drug resistance. ErbB2 has been shown to be amplified in 20% of axillary node-negative ("ANN") breast cancer cases, and this amplification has been identified as an independent prognostic factor for risk of recurrence in ANN breast cancer. (Andrulis, I. L., et al., J Clin Oncol 16: 1340-9, 1998).

Targeted blockade of ErbB signaling with trastuzumab (Herceptin), a monoclonal antibody directed at ErbB2, has been shown to improve survival in women with ErbB2-positive, advanced breast cancer. Other monoclonal antibodies directed against ErbB receptors include cetuximab (Erbitux) and panitumumab (Vectibix).

Several small molecule tyrosine kinase inhibitors (TKIs) have been found to act selectively upon ErbB family members. Notable examples include gefitinib (Iressa) and erlotinib (Tarceva), both of which target the EGFR. These small molecules compete with ATP for binding to the kinase domain of the receptor. Compared to monoclonal antibodies, TKIs have several advantages in that they are orally bioavailable, well-tolerated, and appear to be active against truncated forms of ErbB2 and EGFR receptors (e.g., EGFR vIII) in vitro. In addition, the small size of small molecule TKIs may allow them to penetrate sanctuary sites such as the central nervous system. Finally, the homology between kinase domains of ErbB receptors allows for development of TKIs that target more than one member of the ErbB family simultaneously, the advantages of which are described herein.

Although certain malignancies have been linked to the overexpression of individual receptors, efficient signal transduction relies on the coexpression of ErbB receptor family members. This cooperation of ErbB receptor family members in signal transduction and malignant transformation may limit the success of agents that target individual receptors in the treatment of cancer; a potential mechanism of resistance to agents targeting a single ErbB receptor is upregulation of other members of the receptor family (Britten, C. D., Mol Cancer Ther 3: 1335-42, 2004).

Agents that target two or more ErbB receptors are called pan-ErbB regulators. ERRP is a pan-ErbB negative regulator that is expressed in most benign pancreatic ductal epithelium and islet cells. Tumors have been found to experience a progressive loss in ERRP expression. Pan-ErbB regulators may be more successful in treating tumors than compounds that only target one ErbB receptor. Erbitux and Herceptin show success in a limited patient base (tumors having increased expression of EGFR or ErbB2), which could be partly due to lack of pan-ErbB activity.

In both in vitro and in vivo models, strategies that employ a dual ErbB approach seem to have greater antitumor activity than agents targeting a single ErbB receptor. Thus, agents that target multiple members of the ErbB family are likely to provide therapeutic benefit to a broader patient population (Zhang, Y., et al., Cancer Res 66: 1025-32, 2006). In certain embodiments, provided compounds inhibit one or more of ErbB1, ErbB2, ErbB3, and ErbB4. In some embodiments, provided compounds inhibit two or more of ErbB1, ErbB2, ErbB3, and ErbB4, or a mutant thereof, and are therefore pan-ErbB inhibitors.

Clearly, there is growing evidence to support the concurrent inhibition of two or more ErbB (i.e., pan-erbB) receptors in cancer therapy. Possible pan-ErbB approaches with small molecules include using combinations of agents that target individual ErbB receptors, using single agents that target multiple ErbB receptors, or using agents that interfere with ErbB receptor interactions (e.g., dimerization). Additional strategies include therapies utilizing a small molecule in combination with antibodies, or chemoprevention therapies (Lin, N. U.; Winer, E. P., Breast Cancer Res 6: 204-210, 2004).

An example of small molecule pan-ErbB inhibition is CI-1033, an irreversible pan-ErbB inhibitor that covalently binds to the ATP binding site of the intracellular kinase domain. Another irreversible pan-ErbB receptor tyrosine kinase inhibitor is HKI-272, which inhibits the growth of tumor cells that express ErbB-1 (EGFR) and ErbB-2 (HER-2) in culture and xenografts, and has antitumor activity in HER-2-positive breast cancer (Andrulis, I. L., et al., J Clin Oncol 16: 1340-9, 1998). Irreversible inhibitors have demonstrated superior antitumor activity in comparison with reversible inhibitors.

Neurofibromatosis type I (NF1) is a dominantly inherited human disease affecting one in 2500-3500 individuals. Several organ systems are affected, including bones, skin, iris, and the central nervous system, as manifested in learning disabilities and gliomas. A hallmark of NF1 is the development of benign tumors of the peripheral nervous system (neurofibromas), which vary greatly in both number and size among patients. Neurofibromas are heterogeneous tumors composed of Schwann cells, neurons, fibroblasts and other cells, with Schwann cells being the major (60-80%) cell type.

Abberant expression of the EGFR is associated with tumor development in NF1 and in animal models of NF1, suggesting a role in pathogenesis and representing a novel potential therapeutic target. EGFR expression affects the growth of tumor cell lines derived from NF1 patients under conditions where EGF is not the primary factor driving growth of the cells. These data suggest that EGFR may play an important role in NF1 tumorigenesis and Schwann cell transformation (DeClue, J. E., et al., J Clin Invest 105: 1233-41, 2000).

Patients with NF1 develop aggressive Schwann cell neoplasms known as malignant peripheral nerve sheath tumors (MPNSTs). Schwann cells are the major supportive cell population in the peripheral nervous system. Neoplastic Schwann cells within these neoplasms variably express the ErbB tyrosine kinases mediating NRG-1 responses (ErbB2, ErbB3, ErbB4). Neuregulin-1 (NRG-1) proteins promote the differentiation, survival, and/or proliferation of many cell types in the developing nervous system, and overexpression of NRG-1 in myelinating Schwann cells induces the formation of malignant peripheral nerve sheath tumors (MPNSTs) (Fallon, K. B., et al., J Neuro Oncol 66: 273-84, 2004).

Deregulation of Schwann cell growth is a primary defect driving the development of both benign neurofibromas and MPNST in neurofibromatosis type I (NF1) patients. Growth of MPNSTs and transformed mouse Schwann cells in vitro is highly EGF-dependent and can be blocked by EGFR inhibitors under conditions where EGF is the primary growth factor. Some human MPNST cell lines have been found to demonstrate constitutive ErbB phosphorylation. While treatment with ErbB inhibitors abolishes ErbB phosphorylation and reduces DNA synthesis in these lines, effective chemotherapeutic regimens for MPNST remain elusive (Stonecypher, M. S., et al., Oncogene 24: 5589-5605, 2005).

Schwannomas are peripheral nerve tumors comprised almost entirely of Schwann-like cells, and typically have mutations in the neurofibromatosis type II (NF2) tumor suppressor gene. Ninety percent of NF2 patients develop bilateral vestibular schwannomas and/or spinal schwannomas. Enlarging schwannomas can compress adjacent structures, resulting in deafness and other neurologic problems. Surgical removal of these tumors is difficult, often resulting in increased patient morbidity.

Both normal human Schwann cells and schwannoma cells express neuregulin receptors (i.e., ErbB receptors), and schwannoma cells proliferate in response to neuregulin. It is possible that aberrant neuregulin production or response contributes to aberrant schwannoma cell proliferation (Pelton, P. D., et al., Oncogene 17: 2195-2209, 1998).

The NF2 tumor suppressor, Merlin, is a membrane/cytoskeleton-associated protein implicated in the regulation of tyrosine kinase activity. Genetic interactions between a Merlin mutation and EGFR pathway mutations have been documented in *Drosophila* (LaJeunesse, D. R., et al., Genetics 158: 667-79, 2001). Other evidence suggests Merlin can inhibit EGFR internalization and signaling upon cell-cell contact by restraining the EGFR into a membrane compartment from which it can neither signal nor be internalized (McClatchey, A. I., et al., Genes and Development 19: 2265-77, 2005; Curto, M. C., et al., J Cell Biol 177: 893-903, 2007).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of one of more of ErbB1, ErbB2, ErbB3, and ErbB4 and are therefore useful for treating one or more disorders associated with activity of one of more of ErbB1, ErbB2, ErbB3, and ErbB4. Thus, in certain embodiments, the present invention provides a method for treating an ErbB1-mediated, an ErbB2-mediated, an ErbB3-mediated, and/or ErbB4-mediated disorder comprising the step of administering to a patient in need thereof a compound of the present invention, or pharmaceutically acceptable composition thereof.

As used herein, the terms "ErbB1-mediated", "ErbB2-mediated," "ErbB3-mediated," and/or "ErbB4-mediated" disorders or conditions as used herein means any disease or other deleterious condition in which one or more of ErbB1, ErbB2, ErbB3, and/or ErbB4, or a mutant thereof, are known to play a role. Accordingly, another embodiment of the present invention relates to treating or lessening the severity of one or more diseases in which one or more of ErbB1, ErbB2, ErbB3, and/or ErbB4, or a mutant thereof, are known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from a cancer. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer.

In certain embodiments, the present invention provides a method for treating or lessening the severity of neurofibromatosis type I (NF1), neurofibromatosis type II (NF2) Schwann cell neoplasms (e.g. MPNST's), or Schwannomas.

The TEC family of non-receptor tyrosine kinases, referred to herein as "TEC-kinases," plays a central role in signaling through antigen-receptors such as the TCR, BCR and Fee receptors (reviewed in Miller A, et al. Current Opinion in Immunology 14; 331-340 (2002). TEC-kinases are essential for T cell activation. Three members of the family, Itk, Rlk and, are activated downstream of antigen receptor engagement in T cells and transmit signals to downstream effectors, including PLC-g. Combined deletion of Itk and Rlk in mice leads to a profound inhibition of TCR responses including proliferation, cytokine production and immune responses to an intracellular parasite (*Toxoplasma gondii*) (Schaeffer et al, Science 284; 638-641 (1999)). Intracellular signalling following TCR engagement is effected in ITK/RLK deficient T cells; inositol triphosphate production, calcium mobilization and MAP kinase activation are all reduced. Tec-kinases are also essential for B cell development and activation.

TEC-kinases include five family members, which are expressed primarily in hematopoietic cells: TEC, BTK, ITK (also known as TSK and EMT), RLK (also known as TXK), and BMX (also known as ETK). Additional related TEC-kinases have been found in *Drosophila melanogaster*, zebrafish (*Danio rerió*), skate (*Raja eglanteria*), and sea urchin (*Anthocidaris crassispina*).

Provided compounds are inhibitors of one of more TEC-kinases and are therefore useful for treating one or more disorders associated with activity of one or more TEC-kinases. Thus, in certain embodiments, the present invention provides a method for treating a TEC-mediated disorder comprising the step of administering to a patient in need thereof a compound of the present invention, or pharmaceutically acceptable composition thereof.

The term "TEC-mediated condition", as used herein means any disease or other deleterious condition in which TEC-kinases are known to play a role. Such conditions include those described herein and in Melcher, M et al., "The Role of TEC Family Kinases in Inflammatory Processes", *Anti-Inflammatory & Anti-Allergy Agents in Medicinal Chemistry*, Vol. 6, No. 1, pp. 61-69 (February 2007). Accordingly, another embodiment of the present invention relates to treating or lessening the severity of one or more diseases in which TEC-kinases are known to play a role. Specifically, the present invention relates to a method of treating or lessening the severity of a disease or condition selected from autoimmune, inflammatory, proliferative, and hyperproliferative diseases and immunologically-mediated diseases including rejection of transplanted organs or tissues and Acquired Immunodeficiency Syndrome (AIDS), wherein said method comprises administering to a patient in need thereof a composition of the present invention.

In some embodiments, the present invention provides a method for treating or lessening the severity of one or more diseases and conditions associated with TEC-kinases including diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. In some embodiments, the present invention provides a method for treating or lessening the severity of one or more diseases and conditions associated with Tec-kinases including those conditions characterized by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

In some embodiments, the present invention provides a method for treating or lessening the severity of one or more diseases and conditions associated with TEC-kinases including diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

In some embodiments, the present invention provides a method for treating or lessening the severity of one or more diseases and conditions associated with TEC-kinases including diseases and disorders of the skin, including, without limitation, psoriasis, systemic sclerosis, atopical dermatitis, contact dermatitis and other eczematous dermatitis, seborrhoetic dermatitis, lichen planus, pemphigus, bullous pemphigus, epidermolysis bullosa, urticaria, angiodermas, vasculitides, erythemas, cutaneous eosinophilias, uveitis, Alopecia, greata and vernal conjunctivitis.

In some embodiments, the present invention provides a method for treating or lessening the severity of one or more diseases and conditions associated with TEC-kinases including diseases and disorders of the gastrointestinal tract, including, without limitation, celiac disease, proctitis, eosinophilic gastro-enteritis, mastocytosis, pancreatitis, Crohn's disease, ulcerative colitis, food-related allergies which have effects remote from the gut, e.g., migraine, rhinitis and eczema.

In some embodiments, the present invention provides a method for treating or lessening the severity of one or more diseases and conditions associated with TEC-kinases including those diseases and disorders of other tissues and systemic disease, including, without limiation, multiple sclerosis, artherosclerosis, lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas including prostate cancers), artherosclerosis, and systemic lupus erythematosus.

In some embodiments, the present invention provides a method for treating or lessening the severity of one or more diseases and conditions associated with TEC-kinases including allograft rejection including, without limitation, acute and chronic allograft rejection following for example transplantation of kidney, heart, liver, lung, bone marrow, skin and cornea; and chronic graft versus host disease.

In some embodiments, the present invention relates to a method of treating or lessening the severity of one or more of the diseases or conditions associated with TEC-kinases, as recited above, wherein said method comprises administering to a patient in need thereof a compound or composition according to the present invention.

Bruton's tyrosine kinase ("BTK"), a member of TEC-kinases, is a key signaling enzyme expressed in all hematopoietic cells types except T lymphocytes and natural killer cells. BTK plays an essential role in the B-cell signaling pathway linking cell surface B-cell receptor (BCR) stimulation to downstream intracellular responses.

BTK is a key regulator of B-cell development, activation, signaling, and survival (Kurosaki, Curr Op Imm, 2000, 276-281; Schaeffer and Schwartzberg, Curr Op Imm 2000, 282-288). In addition, BTK plays a role in a number of other hematopoietic cell signaling pathways, e.g., Toll like receptor (TLR) and cytokine receptor-mediated TNF-αproduction in macrophages, IgE receptor (FcepsilonRI) signaling in mast cells, inhibition of Fas/APO-1 apoptotic signaling in B-lineage lymphoid cells, and collagen-stimulated platelet aggregation. See, e.g., C. A. Jeffries, et al., (2003), Journal of Biological Chemistry 278:26258-26264; N. J. Horwood, et al., (2003), The Journal of Experimental Medicine 197: 1603-1611; Iwaki et al. (2005), Journal of Biological Chemistry 280(48):40261-40270; Vassilev et al. (1999), Journal of Biological Chemistry 274(3): 1646-1656, and Quek ei al/. (1998), Current Biology 8(20): 1137-1140.

Patients with mutations in BTK have a profound block in B cell development, resulting in the almost complete absence of B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (FceRI). BTK deficient murine mast cells have reduced degranulation and decreased production of proinflammatory cytokines following FceRI cross-linking (Kawakami et al. Journal of leukocyte biology 65: 286-290).

Provided compounds are inhibitors of BTK and are therefore useful for treating one or more disorders associated with activity of BTK. Thus, in some embodiments, the present invention provides a method for treating an BTK-mediated disorder comprising the step of administering to a patient in need thereof a compound of the present invention, or pharmaceutically acceptable composition thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphorna/leukemia, or lymphomatoid granulomatosis. In some embodiments, the cancer is breast cancer or prostate cancer.

In some embodiments, the present invention provides a method for treating or lessening the severity of one or more diseases and conditions associated with BTK, wherein the disease or condition is selected from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irrtiable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherslcerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In some embodiments, the present invention provides a method for treating or lessening the severity of one or more diseases and conditions associated with BTK, selected from rheumatoid arthritis, multiple sclerosis, B-cell chromic lymphocytic leukemia, hairy cell leukemia, non-Hodgkin's lymphoma, irritable bowel syndrome, Crohn's Disease, lupus and renal transplant.

Interleukin-2 tyrosine kinase ("ITK") is expressed in T cells, mast cells and natural killer cells. It is activated in T cells upon stimulation of the T cell receptor (TCR), and in mast cells upon activation of the high affinity IgE receptor. Following receptor stimulation in T cells, Lck, a src tyrosine kinase family member, phosphorylates Y511 in the kinase domain activation loop of Itk (S. D. Heyeck et al., 1997, J. Biol. Chem., 272, 25401-25408). Activated Itk, together with Zap-70 is required for phosphorylation and activation of PLC-.gamma. (S. C. Bunnell et al., 2000, J. Biol. Chem., 275, 2219-2230). PLC-.gamma. catalyzes the formation of inositol 1,4,5-triphosphate and diacylglycerol, leading to calcium mobilization and PKC activation, respectively. These events activate numerous downstream pathways and lead ultimately to degranulation (mast cells) and cytokine gene expression (T cells) (Y. Kawakami et al., 1999, J. Leukocyte Biol., 65, 286-290).

The role of ITK in T cell activation has been confirmed in ITK knockout mice. CD4$^+$ T cells from ITK knockout mice have a diminished proliferative response in a mixed lymphocyte reaction or upon Con A or anti-CD3 stimulation. (X. C. Liao and D. R. Littman, 1995, Immunity, 3, 757-769). Also, T cells from ITK knockout mice produced little IL-2 upon TCR stimulation resulting in reduced proliferation of these cells. In another study, ITK deficient CD4$^+$ T cells produced reduced levels of cytokines including IL-4, IL-5 and IL-13 upon stimulation of the TCR, even after priming with inducing conditions. (D. J. Fowell, 1999, Immunity, 11, 399-409).

The role of ITK in PLC-gamma activation and in calcium mobilization was also confirmed in the T cells of these knock-out mice, which had severely impaired IP$_3$ generation and no extracellular calcium influx upon TCR stimulation (K. Liu et al., 1998, J. Exp. Med. 187, 1721-1727). Such studies support a key role for ITK in activation of T cells and mast cells. Thus an inhibitor of ITK would be of therapeutic benefit in diseases mediated by inappropriate activation of these cells.

It has been well established that T cells play an important role in regulating the immune response (Powrie and Coffman, 1993, Immunology Today, 14, 270-274). Indeed, activation of T cells is often the initiating event in immunological disorders. Following activation of the TCR, there is an influx of calcium that is required for T cell activation. Upon activation, T cells produce cytokines, including IL-2, 4, 5, 9, 10, and 13 leading to T cell proliferation, differentiation, and effector function. Clinical studies with inhibitors of IL-2 have shown that interference with T cell activation and proliferation effectively suppresses immune response in vivo (Waldmann, 1993, Immunology Today, 14, 264-270). Accordingly, agents that inhibit T lymphocyte activation and subsequent cytokine production, are therapeutically useful for selectively suppressing the immune response in a patient in need of such immunosuppression.

Mast cells play a critical roll in asthma and allergic disorders by releasing pro-inflammatory mediators and cytokines. Antigen-mediated aggregation of Fc.epsilon.RI, the high-affinity receptor for IgE results in activation of mast cells (D. B. Corry et al., 1999, Nature, 402, B18-23). This triggers a series of signaling events resulting in the release of mediators, including histamine, proteases, leukotrienes and cytokines (J. R. Gordon et al., 1990, Immunology Today, 11, 458-464.) These mediators cause increased vascular permeability, mucus production, bronchoconstriction, tissue degradation and inflammation thus playing key roles in the etiology and symptoms of asthma and allergic disorders.

Published data using ITK knockout mice suggests that in the absence of ITK function, increased numbers of memory T cells are generated (A. T. Miller et al., 2002 The Journal of Immunology, 168, 2163-2172). One strategy to improve vaccination methods is to increase the number of memory T cells generated (S. M. Kaech et al., Nature Reviews Immunology, 2, 251-262). In addition, deletion of ITK in mice results in reduced T cell receptor (TCR)-induced proliferation and secretion of the cytokines IL-2, IL-4, IL-5, IL-10 and IFN-y (Schaeffer et al, Science 284; 638-641 (1999)), Fowell et al, Immu7lity 11, 399-409 (1999), Schaeffer et al, Nature Immunology 2 (12): 1183-1188 (2001))). The immunological symptoms of allergic asthma are attenuated in ITK−/−mice. Lung inflammation, eosinophil infiltration and mucous production are drastically reduced in ITK−/−mice in response to challenge with the allergen OVA (Mueller et al, Journal of Immunology 170: 5056-5063 (2003)). ITK has also been implicated in atopic dermatitis. This gene has been reported to be more highly expressed in peripheral blood T cells from patients with moderate and/or severe atopic dermatitis than in controls or patients with mild atopic dermatitis (Matsumoto et al, International arcllives of Allergy and Immunology 129: 327-340 (2002)).

Splenocytes from RLK−/−mice secrete half the IL-2 produced by wild type animals in response to TCR engagement (Schaeffer et al, Science 284: 638-641 (1999)), while combined deletion of ITK and RLK in mice leads to a profound inhibition of TCR-induced responses including proliferation and production of the cytokines IL-2, IL-4, IL-5 and IFN-y (Schaeffer et al, Nature Immunology 2 (12): 1183-1188 (2001)), Schaeffer et al, Science 284: 638-641 (1999)). Intracellular signalling following TCR engagement is effected in ITK/RLK deficient T cells; inositol triphosphate production, calcium mobilization, MAP kinase activation, and activation of the transcription factors NFAT and AP-1 are all reduced (Schaeffer et al, Science 284: 638-641 (1999), Schaeffer et al, Nature Immunology 2 (12): 1183-1188 (2001)).

Provided compounds are inhibitors of ITK and are therefore useful for treating one or more disorders associated with activity of ITK. Thus, in some embodiments, the present invention provides a method for treating an ITK-mediated disorder comprising the step of administering to a patient in need thereof a compound of the present invention, or pharmaceutically acceptable composition thereof.

As used herein, the term "ITK-mediated" disorders or conditions as used herein means any disease or other deleterious condition in which ITK, or a mutant thereof, is known to play a role. Accordingly, another embodiment of the present invention relates to treating or lessening the severity of one or more diseases in which ITK, or a mutant thereof, is known to play a role. Specifically, the present invention relates to a method of treating or lessening the severity of a disease or condition selected from a mast cell-mediated condition, a basophil-mediated disorder, an immune or allergic disorder, wherein said method comprises administering to a patient in need thereof a compound or composition according to the present invention.

In some embodiments, the present invention provides a method for treating or lessening the severity of one or more diseases and conditions associated with ITK, wherein the disease or condition is an immune disorder, including inflammatory diseases, autoimmune diseases, organ and bone marrow transplant rejection and other disorders associated with T cell-mediated immune response or mast cell-mediated immune response.

In certain embodiments, the present invention provides a method for treating or lessening the severity of one or more diseases and conditions associated with ITK, wherein the disease or condition is acute or chronic inflammation, an allergy, contact dermatitis, psoriasis, rheumatoid arthritis, multiple sclerosis, type 1 diabetes, inflammatory bowel disease, Guillain-Barre syndrome, Crohn's disease, ulcerative colitis, cancer, graft versus host disease (and other forms of organ or bone marrow transplant rejection) or lupus erythematosus.

In certain embodiments, the present invention provides a method for treating or lessening the severity of one or more diseases and conditions associated with ITK, wherein the disease or condition is a mast cell driven conditions, a basophil-mediated disorder, reversible obstructive airway disease, asthma, rhinitis, chronic obstructive pulmonary disease (COPD), peripheral T-cell lymphomas or HIV. Such conditions include those described in Readinger, J. A. et al., "Selective Targeting of ITK Blocks Multiple Steps of HIV Replication", PNAS 2008, Vol. 105, No. 18 (May 6, 2008).

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. The pharmaceutical intervention in the JAK/STAT pathway has been reviewed [Frank Mol. Med. 5: 432-456 (1999) & Seidel, et al, Oncogene 19: 2645-2656 (2000)].

JAK1, JAK2, and TYK2 are ubiquitously expressed, while JAK3 is predominantly expressed in hematopoietic cells. JAK3 binds exclusively to the common cytokine receptor gamma chain (yc) and is activated by IL-2, IL-4, IL-7, IL-9, and IL-15.

The proliferation and survival of murine mast cells induced by IL-4 and IL-9 have, in fact, been shown to be dependent on JAK3- and yc-signaling [Suzuki et al, Blood 96: 2172-2180 (2000)].

Cross-linking of the high-affinity immunoglobulin (Ig) E receptors of sensitized mast cells leads to a release of proinflammatory mediators, including a number of vasoactive cytokines resulting in acute allergic, or immediate (type I) hypersensitivity reactions [Gordon et al, Nature 346: 274-276 (1990) & Galli, N. Engl. J. Med., 328: 257-265 (1993)]. A crucial role for JAK3 in IgE receptor-mediated mast cell responses in vitro and in vivo has been established [Malaviya, et al, Biochem. Biophys. Res. Commun. 257: 807-813 (1999)]. In addition, the prevention of type I hypersensitivity reactions, including anaphylaxis, mediated by mast cell-activation through inhibition of JAK3 has also been reported [Malaviya et al, J. Biol. Chem. 274: 27028-27038 (1999)]. Targeting mast cells with JAK3 inhibitors modulated mast cell degranulation in vitro and prevented IgE receptor/antigen-mediated anaphylactic reactions in vivo.

A recent study described the successful targeting of JAK3 for immune suppression and allograft acceptance. The study demonstrated a dose-dependent survival of Buffalo heart allograft in Wistar Furth recipients upon administration of inhibitors of JAK3 indicating the possibility of regulating unwanted immune responses in graft versus host disease [Kirken, transpl. proc. 33: 3268-3270 (2001)].

IL-4-mediated STAT-phosphorylation has been implicated as the mechanism involved in early and late stages of rheumatoid arthritis (RA). Up-regulation of proinflammatory cytokines in RA synovium and synovial fluid is a characteristic of the disease. It has been demostrated that IL-4-mediated activation of IL-4/STAT pathway is mediated through the Janus kinases (JAK 1 & 3) and that IL-4-associated JAK kinases are expressed in the RA synovium [Muller-Ladner, et al, J. Immunol. 164: 3894-3901 (2000)].

Familial amyotrophic lateral sclerosis (FALS) is a fatal neurodegenerative disorder affecting about 10% of ALS patients. The survival rates of FALS mice were increased upon treatment with a JAK3 specific inhibitor. This confirmed that JAK3 plays a role in FALS [Trieu, et al, Biochem. Biophys. Res. Commun. 267: 22-25 (2000)].

Signal transducer and activator of transcription (STAT) proteins are activated by, among others, the JAK family kinases. Results form a recent study suggested the possibility of intervention in the JAK/STAT signaling pathway by targeting JAK family kinases with specific inhibitors for the treatment of leukemia [Sudbeck, et al, Clin. Cancer Res. 5: 1569-1582 (1999) ]. JAK3 specific compounds were shown to inhibit the clonogenic growth of JAK3-expressing cell lines DAUDI, RAMOS, LC1; 19, NALM-6, MOLT-3 and HL-60. Inhibition of JAK3 and TYK 2 abrogated tyrosine phosphorylation of STAT3, and inhibited cell growth of mycosis fungoides, a form of cutaneous T cell lymphoma.

According to another embodiment, the invention provides a method for treating or lessening the severity of a JAK3-mediated disease or condition in a patient comprising the step of administering to said patient a composition according to the present invention.

The term "JAK3-mediated disease", as used herein means any disease or other deleterious condition in which a JAK3 kinase is known to play a role. Accordingly, another embodiment of the present invention relates to treating or lessening the severity of one or more diseases in which JAK3 is known to play a role. Specifically, the present invention relates to a method of treating or lessening the severity of a disease or condition selected from immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas, wherein said method comprises administering to a patient in need thereof a composition according to the present invention.

The compounds and compositions, according to the method of the present invention, may be administered using any amount and any route of administration effective for treating or lessening the severity of cancer, an autoimmune disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting ErbB1, ErbB2, ErbB3, ErbB4, a TEC-kinase, and/or JAK3, or a mutant thereof, activity in a biological sample comprising the step of contacting said biological sample with a compound of this invention, or a composition comprising said compound. In certain embodiments, the invention relates to a method of irreversibly inhibiting ErbB1, ErbB2, ErbB3, ErbB4, a TEC-kinase, and/or JAK3, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of protein kinase, or a protein kinase selected from ErbB1, ErbB2, ErbB3, ErbB4, a TEC-kinase, and/or JAK3, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting one or more of ErbB1, ErbB2, ErbB3, ErbB4, a TEC-kinase, and/or JAK3, or a mutant thereof, activity in a patient comprising the step of administering to said patient a compound of the present invention, or a composition comprising said compound. According to certain embodiments, the invention relates to a method of irreversibly inhibiting one or more of ErbB1, ErbB2, ErbB3, ErbB4, a TEC-kinase, and/or JAK3, or a mutant thereof, activity in a patient comprising the step of administering to said patient a compound of the present invention, or a composition comprising said compound. In other embodiments, the present invention provides a method for treating a disorder mediated by one or more of ErbB1, ErbB2, ErbB3, ErbB4, a TEC-kinase, and/or JAK3, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of Abarelix, aldesleukin, Aldesleukin, Alemtuzumab, Alitretinoin, Allopurinol, Altretamine, Amifostine, Anastrozole, Arsenic trioxide, Asparaginase, Azacitidine, BCG Live, Bevacuzimab, Fluorouracil, Bexarotene, Bleomycin, Bortezomib, Busulfan, Calusterone, Capecitabine, Camptothecin, Carboplatin, Carmustine, Celecoxib, Cetuximab, Chlorambucil, Cladribine, Clofarabine, Cyclophosphamide, Cytarabine, Dactinomycin, Darbepoetin alfa, Daunorubicin, Denileukin, Dexrazoxane, Docetaxel, Doxorubicin (neutral), Doxorubicin hydrochloride, Dromostanolone Propionate, Epirubicin, Epoetin alfa, Erlotinib, Estramustine, Etoposide Phosphate, Etoposide, Exemestane, Filgrastim, floxuridine fludarabine, Fulvestrant, Gefitinib, Gemcitabine, Gemtuzumab, Goserelin Acetate, Histrelin Acetate, Hydroxyurea, Ibritumomab, Idarubicin, Ifosfamide, Imatinib Mesylate, Interferon Alfa-2a, Interferon Alfa-2b, Irinotecan, Lenalidomide, Letrozole, Leucovorin, Leuprolide Acetate, Levamisole, Lomustine, Megestrol Acetate, Melphalan, Mercaptopurine, 6-MP, Mesna, Methotrexate, Methoxsalen, Mitomycin C, Mitotane, Mitoxantrone, Nandrolone, Nelarabine, Nofetumomab, Oprelvekin, Oxaliplatin, Paclitaxel, Palifermin, Pamidronate, Pegademase, Pegaspargase, Pegfilgrastim, Pemetrexed Disodium, Pentostatin, Pipobroman, Plicamycin, Porfimer Sodium, Procarbazine, Quinacrine, Rasburicase, Rituximab, Sargramostim, Sorafenib, Streptozocin, Sunitinib Maleate, Talc, Tamoxifen, Temozolomide, Teniposide, VM-26, Testolactone, Thioguanine, 6-TG, Thiotepa, Topotecan, Toremifene, Tositumomab, Trastuzumab, Tretinoin, ATRA, Uracil Mustard, Valrubicin, Vinblastine, Vincristine, Vinorelbine, Zoledronate, or Zoledronic acid.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immuno-modulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

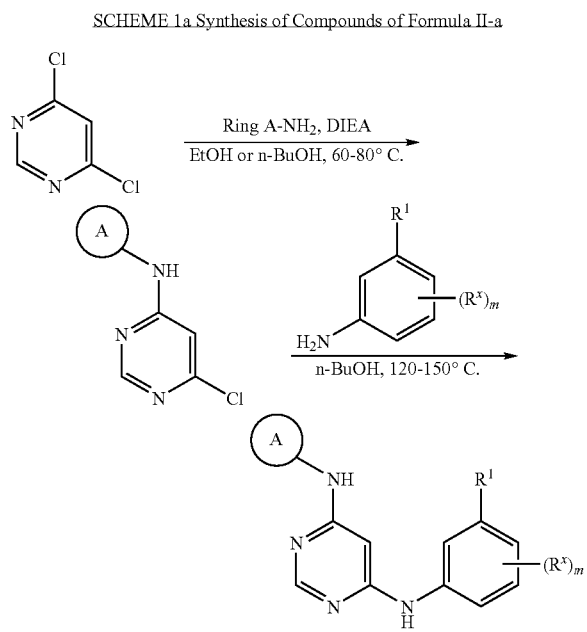

Synthesis of (6-chloro-pyrimidin-4-yl)-(3-bromo-phenyl)-amine: A solution of 4,6-dichloropyrimidine (5 g, 33.6 mmol), 3-bromoaniline (5.8 g, 33.7 mmol) and N,N-diisopropylethylamine (DIEA) (5.2 g, 40.2 mmol) in ethanol (40 mL) was heated at 80° C. for 16 hr. The reaction mixture was cooled to ambient temperature, diethylether (35 mL) was added while the mixture was being stirred. The product was precipitated, filtered, washed with water and dried to afford 5.9 g (62% yield) of a light colored solid. MS (m/z): $MH^+$=284, 286, 288.

Synthesis of 3-[6-(3-bromophenylamino)-pyrimidin-4-ylamino]-phenylamine: A mixture of (6-chloro-pyrimidin-4-yl)-(3-bromo-phenyl)-amine (300 mg, 1.1 mmol) and benzene-1,3-diamine (300 mg, 2.75 mmol) in 3 mL of n-BuOH was heated in a sealed tube to 150° C. for 16 hr. Solvent was removed by vacuum evaporation and the crude product was purified by flash chromatography on silica gel with EtOAc/DCM solvent system to afford 255 mg (65% yield) of the title compound as a yellow solid. MS (m/z): $MH^+$=356, 358.

The following compounds were prepared in a manner substantially similar to that described in Scheme 1a and the Examples above:

(a) 3-Bromoaniline and benzene-1,4-diamine gave 4-[6-(3-bromophenylamino)-pyrimidin-4-ylamino]phenylamine: MS (m/z): $MH^+$=356, 358.

(b) 3-Chloro-4-fluoroaniline and benzene-1,3-diamine gave 3-[6-(3-chloro-4-fluorophenylamino)-pyrimidin-4-ylamino]phenylamine ($I^R$-4). MS (m/z): $MH^+$=330, 332.

(c) 3-Methylaniline and benzene-1,3-diamine gave 3-[6-(3-methylphenylamino)-pyrimidin-4-ylamino]phenylamine ($I^R$-5). MS (m/z): $MH^+$=292.

(d) 3-Chloro-4-(3-fluorophenyl)methoxyaniline and benzene-1,3-diamine gave 3-{6-[3-chloro-4-(3-fluorophenyl)methoxyphenylamino]-pyrimidin-4-ylamino}phenylamine ($I^R$-6). MS (m/z): $MH^+$=436, 438.

(e) 3-Bromoaniline and 3-ethynylaniline gave $N^4$-(3-Bromophenyl)-$N^6$-(3-ethynylphenyl)pyrimidine-4,6-diamine (I-12). MS $(M+H^+)$ 365, 367; $^1$H NMR (400 MHz, $d^6$-DMSO) δ 9.73 (s, 1H), 9.60 (s, 1H), 8.67 (s, 1H), 7.95 (t, 1H), 7.76 (s, 1H), 7.50 (d, 1H), 7.46 (d, 1H), 7.55 (t, 1H), 7.40 (t, 1H), 7.20 (d, 1H), 7.10 (d, 1H), 6.30 (s, 1H), 4.25 (s, 1H) ppm.

(f) 3-Ethynylaniline gave $N^4$,$N^6$-bis(3-ethynylphenyl)pyrimidine-4,6-diamine (I-11). MS $(M+H^+)$ 311, 312; $^1$H NMR (400 MHz, $d^6$-DMSO) δ 9.24 (s, 2H), 8.32 (s, 1H), 7.78 (s, 2H), 7.52 (d, 2H), 7.25 (t, 2H), 7.02 (d, 2H), 6.13 (s, 1H), 4.12 (s, 2H) ppm.

(g) 4-Phenoxyaniline and 2,6-diaminopyridine gave 2-[6-(4-phenoxyphenyl)-aminopyrimidin-4-yl]amino-6-aminopyridine ($I^R$-11) MS (m/z): $MH^+$=372, 371.

(h) 4-Phenoxyaniline and 1,4-diaminobenzene gave 4-[6-(4-phenoxyphenyl)amino-pyrimidin-4-yl]amino-aminobenzene ($I^R$-14) MS (m/z): $MH^+$=370

Example 2

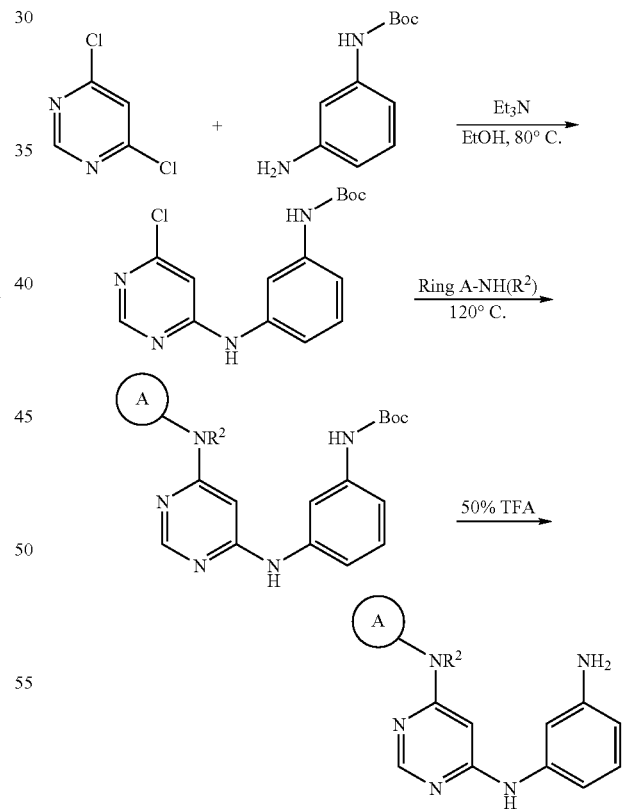

SCHEME 2a
Sequence A for Synthesis of 3-(6-mono- or disubstituted-amino) pyrimidin-4-ylamino)-phenylamines Although a BOC protecting group is depicted in Scheme 2a above and the ensuing schemes below, one of ordinary skill in the art will recognize that other amine protecting groups are amenable for use in preparing compounds of the present invention. Accordingly, a variety of amine protecting groups is contemplated.

Synthesis of tert-butyl 3-(6-chloropyrimidin-4-ylamino) phenylcarbamate 4,6-Dichloropyrimidine (1.5 g, 10 mmol), tert-butyl 3-aminophenylcarbamate (2.1 g, 10 mmol) and triethylamine (2.2 g, 20 mmol) were mixed in ethanol (20 mL), heated at 80° C. for 16 hr. The reaction mixture was cooled to RT and solvent was removed in vacuo. The gummy crude product was mixed with 20 mL of DCM and was stirred at RT to give an off-white solid, which was filtered and dried under vacuum (1.6 g, 5 mmol). MS (m/z): MH$^+$=321, 323.

Synthesis of tert-butyl 3-(6-[N-methyl-N-phenylamino] pyrimidin-4-ylamino)phenyl-carbamate A mixture of tert-butyl 3-(6-chloropyrimidin-4-ylamino)phenylcarbamate (1.6 g, 5 mmol) and N-methylaniline (1.07 g, 10 mmol) was heated at 120° C. in a sealed tube for 2 hr. The reaction mixture was cooled to RT, mixed with 1 mL of 1N NaOH and 5 mL of DCM, stirred for 30 min, the product was filtered and dried under vacuum to give a solid product. MS (m/z): MH$^+$=392.

Synthesis of 3-[6-(N-methyl-N-phenylamino)-pyrimidin-4-ylamino]phenylamine (I$^R$-8) A mixture of tert-butyl 3-(6-[N-methyl-N-phenylamino]pyrimidin-4-ylamino)phenyl-carbamate (1.17 g, 3 mmol) and TFA (50% in DCM, 10 mL) was stirred at RT for 4 hr. The reaction solvent was removed under vacuum. The crude product was mixed with 1 mL of 2N NaOH and 5 mL of EtOAc, was stirred for 30 min, was filtered, and was dried under vacuum to give 0.65 g (75%) of the title compound, an off-white solid. (I$^R$-8) MS (m/z): MH$^+$=292.

The following compounds were prepared in a manner substantially similar to that described in Scheme 2a:

(a) 4-Phenoxyphenyl amine gave 3-[6-(4-phenoxyphenylamino) -pyrimidin-4-ylamino]phenylamine. (I$^R$-7) MS (m/z): MH$^+$=370.

(b) 3-Chloro-4-(2-pyridyl)methoxyaniline gave 3-{[6-(3-chloro-4-(2-pyridyl)methoxyphenylamino)-pyrimidin-4-ylamino]phenylamine. (I$^R$-9) MS (m/z): MH$^+$=419, 421.

(c) 3-Chloro-4-(3-fluorobenzyloxy)aniline gave 3-[6-(3-chloro-4-{3-fluorobenzyloxy}phenylamino)-pyrimidin-4-ylamino]-phenyl amine. (I$^R$-6) MS (m/z): M$^+$=436, 438.

(d) Aniline gave 3-[6-(phenylamino)-pyrimidin-4-yl]aminophenylamine. (I$^R$-15) MS (m/z): MH$^+$=278.

SCHEME 2b
Sequence B for Synthesis of 3-(6-mono- or disubstituted-aminopyrimidin-4-yl)amino-phenylamines

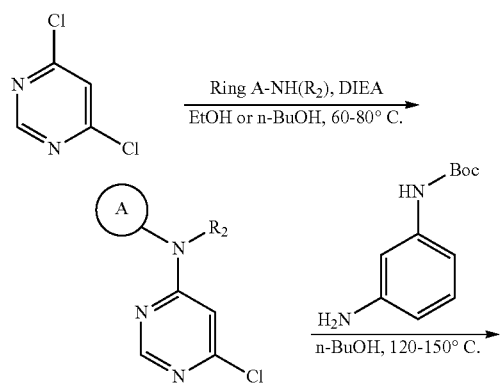

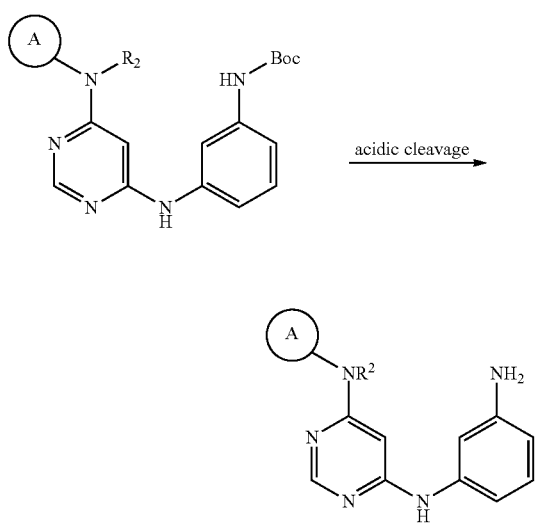

Synthesis of 3-[6-(4-bromo-2-fluorophenylamino)-pyrimidin-4-yl-amino]-phenylamine (I$^R$-17). A solution of 4-bromo-2-fluoroaniline (701 mg, 3.69 mmol), diisopropylethylamine (0.70 mL, 4.03 mmol), and 4,6-dichloropyrimidine (500 mg, 3.36 mmol) in EtOH (10 mL) was heated in an 85° C. oil bath for 5 d. Flash chromatography (2% MeOH/CHCl$_3$) of the residue gave 380 mg (37%) of N-(4-bromo-2-fluorophenyl)-6-chloropyrimidin-4-amine as a pale yellow solid. MS (m/z): 304, 302. A suspension of N-(4-bromo-2-fluorophenyl)-6-chloropyrimidin-4-amine (0.37 g, 1.22 mmol) and tert-butyl 3-aminophenylcarbamate (0.28 g, 1.35 mmol) in n-BuOH (4 mL) was heated in an oil bath at 120-130° C. for 6 h. The reaction mixture was cooled and concentrated to give 0.68 g of a brown foam. Flash chromatography gave 0.16 g (28%) tert-butyl 3-(6-[4-bromo-2-fluorophenyl]aminopyrimidin-4-yl)aminophenylcarbamate as a white solid. MS (m/z): (M+H) 476, 474. tert-Butyl 3-(6-[4-bromo-2-fluorophenyl]aminopyrimidin-4-yl)aminophenylcarbamate (0.15 g, 0.32 mmol) was taken up in 4M HCl in dioxane (5 mL). After several minutes a white solid began to precipitate. The mixture was allowed to stand for 3 h and was concentrated via rotary evaporation. Saturated aqueous sodium bicarbonate (5 mL) was added and the mixture was sonicated for several minutes. The solid was collected by filtration, was washed with water (5 mL), and was dried overnight under vacuum to give 0.12 g (100%) of 3-[6-(4-bromo-2-fluorophenylamino)-pyrimidin-4-yl-amino]-phenylamine (I$^R$-17) as a white powder. MS (m/z): (M+H) 376, 374.

SCHEME 2c
Synthesis of 3-(6-mono or disubstituted-aminopyrimidin-4-yl) amino-N-substituted phenylamines

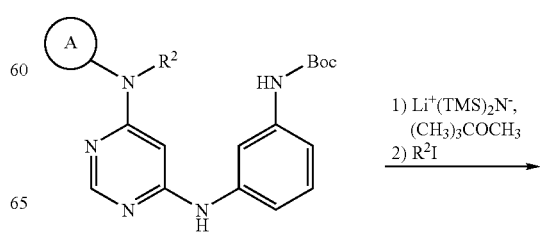

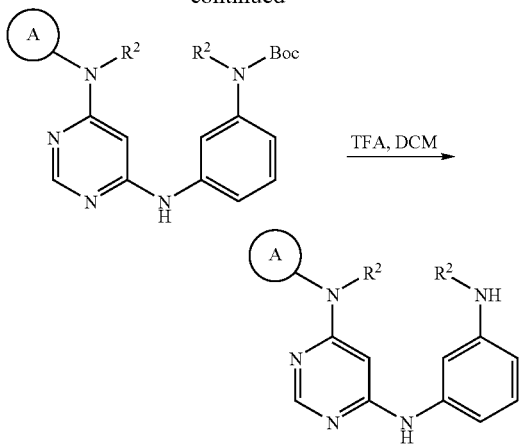

Synthesis of tert-butyl N-3-(6-chloropyrimidin-4-ylamino)phenyl -N-methylcarbamate To a stirring solution of tert-butyl 3-(6-chloropyrimidin-4-ylamino)phenyl carbamate (2.000 g, 6.235 mmol) in 10 mL of THF at 0° C. under $N_2$ was added drop-wise a solution of 1.0 M lithium bis(trimethylsilyl)amide in tert-butyl methyl ether (6.23 mL, 6.23 mmol). The light yellow solution was stirred at 0° C. for 30 min then iodomethane (0.43 mL, 6.892 mmol, 1.1 eq) was added. The solution was allowed to slowly warm to room temperature overnight, was concentrated, and was then partitioned between EtOAc and saturated $KH_2PO_4$ solution. The organic extract was washed with brine solution, dried ($MgSO_4$), was filtered, was concentrated in vacuo and was chromatographed (silica gel, 2% MeOH in $CH_2Cl_2$) to give 0.904 g of tert-butyl N-3-(6-chloropyrimidin-4-ylamino)phenyl-N-methylcarbamate as an off-white solid. MS (m/z) M+1=335/337 (100/44%), $^1$H NMR ($CDCl_3$) δ 8.48 (s, 1H), 7.49 (bs, 1H), 7.38 (m, 1H), 7.24 (m, 1H), 6.91 (m, 1H), 6.71 (bs, 1H), 6.30 (s, 1H), 3.48 (s, 3H), 1.53 (s, 9H).

Synthesis of N-3-[6-(3-Chloro-4-fluorophenylamino)-pyrimidin-4-ylamino]phenyl-N-methylamine (Int-C) A solution of tert-butyl N-3-(6-chloropyrimidin-4-ylamino)phenyl-N-methylcarbamate (0.486 g, 1.095 mmol) in 25 mL of $CH_2Cl_2$ was treated with trifluoroacetic acid (5 mL). The solution was stirred at room temperature under $N_2$ for 2 h, was concentrated and was partitioned between $CHCl_3$ and 10% aq. $NH_4OH$ solution. The organic extract was washed with brine solution, was dried ($MgSO_4$), was filtered and was concentrated to give 0.630 g of N-3-[6-(3-chloro-4-fluorophenylamino) -pyrimidin-4-ylamino]phenyl-N-methylamine (Int-C) as yellow oil. MS (m/z): 344/346 (M+1, 100/68%). TLC ($SiO_2$, 10% MeOH in $CHCl_3$): $R_f$ 0.44.

Example 3

SCHEME 3a
Sequence B for Synthesis of 3-(6-mono- or disubstituted-aminopyrimidin-4-yl)amino-phenylamines

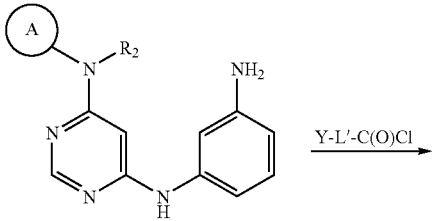

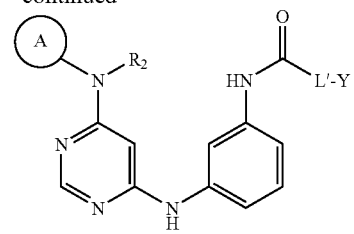

wherein L' is a subset of L, as defined herein, such that Y-L'C(O)Cl results in formation of provided compounds wherein $R^1$ is -L-Y wherein a terminal methylene unit of L is replaced with —NHC(O)—.

Synthesis of N-{3-[6-(3-bromophenylamino) -pyrimidin-4-ylamino]-phenyl}-2-propenamide (I-1) A solution of 3-[6-(3-bromophenylamino)-pyrimidin-4-ylamino]phenylamine (250 mg, 0.7 mmol) and triethylamine (180 mg, 1.75 mmol) in 5 mL of THF was stirred at RT. Acryloyl chloride (80 mg, 0.9 mmol) was added into the reaction mixture and it was stirred at RT for 1 h. The solvent was removed by vacuum evaporation and the crude product was purified by flash chromatography on silica gel with EtOAc/DCM solvent system to afford 115 mg (40% yield) of the title compound as a light colored solid. MS (m/z): $MH^+$=410, 412. $^1$H NMR (DMSO): 10.15 (s, 1H), 9.36 (s, 1H), 9.28 (s, 1H), 8.34 (s, 1H), 8.02 (s, 1H), 8.00 (s, 1H), 7.51-7.11 (m, 5H), 6.47 (dd, 1H, $J_1$=10.1 Hz, $J_2$=17.0 Hz), 6.27 (dd, 1H, $J_1$=1.9 Hz, $J_2$=17.0 Hz), 6.20 (s, 1H), 5.76 (dd, 1H, $J_1$=10.1 Hz, $J_2$=1.9 Hz) ppm.

The following compounds were prepared in a manner substantially similar to those described in Schemes 3a:

(a) 4-[6-(3-Bromophenylamino)-pyrimidin-4-ylamino] phenylamine and acryoyl chloride gave N-{4-[6-(3-bromophenylamino) -pyrimidin-4-ylamino]phenyl}-2-propenamide (I-93). MS (m/z): $MH^+$=410, 412. $^1$H NMR (DMSO): 10.10 (s, 1H), 9.33 (s, 1H), 9.17 (s, 1H), 8.30 (s, 1H), 8.02 (s, 1H), 7.62 (m, 2H), 7.46 (m, 3H), 7.22 (t, 1H, J=8.0 Hz), 7.10 (d, 1H, J=8.0 Hz), 6.43 (dd, 1H, $J_1$=10.0 Hz, $J_2$=17.0 Hz), 6.24 (d, 1H, J=17.0 Hz), 6.13 (s, 1H), 5.73 (d, 1H, J=10.0 Hz) ppm.

(b) 3-[6-(3-Bromophenylamino)-pyrimidin-4-ylamino] phenylamine and propionyl chloride gave N-{3-[6-(3-bromophenylamino)-pyrimidin-4-ylamino]phenyl}-propionamide ($I^R$-3). MS (m/z): $MH^+$=412, 414. $^1$H NMR (DMSO): 9.78 (s, 1H), 9.28 (s, 1H), 9.16 (s, 1H), 8.26 (s, 1H), 7.96 (s, 1H), 7.76 (s, 1H), 7.43 (d, 1H, J=8.2 Hz), 7.20 (m, 2H), 7.05 (m, 3H), 6.12 (s, 1H), 2.27 (q, 2H, J=7.6 Hz), 1.03 (t, 3H, J=7.6 Hz) ppm.

(c) 3-[6-(3-Bromophenylamino)-pyrimidin-4-ylamino] phenylamine and (E)-2-butenoylchloride gave (E)-N-{3-[6-(3-bromophenylamino)-pyrimidin-4-ylamino]-phenyl}-2-butenamide (I-8). MS (m/z): $M+H^+$=424, 426. $^1$H NMR (DMSO): 9.87 (s, 1H), 9.29 (s, 1H), 9.18 (s, 1H), 8.27 (s, 1H), 7.96 (s, 1H), 7.82 (s, 1H), 7.44 (d, 1H, J=8.2 Hz) 7.20 (m, 4H), 7.05 (dd, 1H, $J_1$=1.0 Hz, $J_2$=7.8 Hz), 6.75 (m, 1H), 6.15 (m, 2H), 1.81 (d, 3H, J=7.8 Hz) ppm.

(d) 3-[6-(3-Chloro-4-fluorophenylamino)-pyrimidin-4-ylamino]phenylamine ($I^R$-4) and acryoyl chloride gave N-{3-[6-(3-chloro-4-fluorophenylamino) -pyrimidin-4-ylamino]phenyl}-2-propenamide (I-2). MS (m/z): $MH^+$=384, 386. $^1$H NMR (DMSO): 9.29 (s, 1H), 9.20 (s, 1H), 8.27 (s, 1H), 7.93 (m, 1H), 7.86 (s, 1H), 7.41 (m, 1H), 7.25 (m, 5H), 6.42 (dd, 1H, $J_1$=10.1 Hz, $J_2$=17.0

Hz), 6.22 (dd, 1H, $J_1=1.9$ Hz, $J_2=17.0$ Hz), 6.09 (d, 1H, $J_1=0.7$ Hz), 5.69 (dd, 1H, $J_1=10.1$ Hz, $J_2=1.9$ Hz) ppm.

(e) 3-[6-(3-Methylphenylamino)-pyrimidin-4-ylamino]phenylamine and acryolyl chloride gave N-{3-[6-(3-methylphenylamino)-pyrimidin-4-ylamino]phenyl}-2-propenamide (I-4). MS (m/z): $M+H^+=346$. $^1$H NMR (DMSO): 9.11 (s, 1H), 9.00 (s, 1H), 8.21 (s, 1H), 7.86 (d, 1H, J=1.7 Hz), 7.31-7.05 (m, 7H), 6.74 (d, 1H, J=7.6 Hz), 6.41 (dd, 1H, $J_1=10.0$ Hz, $J_2=17.0$ Hz), 6.20 (dd, 1H, $J_1=2.0$ Hz, $J_2=17.0$ Hz), 6.14 (s, 1H), 5.69 (dd, 1H, $J_1=10.1$ Hz, $J_2=2.0$ Hz), 2.23 (s, 3H) ppm.

(f) 3-{6-[3-Chloro-4-(3-fluorophenyl)methoxyphenylamino]-pyrimidin-4-ylamino}phenylamine ($I^R$-6) and acryolyl chloride gave N-{3-[6-(3-chloro-4-(3-fluorophenyl)methoxyphenylamino)-pyrimidin-4-ylamino]phenyl}-2-propenamide (II-6). MS (m/z): $M+H^+=490$, 492. $^1$H NMR (DMSO): 9.13 (s, 1H), 9.07 (s, 1H), 8.22 (s, 1H), 7.85 (d, 1H, J=1.5 Hz), 7.40-7.10 (m, 10H), 6.41 (dd, 1H, $J_1=10.0$ Hz, $J_2=17.0$ Hz), 6.20 (dd, 1H, $J_1=2.0$ Hz, $J_2=17.0$ Hz), 6.05 (s, 1H), 5.70 (dd, 1H, $J_1=10.1$ Hz, $J_2=2.0$ Hz), 5.14 (s, 2H) ppm.

(g) 4-Phenoxyphenyl amine gave 3-[6-(4-phenoxyphenylamino)-pyrimidin-4-ylamino]phenylamine. ($I^R$-7) and acryolyl chloride gave N-{3-[6-(4-phenoxyphenylamino)-pyrimidin-4-ylamino]phenyl}-2 propenamide (I-13). MS (m/z): $MH^+=424$. $^1$H NMR (DMSO): 9.14 (s, 1H), 9.10 (s, 1H), 8.22 (s, 1H), 7.89 (s, 1H), 7.52 (d, 2H, J=9.0 Hz), 7.35-6.92 (m, 11H), 6.42 (dd, 1H, $J_1=10.1$ Hz, $J_2=16.9$ Hz), 6.22 (dd, 1H, $J_1=1.9$ Hz, $J_2=16.9$ Hz), 6.12 (s, 1H), 5.70 (dd, 1H, $J_1=1.9$ Hz, $J_2=10.1$ Hz) ppm.

(h) 3-[6-(N-methyl-N-phenylamino)-pyrimidin-4-ylamino]phenylamine ($I^R$-8) and acryoyl chloride gave N-{3-[6-(N-methyl-N-phenylamino)-pyrimidin-4-ylamino]phenyl}-2 propenamide (I-15): an off-white solid; 70 mg; 20%; MS (m/z): $MH^+=346$. $^1$H NMR (DMSO): 10.02 (s, 1H), 9.00 (s, 1H), 8.25 (s, 1H), 7.85 (s, 1H), 7.45-7.12 (m, 6H), 6.45 (dd, 1H), 6.20 (d, 1H), 5.70 (m, 1H), 3.35 (s, 3H) ppm.

(i) 3-{[6-(3-Chloro-4-(2-pyridyl)methoxyphenylamino)-pyrimidin-4-ylamino]phenylamine ($I^R$-9) and acryolyl chloride gave N-(3-(6-(3-chloro-4-(pyridin-2-ylmethoxy)phenylamino)pyrimidin-4-ylamino)phenyl)-2-propenamide (I-16). MS (m/z): $MH^+=473$, 475 (3:1). $^1$H NMR (DMSO): 10.10 (s, 1H), 9.17 (s, 1H), 9.08 (s, 1H), 8.55 (m, 1H), 8.24 (s, 1H), 7.92-7.73 (m, 4H), 7.57 (d, 1H), 7.38-7.06 (m, 5H), 6.45 (dd, 1H), 6.23 (dd, 1H), 6.08 (s, 1H), 5.72 (dd, 1H), 5.20 (s, 2H) ppm.

(j) 3-[6-(3-Chloro-4-fluorophenylamino)-pyrimidin-4-ylamino]phenylamine ($I^R$-4) and 1-cyanocyclopropanecarbonyl chloride gave N-[3-(6-{3-chloro-4-fluorophenyl}pyrimidin-4-yl)amino]phenyl-1-cyanocyclopropanecarboxamide (I-47). MS (m/z): $M+1=423/425$, H NMR (DMSO-$d_6$) δ 10.04 (s, 1H), 9.18 (s, 1H), 9.12 (s, 1H), 8.27 (d, 1H), 7.88 (s, 1H), 7.8 (s, 1H), 7.47-7.16 (m, 9H), 6.74 (b, 1H), 6.28 (d, 1H), 6.1 (s, 1H), 5.19 (s, 2H), 3.05 (s, 2H), 2.18 (s, 6H).

(k) 3-[6-(3-Chloro-4-fluorophenylamino)-pyrimidin-4-ylamino]phenylamine ($I^R$-4) and chloroacetyl chloride gave 2-chloro-N-{3-[6-(3-chloro-4-fluorophenylamino)-pyrimidin-4-ylamino]-phenyl}-acetamide (I-49). MS (ES$^+$): $(M+1)^+=406$ (100%), $(M+3)^+=408$ (75%). $^1$H-NMR (DMSO-$d_6$, δ 10.31 (s, 1H), 9.37 (s, 1H), 9.30 (s, 1H), 8.33 (s, 1H), 8.00 (m, 1H), 7.87 (s, 1H), 7.47-7.24 (m, 5H), 6.15 (s, 1H), 4.26 (s, 2H).

(l) 3-[6-(3-Chloro-4-fluorophenyl)aminopyrimidin-4-yl]aminophenylamine ($I^R$-4) and 2-chloropropionyl chloride gave 2-chloro-N-[3-(6-{3-chloro-4-fluorophenyl}aminopyrimidin-4-yl)aminophenyl]propionamide (I-50). MS (ES$^+$): $(M+1)^+=420$ (100%), $(M+3)^+=422$ (75%). $^1$H-NMR (DMSO-$d_6$, δ 10.32 (s, 1H), 9.37 (s, 1H), 9.28 (s, 1H), 8.33 (s, 1H), 8.00-7.98 (m, 1H), 7.87 (s, 1H), 7.47-7.26 (m, 5H), 6.14 (s, 1H), 4.69 (quartet, 1H), 1.61 (d, 3H).

(m) 3-[6-(3-Chloro-4-fluorophenylamino)pyrimidin-4-ylamino]phenylamine ($I^R$-4) and 1-trifluoromethylcyclopropanecarbonyl chloride gave N-[3-(6-{3-chloro-4-fluorophenyl}aminopyrimidin-4-yl)aminophenyl]-1-trifluoromethylcyclopropanecarboxamide (I-51). MS (ES) (m/z): 466/468 [M+1, 100/45%]. $^1$H NMR (DMSO-$d_6$) δ 9.61 (m, 1H), 9.07-9.18 (m, 2H), 8.14 (m, 1H), 7.63-7.8 (m, 2H), 7.03-7.21 (m, 5H), 5.94 (bs, 1H), 1.12-1.27 (m, 4H).

(n) N-3-[6-(3-Chloro-4-fluorophenylamino)-pyrimidin-4-ylamino]phenyl-N-methylamine (Int-D) and acryolyl chloride gave N-3-[6-(3-chloro-4-fluorophenylamino)pyrimidin-4-yl]aminophenyl-N-methyl-2-propenamide (I-53). MS (m/z): 398/400 (M+1, 100/63%). $^1$H NMR (DMSO-$d_6$) δ 10.32 (s, 1H), 9.21 (s, 1H), 8.33 (s, 1H), 7.99 (bs, 1H), 7.25-7.68 (m, 5H), 7.06 (bs, 1H), 6.41-6.47 (m, 2H), 6.26-6.29 (m, 1H), 5.71-5.80 (m, 2H).

(o) 3-[6-(4-Bromo-2-fluorophenyl)aminopyrimidin-4-yl]aminophenyl amine ($I^R$-17) and acryloyl chloride gave N-3-[6-(4-bromo-2-fluorophenylamino)pyrimidin-4-yl]aminophenyl]-2-propenamide (I-55). MS $(M+H^+)$ 430, 428. $^1$H NMR ($d^6$-DMSO) δ 10.13 (s, 1H), 9.25 (s, 1H), 9.02 (s, 1H), 8.26 (s, 1H), 7.91 (m, 2H), 7.57 (d, J=11 Hz, 1H), 7.45-7.15 (m, 4H), 6.46 (dd, J=12 and 10 Hz, 1H), 6.26 (d, J=12 Hz, 1H), 6.23 (s, 1H), 5.75 (d, J=10 Hz, 1H).

(p) 2-[6-(4-phenoxyphenyl)amino-pyrimidin-4-yl]amino-6-aminopyridine ($I^R$-11) and acryolyl chloride gave N-6-[6-(4-phenoxyphenyl)amino-pyrimidin-4-yl)]aminopyridin-2-ylpropenamide (I-63) $^1$H NMR (DMSO-$d_6$) δ ppm: 5.75 (d, J=10.20 Hz, 1H), 6.29 (d, J=17.04 Hz, 1H), 6.62 (dd, J=10.08 & 16.92 Hz, 1H), 6.96-7.00 (m, 4H), 7.07-7.11 (m, 1H), 7.18 (bd, J=3.28 Hz, 1H), 7.33-7.38 (m, 3H), 7.62-7.69 (m, 4H), 8.29 (s, 1H), 9.13 (s, 1H), 9.66 (s, 1H), 10.15 (s, 1H); MS: m/z 425.3 (M+1).

(q) 2-[6-(3-methylphenoxy)-pyrimidin-4-yl]amino-6-aminopyridine ($I^R$-12) and acryolyl chloride gave N-6-[6-(3-methylphenoxy)-pyrimidin-4-yl)]aminopyridin-2-ylpropenamide (I-65) $^1$H NMR (CDCl$_3$) δ ppm: 2.40 (s, 3H), 5.86 (d, J=9.44 Hz, 1H), 6.49-6.61 (m, 2H), 6.83 (bs, 1H), 6.95-7.05 (m, 3H), 7.15 (d, J=7.48 Hz, 1H), 7.34 (t, J=15.08 Hz, 2H), 7.54 (bd, J=5.56 Hz, 1H), 8.78 (s, 1H), 10.78 (s, 1H); LCMS: m/z 348.8 (M+1).

(r) 2-[6-(4-phenoxyphenoxy)-pyrimidin-4-yl]amino-6-aminopyridine ($I^R$-13) and acryolyl chloride gave N-6-[6-(4-phenoxyphenoxy)-pyrimidin-4-yl)]aminopyridin-2-yl}propenamide (I-66) $^1$H NMR (MeOD) δ ppm: 5.92 (dd, J=11.60, Hz, 1H), 6.50-6.54 (m, 2H), 6.75-7.28 (m, 10H), 7.37-7.41 (m, 2H), 7.91 (t, J=16.08 Hz, 1H), 8.63 (s, 1H); LCMS: m/z 426 (M+1).

(s) 3-[6-(phenylamino)-pyrimidin-4-ylamino]phenylamine. ($I^R$-15) acryolyl chloride gave N-3-[6-(phenylamino)-pyrimidin-4-yl]aminophenylpropenamide (I-67) $^1$H NMR (DMSO-$d_6$) δ ppm: 5.72 (dd, J=2.04 & 10.04 Hz, 1H), 6.19 (s, 1H), 6.25 (dd, J=2 & 16.92 Hz, 1H), 6.46 (dd, J=10.04 & 16.88 Hz, 1H), 6.96 (t, J=7.36 Hz, 1H), 7.19-7.31 (m, 4H), 7.54 (d, J=7.68 Hz, 2H), 7.91 (s, 1H), 8.26 (s, 1H), 9.13 (s, 1H), 9.18 (s, 1H), 10.11 (s, 1H); MS: m/z 332.8 (M+1).

Example 4

SCHEME 4a
Sequence A for Synthesis of N-3-(6-mono- or disubstituted-aminopyrimidin-4-yl)amino-N-mono- or unsubstituted-phenyl-4-amino-substituted-2-butenamides

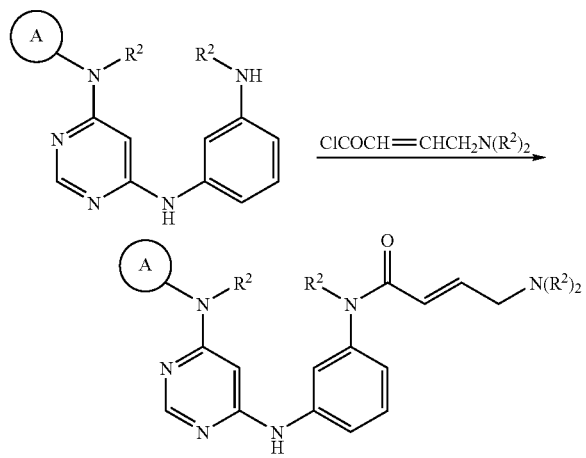

SCHEME 4b
Sequence B for Synthesis of N-3-(6-mono or disubstituted-aminopyrimidin-4-yl)amino-N-mono- or unsubstituted-phenyl-4-amino-substituted-2-butenamides

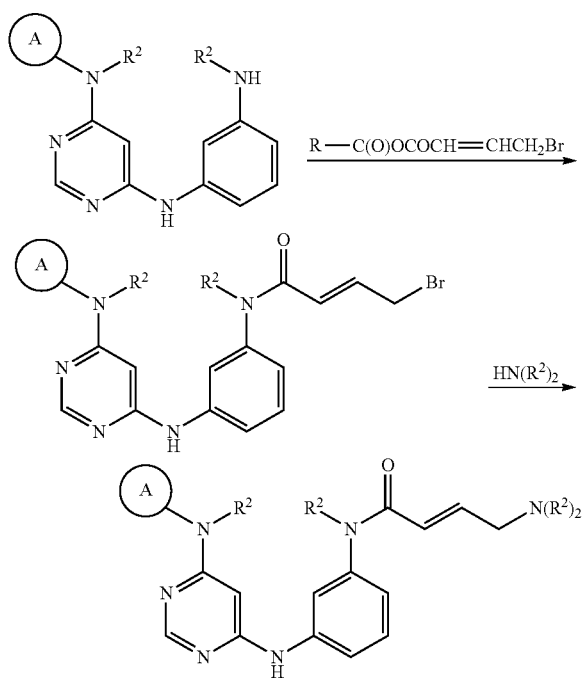

Synthesis of (E)-N-(3-(6-(3-chloro-4-(pyridin-2-ylmethoxy)phenylamino)-pyrimidin-4-ylamino)phenyl)-4-(dimethylamino)but-2-enamide (I-19). 3-{[6-(3-chloro-4-(2-pyridyl)methoxyphenylamino)-pyrimidine-4-ylamino] phenylamine ($I^R$-9) was dissolved in N-methylpyrrolidinone (1.2 mL) and added dropwise over 10 minutes to the ice-cold solution of (E)-4-(dimethylamino)but-2-enoyl chloride hydrochloride in acetonitrile. The reaction was stirred in an ice bath for 2 hr. To the mixture was added sodium bicarbonate to pH greater than 9. The oil that formed was extracted with EtOAc (3×25 mL). A portion of the material was insoluble and set aside. The organic layer was dried (MgSO$_4$) filtered and evaporated to a dark red oil. Both oils contained substantial amount of product as shown by TLC:SiO$_2$ CHCl$_3$: MeOH/NH$_4$OH (8:1) 19:1. The oils were combined and purified by flash column chromatography silica gel (25×300 mm) eluted first with 5% methanol/ammonium hydroxide 8/1 to remove non-polar impurities followed by 10% methanol/ammonium hydroxide 8/1 to elute 59 mg of product. The sample was further purified by a second flash column chromatography silica gel (25×250 mm) eluted with 10% methanol/ammonium hydroxide 8/1 to give the title compound (16.3 mg, 0.03 mmol, 6.4% yield). MS (ES+) 530 (M+): 552, (M+Na); $^1$H NMR (DMSO-d$_6$, 500 MHz) δ (ppm): 10.04 (s, 1H), 9.19 (s, 1H), 9.14 (s, 1H), 8.60 (s, 1H), 8.27 (s, 1H), 7.88 (s, 2H), 7.57 (s, 1H), 7.36 (d, 1H, J=7.4 Hz), 7.29 (d, 2H, J=7.8 Hz), 7.22 (d, 2H, J=7.9 Hz), 7.18 (m, 2H), 6.74 (m, 1H), 6.30 (d, 1H, J=15 Hz) 6.10 (s, 1H), 5.24 (s, 2H), 3.06 (s, 2H), 2.18 (s, 6H) ppm; HPLC: t$_R$=5.15 min, 97.5% (YMC-Pack ODS-A 4.6×100 mm, 80% water/20% acetonitrile to 5% water/95% acetonitrile over 5.5 min, hold to 9 min.).

Synthesis of (E)-N-3-(6-[3-methylphenyl]aminopyrimidin-4-yl)aminophenyl-4-bromo-2-butenamide (Int-D) To a stirring solution of 4-bromo-but-2-enoic acid (0.72 g) at 0° C. under nitrogen atmosphere and triethylamine (0.61 mL, 4.38 mmol) in 5 mL of THF was added iso-butyl chloroformate (0.56 mL, 4.32 mmol). The mixture was stirred for 15 min followed by dropwise addition of a solution of N-(3-aminophenyl)-N'-3-methylphenylamino-pyrimidine-4,6-diamine (1.015 g, 3.483 mmol) in 50 mL of THF. The reaction was allowed to warm to room temperature overnight. The sample was concentrated then partitioned between EtOAc and sat. NaHCO$_3$ solution. The organic extract was washed with brine solution, dried (MgSO$_4$), filtered and was concentrated. The resultant brown foamy solid was washed with diethyl ether and vacuum dried to give 0.960 g of crude (E)-N-3-(6-[3-methylphenyl]aminopyrimidin-4-yl)aminophenyl-4-bromo-2-butenamide (Int-D) as brick-brown solid. MS (m/z): (M+1) 438/440 (71/75%).

Synthesis of (E)-N-3-(6-[3-methylphenyl]aminopyrimidin-4-yl)aminophenyl-4-(methyl-prop-2-ynyl)amino-2-butenamide (I-58) To a stirring solution at 0° C. under N$_2$ of N-[3-(6-{3-methylphenyl}amino-pyrimidin-4-ylamino)-4-bromo-2-butenamide (Int-D) (0.492 g, 1.122 mmol) and triethylamine (0.20 mL, 1.44 mmol) in 10 mL of THF was added (via syringe) N-methyl-propargylamine (0.11 mL, 1.173 mmol). The solution was allowed to warm to room temperature overnight, was concentrated and was then partitioned between EtOAc and sat. NaHCO$_3$ solution. The organic extract was washed with brine solution, was dried (MgSO$_4$), was filtered and was concentrated. The residue was chromatographed (silica gel, 10% MeOH in CHCl$_3$) to give 0.110 g of (E)-N-3-(6-[3-methylphenyl]aminopyrimidin-4-yl)aminophenyl-4-(methyl-prop-2-ynyl)amino-2-butenamide (I-58). MS (APCI) m/z 427 (M+1, 100%). $^1$H NMR (DMSO-d$_6$) δ 10.06 (s, 1H), 9.07 (s, 1H), 9.17 (s, 1H), 8.27 (s, 1H), 7.90 (s, 1H), 7.16-7.36 (m, 6H), 6.70-6.73 (m, 1H), 6.79 (d, 1H), 6.20 (s, 1H), 6.32 (d, 1H), 3.30-3.49 (m), 3.14-3.27 (m, 3H), 2.18-2.39 (m, 7H which contain singlets at δ 2.25 [3H] and δ 2.29 [3H]).

Synthesis of (E)-N-3-(6-[3-methylphenyl]aminopyrimidin-4-yl)aminophenyl-4-piperazinyl-2-butenamide (I-57) To a stirring solution at 0° C. under N₂ of N-[3-(6-{3-methylphenyl}amino-pyrimidin-4-ylamino)-4-bromo-2-butenamide (Int-D) (2.15 g, 4.91 mmol) and triethylamine (0.86 mL, 6.17 mmol) in 10 mL of THF was added dropwise a solution of 1-Boc-piperazine (0.92 g, 4.91 mmol) in 10 mL of THF. The solution was allowed to warm to room temperature overnight, was concentrated and was then partitioned between EtOAc and sat. NaHCO₃ solution. The organic extract was washed with brine solution, was dried (MgSO₄), was filtered and was concentrated to give 2.76 g of 4-{3-[3-(6-{3-methylphenyl}amino-pyrimidin-4-ylamino)-phenylcarbamoyl]-allyl}-piperazine-1-carboxylic acid tert-butyl ester as gummy brown solid. This material was dissolved in 100 mL of CH₂Cl₂. 20 mL of trifluoroacetic acid was added and the mixture was stirred at room temperature under N₂ for 2 h. The mixture was concentrated in vacuo, was basified with sat. NaHCO₃ solution and was extracted with EtOAc (2×100 ml). The combined organic extract was dried (MgSO₄), was filtered and was concentrated in vacuo. The residue was chromatographed (silica gel, 5% MeOH in CHCl₃ [500 mL] then 1% NH₄OH-10% MeOH in CHCl₃) to give 0.404 g of (E)-N-3-(6-[3-methylphenyl]aminopyrimidin-4-yl)aminophenyl-4-piperazinyl-2-butenamide. (I-57) MS (m/z): 444 (M+1, 100%). ¹H NMR (DMSO-d₆) δ 10.03 (s, 1H), 9.17 (s, 1H), 9.07 (s, 1H), 8.27 (s, 1H), 7.90 (s, 1H), 7.17-7.36 (m, 6H), 6.79-6.80 (d, 1H), 6.72-6.75 (m, 1H), 6.29 (d, 1H), 6.20 (s, 1H), 3.08-3.39 (m, containing water and ~3H), 2.70-2.72 (m, 4H), 2.30-2.42 (m, 4H), 2.29 (s, 3H.

The following compounds were prepared in a manner substantially similar to those described in Scheme 4a, above:

(a) 3-(6-[3-chloro-4-{3-fluorobenzyloxy}]phenylaminopyrimidin-4-yl)aminophenylamine (I$^R$-6) and 4-dimethylamino-2-butenoyl chloride gave (E)-N-3-([6-(3-chloro-4-{3-fluorobenzyloxy}phenylamino)-pyrimidin-4-yl)aminophenyl-4-(dimethylamino)but-2-enamide (I-46). MS (m/z): M⁺=547, 549 (3:1), H-NMR (DMSO-d₆) δ 10.04 (s, 1H), 9.18 (s, 1H), 9.12 (s, 1H), 8.27 (d, 1H), 7.88 (s, 1H), 7.8 (s, 1H), 7.47-7.16 (m, 9H), 6.74 (b, 1H), 6.28 (d, 1H), 6.1 (s, 1H), 5.19 (s, 2H), 3.05 (s, 2H), 2.18 (s, 6H).

(b) 3-[6-(3-methylphenylamino)-pyrimidin-4-ylamino]phenylamine (I$^R$-5) and 4-(dimethylamino)-2-butenoyl chloride gave (E)-N-{3-[6-(3-methylphenylamino)-pyrimidin-4-ylamino]phenyl}-4-dimethylamino-2-butenamide (I-17). MS (m/z): MH⁺=403.

(c) 3-[6-(3-chloro-4-fluorophenylamino)-pyrimidin-4-ylamino]phenylamine (I$^R$-4) and 4-(dimethylamino)-2-butenoyl chloride gave (E)-N-{3-[6-(3-chloro-4-fluorophenylamino)-pyrimidin-4-ylamino]phenyl}-4-dimethylamino-2-butenamide (I-18). MS (M+H⁺) 441, 443; ¹H NMR (400 MHz, d⁶-DMSO) δ 10.01 (s, 1H), 9.30 (s, 1H), 9.20 (s, 1H), 8.28 (s, 1H), 7.95 (dd, J=7 and 3 Hz, 1H), 7.86 (s, 1H), 7.41 (m, 1H), 7.35-7.10 (m, 3H), 6.69 (dt, J=15 and 5 Hz, 1H), 6.26 (d, J=15 Hz, 1H), 6.11 (s, 1H), 3.02 (d, J=5 Hz, 2H), 2.14 (s, 6H) ppm.

(d) N-3-[6-(3-chloro-4-fluorophenylamino)-pyrimidin-4-ylamino]phenyl-N-methylamine (Int-C) and 4-dimethylamino-2-butenoyl chloride gave (E)-N-(3-[6-(3-chloro-4-fluorophenylamino)-pyrimidin-4-ylamino]phenyl-N-methyl-4-(dimethylamino)but-2-enamide (I-48) MS (ES) (m/z): 455/457 (M+1, 37/13%) and 228 (100%). ¹H NMR (DMSO-d₆) δ 10.22 (s, 1H), 9.20 (s, 1H), 8.33 (s, 1H), 7.99 (bs, 1H), 7.25-7.68 (m, 5H), 7.05 (bs, 1H), 6.73-6.76 (m, 1H), 6.26-6.29 (m, 1H), 5.71 (s, 1H), 3.06 (bs, 2H), 1.99 (s, 6H).

(e) 3-[6-(4-phenoxyphenylamino)-pyrimidin-4-yl]aminophenylamine (I$^R$-7) and 4-dimethylamino-2-butenoyl chloride gave (E)-N-3-[6-(4-phenoxyphenyl)amino-pyrimidin-4-yl]aminophenyl-4-(dimethylamino)but-2-enamide (I-62) ¹H NMR (DMSO-d₆) δ ppm: 2.19 (s, 6H), 3.07 (d, J=5.36 Hz, 2H), 6.16 (s, 1H), 6.29 (d, J=15.4 Hz, 1H), 6.68-6.75 (m, 1H), 6.95-6.98 (m, 4H), 7.06-7.10 (m, 1H), 7.20 (dd, J=7.88 & 8.12 Hz, 1H), 7.24 (d, J=8.32 Hz, 2H), 7.36 (dd, J=7.52 & 7.84 Hz, 2H), 7.55 (d, J=8.76 Hz, 2H), 7.90 (s, 1H), 8.24 (s, 1H), 9.15 (d, J=8.84 Hz, 2H), 10.04 (s, 1H); LCMS: m/z 481 (M+1).

Example 5

SCHEME 5a
Synthesis of N-{3-[6-(arylamino)-pyrimidin-4-ylamino]-phenyl}-ethensulfonamides

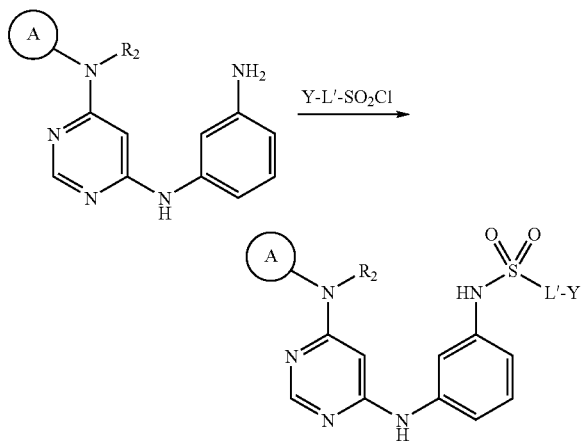

wherein L' is a subset of L, as defined herein, such that Y-L'SO₂Cl results in formation of provided compounds wherein R¹ is -L-Y wherein a terminal methylene unit of L is replaced with —NHSO₂—.

Synthesis of N-{3-[6-(3-chloro-4-fluorophenylamino)-pyrimidin-4-ylamino]phenyl}-ethenesulfonamide (I-3) A solution of 3-[6-(3-chloro-4-fluorophenylamino)-pyrimidin-4-ylamino]phenylamine (I$^R$-4) (300 mg, 0.9 mmol) and triethylamine (500 mg, 5 mmol) in 10 mL of THF was stirred at RT. 2-Chloroethanesulfonyl chloride (360 mg, 2.25 mmol) was added into the reaction mixture and stirring was continued at RT for 1 hr. The crude product was purified by flash chromatography on silica gel with EtOAc/heptane solvent system to afford 35 mg (9%) of the title compound, a brown colored solid. MS (m/z): MH⁺=420, 422. ¹H NMR (DMSO): 9.92 (s, 1H), 9.29 (s, 1H), 9.21 (s, 1H), 8.26 (s, 1H), 7.92 (m, 1H), 7.40-7.22 (m, 4H), 7.14 (m, 1H), 6.20 (m, 2H), 6.05 (m, 3H) ppm.

The following compounds were prepared in a manner substantially similar to Schemes 5a:

(a) 3-{6-[3-chloro-4-(3-fluorophenyl)methoxyphenylamino]-pyrimidin-4-ylamino}phenylamine (I$^R$-6) gave N-{3-[6-(3-chloro-4-(3-fluorophenyl)methoxy-phenylamino)-pyrimidin-4-ylamino]phenyl}-ethenesulfonamide (I-7). MS (m/z): M+H⁺=526, 528 (2:1). MS (m/z): M+H⁺=490, 492 (2:1). ¹H NMR (DMSO): 9.91 (s, 1H), 9.16 (s, 1H), 9.07 (s, 1H), 8.22 (s, 1H), 7.73 (s, 1H), 7.40-7.10 (m, 9H), 6.70 (m, 2H), 6.12 (d, 1H, J=17.0 Hz), 6.02 (m, 2H), 5.14 (s, 2H) ppm.

(b) 3-[6-(3-methylphenylamino)-pyrimidin-4-ylamino]phenylamine (I$^R$-5) gave N-{3-[6-(3-methylphenylamino)-pyrimidin-4-ylamino]phenyl}-ethenesulfonamide (II-5). MS (m/z): M+H$^+$=382. $^1$H NMR (DMSO): 9.90 (s, 1H), 9.12 (s, 1H), 9.00 (s, 1H), 8.21 (s, 1H), 7.37 (d, 1H, J=1.7 Hz), 7.26 (m, 3H), 7.13 (m, 2H), 6.70 (m, 3H), 6.13 (m, 2H), 6.00 (d, 1H, J=10.0 Hz), 2.24 (s, 3H) ppm.

Example 6

SCHEME 6a
Synthesis of N$^2$-acylated
6-(6-mono or disubstituted-aminopyrimidin-4-yl)amino-2-aminopyridines

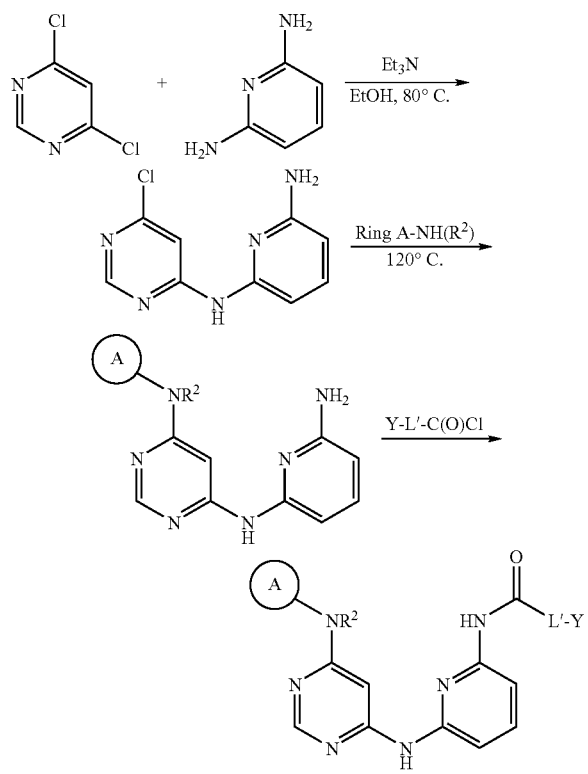

Synthesis of N-(6-chloro-pyrimidin-4-yl)-pyridine-2,6-diamine A mixture of 2,6-diaminopyridine (1.530 g, 14.020 mmol) and 4,6-dichloropyrimidine (2.610 g, 17.519 mmol) in 15 mL of n-butanol in a sealed vial was heated at 100° C. for 72 h. The dark brown sample was cooled, was concentrated to remove most of the n-butanol, and was then partitioned between EtOAc and sat. NaHCO$_3$ solution. An emulsion formed, the sample was filtered through a pad of Celite and the layers were separated. The organic extract was washed with sat. KH$_2$PO$_4$ and brine solutions, was dried (MgSO$_4$), was filtered and was concentrated to brown oily-solid. The sample was suspended into 50 mL of CH$_2$Cl$_2$, was cooled and was filtered to give 1.017 g of N-(6-chloro-pyrimidin-4-yl)-pyridine-2,6-diamine as yellow-orange solid. MS (ES) (m/z) 222/224 (M+1, 100/63%). TLC (SiO$_2$, 50% EtOAc in hexanes): R$_f$ 0.33.

Synthesis of N-(6-amino-pyridin-2-yl)-N'-(3-chloro-4-fluorophenyl)-pyrimidine-4,6-diamine (Int-E) A mixture of N-(6-chloro-pyrimidin-4-yl)-pyridine-2,6-diamine (1.000 g, 4.512 mmol) and 3-chloro-4-fluoroaniline (1.380 mmol) in 10 mL of n-butanol in a sealed vial was heated at 120° C. for 24 h. The sample was cooled, was concentrated to remove most of the n-butanol, and was then diluted with EtOAc and sat. NaHCO$_3$ solution. The sample was stirred at room temperature for 30 min and was filtered. The solid was washed with fresh EtOAc and water and vacuum dried to give 1.063 g of N-(6-amino-pyridin-2-yl)-N'-(3-chloro-4-fluorophenyl)-pyrimidine-4,6-diamine (Int-E) as tan solid. MS (ES) (m/z) 331/333 (M+1, 100/65%). TLC (SiO$_2$, 10% MeOH in CHCl$_3$): R$_f$ 0.25.

Synthesis of (E)-N-[6-(3-chloro-4-fluorophenylamino)pyrimidin-4-ylaminopyridin-2-yl]-4-(dimethylamino)but-2-enamide (I-52).

To a stirring suspension at 0° C. under N$_2$ of 4-dimethylamino-but-2-enoic acid, hydrochloride (0.500 g, 3.019 mmol) in 15 mL of THF containing 5 drops of DMF was added drop-wise (via syringe) oxalyl chloride (0.28 mL, 3.210 mmol). Gas formation started immediately. The sample was stirred at 0° C. for ~30 min, room temperature for ~2 h, re-cooled to 0° C., then treated with drop-wise addition of a solution of N-(6-amino-pyridin-2-yl)-N'-(3-chloro-4-fluorophenyl)-pyrimidine-4,6-diamine (Int-E) (0.500 g, 1.512 mmol) in 15 mL of THF and 3 mL of NMP. The ice-bath was removed, the sample was stirred at room temperature for 2 h then was partitioned between EtOAc and sat. NaHCO$_3$ solution. The organic extract was washed with brine solution, dried (MgSO$_4$), filtered and concentrated to a yellow solid. The solid was suspended into EtOAc (~25 mL), stirred at room temperature for ~12 h, filtered and vacuum dried to give 0.459 g (69%) of (E)-N-[6-(3-chloro-4-fluorophenylamino)pyrimidin-4-ylaminopyridin-2-yl]-4-(dimethylamino)but-2-enamide (I-52) as light yellow solid. MS (m/z): 442/444 (M+1, 100/37%). $^1$H NMR (DMSO-d$_6$) δ 10.19 (s, 1H), 9.78 (s, 1H), 9.43 (s, 1H), 8.36 (s, 1H), 8.05-8.07 (m, 1H), 7.54-7.72 (m, 4H), 7.32-7.35 (m, 1H), 7.10 (bs, 1H), 6.79-6.82 (m, 1H), 6.54-6.57 (m, 1H), 3.14 (bs, 2H), 2.23 (bs, 6H).

Example 7

SCHEME 7a
Synthesis of N-acylated
3-(6-mono or disubstituted-aminopyrimidin-4-yl)amino-mono-substituted-phenylamines

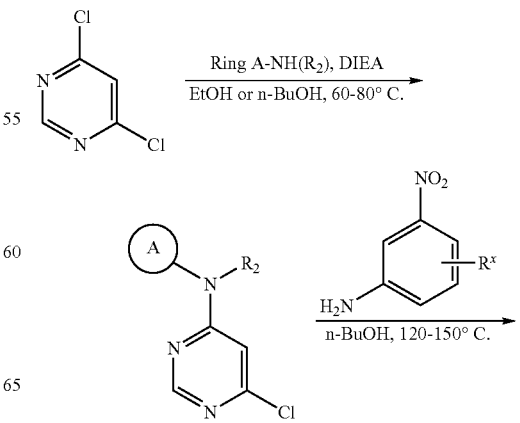

-continued

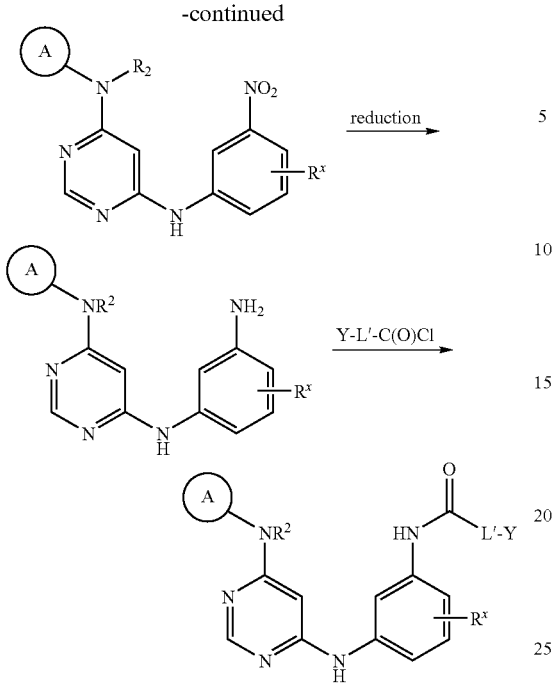

Synthesis of N-(5-Amino-2-methylphenyl)-N'-(3-chloro-4-fluorophenyl)-pyrimidine-4,6-diamine (Int-F) A mixture of 4-(3-chloro-4-fluorophenyl)-6-chloropyrimidin-4-ylamine ($I^R$-4) (1.2 g, 4.6 mmol), 2-methyl-5-nitroaniline (0.85 g, 5.5 mmol) and 1 mL of concentrated HCl in 10 mL of n-butanol was heated at 120° C. for 16 h. With stirring, 5 mL of EtOAc was added to the reaction mixture. The light yellow colored product that precipitated was filtered and dried under vacuum to give N-(3-chloro-4-fluorophenyl)-N'-(2-methyl-5-nitrophenyl)pyrimidine-4,6-diamine. MS (APCI) (m/z): 374/376 (M+1). A mixture of N-(3-chloro-4-fluorophenyl)-N'-(2-methyl-5-nitrophenyl)pyrimidine-4,6-diamine (0.55 g, 1.5 mmol) and iron powder (35 mesh, 0.5 g, 5 eq) in 5 mL of HOAc and 2 mL of MeOH was heated at reflux for 2 h. The solvent was removed in vacuo and the dark colored residue was mixed with 150 mL of $CH_2Cl_2$ and 15 mL of sat. $K_2CO_3$ solution and was stirred at room temperature for 30 min. The organic layer was dried ($MgSO_4$), was concentrated, and was then purified by flash chromatography (silica gel, MeOH/$NH_4OH/CH_2Cl_2$) to afford 0.115 g of N-(5-amino-2-methylphenyl)-N'-(3-chloro-4-fluorophenyl)pyrimidine-4,6-diamine as a light colored solid. (Int-F) MS (m/z): 344/346 (M+1).

In a manner substantially similar to that described above 4-(3-chloro-4-fluorophenylamino)-6-chloropyrimidine and 2-methoxy-5-nitroaniline gave N-(5-amino-2-methoxyphenyl)-N'-(3-chloro-4-fluorophenyl)pyrimidine-4,6-diamine. (Int-G) MS (m/z): 360/362 (M+1).

Synthesis of (E)-N-[3-(6-{3-Chloro-4-fluorophenyl}amino-pyrimidin-4-ylamino)-4-methylphenyl]-4-(dimethylamino)but-2-enamide (I-54) N-(5-amino-2-methylphenyl)-N'-(3-chloro-4-fluorophenyl)pyrimidine-4,6-diamine (Int-F) and 4-dimethylamino-2-butenoyl chloride were combined in a manner similar to that described in Scheme 4a to give (E)-N-[3-(6-{3-chloro-4-fluorophenyl}amino-pyrimidin-4-ylamino)-4-methylphenyl]-4-(dimethylamino)but-2-enamide (I-54). MS (m/z): 455/457 (M+1, 100/39%). $^1$H NMR (DMSO-$d_6$) δ 11.02 (bs, 1H), 10.66 (bs, 1H), 9.92 (bs, 1H), 9.39 (bs, 1H), 7.92-7.94 (m, 1H), 7.75 (bs, 1H), 7.27-7.56 (m, 4H), 6.80 (m, 1H), 6.54 (d, 1H), 5.89 (bs, 1H), 3.92 (bs, 2H), 2.75 (bs, 6H), 2.17 (bs, 3H).

In a manner substantially similar to that described for the synthesis of (I-54) N-(5-Amino-2-methoxyphenyl)-N'-(3-chloro-4-fluorophenyl)pyrimidine-4,6-diamine (Int-G) and 4-dimethylamino-2-butenoyl chloride gave (E)-N-[3-(6-[3-chloro-4-fluorophenyl)-aminopyrimidin-4-ylamino-4-methoxyphenyl]-4-(dimethylamino)but-2-enamide (I-59). MS (m/z): 471/473 (M+1, 100/41%). $^1$H NMR (DMSO-$d_6$) δ 9.97 (s, 1H), 9.28 (s, 1H), 8.46 (s, 1H), 8.26 (s, 1H), 7.93-7.98 (m, 2H), 7.44-7.51 (m, 2H), 7.30-7.33 (m, 1H), 7.02 (d, 1H), 6.69-6.72 (m, 1H), 6.26 (d, 1H), 6.03 (s, 1H), 3.80 (s, 3H), 3.05 (m, 2H), 2.17 (s, 6H).

Example 8

Synthesis of 2-[6-(3-methylphenoxy)-pyrimidin-4-yl]amino-6-aminopyridine ($I^R$-12)

A mixture of 2,6-diaminopyridine (1.530 g, 14.020 mmol) and 4,6-dichloropyrimidine (2.610 g, 17.519 mmol) in 15 mL of n-butanol in a sealed vial was heated at 100° C. for 72 h. The dark brown sample was cooled and was concentrated at reduced pressure to remove most of the n-butanol. The residue was then partitioned between EtOAc and saturated. NaHCO3 solution. An emulsion formed, the sample was filtered through a pad of Celite and the layers were separated. The organic extract was washed with sat. $KH_2PO_4$ and brine solutions, dried ($MgSO_4$), filtered and concentrated to brown oily-solid. The sample was suspended into ~50 mL of $CH_2Cl_2$, cooled and filtered to give 1.017 g (36%) of N-(6-chloro-pyrimidin-4-yl)-pyridine-2,6-diamine as yellow-orange solid. MS: m/z 222/224 (M+1, 100/63%). To a solution of N-(6-chloro-pyrimidin-4-yl)-pyridine-2,6-diamine (100 mg, 0.45 mmol) in DMF (1 mL) was added 3-methylphenol (88 mg, 0.8 mmol) and anhydrous $K_2CO_3$ (93 mg, 0.6 mmol). The reaction mixture was heated at 145° C. for 16 h. It was then cooled and DMF was removed under reduced pressure to get a yellow gummy residue. The residue was taken in EtOAc (20 mL), was washed sequentially with water (5 mL) and brine (5 mL) and was dried over $Na_2SO_4$. Filtration followed by concentration under reduced pressure afforded a yellow gum which was further purified by column chromatography ($SiO_2$, 60-120, EtOAc/hexane, 5/5) to give 100 mg of 2-[6-(3-methylphenoxy)-pyrimidin-4-yl]amino-6-aminopyridine ($I^R$-12) as a pale yellow solid. MS: m/z 294 (M+H)

The following compounds were prepared in a manner substantially similar to the procedure described above:
(a) 4-Phenoxyphenol and 2,6-diaminopyridine gave 2-[6-(4-phenoxyphenoxy)-pyrimidin-4-yl]amino-6-aminopyridine ($I^R$-13) MS (m/z): $MH^+$=372.
(b) 4-nitrophenol and 1,3-diaminobenzene gave 3-[6-(4-nitrophenoxy)-pyrimidin-4-yl]amino-aminobenzene ($I^R$-16) MS (m/z): $MH^+$=324

Example 9

Synthesis of N-3-[6-(3-ethynylphenylamino)-pyrimidin-4-yl]aminophenyl-2-propenamide (I-68) To a stirred solution of $I^R$-1 (150 mg, 0.42 mmol) in dry DMF (4.0 mL) under $N_2$ was added Pd(PPh$_3$)$_2$Cl$_2$ (14.7 mg, 0.021 mmol), CuI (3.9 mg, 0.021 mmol), PPh$_3$ (22.07 mg, 0.08 mmol), and diethylamine (94.8 mg, 6.3 mmol). The reaction mixture was purged with $N_2$ for additional 10 min, trimethylsilylacetylene (45.5 mg, 0.46 mmol) was added, and it was then subjected to microwave irradiation at 120° C. for 30 min. The mixture was cooled, was diluted with 5 mL water, was filtered through Celite® and was extracted with EtOAc (2×10 mL). The combined EtOAc extract was washed with water, then with brine and was dried over $Na_2SO_4$. Concentration under reduced pressure gave a crude product that was purified by column chromatography ($SiO_2$, MeOH/$CHCl_3$, 1/99) to give 100 mg of a brown solid. A solution of this material in 2 mL of dry methanol under nitrogen atmosphere containing anhydrous $K_2CO_3$ (73.9 mg, 0.53 mmol) was stirred at rt for 16 h. The reaction mixture was filtered and the filtrate was concentrated under reduced pressure to give a residue, which was further purified by column chromatography ($SiO_2$, 230-400, MeOH/$CHCl_3$, 1/99) to give 70 mg of a light brown solid. To a stirred solution of this material in NMP (1.0 mL) at 0° C. was added acryloyl chloride (105 mg, 1.16 mmol), and the reaction mixture was stirred at 0° C. for 1 h. The reaction mixture was then quenched with water, was basified with 10% $NaHCO_3$ sol and was extracted with EtOAc. The combined EtOAc extract was washed sequentially with water and brine, was dried over $Na_2SO_4$ and was concentrated under reduced pressure. The residue obtained was further purified by preparative HPLC to give 8 mg of N-3-[6-(3-ethynylphenyl)aminopyrimidin-4-yl]amino-phenyl-2-propenamide (I-68) as an off white solid. $^1$H NMR (DMSO-$d_6$) δ ppm: 4.15 (s, 1H), 5.73-5.76 (m, 1H), 6.19 (s, 1H), 6.25 (dd, J=1.96 & 17.00 Hz, 2H), 6.46 (dd, J=10.2 & 16.96 Hz, 1H), 7.05 (d, J=7.64 Hz, 1H), 7.21-7.33 (m, 3H), 7.54 (d, J=7.96 Hz, 1H), 7.81 (s, 1H), 7.91 (s, 1H), 8.32 (s, 1H), 9.28 (d, J=11.08 Hz, 2H), 10.13 (s, 1H); MS: m/z 356.8 (M+1).

Example 10

Synthesis of N-3-[6-(4-[4-[[4-chloro-3-(trifluoromethyl)phenyl]amino]-carbonyl]amino)phenoxy pyrimidin-4-yl]aminophenylchloroacetamide (I-69)

Step 1: To a solution of 3-[6-(4-nitrophenoxy)-pyrimidin-4-yl]amino-aminobenzene ($I^R$-16) (650 mg, 2.01 mmol) in THF (10 mL) was added $Et_3N$ (305 mg, 3.01 mmol) and $(Boc)_2O$ (525 mg, 2.4 mmol) under $N_2$ atmosphere. The reaction mixture was further heated at 60° C. for 16 h. A residue was obtained after cooling to room temperature and removal of solvent under vacuum. The residue was dissolved in EtOAc (10 mL). The EtOAc extract was washed sequentially with water (5 mL) and brine (2 mL), was dried over $Na_2SO_4$. Concentration under reduced pressure followed by purification by column chromatography ($SiO_2$, 60-120, CHCl3/MeOH, 9/1) gave 400 mg of the Boc derivative as a yellow solid.

Step 2: The material from Step 1 was dissolved in MeOH (8 mL) and 10% Pd/C (40 mg) was added under $N_2$ atmosphere. The reaction mixture was hydrogenated in a Parr apparatus ($H_2$, 3 Kg, rt, 16 h). The reaction mixture was filtered through Celite® and the solvent was removed under reduced pressure to give 250 mg, of the amine as a yellow solid.

Step 3: To the material from Step 2 was added a toluene solution of 4-chloro-3-trifluoromethylphenylisocyanate prepared by reacting under nitrogen atmosphere at 0° C. 24 mg of 4-chloro-3-trifluoromethylaniline in 10 mL toluene with 0.08 mL of a 20%-solution of phosgene in toluene followed by addition of $Et_3N$ (0.07 mL) and at 110° C. for 16 h. The reaction mixture of the amine and the isocyanate was further heated at 110° C. for 4 h and then was quenched with water (1 mL) and was extracted with EtOAc (2×20 mL). The EtOAc extract was washed with water (5 mL), brine (2 mL) and dried over $Na_2SO_4$. Filtration followed by concentration under vacuum offered a residue which was purified by a column chromatography ($SiO_2$, 230-400, hexane/EtOAc, 9/1) to 20 mg of the Boc/urea intermediate as a yellow solid.

Step 4: To a solution of 45 mg of this intermediate in $CH_2Cl_2$ (2 mL) at 0° C. was added TFA (0.01 mL) under $N_2$ atmosphere. The reaction mixture stirred at room temperature for 4 h, was washed sequentially with 10% $NaHCO_3$ solution (1 mL) and brine (1 mL) and was dried over $Na_2SO_4$. Concentration under reduced pressure gave 25 mg of the amine/urea intermediate as a brownish solid.

Step 5: To a solution of the amine/urea intermediate from Step 4 (45 mg, 0.05 mmol), in THF (2 mL) and $Et_3N$ (10 mg, 0.1 mmol) at 0° C. under $N_2$ atmosphere was added chloroacetyl chloride (55 mg, 0.1 mmol). The reaction mixture was allowed to come to rt and with stirring for 2 h. The reaction mixture was concentrated under reduced pressure and the residue was partitioned between EtOAc (4 mL) and water (1 mL). The EtOAc layer was separated, was washed with brine (2 mL) and was dried over $Na_2SO_4$. Filtration followed by concentration under reduced pressure gave a residue which was further purified by column chromatography ($SiO_2$, 230-400, $CHCl_3$/MeOH, 9/1) to give N-3-[6-(4-[4-[[[[4-chloro-3-(trifluoromethyl)phenyl]amino]carbonyl]amino]phenoxy]phenyl]amino-pyrimidin-4-yl]aminophenylchloroacetamide (I-69) as a pale yellow solid. $^1$H NMR (MeOD) δ ppm: 4.19 (s, 2H), 6.61 (s, 1H), 7.13 (d, J=6.92 Hz, 2H), 7.14-7.23 (m, 3H), 7.50-7.55 (m, 3H), 7.63-7.66 (m, 1H), 7.95 (s, 1H), 8.00 (s, 1H), 8.30 (s, 1H); MS: m/z 593 (M+1).

Example 11

Synthesis of (E)-N-3-(6-[3-methylphenylamino]-pyrimidin-4-yl)aminophenyl-4-(4-acetylpiperazin-1yl)-2-butenamide (I-60)

To a stirring solution at 0° C. under $N_2$ of (E)-N-3-(6-[3-methylphenyl]aminopyrimidin-4-yl)aminophenyl-4-piperazinyl-2-butenamide (I-57) (0.291 g, 0.655 mmol) and triethylamine (0.14 mL, 1.004 mmol) in 10 mL of THF was added (via syringe) acetyl chloride (0.05 mL, 0.70 mmol). The sample was allowed to warm to room temperature overnight, was concentrated and was then partitioned between EtOAc and sat. $NaHCO_3$ solution. The organic extract was washed with brine solution, was dried ($MgSO_4$), was filtered, was concentrated and was chromatographed (silica gel, 1% $NH_4OH$-10% MeOH in $CHCl_3$) to give 0.0705 g of (E)-N-3-(6-[3-methylphenyl]aminopyrimidin-4-yl)aminophenyl-4-(4-acetylpiperazin-1yl)-2-butenamide (I-60), a white solid. $^1$H NMR (DMSO-$d_6$ δ 2.00 (s, 3H), 2.29 (s, 3H), 2.35-2.41 (m, 4H), 3.15-3.16 (m, 2H), 3.31-3.46 (m, containing water and ~4H), 6.19 (s, 1H), 6.32 (d, 1H), 6.73-6.80 (m, 2H), 7.16-7.35 (m, 6H), 7.90 (s, 1H), 8.27 (s, 1H), 9.07 (s, 1H), 9.17 (s, 1H) and 10.05 (s, 1H) MS: m/z 486 (M+1, 100%).

Example 12

Synthesis of (E)-N-(3-[6-(3-chloro-4fluorophenylamino)-pyrimidin-4-ylamino]phenyl-N-methyl-4-(dimethyl-$d_6$-amino)but-2-enamide (I-61)

To a stirring solution of 4-bromo-but-2-enoic acid (0.28 g) at 0° C. under nitrogen atmosphere and triethylamine (0.25 mL) in 3 mL of THF was added iso-butyl chloroformate (0.22 mL). The mixture was stirred for 15 min followed by dropwise addition of a solution of 3-[6-(3-chloro-4-fluorophenyl)aminopyrimidine-4-yl]aminophenylamine ($I^R$-4) (0.46 g) in 50 mL of THF. The reaction was allowed to warm to room temperature overnight. The sample was concentrated then partitioned between EtOAc and sat. $NaHCO_3$ solution. The organic extract was washed with brine solution, dried ($MgSO_4$), filtered and was concentrated. The resultant brown foamy solid was washed with diethyl ether and vacuum dried to give 0.378 g of (E)-N-3-(6-[3-chloro-4-fluorophenylamino]pyrimidin-4-ylaminophenyl-4-bromo-2-butenamide (Int-E). MS (m/z): 480, 478, 476 (25/100/80%). To a stirring solution at 0° C. under N₂ of Int-E (0.378 g, 0.794 mmol) and triethylamine (0.28 mL, 2.01 mmol) in 10 mL of THF was added in one portion dimethyl-d₆-amine hydrochloride (0.070 g, 0.799 mmol). The sample was allowed to warm to room temperature overnight and then was partitioned between EtOAc and sat. NaHCO₃ solution. The organic extract was washed with brine solution, was dried (MgSO₄), was filtered and was concentrated. The residue was chromatographed (silica gel, 1% NH₄OH-10% MeOH in CHCl₃) to give 0.0582 g (16%) of (E)-N-(3-[6-(3-chloro-4-fluorophenylamino)-pyrimidin-4-yl]aminophenyl-4-(dimethyl-d₆-amino)but-2-enamide (I-61), a tan solid. $^1$H NMR (DMSO-d₆) δ 3.05-3.07 (m, 2H), 6.16 (s, 1H), 6.29-6.32 (m, 1H), 6.72-6.75 (m, 1H), 7.21-7.47 (m, 5H), 7.90 (s, 1H), 7.92-8.01 (m, 1H), 8.32 (s, 1H), 9.26 (s, 1H), 9.36 (s, 1H) and 10.06 (s, 1H); MS: m/z 447/449 (M+1, 100/49%).

Example 13

I-80 may be prepared in a manner substantially similar to that described in Scheme 4a, above:

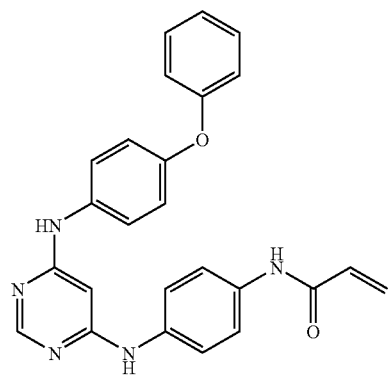

4-[6-(4-phenoxyphenyl)amino-pyrimidin-4-yl]amino-aminobenzene (I$^R$-14) and acryloyl chloride gave N-4-[6-(4-phenoxyphenyl)amino-pyrimidin-4-yl]aminophenylpropenamide (I-80), an off white solid. $^1$H NMR (DMSO-d₆) δ ppm: 5.73 (dd, J=1.6 & 10.0 Hz, 1H), 6.08 (d, J=5.6 Hz, 1H), 6.24 (dd, J=2 & 16.8 Hz, 1H), 6.43 (dd, J=10 & 16.8 Hz, 1H), 6.95-6.70 (m, 4H), 7.09 (t, J=7.6 Hz, 1H), 7.35-7.39 (m, 2H), 7.45-7.49 (m, 2H), 7.55-7.61 (m, 4H), 8.23 (s, 1H), 9.08 (s, 1H), 9.1 (s, 1H), 10.1 (s, 1H); LCMS: m/e 423.8 (M+).

Example 14

SCHEME 14a

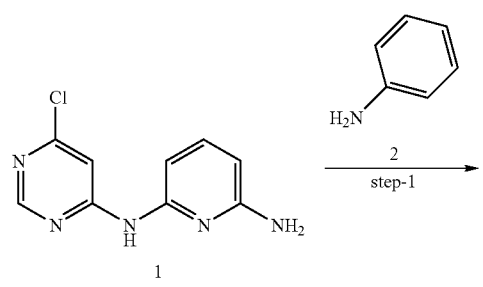

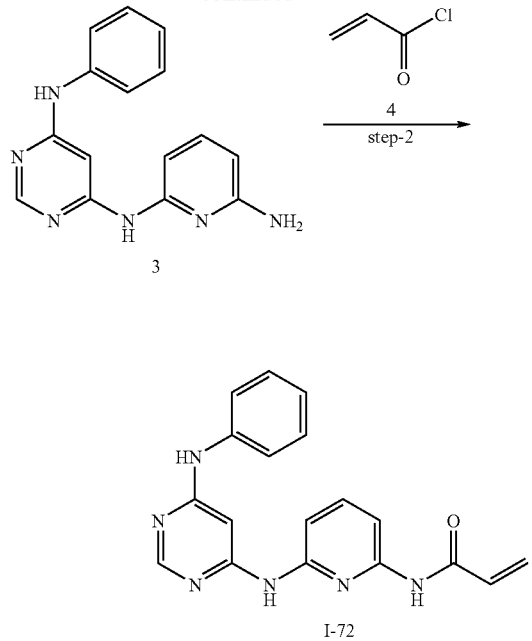

Synthesis of N-6-(6-(phenylamino)pyrimidin-4-ylamino)pyridine-2-yl)acrylamide (I-72)

Step-1 A solution of N²-(6-chloropyrimidin-4-yl)pyridine-2,6-diamine (1) (0.25 g, 1.1 mmol) and aniline (2) (0.16 g, 1.7 mmol) in n-BuOH (25 mL) was heated at 120° C. for 12 h in a pressure tube. The reaction mixture was cooled, was dissolved in methanol (10 mL) and was concentrated under reduced pressure. The residue was dissolved in ethyl acetate (35 mL) and was washed successively with 10% sodium bicarbonate solution (20 mL), water (20 mL), and saturated brine (20 mL). The ethyl acetate extract was dried over Na₂SO₄ and was concentrated under reduced pressure to give a residue, which was triturated with diethyl ether to give (260 mg, 83%) N⁴-(6-aminopyridin-2-yl)-N⁶-phenylpyrimidine-4,6-diamine (3) as an off-white solid.

Step-2 To a stirred solution of 3 (0.2 g, 0.7 mmol) in NMP (10 mL) was added acryloyl chloride (0.097 g, 1 mmol), drop wise at 0° C. The reaction mixture was allowed to stir at the same temperature for 20 min and then warmed to rt for 1.5 h. It was quenched with 10% sodium bicarbonate solution (4 mL) and was extracted with ethyl acetate (2×35 mL). The combined ethyl acetate layer was washed with water (20 mL), saturated brine (20 mL), was dried over Na₂SO₄ and was concentrated under reduced pressure. The residue was further purified by column chromatography (SiO₂, 60-120, Petroleum ether/EtOAc: 90/10) to give N-6-(6-(phenylamino)pyrimidin-4-ylamino)pyridine-2-yl)acrylamide (I-72) as a brown solid. $^1$H NMR (DMSO-d₆) δ ppm: 5.80 (dd, J=1.84 & 10.12 Hz, 1H), 6.31 (dd, J=1.8 & 16.96 Hz, 1H), 6.64 (dd, J=10.08 & 16.88 Hz, 1H), 6.96 (t, J=7.32 Hz, 1H), 7.15-7.20 (m, 1H), 7.28 (t, J=7.52 Hz, 2H), 7.34 (s, 1H), 7.60-7.70 (m, 4H), 8.30 (s, 1H), 9.08 (s, 1H), 9.66 (s, 1H), 10.06 (s, 1H); LCMS: m/e 332.6 (M+).

Example 15

SCHEME 15a

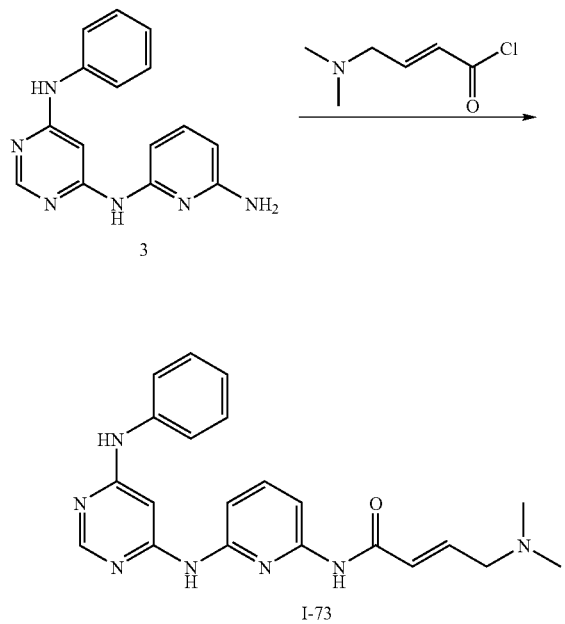

Synthesis of (E)-4-(dimethylamino)-N-(6-(6-(phenylamino)pyrimidin-4-ylamino)pyridine-2-yl)but-2-enamide (I-73)

To a stirred solution of acetonitrile (20 mL) and DMF (0.05 mL) under $N_2$ was added N,N-dimethylamino crotonic acid hydrochloride (0.47 g, 2.8 mmol). After 10 min this solution was cooled to 0-5° C. Oxalyl chloride (0.44 g, 3.5 mmol) was added and the reaction mixture was maintained at 0-5° C. for 30 min. It was allowed to warm to rt and stirring was continued for 2 h. It was then heated to 40° C. for 5 min and again brought to rt and stirred for 10 min to get a light greenish colored solution of dimethylaminocrotonyl chloride that was used as such for next step. To a stirred solution of $N^4$-(6-aminopyridin-2-yl)-$N^6$-phenylpyrimidine-4,6-diamine (0.2 g, 0.7 mmol) in NMP (10 mL) was added dropwise under $N_2$ atmosphere at 0° C. the solution of dimethylaminocrotonyl chloride. The reaction mixture was maintained at this temperature for 30 min and was warmed to rt and stirred for 2 h. The mixture was quenched with sodium bicarbonate solution (1 mL) and was extracted with EtOAc (2×35 mL). The combined ethyl acetate extract was washed with water (20 mL) and brine (20 mL), was dried over $Na_2SO_4$ and was concentrated under reduced pressure. The residue was purified by column chromatography (SiO$_2$, 60-120, product was eluted at 4-6% methanol in chloroform) to give (E)-4-(dimethylamino)-N-(6-(6-(phenylamino)pyrimidin-4-ylamino)pyridine-2-yl)but-2-enamide (I-73) as a yellowish solid. $^1$H NMR (DMSO-d$_6$) δ ppm: 2.24 (s, 6H), 3.13 (d, J=5.76 Hz, 2H), 6.56 (d, J=15.52 Hz, 1H), 6.80 (d, J=15.36 Hz, 1H), 6.95 (t, J=7.36 Hz, 1H), 7.11 (t, J=1.16 Hz, 1H), 7.29 (t, J=7.56 Hz, 2H), 7.58 (s, 1H), 7.65-7.7 (m, 4H), 8.31 (d, J=2.44 Hz, 1H), 9.23 (s, 1H), 9.68 (s, 1H), 10.16 (s, 1H); LCMS: m/e 390.3 (M+1).

Example 16

SCHEME 16a

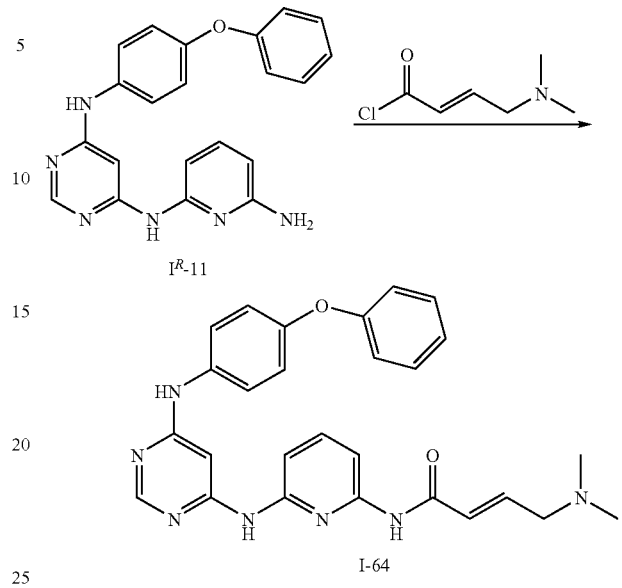

Synthesis of (E)-4-(dimethylamino)-N-(6-(6-(4-phenoxyphenylamino)pyrimidin-4-ylamino)pyridine-2-yl)but-2-enamide (I-64)

A solution of dimethylaminocrotonyl chloride was prepared by reaction of dimethylaminocrotonic acid hydrochloride (0.36 g, 2.16 mmol) in CH$_3$CN (4 mL) containing DMF (1 drop) with oxalyl chloride (0.34 g, 2.70 mmol) according to the procedure in Example 15a. This acid chloride was added drop wise at 0° C. in to a stirred solution of $N^4$-(6-aminopyridin-2-yl)-$N^6$-4-phenoxyphenylpyrimidine-4,6-diamine ($I^R$-11) (0.2 g, 0.54 mmol) in NMP (8 mL). The reaction was stirred at 0° C. for 1 h, was diluted with EtOAc (5 mL), and was washed with 10% NaHCO$_3$ (2 mL), water (2 mL) and brine (2 mL). Drying over Na$_2$SO$_4$ followed by concentration under reduced pressure offered a residue which was further purified by column chromatography (SiO$_2$, 60-120, chloroform/methanol, 9/1) to give (E)-4-(dimethylamino)-N-(6-(6-(4-phenoxyphenylamino)pyrimidin-4-ylamino)pyridine-2-yl)but-2-enamide (I-64) as a yellow solid. $^1$H NMR (DMSO-d$_6$) δ ppm: 2.18 (s, 6H), 3.05 (d, J=5.2 Hz, 2H), 6.48 (d, J=15.2 Hz, 1H), 6.79 (d, J=6 & 15.6 Hz, 1H), 6.96-6.99 (m, 4H), 7.07-7.15 (m, 2H), 7.36 (t, J=7.6 Hz, 2H), 7.42 (s, 1H), 7.64-7.7 (m, 4H), 8.30 (s, 1H), 9.12 (s, 1H), 9.69 (s, 1H), 10.07 (s, 1H); LCMS: m/e 482.4 (M+1).

Example 17

SCHEME 17a

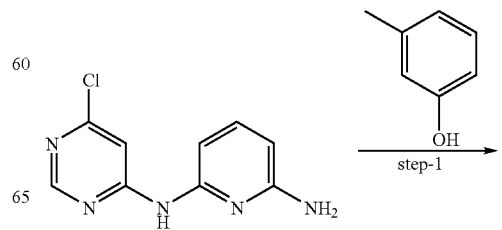

3H), 7.12 (t, J=8.12 Hz, 2H), 7.34 (t, J=7.84 Hz, 1H), 7.54 (s, 1H), 7.69 (t, J=6.24 Hz, 1H), 7.79 (d, J=8 Hz, 1H), 8.30 (s, 1H); LCMS: m/e 404.8 (M+).

Example 18

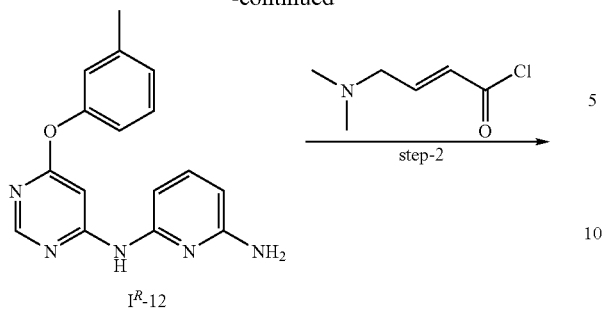
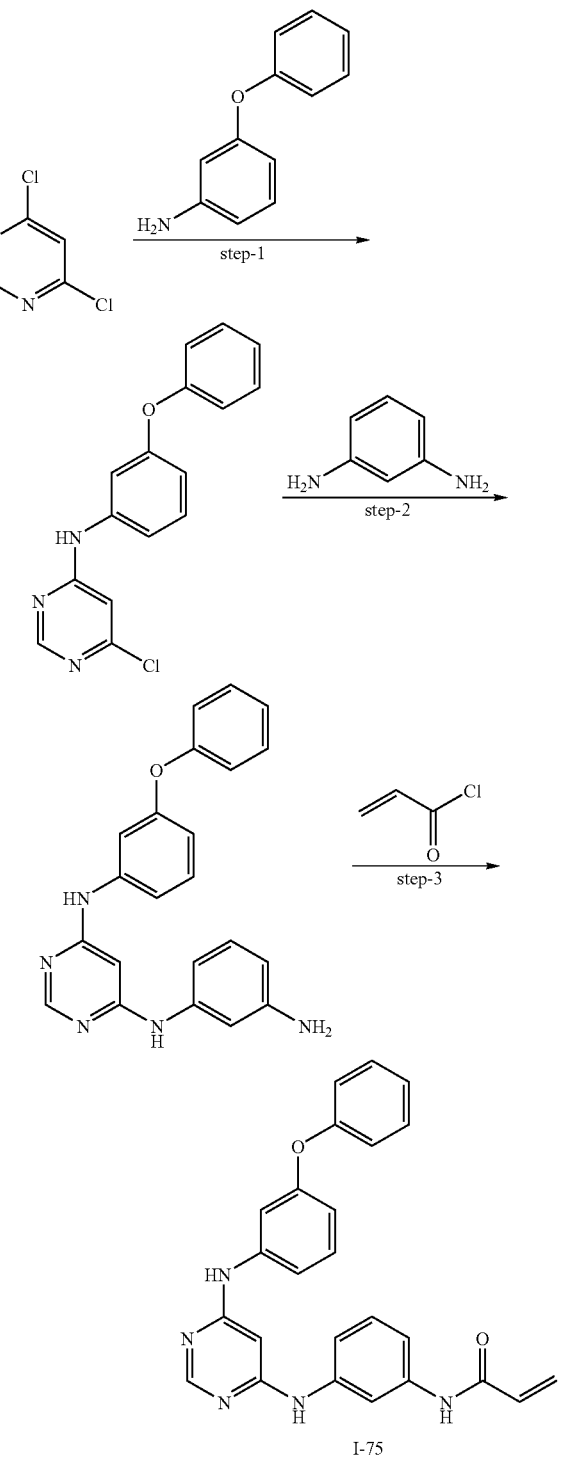

Synthesis of (E)-4-(dimethylamino)-N-(6-(6-(3-methylphenoxy)pyrimidin-4-ylamino)pyridine-2-yl)but-2-enamide (I-74)

Step 1

To a solution of $N^2$-(6-chloropyrimidin-4-yl)pyridine-2,6-diamine (100 mg, 0.45 mmol) in DMF (1 mL) was added 3-methylphenol (88 mg, 0.8 mmol) and anhydrous $K_2CO_3$ (93 mg, 0.6 mmol). The reaction mixture was heated at 145° C. for 16 h. It was then cooled and DMF was removed under reduced pressure to get a yellow gummy residue. The residue was taken in EtOAc (20 mL) and washed with water (5 mL), brine (5 mL) and dried over $Na_2SO_4$. Filtration followed by concentration under reduced pressure afforded a yellow gum which was further purified by column chromatography ($SiO_2$, 60-120, EtOAc/hexane, 5/5) to give $N^2$-(6-(3-methylphenoxy)pyrimidin-4-yl)pyridine-2,6-diamine ($I^R$-12) (100 mg, 75%) as a pale yellow solid.

Step 2

To a solution of $I^R$-12 (75 mg, 0.25 mmol) in NMP (2 mL) was added dimethylaminocrotonyl chloride (168 mg, 1.02 mmol) at 0° C. The reaction mixture was stirred at room temperature for 1 h and was then quenched with $NaHCO_3$ solution (2 mL). The mixture was extracted with EtOAc (3×5 mL) and the combined EtOAc extract was washed with water (5 mL), brine (5 mL) and was dried over $Na_2SO_4$. Concentration under reduced pressure afforded a yellow oil, which was further purified by column chromatography ($SiO_2$, 60-120, Chloroform/Methanol, 9/1) to give (E)-4-(dimethylamino)-N-(6-(6-(3-methylphenoxy)pyrimidin-4-ylamino)pyridine-2-yl)but-2-enamide (I-74) as a light brown solid. $^1$H NMR ($CD_3OD$) δ ppm: 2.35 (s, 6H), 2.38 (s, 3H), 3.25 (dd, J=1.2 & 6.6 Hz, 2H), 6.40 (d, J=13.16 Hz, 1H), 6.92-7.01 (m, Synthesis of N-(3-(6-(3-phenoxyphenylamino)pyrimidin-4-ylamino)phenyl)acrylamide (I-75)

Step 1

A solution of 4,6-dichloropyrimidine (0.5 g, 3.3 mmol), 3-phenoxyaniline (0.75 g, 4 mmol) and DIPEA (0.65 g, 5 mmol) in n-butanol (5 mL) was subjected to microwave irradiation (110° C., 30 min). The reaction mixture was cooled, concentrated under reduced pressure and the residue was dissolved in EtOAc (10 mL). This solution was washed with water (5 mL) and brine (5 mL), and was dried over $Na_2SO_4$. Concentrated under reduced pressure gave a residue that was purified by column chromatography ($SiO_2$, 60-120, hexane/ethylacetate, 8/2) to give 6-chloro-N-(3-phenoxyphenyl)pyrimidine-4-amine (0.56 g, 56%) as an off-white solid.

Step 2

A solution of 6-chloro-N-(3-phenoxyphenyl)pyrimidine-4-amine (0.25 g, 0.8 mmol), 1,3-diaminobenzene (0.36 g, 3.3 mmol), n-butanol (10 mL) and conc. HCl (61 mg, 1.6 mmol) was subjected to microwave irradiation (160° C., 15 min). The reaction mixture was cooled, was concentrated under reduced pressure and the residue was taken in EtOAc (10 mL). The EtOAc solution was washed with water (5 mL) and brine (5 mL), and was dried over $Na_2SO_4$. Concentration under reduced pressure gave a residue that was purified by column chromatography ($SiO_2$, 60-120, hexane/ethyl acetate, 6/4) to give $N^4$-(3-aminophenyl)-$N^6$-(3-phenoxyphenyl)pyrimidine-4,6-diamine (0.1 g, 32%) as a brown solid.

Step 3

To a stirred solution of $N^4$-(3-aminophenyl)-$N^6$-(3-phenoxyphenyl)pyrimidine-4,6-diamine (40 mg, 0.1 mmol), $Et_3N$ (0.03 mL, 0.2 mmol) and NMP (0.4 mL) in $CH_2Cl_2$ (2 mL), at 0° C., was added acryloyl chloride (6) (29 mg, 0.3 mmol). The reaction mixture was allowed to come to rt and stirred at this temperature for 3 h. It was washed with 10% $NaHCO_3$ solution (2 mL), water (2 mL), brine (2 mL) and dried over $Na_2SO_4$. Filtration followed by concentration under reduced pressure offered a residue which was purified by column chromatography ($SiO_2$, 230-400, chloroform/methanol, 9/1) to gave N-(3-(6-(3-phenoxyphenylamino)pyrimidin-4-ylamino)phenyl)acrylamide (I-75) as a light brown solid. $^1H$ NMR (DMSO-$d_6$) δ ppm: 5.73 (dd, J=1.72 & 10 Hz, 1H), 6.18 (s, 1H), 6.24 (dd, J=1.92 & 17 Hz, 1H), 6.45 (dd, J=10.04 & 16.88 Hz, 1H), 6.54-6.57 (m, 1H), 7.01-7.05 (m, 2H), 7.11-7.15 (dd, J=0.88 & 7.48 Hz, 1H), 7.19-7.32 (s, 4H), 7.35-7.41 (m, 4H), 7.89 (s, 1H), 8.26 (s, 1H), 9.2 (s, 1H), 9.25 (s, 1H), 10.26 (s, 1H); LCMS: m/e 423.8 (M+1).

Example 19

SCHEME 19a

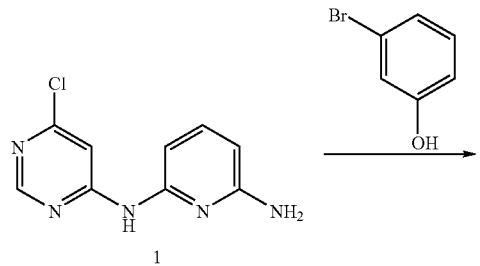

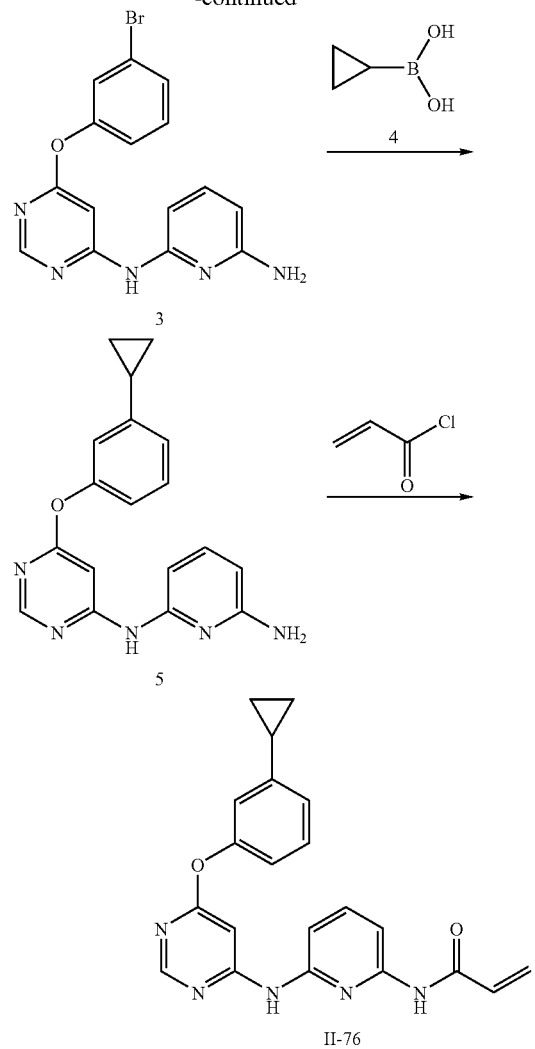

Compound I-76 can be prepared according to Scheme 19a by coupling intermediate 1 with 3-bromophenol, followed by boronic acid coupling of intermediates 3 and 4 to give intermediate 5. Intermediate 5 can then be treated with acryloyl chloride using a protocol similar to that in Example 6 to give compound I-76.

Example 20

SCHEME 20a

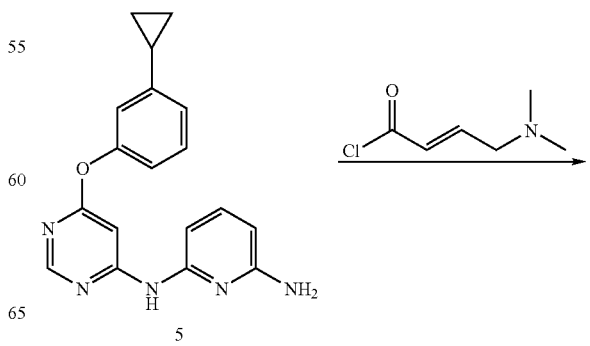

-continued

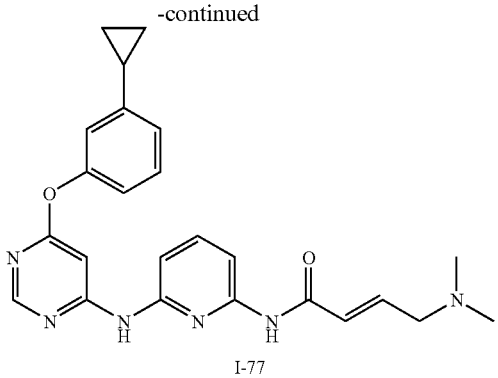

I-77

Compound I-77 can be prepared according to Scheme 20a by treatment of intermediate 5 with (E)-4-(dimethylamino) but-2-enoyl chloride using a protocol similar to that in Example 6.

Example 21

SCHEME 21a

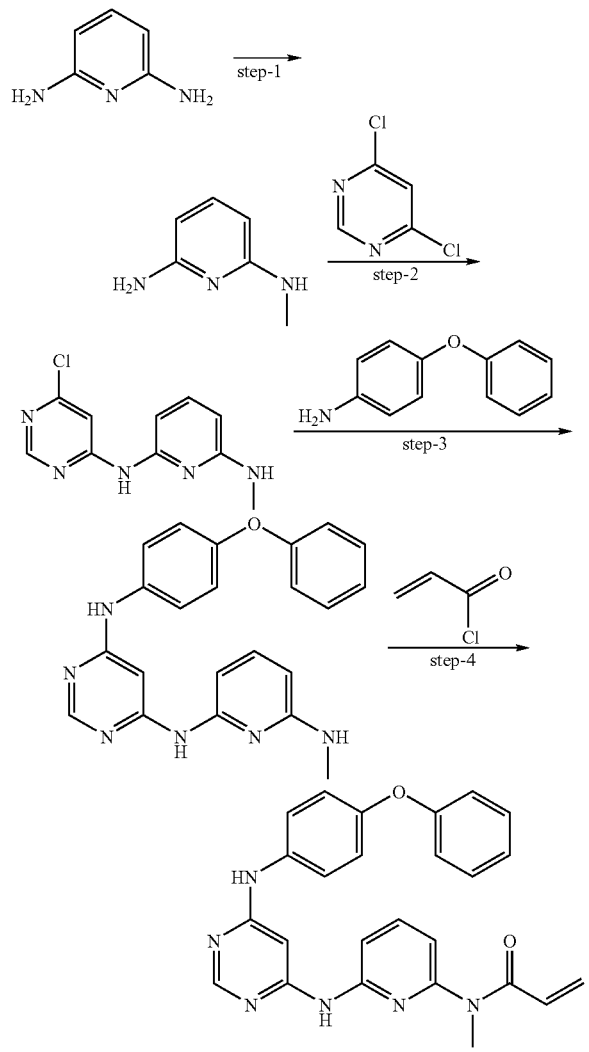

I-78

Synthesis of N-methyl-N-(6-(6-(4-phenoxyphenylamino)pyrimidin-4-ylamino)pyridin-2-yl)acrylamide (I-78)

Step 1

To a solution of 2,6-diaminopyridine (10 g, 91.63 mmol) in dry THF (100 mL) was added $K_2CO_3$ (18.8 g, 136.23 mmol) and $CH_3I$ (13 g, 91.63 mmol) and the reaction mixture was stirred at room temperature for 16 h. Water was added (10 mL) and the mixture was extracted with EtOAc (100 mL). The EtOAc layer was dried and was concentrated under reduced pressure. The residue was further purified by column chromatography ($SiO_2$, 60-120, chloroform) to give 2-methylamino-6-aminopyridine (1.1 g, 10%) as a brown solid.

Step 2

A mixture of 2-methylamino-6-aminopyridine (0.5 g, 4.04 mmol), 4,6-dichloropyrimidine (1.51 g, 10.13 mmol), DIPEA (1.5 g, 12.17 mmol) in n-butanol (5 mL) was heated at 120° C. for 16 h. The reaction mixture was cooled, was concentrated under reduced pressure and the residue was taken in dichloromethane (25 mL). The dichloromethane solution was washed with $NaHCO_3$ solution (2 mL), water (2 mL) and brine (2 mL), was dried over $Na_2SO_4$ and was concentrated under reduced pressure. The residue was purified by column chromatography ($SiO_2$, 60-120, petroleum ether/ethyl acetate, 6/4) to give $N^2$-(6-chloropyrimidin-4-yl)-$N^6$-methylpyridine-2,6,diamine (0.3 g, 33%) as a yellow solid.

Step 3

A solution of $N^2$-(6-chloropyrimidin-4-yl)-$N^6$-methylpyridine-2,6,diamine (0.3 g 1.27 mmol), 4-phenoxy aniline (0.28 g, 1.52 mmol) and conc. HCl (2 drops) in n-butanol (2 mL) was subjected to microwave irradiation (120° C., 1 h). The reaction mixture was cooled, was concentrated under reduced pressure, and the residue was diluted with $CH_2Cl_2$ (5 mL). The dichloromethane solution was washed with $NaHCO_3$ (2 mL), water (2 mL), and brine (2 mL), and was dried over $Na_2SO_4$. Filtration followed by concentration under reduced pressure gave a residue which was purified by column chromatography ($SiO_2$, 60-120, chloroform/methanol, 9/1) to give $N^4$-(6-(methylamino)pyridine-2-yl)-$N^6$-(4-phenoxyphenyl)pyrimidine-4,6-diamine (0.2 g, 41%) as a light brown solid.

Step 4

To a solution of $N^4$-(6-(methylamino)pyridine-2-yl)-$N^6$-(4-phenoxyphenyl)pyrimidine-4,6-diamine (0.07 g, 0.18 mmol) in NMP (1 mL) was added acryloyl chloride (0.032 g, 0.36 mmol) at 0° C. and the reaction mixture was stirred at rt for 1 h. The reaction mixture was diluted with dichloromethane (2 mL), was washed with $NaHCO_3$ (1 mL), water (1 mL), and brine (1 mL). The dichloromethane solution was dried over $Na_2SO_4$ and was concentrated under reduced pressure. The residue was purified by column chromatography ($SiO_2$, 60-120, chloroform/methanol, 9/1) to give N-methyl-N-(6-(6-(4-phenoxyphenylamino)pyrimidin-4-ylamino)pyridin-2-yl)acrylamide (I-78) as a yellow solid. $^1$H NMR (DMSO-$d_6$) δ ppm: 3.22 (s, 3H), 5.60 (dd, J=2.56 & 9.76 Hz, 1H), 6.12-6.16 (m, 2H), 6.79 (d, J=7.56 Hz, 1H), 6.96 (d, J=8.64 Hz, 5H), 7.09 (t, J=7.32 Hz, 1H), 7.23 (s, 1H), 7.33-7.37 (m, 4H), 7.45 (d, J=8.2 Hz, 2H), 7.32 (t, J=7.8 Hz, 1H), 8.24 (s, 1H); LCMS: m/e 439.3 (M+1).

Example 22

SCHEME 22a

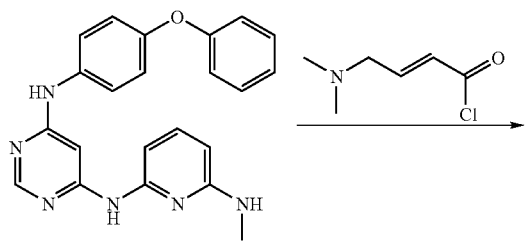

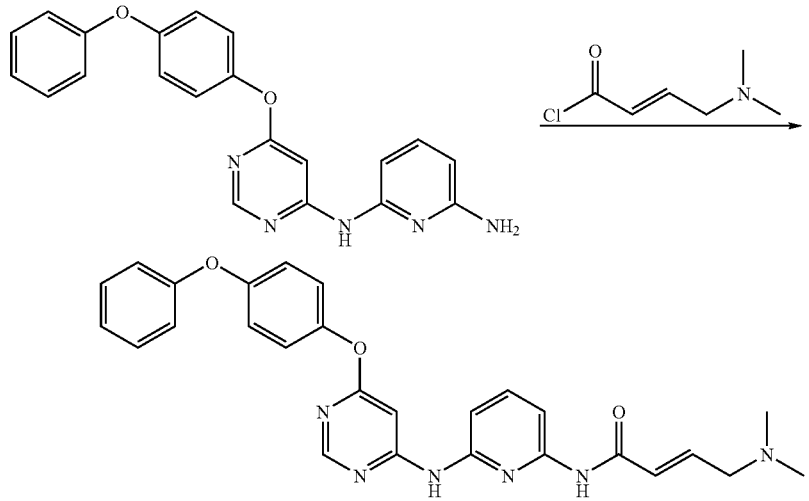

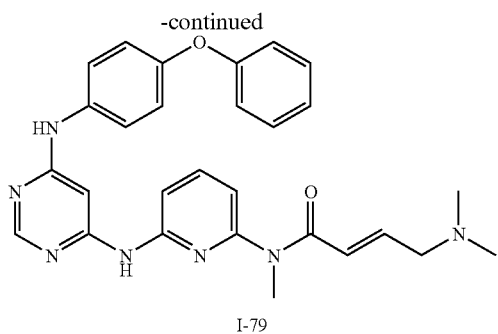
I-79

Synthesis of (E)-4-(dimethylamino)-N-methyl-N-(6-(6-(4-phenoxyphenylamino)pyrimidin-4-ylamino)pyridine-2-yl)but-2-enamide (I-79)

To a solution of dimethylaminocrotonic acid hydrochloride (0.120 g, 0.72 mmol) in CH$_3$CN (1.4 mL) was added DMF (1 drop) followed by oxalyl chloride (0.07 mL, 0.91 mmol) at 0° C. under nitrogen atmosphere. The reaction was allowed to stir at this temperature for 30 min and then at rt for 2 h. This acid chloride was added, drop wise, at 0° C. in to a stirred solution of N$^4$-(6-(methylamino)pyridine-2-yl)-N$^6$-(4-phenoxyphenyl)pyrimidine-4,6-diamine (0.07 g, 0.18 mmol) in NMP (2.8 mL). The reaction was allowed to stir at 0° C. for 1 h, diluted with EtOAc (5 mL), and washed with 10% NaHCO$_3$ (2 mL), water (2 mL) and brine (2 mL). drying over Na$_2$SO$_4$ followed by concentration under reduced pressure gave a residue which was further purified by column chromatography (SiO$_2$, 60-120, chloroform/methanol, 9/1) to give (E) -4-(dimethylamino)-N-methyl-N-(6-(6-(4-phenoxyphenylamino)pyrimidin-4-ylamino)pyridine-2-yl)but-2-enamide (I-79) as a yellow solid. $^1$H NMR (DMSO-d$_6$) δ ppm: 2.05 (s, 6H), 2.91 (d, J=6 Hz, 2H), 3.27 (s, 3H), 6.08 (d, J=15.2 Hz, 1H), 6.65 (dd, J=5.6 & 14.8 Hz, 1H), 6.82 (d, J=7.6 Hz, 1H), 6.97-7.00 (m, 4H), 7.10 (t, J=7.2 Hz, 1H), 7.20 (s, 1H), 7.35-7.39 (m, 2H), 7.46 (d, J=8 Hz, 1H), 7.53 (d, J=8.8 Hz, 2H), 7.75 (t, J=8 Hz, 1H), 8.30 (s, 1H), 9.30 (s, 1H), 9.95 (s, 1H); LCMS: m/e 496 (M+1).

Example 23

Scheme 23a

Synthesis of (E)-4-dimethylamino)-N-(6-(6-(4-phenoxyphenoxy)pyrimidin-4-ylamino)pyridin-2-yl)but-2-enamide (I-82)

To a stirred solution of N$^2$-(6-(4-phenoxyphenoxy)pyrimidin-4-yl)pyridine-2,6-diamine (0.65 g, 1.75 mmol) in NMP (10 mL) was added dimethylaminocrotonyl chloride (1.026 g, 7 mmol) at 0° C. The reaction mixture was allowed to come to room temperature and kept at it for 1 h. It was diluted with dichloromethane (10 mL), was washed with NaHCO$_3$ solution (2 mL) and water (2 mL), and dried over Na$_2$SO$_4$. The dichloromethane solution was filtered and was concentrated under reduced pressure to give a residue that was purified by column chromatography (SiO$_2$, 60-120, chloroform/methanol, 9/1) to give (E)-4-dimethylamino)-N-(6-(6-(4-phenoxyphenoxy)pyrimidin-4-ylamino)pyridin-2-yl)but-2-enamide (I-82) as an off white solid. $^1$H NMR (DMSO-d$_6$) δ ppm: 2.19 (s, 6H), 3.08 (d, J=5.52 Hz, 2H), 6.50 (d, J=15.4 Hz, 1H), 6.77 (td, J=5.92 & 15.4 Hz, 1H), 7.00-7.07 (m, 5H), 7.15 (t, J=7.36 Hz, 1H), 7.21 (dd, J=2.2 & 8.92 Hz, 2H), 7.41 (t, J=7.52 Hz, 2H), 7.68 (t, J=7.96 Hz, 1H), 7.77 (d, J=7.96 Hz, 1H), 7.95 (s, 1H), 8.35 (s, 1H), 10.20 (s, 1H), 10.40 (s, 1H); LCMS: m/e 483 (M+1).

Example 24

Scheme 24a

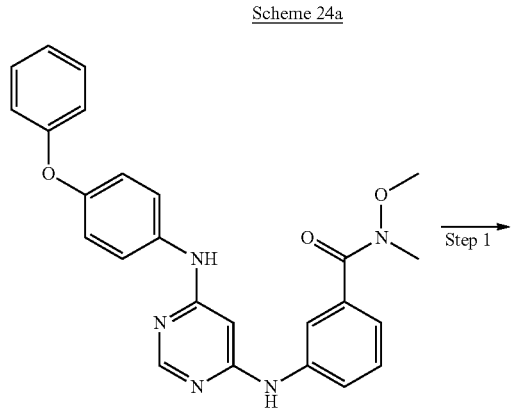

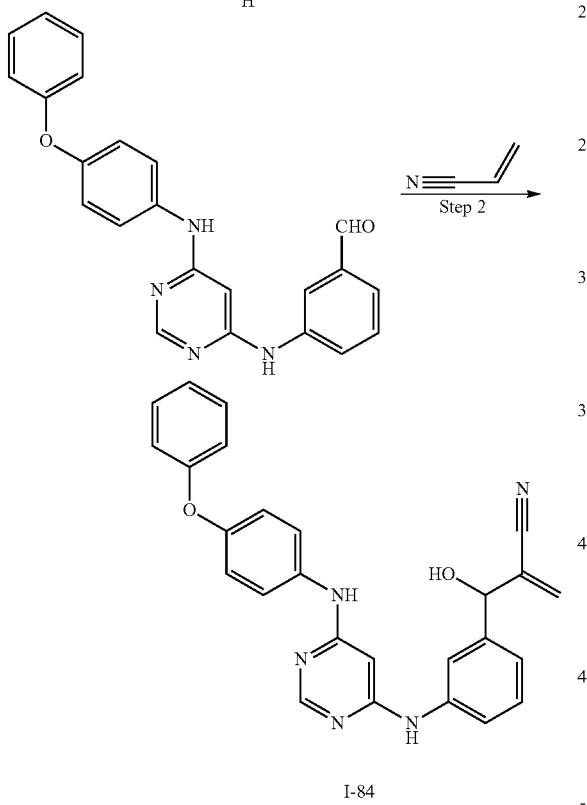

Synthesis of 2-(hydroxy(3-(6-(4-phenoxyphenylamino)pyrimidin-4-ylamino)phenyl)methyl)acrylamide (I-84)

Step 1

To a stirred solution of N-methoxy-N-methyl-3-(6-(4-phenoxyphenylamino)pyrimidin-4-ylamino)benzamide (0.75 g, 1.7 mmol) in THF (10 mL) was added LAH (3.4 mL, 3.4 mmol, 1 M solution in THF) at −60° C. The reaction mixture was stirred at −60° C. for 1 h, was quenched with $Na_2SO_4$ solution (2 mL) and was extracted with ethyl acetate (10 mL). The organic layer was separated and washed with water (2 mL) and with brine solution (2 mL) and was dried over anhydrous $Na_2SO_4$. Filtration followed by concentration under reduced pressure gave a residue that was purified by column chromatography ($SiO_2$, 60-120, chloroform/methanol, 9/1) to give 3-(6-(4-phenoxyphenylamino)pyrimidin-4-ylamino)benzaldehyde (0.6 g, 92%) as an off yellow solid.

Step 2

To a stirred solution of 3-(6-(4-phenoxyphenylamino)pyrimidin-4-ylamino)benzaldehyde (100 mg, 0.26 mmol) and acrylonitrile (36 mg, 0.52 mmol) in 1,4-dioxane/$H_2O$ (0.5 mL/0.5 mL) was added DABCO (29 mg, 0.26 mmol) at rt. Stirring was continued at room temperature for 48 h after which time the reaction mixture was concentrated under reduced pressure. The residue obtained was further purified by column chromatography ($SiO_2$, 60-120, pet ether/ethyl acetate, 6/4) to give 2-(hydroxy(3-(6-(4-phenoxyphenylamino)pyrimidin-4-ylamino)phenyl)methyl)acrylamide (I-84) as a white solid. $^1$H NMR (DMSO-$d_6$) δ ppm: 5.33 (s, 1H), 6.06 (s, 1H), 6.20 (s, 1H), 6.25 (s, 1H), 6.80 (s, 1H), 6.88 (s, 1H), 6.95-7.05 (m, 4H), 7.09-7.13 (m, 2H), 7.16 (bd, J=7.92 Hz, 1H), 7.32-7.39 (m, 5H), 7.47 (s, 1H), 8.31 (s, 1H); LCMS: m/e 436 (M+1).

Example 25

Scheme 25a

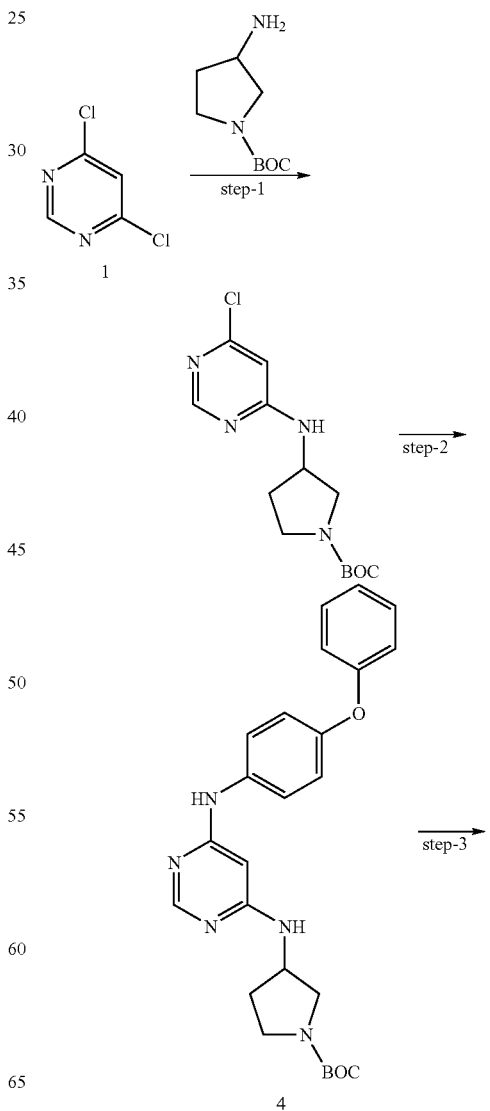

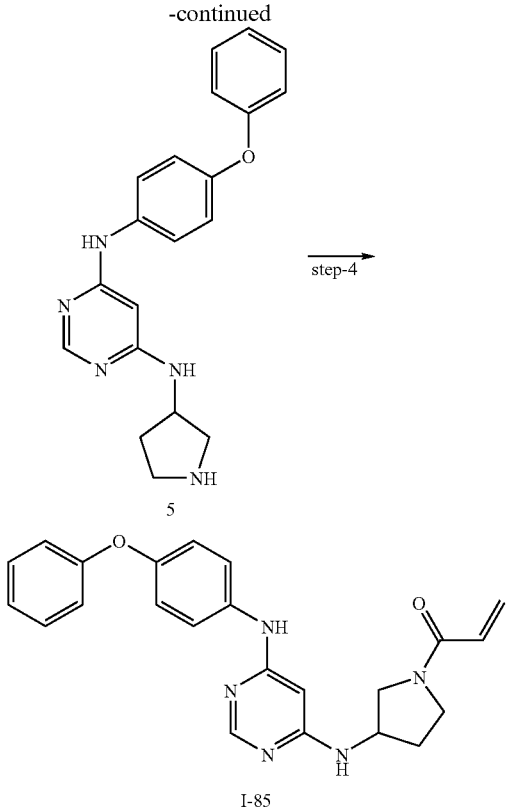

Synthesis of 1-(3-(6-(4-phenoxyphenylamino)pyrimidin-4-ylamino)pyrrolidin-1-yl)prop-2-en-1-one (I-85)

Step 1

A solution of 4,5-dichloropyrimidine (0.6 g, 4.02 mmol), 3-amino-Boc-pyrrolidine (0.5 g, 2.6 mmol) and DIPEA (1.73 g, 13.3 mmol) in n-butanol (5.0 mL) was heated in a pressure tube (120° C., 12 h). It was cooled, quenched with water (10 mL) and was extracted with EtOAc (2×25 mL). The combined EtOAc extract was washed with water (5 mL), brine (5 mL), dried over $Na_2SO_4$ and concentrated under reduced pressure to afford tert-butyl 3-(6-chloropyrimidin-4-ylamino)pyrrolidine-1-carboxylate (0.4 g, 50%) as a yellow solid.

Step 2

To a stirring solution of tert-butyl 3-(6-chloropyrimidin-4-ylamino)pyrrolidin-1-carboxylate (0.5 g, 1.6 mmol) and 4-phenoxy aniline (0.309 g, 1.6 mmol) in ethanol (4 mL) was added acetic acid (0.1 mL) and the reaction mixture was heated at 100° C. for 36 h. The reaction mixture was cooled, ethanol was removed under reduced pressure and the residue was taken in ethyl acetate (10 mL). It was washed with $NaHCO_3$ solution (2 mL), brine (2 mL), dried over $Na_2SO_4$ and concentrated under reduced pressure. The residue was further purified by column chromatography ($SiO_2$, 60-120, chloroform/methanol, 9/1) to yield tert-butyl 3-(6-(4-phenoxyphenylamino)pyrimidin-4-ylamino)pyrrolidine-1-carboxylate (0.3 g, 42.8%) as a white solid.

Step 3

To a stirred solution of tert-butyl 3-(6-(4-phenoxyphenylamino)pyrimidin-4-ylamino)pyrrolidin-1-carboxylate (0.1 g, 0.2 mmol) in dry $CH_2Cl_2$ (2.0 mL) at 0° C. was added $CF_3COOH$ (2 mL, 20 vol.) and the reaction mixture was kept at this temperature for 30 min. It was allowed to come to rt and stir at this temperature for 3 h. The reaction mixture was concentrated under reduced pressure and the residue was quenched with water (2 mL), basified with $NaHCO_3$ solution, and was extracted with ethyl acetate (2×8 mL). The combined ethyl acetate extract was washed with water (2 mL) and brine (2 mL), was dried over $Na_2SO_4$ and was concentrated under reduced pressure to give $N^4$-(4-phenoxyphenyl)-$N^6$-(pyrrolidin-3-yl)pyrimidine-4,6-diamine (0.025 g, 32.4%) as a light a brown solid.

Step 4

To a stirred solution of $N^4$-(4-phenoxyphenyl)-$N^6$-(pyrrolidin-3-yl)pyrimidine-4,6-diamine (0.13 g, 0.3 mmol) in THF (1.5 mL) at −60° C. were added DIPEA (0.07 g, 0.5 mmol) and acryloyl chloride (1 M solution in THF, 0.3 mL, 0.3 mmol), and the reaction mixture was stirred at −60° C. for 5 min. The reaction mixture was quenched by adding water and it was extracted with EtOAc (2×5 mL). The combined EtOAc extract was washed with brine (3 mL), was dried over $Na_2SO_4$ and was concentrated under reduced pressure. The residue obtained was purified by column chromatography ($SiO_2$, 230-400, chloroform/methanol: 98/2) to give 1-(3-(6-(4-phenoxyphenylamino)pyrimidin-4-ylamino)pyrrolidin-1-yl)prop-2-en-1-one (I-85) as a light green solid. $^1$H NMR (DMSO-$d_6$) δ ppm: 1.83-1.86 & 1.90-1.94 (m, 1H), 2.07-3.0 & 2.16-2.20 (m, 1H), 3.38-3.86 (m, 4H), 4.2-4.75 & 4.35-4.5 (bs, 1H), 5.65 (dt, J=2 & 10 Hz, 1H), 5.78 (d, J=3.6 Hz, 1H), 6.11 & 6.15 (dd, J=2.4 & 7.0 Hz & dd, J=2.4 & 7.2 Hz, 1H), 6.51-6.64 (m, together 1H), 6.93-7.00 (m, 4H), 7.07-7.18 (m, 2H), 7.36 (t, J=8 Hz, 2H), 7.51 (d, J=8 Hz, 2H), 8.12 (s, 1H), 8.93 (s, 1H); LCMS: m/e 401.8 (M+1).

Example 26

Scheme 26a

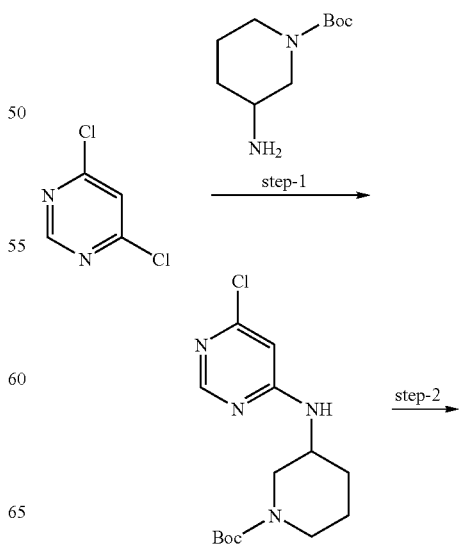

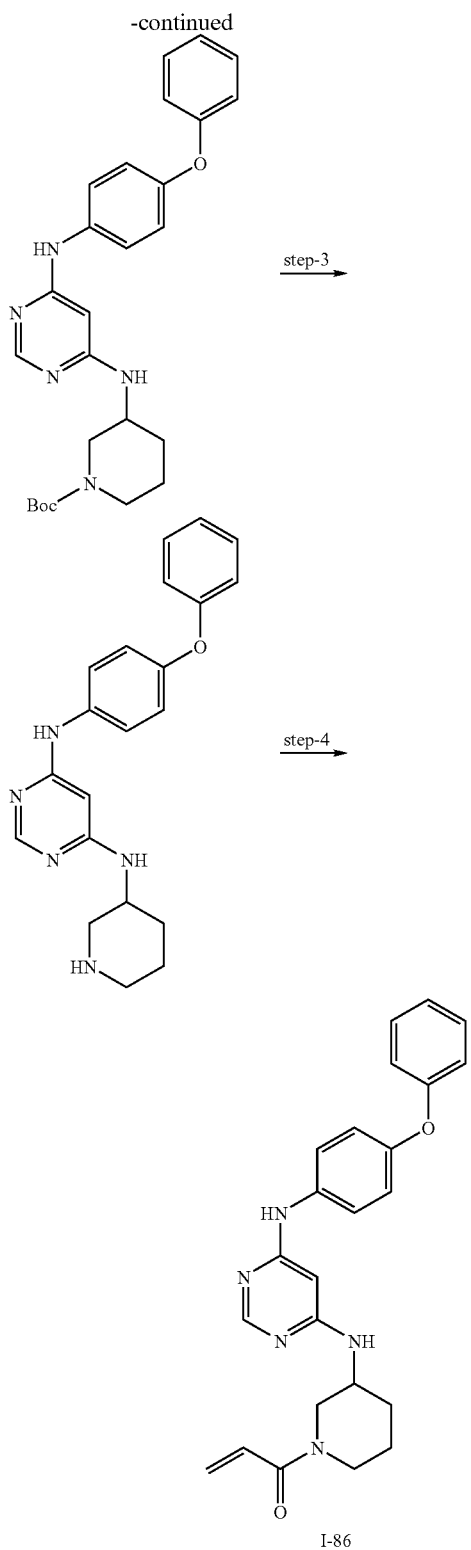

Synthesis of 1-(3-(6-(4-phenoxyphenylamino)pyrimidin-4-ylamino)piperidin-1-yl)prop-2-en-1one (I-86)

Step 1

A solution of 4,6-dichloropyrimidine (0.1 g, 0.671 mmol), 3-amino-Boc-piperidine (0.16 g, 0.80 mmol) and DIPEA (0.086 g, 6.71 mmol) in n-butanol (5.0 mL) was heated in a pressure tube (120° C., 12 h). The solution was cooled, was quenched with water (2 mL) and was extracted with EtOAc (2×15 mL). The combined EtOAc extract was washed with water (5 mL), brine (5 mL), was dried over Na$_2$SO$_4$ and was concentrated under reduced pressure to give tert-butyl 3-(6-chloropyrimidin-4-ylamino)piperidine-1-carboxylate, which was dried under high vacuum and was used as such for next step without further purification.

Step 2

A solution of tert-butyl 3-(6-chloropyrimidin-4-ylamino)piperidine-1-carboxylate (0.15 g, 0.48 mmol), 4-phenoxyaniline (0.089 g, 0.48 mmol), Pd(OAc)$_2$ (0.010 g, 0.048 mmol), BINAP (0.014 g, 0.024 mmol) and Cs$_2$CO$_3$ (0.39 g, 1.2 mmol) in degassed toluene (toluene was purged with N$_2$ for 15 min) was heated for 12 h at 100° C. under N$_2$ atmosphere. The reaction mixture was cooled, was diluted with EtOAc (20 mL) and was washed with water (4 mL) and brine (2 mL) and was dried over Na$_2$SO$_4$. The crude product obtained was purified by column chromatography (SiO$_2$, 230-400, chloroform/methanol: 99/1) to give tert-butyl 3-(6-(4-phenoxyphenylamino)pyrimidin-4-ylamino)piperidine-1-carboxylate (90 mg, 40.9%) as a light yellow solid.

Step 3

To a stirred solution of tert-butyl 3-(6-(4-phenoxyphenylamino)pyrimidin-4-ylamino)piperidine-1-carboxylate (110 mg, 0.238 mmol) in dry CH$_2$Cl$_2$ (1.0 mL) at 0° C. was added CF$_3$COOH (0.5 mL, 5 vol) and the reaction mixture was kept at this temperature for 30 min. It was allowed to come to rt and to stir at this temperature for 3 h. The reaction mixture was concentrated under reduced pressure and the residue was quenched with water (2 mL), was basified with NaHCO$_3$ solution, and was extracted with ethyl acetate (2×8 mL). The combined ethyl acetate extract was washed with water (2 mL), brine (2 mL), dried over Na$_2$SO$_4$ and concentrated under reduced pressure to give N$^4$-(4-phenoxyphenyl)-N$^6$-(piperidin-3-yl)pyrimidine-4,6-diamine (0.07 g, 81%) as a light yellow solid.

Step 4

To a stirred solution of N$^4$-(4-phenoxyphenyl)-N$^6$-(piperidin-3-yl)pyrimidine-4,6-diamine (0.025 g, 0.069 mmol) in NMP (0.5 mL) at 0° C. was added acryloyl chloride (0.007 g, 0.083 mmol), and the reaction mixture was stirred at 0° C. for 5 min. The reaction mixture was quenched by adding 10% NaHCO$_3$ solution and it was extracted with EtOAc (2×5 mL). The combined EtOAc extract was washed with water (3 mL) and brine (3 mL), was dried over Na$_2$SO$_4$ and was concentrated under reduced pressure. The residue obtained was purified by column chromatography (SiO$_2$, 230-400, chloroform/methanol: 98/2) to give 1-(3-(6-(4-phenoxyphenylamino)pyrimidin-4-ylamino)piperidin-1-yl)prop-2-en-1one (I-86) as an off white solid. $^1$H NMR (MeOD) δ ppm: 1.5-1.75 (m, 2H), 1.80-2.00 (m, 1H), 2.0-2.20 (m, 1H), 2.70-2.90 (m, 1H), 2.90-3.05 (m, 1H), 3.80-4.00 (m, 2H), 4.30-4.45 (m, 1H), 5.65 & 5.75 (d, J=10.8 Hz & d, J=10.8 Hz respectively, together 1H), 5.81 (d, J=10.8 Hz, 1H), 6.14 & 6.18 (d, J=17.2 Hz & d, J=19.2 Hz respectively, together 1H), 6.60-6.70 & 6.70-6.85 (m, together 1H), 6.97-7.00 (m, 4H), 7.04 (t, J=7.6 Hz, 1H), 7.32-7.38 (m, 4H), 8.04 & 8.07 (s, together 1H); LCMS: m/e 416.1 (M+1).

Example 27

SCHEME 27a

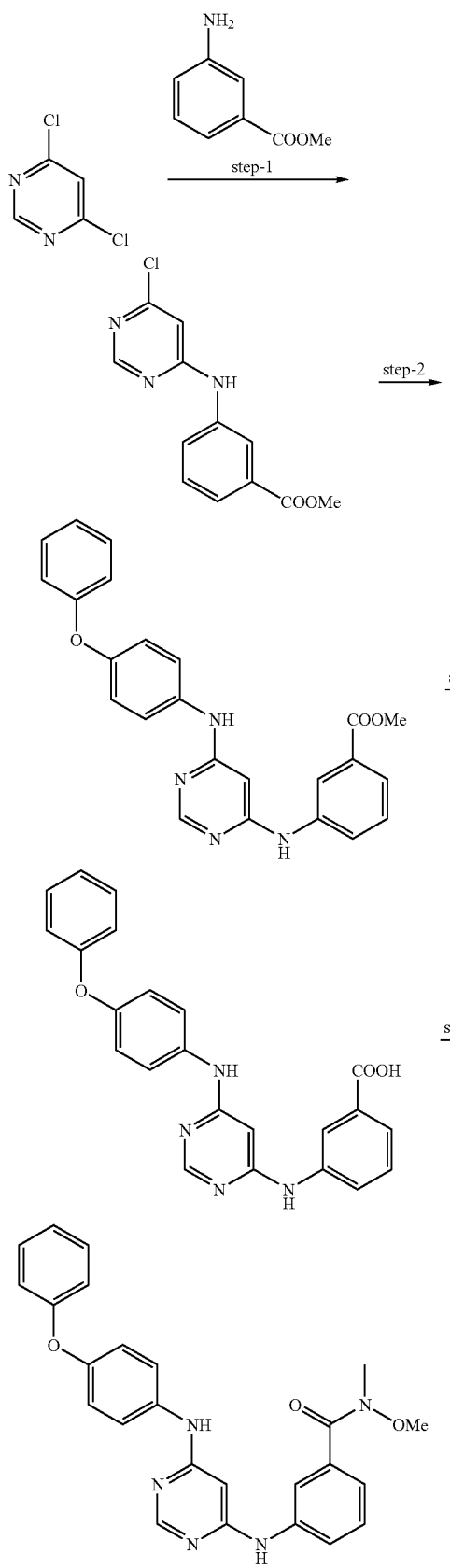

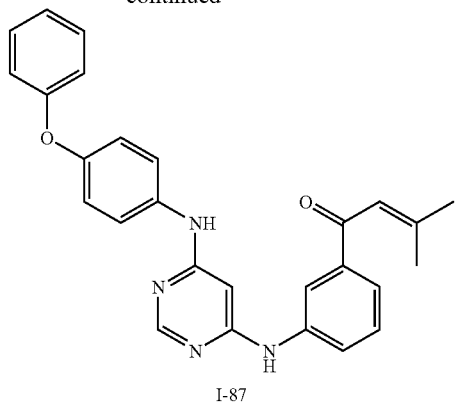

I-87

Synthesis of 3-methyl-1-(3-(6-(4-phenoxyphenylamino) pyrimidin-4-ylamino)phenyl)but-2-en-1-one (I-87)

Step 1

To a stirred solution of 4,6-dichloropyrimidine (0.5 g, 3.7 mmol) in n-butanol (10 mL) was added methyl 3-aminobenzoate (0.498 g, 3.7 mmol) and DIPEA (0.65 g, 5.0 mmol) and the reaction mixture was heated at 110° C. for 12 h. It was cooled and excess n-butanol was removed under reduced pressure. The residue was extracted with EtOAc (2×30 mL) and the combined EtOAc extract was washed with water (5 mL), brine (2.5 mL), dried over $Na_2SO_4$ and concentrated under reduced pressure. The residue was stirred with pet ether (30 mL) for 30 min, the pet ether removed by decantation and the solid obtained was dried under high vacuum to give methyl 3-(6-chloropyrimidin-4-ylamino)benzoate (0.3 g, 34%) as light brown solid.

Step 2

To a stirring solution of methyl 3-(6-chloropyrimidin-4-ylamino)benzoate (1.0 g, 3.8 mmol) and 4-phenoxy aniline (0.703 g, 3.8 mmol) in ethanol (5 mL) was added acetic acid (0.22 mL) and the reaction mixture was heated at 100° C. for 48 h. The reaction mixture was cooled, ethanol was removed under reduced pressure and the residue was dissolved in ethyl acetate (50 mL). It was washed with $NaHCO_3$ solution (5 mL) and brine (5 mL), was dried over $Na_2SO_4$ and was concentrated under reduced pressure. The residue was purified by column chromatography ($SiO_2$, 60-120, chloroform/methanol, 9/1) to yield methyl 3-(6-(4-phenoxyphenylamino)pyrimidin-4-ylamino)benzoate (1 g, 66%) as an off-white solid.

Step 3

To a stirred solution of methyl 3-(6-(4-phenoxyphenylamino)pyrimidin-4-ylamino)benzoate (0.3 g, 0.72 mmol) in methanol/THF (2/2, 4 mL) was added LiOH (0.122 g, 2.9 mmol) in $H_2O$ (4 mL) and the reaction mixture was stirred at rt for 2 h. It was concentrated under reduced pressure. the residue was diluted with water (2 mL) and was extracted with dichloromethane (5 mL). The aqueous layer was separated and was acidified with 1.5 N HCl (pH ~5-6) to get a white precipitate, which was collected by filtration and dried under vacuum to give 3-(6-(4-phenoxyphenylamino)pyrimidin-4-ylamino)benzoic acid (0.2 g 69%) as a white solid.

Step 4

To a stirred solution of 3-(6-(4-phenoxyphenylamino)pyrimidin-4-ylamino)benzoic acid (0.05 g, 0.12 mmol) in DMF (2 mL) were added MeNH—OMe.HCl (0.0084 g, 0.12 mmol), EDCI.HCl (0.0361 g, 0.18 mmol), HOBT (0.0084 g, 0.062 mmol) and DIPEA (0.023 g, 0.18 mmol). The reaction mixture was stirred at room temperature for 1 h and was quenched with water. A white solid was isolated by filtration and dried under vacuum to give N-methoxy-N-methyl-3-(6-(4-phenoxyphenylamino)pyrimidin-4-ylamino)benzamide (0.025 g, 44.5%) as a white solid.

Step 5

To a stirred solution of N-methoxy-N-methyl-3-(6-(4-phenoxyphenylamino)pyrimidin-4-ylamino)benzamide (50 mg, 0.11 mmol) in THF (0.5 mL) at 0° C. was added 2-methylpropenylmagnesium bromide (1.1 mL, 0.55 mmol, 0.5 M in THF). The reaction mixture was allowed to stir at room temperature for 30 min. It was quenched with sat. NH$_4$Cl solution (0.5 mL) and was extracted with EtOAc (3×2 mL). The combined organic layer was washed with brine, was dried over anhydrous Na$_2$SO$_4$, was filtered and was concentrated under reduced pressure to give a white solid, which was further purified by column chromatography (SiO$_2$, 60-120, chloroform/methanol, 9/1) to give 3-methyl-1-(3-(6-(4-phenoxyphenylamino)pyrimidin-4-ylamino)phenyl)but-2-en-1-one (I-87) as an off white solid. $^1$H NMR (CDCl$_3$) δ ppm: 2.01 (s, 3H), 2.20 (s, 3H), 6.14 (s, 1H), 6.71 (s, 1H), 6.95 (s, 1H), 6.99-7.02 (m, 5H), 7.11 (t, J=7.36 Hz, 1H), 7.26-7.28 (m, 2H), 7.34 (t, J=7.56 Hz, 2H), 7.40-7.53 (m, 2H), 7.65 (d, J=7 Hz, 1H), 7.86 (s, 1H), 8.32 (s, 1H); LCMS: m/e 437.2 (M+1).

Example 28

Scheme 28a

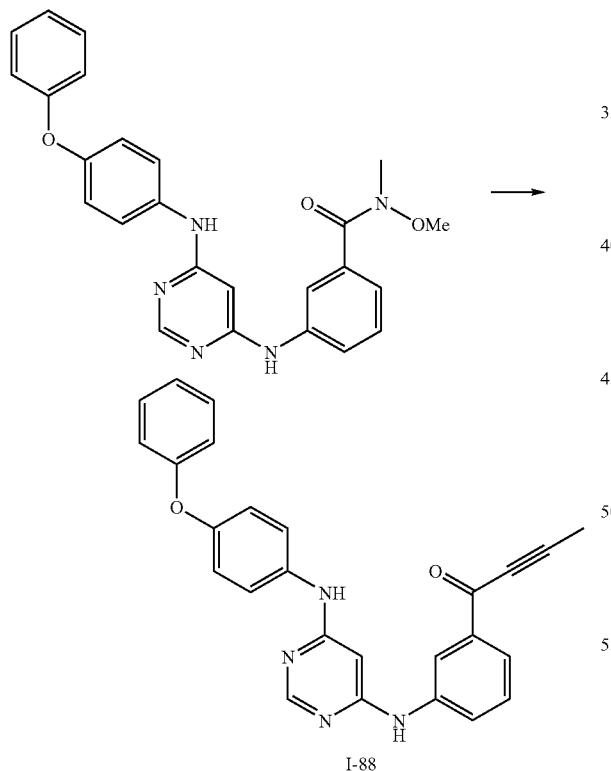

I-88

Synthesis of 1-(3-(6-(4-phenoxyphenylamino)pyrimidin-4-ylamino)phenyl)but-2-yn-1-one (I-88)

To a stirred solution of N-methoxy-N-methyl-3-(6-(4-phenoxyphenylamino)pyrimidin-4-ylamino)benzamide (50 mg, 0.11 mmol) in THF (0.5 mL) at 0° C. was added a THF solution of 1-butynylmagnesium bromide (1.1 mL, 1.1 mmol). The reaction mixture was allowed to come to rt and was stirred at rt for 30 min. The reaction mixture was quenched with saturated NH$_4$Cl solution (0.5 mL) and was extracted with EtOAc (2×3 mL). The combined EtOAc layer was washed with brine, was dried over anhydrous Na$_2$SO$_4$, was filtered and was concentrated under reduced pressure to give a white solid, which h was further purified by column chromatography (SiO$_2$, 60-120, chloroform/methanol, 9/1) to give 1-(3-(6-(4-phenoxyphenylamino)pyrimidin-4-ylamino)phenyl)but-2-yn-1-one (I-88) as an off-yellow solid. $^1$H NMR (DMSO-d$_6$) δ ppm: 2.22 (s, 3H), 6.16 (s, 1H), 6.97 (d, J=8.6 Hz, 2H), 7.01 (d, J=8.8 Hz, 2H), 7.1 (t, J=7.2 Hz, 1H), 7.35-7.39 (m, 2H), 7.48 (t, J=8 Hz, 1H), 7.56 (d, J=8.8 Hz, 2H), 7.66 (d, J=7.2 Hz, 1H), 7.95 (d, J=7.6 Hz, 1H), 8.32 (s, 1H), 8.39 (s, 1H), 9.22 (s, 1H), 9.47 (s, 1H); LCMS: m/e 421.1 (M+1).

Example 29

Scheme 29a

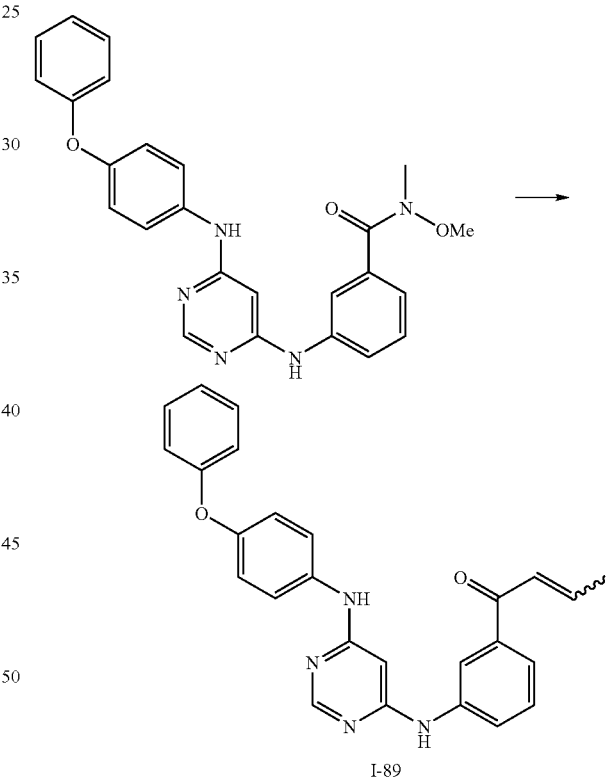

I-89

Synthesis of (E,Z)-1-(3-(6-(4-phenoxyphenylamino)pyrimidin-4-ylamino)phenyl)but-2-en-1-one (I-89)

To a stirred solution of N-methoxy-N-methyl-3-(6-(4-phenoxyphenylamino)pyrimidin-4-ylamino)benzamide (50 mg, 0.11 mmol) in THF (0.5 mL) at 0° C. was added a THF solution of propenylmagnesium bromide (2.2 mL, 1.1 mL, 0.5 M soln. in THF). The reaction mixture was allowed to stir at room temperature for 30 min. It was quenched with saturated NH$_4$Cl solution (0.5 mL) and was extracted with EtOAc (2×3 mL). The combined organic layer was washed with brine, was dried over anhydrous Na$_2$SO$_4$, was filtered and was concentrated under reduced pressure to get a white solid, which was further purified by column chromatography (SiO$_2$, 60-120, chloroform/methanol, 9/1) to give (E,Z)-1-(3-(6-(4-phenoxyphenylamino)pyrimidin-4-ylamino)phenyl)but-2-en-1-one (I-89) as a pale yellow solid. $^1$H NMR (DMSO-d$_6$) δ ppm: 1.98 (dd, J=1.6 & 6.8 Hz, 3H) & 2.13 (dd, J=1.6 & 7.2 Hz, 3H), 6.10-6.13 (m, 1H), 6.75-6.90 (m, 1H), 6.90-7.13 (m, 7H), 7.25-7.27 (m, 1H), 7.32-7.34 (m, 2H), 7.34-7.50 (m, 2H), 7.63-7.65 (m, 1H), 7.86-7.88 (m, 1H), 8.32 (s, 1H); LCMS: m/e 423 (M+1).

Example 30

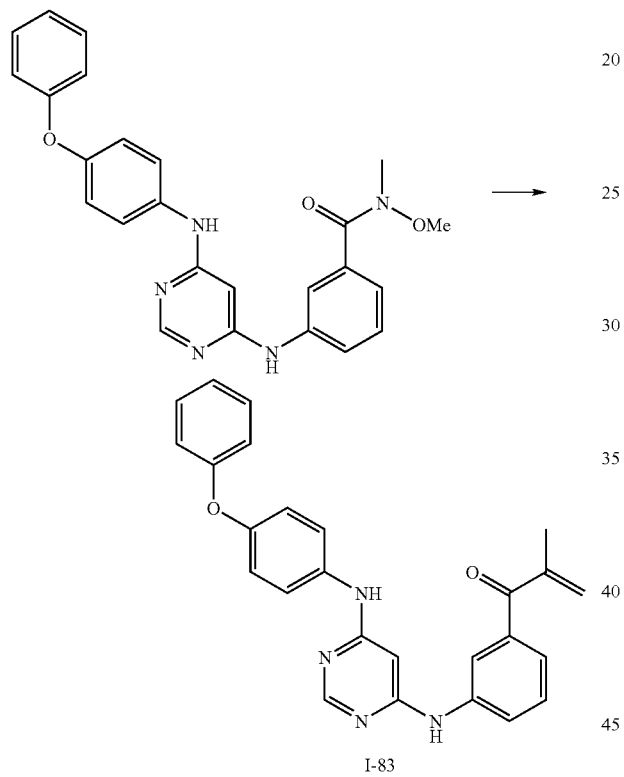

Synthesis of 2-methyl-1-(3-(6-(4-phenoxyphenylamino) pyrimidin-4-ylamino)phenyl)prop-2-en-1-one (I-83)

To a N-methoxy-N-methyl-3-(6-(4-phenoxyphenylamino) pyrimidin-4-ylamino)benzamide (0.150 g, 0.340 mmol) at 0° C. was added 2-methylpropenylmagnesium bromide (6.8 mL, 3.4 mmol, 0.5 M solution in THF). The reaction mixture was allowed to stir at room temperature for 30 min. It was quenched with saturated NH$_4$Cl solution (0.5 mL) and was extracted with EtOAc (2×3 mL). The combined organic layer was washed with brine, dried over Na$_2$SO$_4$, filtered and concentrated under reduced pressure to get a white solid, which was further purified by column chromatography (SiO$_2$, 60-120, product getting eluted in methanol/chloroform: 2/98) to give 2-methyl-1-(3-(6-(4-phenoxyphenylamino)pyrimidin-4-ylamino)phenyl)prop-2-en-1-one (I-83) as a white solid. $^1$H NMR (DMSO-d$_6$) δ ppm: 1.99 (s, 3H), 5.64 (s, 1H), 6.03 (s, 1H), 6.14 (s, 1H), 6.96-7.02 (m, 4H), 7.10 (t, J=7.6 Hz, 1H), 7.25 (d, J=7.6 Hz, 1H), 7.35-7.43 (m, 3H), 7.56 (d, J=8.8 Hz, 2H), 7.88 (d, J=8 Hz, 1H), 7.92 (s, 1H), 8.29 (s, 1H), 9.21 (s, 1H), 9.38 (s, 1H); LCMS: 423 m/e (M+1).

Example 31

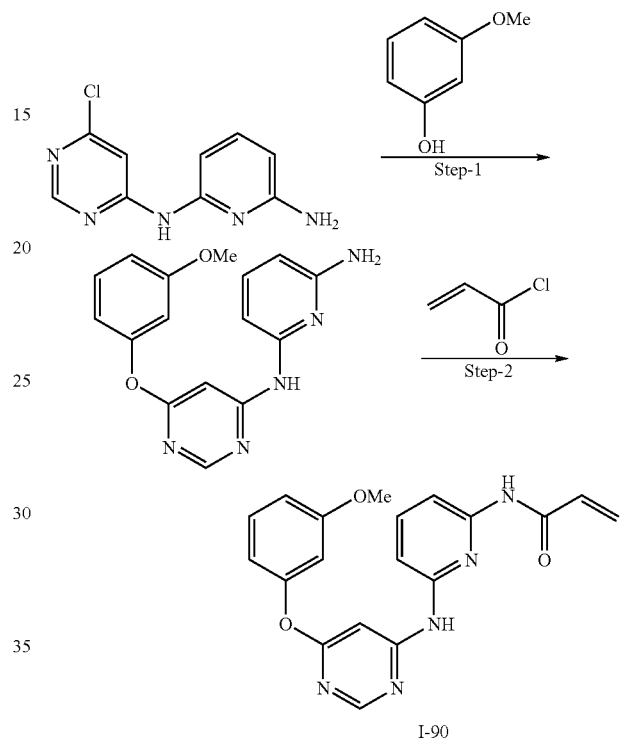

Synthesis of N-(6-(6-(3-methoxyphenoxy)pyrimidin-4-ylamino) yridine-2-yl)acrylamide (I-90)

Step 1

To a solution of N$^2$-(6-chloropyrimidin-4-yl)pyridine-2,6-diamine (200 mg, 0.90 mmol) in dry DMF (2 mL) was added 3-methoxyphenol (112 mg, 0.90 mmol) and anhydrous K$_2$CO$_3$ (186 mg, 1.353 mmol). The reaction mixture was heated at 100° C. for 16 h under N$_2$ atmosphere. It was then cooled and DMF removed under reduced pressure to give a yellowish gummy residue that was taken in EtOAc (10 mL). It was washed with water (5 mL), brine (5 mL), dried over Na$_2$SO$_4$ and then concentrated under reduced pressure to give a crude product. This was further purified by column chromatography (SiO$_2$, 60-120, hexane/EtOAc, 5/5) to give N$^2$-(6-(3-methoxylphenoxy)pyrimidin-4-yl)pyridine-2,6-diamine (110 mg, 40.7%) as a pale yellow solid.

Step 2

To a stirred solution of N$^2$-(6-(3-methoxylphenoxy)pyrimidin-4-yl)pyridine-2,6-diamine (100 mg, 0.323 mmol) in THF/NMP (1 mL/0.5 mL) was added acryloyl chloride (0.029 g, 0.3 mmol) under N$_2$ atmosphere at −10° C. The stirring was continued at the same temperature for 2 h and the reaction mixture was concentrated under reduced pressure to give a residue that was further purified by column chromatography (SiO$_2$, 60-120, chloroform/methanol) to give N-(6-

(6-(3-methoxyphenoxy)pyrimidin-4-ylamino)pyridine-2-yl) acrylamide (I-90) as a pale yellow solid. $^1$H NMR (DMSO-$d_6$) δ ppm: 3.75 (s, 3H), 5.79 (dd, J=1.8 & 10.08 Hz, 1H), 6.30 (dd, J=1.8 & 16.96 Hz, 1H), 6.65 (dd, J=10.12 & 16.96 Hz, 1H), 6.74-6.76 (m, 2H), 6.82 (td, J=1.52 & 9.24 Hz, 1H), 7.04 (d, J=7.92 Hz, 1H), 7.33 (t, J=8.28 Hz, 1H), 7.70 (t, J=7.96 Hz, 1H), 7.76 (d, J=8 Hz, 1H), 7.90 (s, 1H), 8.34 (s, 1H), 10.20 (s, 1H), 10.48 (s, 1H); LCMS: m/e 364 (M+1).

Example 32

Scheme 32a

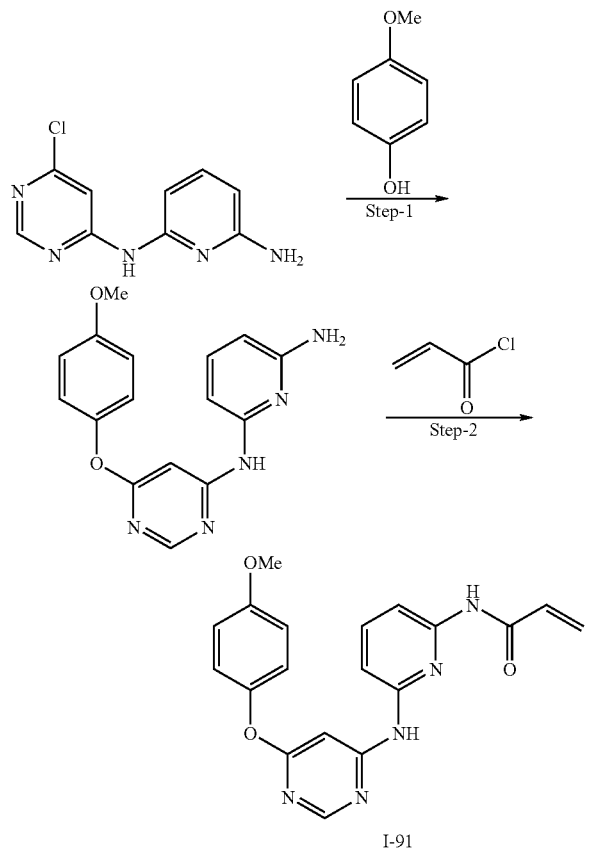

I-91

Synthesis of N-(6-(6-(4-methoxyphenoxy)pyrimidin-4-ylamino) pyridine-2-yl)acrylamide (I-91)

Step 1

To a solution of N$^2$-(6-chloropyrimidin-4-yl)pyridine-2,6-diamine (200 mg, 0.90 mmol) in dry DMF (2 mL) was added 4-methoxyphenol (168 mg, 1.3 mmol) and anhydrous K$_2$CO$_3$ (179 mg, 1.3 mmol). The reaction mixture was heated at 100° C. for 16 h under N$_2$ atmosphere. It was then cooled and DMF removed under reduced pressure to give a yellowish gummy residue that was taken in EtOAc (10 mL). The solution was washed with water (5 mL) and brine (5 mL), was dried over Na$_2$SO$_4$ and was then concentrated under reduced pressure to get crude product. This was further purified by column chromatography (SiO$_2$, 60-120, hexane/EtOAc, 5/5) to give N$^2$-(6-(4-methoxylphenoxy)pyrimidin-4-yl)pyridine-2,6-diamine (160 mg, 59.2%) as a pale yellow solid.

Step 2

To a stirred solution of N$^2$-(6-(4-methoxylphenoxy)pyrimidin-4-yl)pyridine-2,6-diamine (150 mg, 0.474 mmol) in THF/NMP (1 mL/0.5 mL) was added acryloyl chloride (64 mg, 0.712 mmol) at −10° C. under N$_2$ atmosphere. After stirring at this temperature for 30 min, the reaction was stopped and the reaction mixture was slowly added to NaHCO$_3$ solution (10 mL). A white solid was precipitated which was isolated by filtration and was dissolved in a mixture of ethyl acetate (5 mL) and Et$_3$N (0.5 mL). The solution was washed with water (2 mL) and brine (2 mL). Drying over Na$_2$SO$_4$ followed by filtration and concentration under reduced pressure afforded a yellow solid. It was further purified by column chromatography (SiO$_2$, 60-120, chloroform/methanol, 9/1) to give N-(6-(6-(4-methoxyphenoxy)pyrimidin-4-ylamino)pyridine-2-yl)acrylamide (I-91) as an off white solid. $^1$H NMR (DMSO-$d_6$) δ ppm: 3.76 (s, 3H), 5.79 (dd, J=1.84 & 10.16 Hz, 1H), 6.30 (dd, J=1.84 & 17 Hz, 1H), 6.65 (dd, J=10.12 & 16.92 Hz, 1H), 6.96-6.99 (m, 2H), 7.02 (d, J=7.88 Hz, 1H), 7.09-7.13 (m, 2H), 7.69 (t, J=7.96 Hz, 1H), 7.76 (d, J=7.44 Hz, 1H), 7.86 (s, 1H), 8.30 (d, J=0.88 Hz, 1H), 10.17 (s, 1H), 10.17 (s, 1H); LCMS m/e 364 (M+1).

Example 33

Scheme 33a

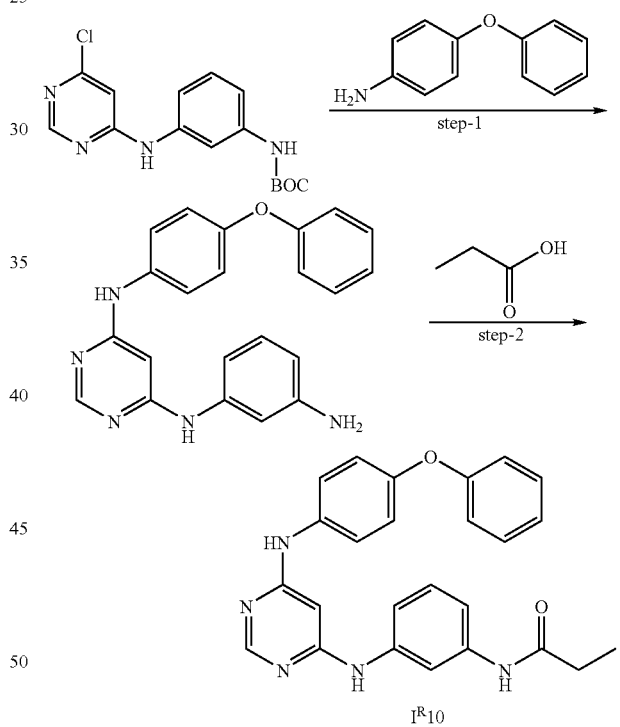

I$^R$10

Synthesis of N-(3-(6-(4-phenoxyphenylamino)pyrimidin-4-ylamino)phenyl)propionamide (I$^R$-10)

Step 1

A solution of tert-butyl 3-(6-chloropyrimidin-4-ylamino)phenylcarbamate (200 mg, 0.6 mmol), 4-phenoxyaniline (346 mg, 1.8 mmol) and concentrated HCl (45 mg, 1.2 mmol) in n-butanol (8 mL) was subjected to microwave irradiation (160° C., 20 min). The reaction mixture was quenched with NaHCO$_3$ solution (2 mL) and extracted with EtOAc (2×10 mL). The combined EtOAc extract was washed with water (5 mL), brine (5 mL), was dried over Na$_2$SO$_4$ and was concentrated under reduced pressure. The residue was further purified by column chromatography (SiO$_2$, 60-120, Chloroform/methanol, 9/1) to give N$^4$-(3-aminophenyl)-N$^6$-(4-phenoxyphenyl)pyrimidine-4,6-diamine (87 mg, 37.8%) as a brown solid.

Step 2

To a solution of propionic acid (12 mg, 0.1 mmol) in DMF (0.6 mL) was added HATU (92 mg, 0.2 mmol) and the reaction mixture was stirred at room temperature for 30 min. To it was added N$^4$-(3-aminophenyl)-N$^6$-(4-phenoxyphenyl)pyrimidine-4,6-diamine (60 mg, 0.1 mmol) followed by DIPEA (41 mg, 0.3 mmol) and the reaction mixture was stirred at this temperature for 16 h. It was concentrated under reduced pressure. The residue was diluted with CH$_2$Cl$_2$ (5 mL) and was washed with NaHCO$_3$ solution (2 mL), water (2 mL), and brine (2 mL). Drying over Na$_2$SO$_4$ followed by concentration under reduced pressure offered a residue that was purified by column chromatography (SiO$_2$, 230-400, chloroform/methanol:9/1) to give N-(3-(6-(4-phenoxyphenylamino)pyrimidin-4-ylamino)phenyl)propionamide (I$^R$-10) as a brown solid. $^1$H NMR (DMSO-d$_6$) δ ppm: 1.06 (t, J=7.56 Hz, 3H), 2.30 (q, J=7.48 Hz, 2H), 6.13 (s, 1H), 6.94-6.99 (m, 4H), 7.08 (t, J=7.36 Hz, 1H), 7.16-7.24 (m, 3H), 7.36 (t, J=7.44 Hz, 2H), 7.54 (d, J=8.88 Hz, 2H), 7.81 (s, 1H), 8.23 (s, 1H), 9.12 (s, 2H), 9.81 (s, 1H); LCMS: m/e 426.3 (M+1).

Example 34

Scheme 34a

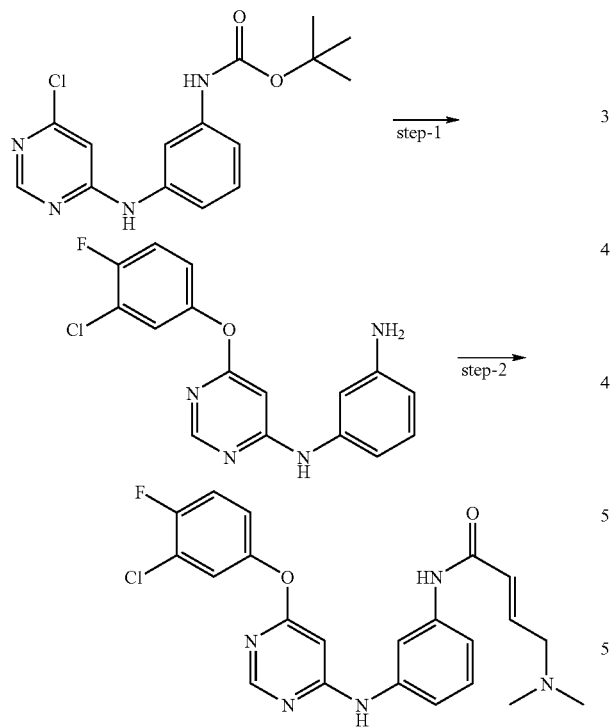

Synthesis of (E)-N-(3-(6-(3-chloro-4-fluorophenoxy)pyrimidin-4-ylamino)phenyl)-4-(dimethylamino)but-2-enamide (I-92)

Step 1

A solution of tert-butyl 3-(6-chloropyrimidin-4-ylamino)phenylcarbamate (1.6 g, 5 mmol), 3-chloro-4-fluorophenol (1.4 g, 10 mmol) and potassium carbonate (1.4 g, 10 mmol) in 15 mL of DMF was heated to 120° C. for 16 h. The reaction mixture was mixed in 15 mL of water, the crude product was precipitated, filtered, purified by flash chromatography on silica gel with MeOH/DCM solvent system to afford 750 mg (45% yield) of N$^1$-(6-(3-chloro-4-fluorophenoxy)pyrimidin-4-yl)benzene-1,3-diamine as an off-white solid. MS (m/z): MH$^+$=331.

Step 2

Oxalyl chloride (155 mg, 1.2 mmol) was added dropwise to a mixture of 4-N, N-dimethyl aminocrotonic acid HCl salt (200 mg, 1.2 mmol) in 5 mL of THF at 0° C. To this mixture was added 3 drops of DMF/THF solution (made from 5 drops of DMF in 1 mL of THF). The reaction mixture was stirred at RT for 2 h, then was cooled to 0° C. ice bath. A solution of N$^1$-(6-(3-chloro-4-fluorophenoxy)pyrimidin-4-yl)benzene-1,3-diamine (200 mg, 0.6 mmol) 2 mL of NMP) was added to the dimethylaminocrotonyl chloride solution and the resulting mixture was stirred for 3 h at 0° C. The reaction was quenched with 3 mL of 1N NaOH, and was extracted with EtOAc (2×25 mL). The crude product mixture was purified by flash chromatography on silica gel with MeOH/NH$_4$OH/DCM solvent system to afford (E)-N-(3-(6-(3-chloro-4-fluorophenoxy)pyrimidin-4-ylamino)phenyl)-4-(dimethylamino)but-2-enamide (I-92) as a light colored solid. MS (m/z): MH$^+$=442, 444 (3:1), H-NMR (DMSO) δ 10.08 (s, 1H), 9.67 (s, 1H), 8.36 (s, 1H), 7.98 (s, 1H), 7.59 (d, 1H), 7.57 (t, 1H), 7.53-7.24 (m, 4H), 6.29 (b, 1H), 6.23 (s, 1H), 3.51 (d, 2H), 2.21 (s, 6H).

Example 35

Scheme 35a

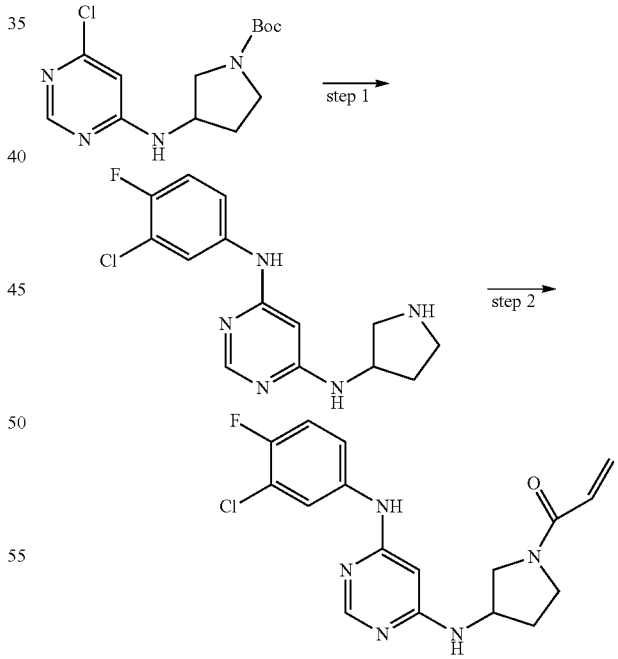

Synthesis of 1-(3-(6-(3-chloro-4-fluorophenyamino)pyrimidin-4-ylamino)pyrrolidin-1-yl)prop-2-en-1-one (I-70)

Step 1

A neat mixture of tert-butyl 3-(6-chloropyrimidin-4-ylamino)pyrrolidin-1-carboxylate (354 mg, 1.18 mmol) and 3-chloro-4-fluoroaniline (3.03 g, 20.8 mmol) was heated at 140° C. for 21 hours. Upon cooling to ambient temperature, the melt was diluted with EtOAc and the mixture was stirred for 1 hour. A beige, amorphous precipitate was collected, washed with water and dried in vacuo at 50-60° C. giving 292 mg (80%) of $N^4$-(3-chloro-4-fluorophenyl)-$N^6$-(pyrrolidin-3-yl)pyrimidine-4,6-diamine. MS (APCI): (M+1)=308, (M−1)=306.

Step 2

To a solution of $N^4$-(3-chloro-4-fluorophenyl)-$N^6$-(pyrrolidin-3-yl)pyrimidine-4,6-diamine (287 mg, 0.93 mmol) and triethylamine (0.32 ml, 2.33 mmol) in anhydrous THF (5 ml) under nitrogen was added acryloyl chloride (91 μl, 1.12 mmol). The reaction mixture was stirred at room temperature for 1 hour and was concentrated under reduced pressure. The residue was eluted through a flash column (silica gel 60, 230-400 mesh, 5% MeOH in EtOAc to 10% MeOH in EtOAc) to give two products. The less polar product ($R_f$=0.24 in 1:9 MeOH:EtOAc) was found to be a diacrylated analog. The more polar product ($R_f$=0.14 in 1:9 MeOH:EtOAc) was 1-(3-(6-(3-chloro-4-fluorophenyamino)pyrimidin-4-ylamino)pyrrolidin-1-yl)prop-2-en-1-one (I-70). MS (APCI) $(M+1)^+$=362, $(M−1)^+$=360: $^1$H-NMR DMSO-$d_6$) δ 9.11 (s, 1H), 8.14 (s, 1H), 7.92 (d, 1H), 7.38-7.23 (m, 3H), 6.58-6.48 (m, 1H), 6.13-6.08 (m, 1H), 5.75 (d, 1H) 5.63-5.59 (m, 1H), 3.64-3.59 (m, 2H), 2.17-1.81 (m, 6H).

Example 36

Scheme 36a

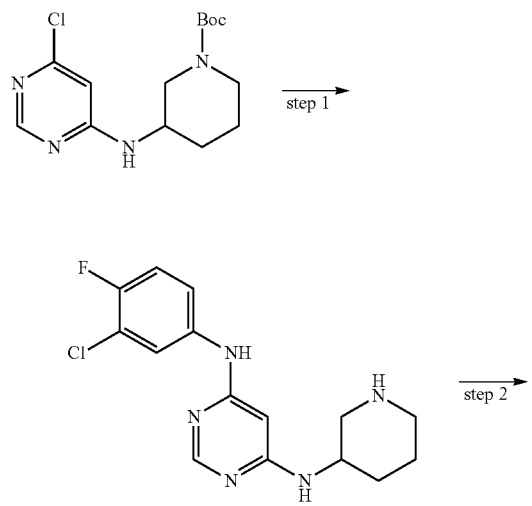

Synthesis of 1-(3-(6-(3-chloro-4-fluorophenyamino) pyrimidin-4-ylamino)piperidin-1-yl)prop-2-en-1-one (I-71)

Step 1

N-(3-Chloro-4-fluorophenyl)-N'-piperidin-3-yl pyrimidine-4,6-diamine

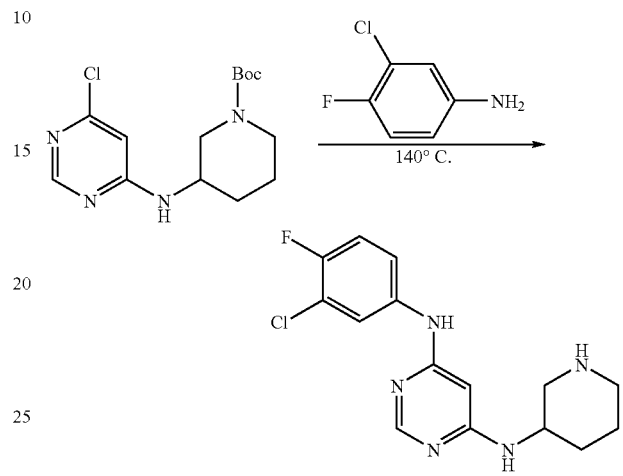

A mixture of tert-butyl 3-(6-chloropyrimidin-4-ylamino) piperidine-1-carboxylate (295 mg, 0.94 mmol) and 3-chloro-4-fluoroaniline (2.83 g, 19.4 mmol) was heated neat at 140° C. for 19 hours. Upon cooling, the melt was stirred in EtOAc and allowed to stand at room temperature for 1 hour. The precipitate was collected, washed with EtOAc and dried to give 256 mg (85%) of $N^4$-(3-chloro-4-fluorophenyl)-$N^6$-(piperidin-3-yl)pyrimidine-4,6-diamine, a grayish-violet amorphous solid. MS (APCI): $(M+1)^+$=322.

Step 2

To a solution of $N^4$-(3-chloro-4-fluorophenyl)-$N^6$-(piperidin-3-yl)pyrimidine-4,6-diamine (251 mg, 0.78 mmol) and triethylamine (0.27 ml, 1.95 mmol) in anhydrous THF (7 ml) under nitrogen was added acryloyl chloride (76 μl, 0.94 mmol). The reaction mixture was stirred at room temperature for 1 hour and was concentrated under reduced pressure. The residue was eluted through a flash column (silica gel 60, 230-400 mesh with 5% MeOH in EtOAc to give two products. The less polar product ($R_f$=0.33 in 1:9 MeOH:EtOAc) was found to be a diacrylated analog. The more polar product ($R_f$=0.24 in 1:9 MeOH:EtOAc) was 1-(3-(6-(3-chloro-4-fluorophenyamino)pyrimidin-4-ylamino)piperidin-1-yl)prop-2-en-1-one (I-71). MS (APCI) $(M+1)^+$=376, $(M−1)^+$=374: $^1$H-NMR DMSO-$d_6$, δ 9.15 (br s, 1H), 8.18 (d, 1H), 7.95 (br s, 1H), 7.43-7.20 (m, 2H), 7.03-6.48 (m, 3H), 6.26-5.97 (m, 2H), 5.86-5.51 (m, 3H), 3.90-3.66 (m, 2H), 1.98-1.66 (m, 2H), 1.59-1.12 (m, 2H).

Example 37

Scheme 37a

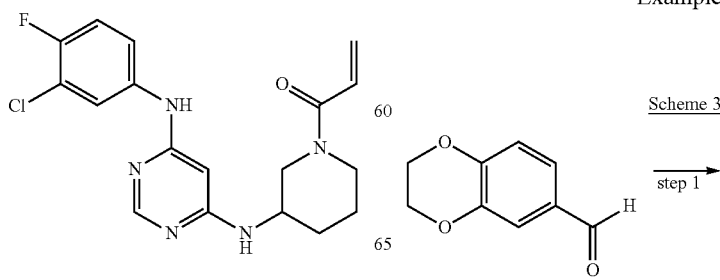

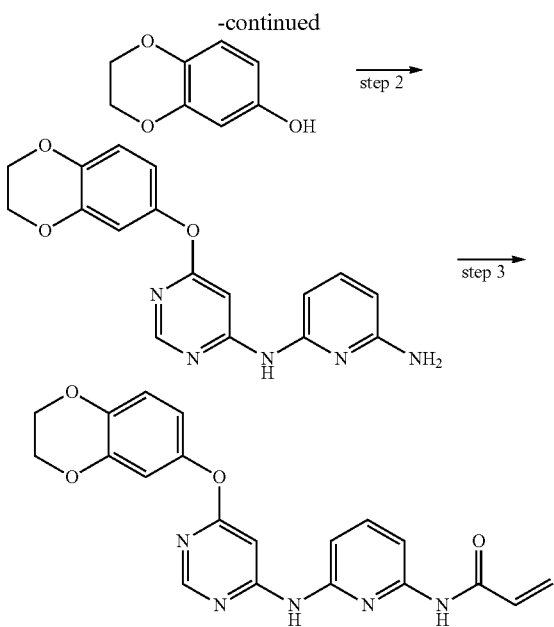

Synthesis of N-(6-(6-(2,3-dihydrobenzo[b][1,4]dioxin-6-yloxy)pyrimidin-4-ylamino)pyridin-2-yl)acrylamide (I-95)

Step 1

To a stirred solution of 2,3-dihydrobenzo[b][1,4]dioxine-6-carbaldehyde (1 g, 6.09 mmol) in $CH_2Cl_2$ (16 mL) was added m-CPBA (4.204 g, 24.36 mmol). The suspension was heated at 50° C. for 2 days, was cooled to rt, was quenched with saturated $NaHCO_3$ soln. and was extracted with $CH_2Cl_2$ (3×10 mL). The combined extract was concentrated under reduced pressure, and then was dissolved in MeOH containing NaOH. The solution was stirred at rt for 2 h, was acidified with HCl and was extracted with ethyl acetate (3×10 mL). The combined extract was washed with saturated $NaHCO_3$ solution and brine, was dried over anhydrous $Na_2SO_4$, was filtered and was concentrated under reduced pressure. The residue was dissolved in $CH_2Cl_2$ and was filtered. The DCM solution was dried over anhydrous $Na_2SO_4$, was filtered and was concentrated under reduced pressure to give 2,3-dihydrobenzo[b][1,4]dioxin-6-ol (0.591 g, 63%) as a reddish brown oily liquid.

Step 2

A stirred mixture of 2,3-dihydrobenzo[b][1,4]dioxin-6-ol (0.137 g, 0.90 mmol), $Cs_2CO_3$ (0.734 g, 2.25 mmol), CuI (0.02 g, 10% w/w), and $N^2$-(6-chloropyrimidin-4-yl)pyridine-2,6-diamine (0.29 g, 0.90 mmol) in NMP (1 mL) was heated at 100° C. for 16 h. The reaction mixture was cooled to rt and slowly added to demineralised water. The solid that precipitated was collected by filtration and was further purified by column chromatography ($SiO_2$, 60-120, pet ether/ethyl acetate, 7/3) to give $N^2$-(6-(2,3-dihydrobenzo[b][1,4]dioxin-6-yloxy)pyrimidin-4-yl)pyridine-2,6-diamine (0.088 g, 29%) as yellow solid.

Step 3

To a stirred solution of $N^2$-(6-(2,3-dihydrobenzo[b][1,4]dioxin-6-yloxy)pyrimidin-4-yl)pyridine-2,6-diamine (0.080 g, 0.23 mmol) and potassium carbonate (0.065 g, 0.47 mmol) in NMP (0.8 mL) at 0° C. was added acryloyl chloride (0.026 g, 0.29 mmol) and the reaction mixture was stirred at 0° C. for 30 min. The reaction mixture was added dropwise to a cold, stirring solution of 10% $NaHCO_3$ and was stirred at 0° C. for 30 min. A white solid was isolated by filtration. The solid was washed with cold water and hexane and dissolved in a 2 mL of methanol/dichloromethane (1/1). This solution was concentrated under reduced pressure. The residue obtained was suspended in cold water (5 mL), $Et_3N$ was added to it and it was extracted with ethyl acetate (2×5 mL). The combined ethyl acetate extract was washed with water (2 mL) and brine (2 mL), was dried over $Na_2SO_4$ and was concentrated under reduced pressure to obtain N-(6-(6-(2,3-dihydrobenzo[b][1,4]dioxin-6-yloxy) pyrimidin-4-ylamino)pyridin-2-yl)acrylamide (I-95) as a light yellow solid. $^1$H NMR (DMSO-$d_6$) δ ppm: 4.25 (s, 4H), 5.79 (dd, J=1.84 & 10.08 Hz, 1H), 6.30 (dd, J=1.84 & 16.96 Hz, 1H), 6.62-6.72 (m, 3H), 6.88 (d, J=8.72 Hz, 1H), 7.03 (d, J=7.84 Hz, 1H), 7.69 (t, J=7.96 Hz, 1H), 7.70 (d, J=7.84 Hz, 1H), 7.85 (s, 1H), 8.32 (d, J=0.4 Hz, 1H), 10.16 (s, 1H), 10.47 (s, 1H); LCMS: m/e 392.

Described below are assays used to measure the biological activity of provided compounds as inhibitors of ErbB1 (EGFR), ErbB2, ErbB4, TEC, BTK, ITK, BMX, and JAK3.

Example 38

Cloning, Expression and Purification of EGFR-WT and EGFR C797S Mutant Using Baculovirus and Insect Cells (i) Subcloning of EGFR-WT and Mutant Kinase Domains Amino acids 696 to 1022 of the EGFR-WT kinase domain (NM_005228, NP_005219.2) was subcloned into the NcoI and HindIII sites of the pFastHTa vector (Invitrogen, Carlsbad, Calif.). To make the EGFR-mutant protein, the cysteine at position 797 was changed to a serine using the Stratagene QuikChange kit (Stratagene, Cedar Creek, Tex.), according to manufacturer's instructions.

(ii) Expression

P1 baculovirus stocks were generated in SF9 cells via Blue Sky Biotech's suspension transfection protocol (Worcester, Mass.). Expression analysis was conducted in 125 ml culture of SF21 insect cells ((grown in SF900I SFM (Invitrogen cat #10902-088), supplemented with 10 mg/L gentamicin (Invitrogen, Carlsbad, Calif., cat# 15710-064)) using a viral load of 0.1 ml of virus per 100 ml of cell suspension. Expression was optimized using Blue Sky Biotech's Infection Kinetics Monitoring system (Worcester, Mass.).

(iii) Purification

Infected insect cells were pelleted. Cell pellets were resuspended in Blue Sky Biotech's lysis buffer (Worcester, Mass., 1×WX; solubilization buffer, containing a protease inhibitor cocktail of leupeptin, pepstatin, PMSF, aprotinin and EDTA) at a ratio of 10 ml per gram of wet cell paste. Cells were lysed by sonication and the lysate was clarified by centrifugation at 9,000 RPM for 30 minutes in a GSA rotor. 500 μl bed volume of NiNTA resin (Qiagen, Valencia, Calif.) was added to the supernatants and batch bound for two hours with constant agitation. The material was transferred by gravity into an empty 2 ml column. The column was washed with 2 ml of wash buffer (Blue Sky Biotech, Worcester, Mass., 1×WX, 25 mM imidazole).The protein was eluted with 1×WX+imidazole at varying concentrations: Elution 1: 75 mM imidazole (2 fractions, 1 column volume); Elution 2: 150 mM imidazole (2 fractions, 1 column volume); Elution 3: 300 mM imidazole (2 fractions, 1 column volume). All the elution fractions were analyzed by SDS page followed by Coomassie staining and Western Blotting using anti-penta-his antibody (Qiagen, Valencia, Calif.). The carboxy-terminal six-histidine "tag" was removed from some of the purified protein using AcTEV Protease kit (Invitrogen, Carlsbad, Calif., Cat# 12575-015), following manufacturer's instructions. All the samples (pre- and post-Tev cut) were analyzed by SDS page followed by Coomassie staining and Western Blotting, as described above.

Example 39

Mass Spectrometry for EGFR

Figure 8:
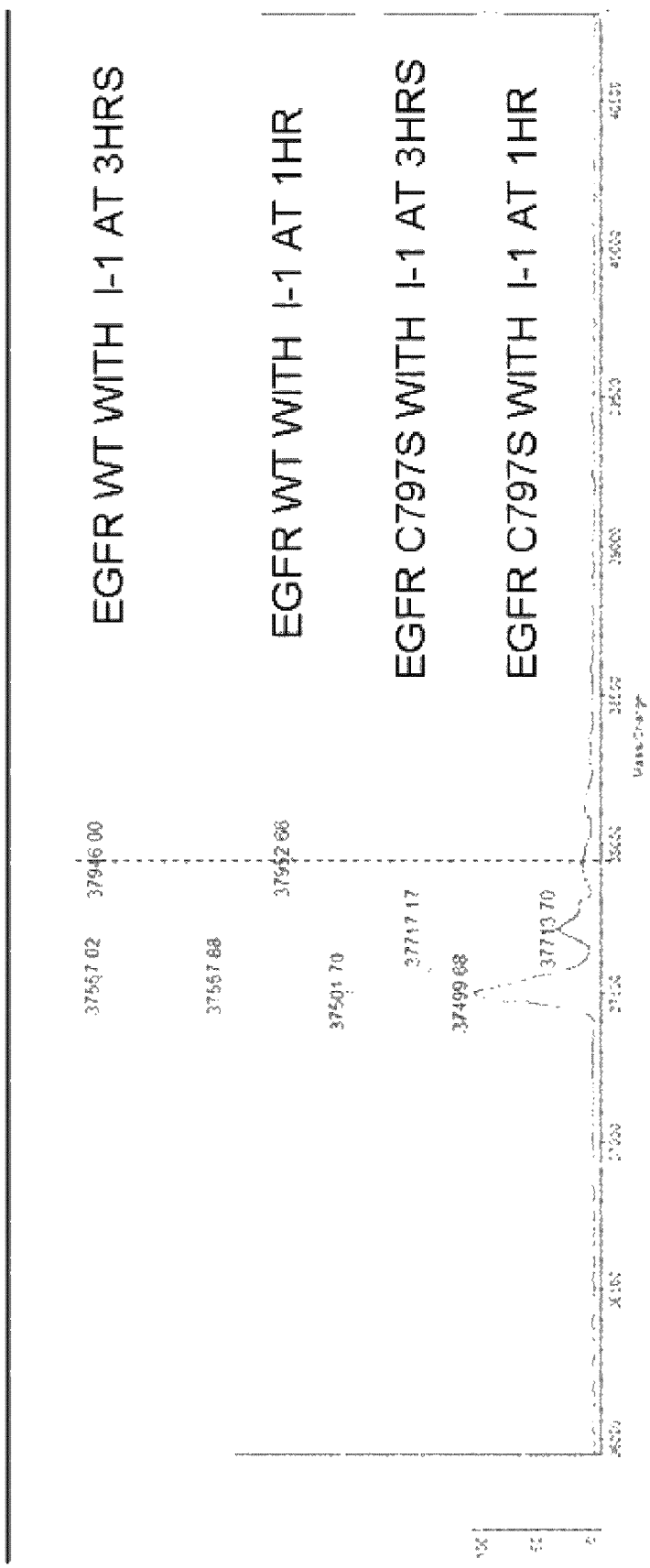
FIG. 8 depicts MS analysis confirming covalent modification of ErbB1 at Cys797 by compound I-1.

EGFR wild type and EGFR mutant (C797S) was incubated with 10-fold excess of compound I-1 for 1 hr and 3 hrs. 1 ul aliquots of the samples (total volume 5-8 ul) were diluted with 10 ul of 0.1% TFA prior to micro C4 ZipTipping directly onto the MALDI target using Sinapinic acid as the desorption matrix (10 mg/ml in 0.1% TFA:Acetonitrile 50:50). Intact mass measurement reveals that the wild type has a nominal mass of about 37557 and the mutant slightly lower at 37500. Reactivity was only observed for the wild type EGFR with a new peak appearing at a mass consistent with a single site covalent modification with compound I-1 which has a mass of 410 Da. (See FIG. 8). The mutant EGFR(C797S) showed no significant reactivity even after 3 hrs, confirming modification of the cysteine of interest, Cys797.

Example 40

Omnia Assay Protocol for Potency Assessment Against EGFR (WT) and EGFR (T790M/L858R) Active Enzymes The protocol below describes continuous-read kinase assays to measure inherent potency of compounds against active forms of EGFR (WT) and EGFR (T790M/L858R) enzymes. The mechanics of the assay platform are best described by the vendor (Invitrogen, Carlsbad, Calif.) on their website at the following URL: http://www.invitrogen.com/content.cfm?pageid=11338 or http://www.invitrogen.com/site/us/en/home/Products-and-Services/Applications/Drug-Discovery/Target-and-Lead-Identification-and-Validation/KinaseBiology/KB-Misc/ Biochemical-Assays/Omnia-Kinase-Assays.html Briefly, 10× stocks of EGFR-WT (PV3872) from Invitrogen and EGFR-T790M/L858R (40350) from BPS Bioscience, San Diego, Calif., 1.13× ATP (AS001A) and appropriate Tyr-Sox conjugated peptide substrates (KCZ1001) were prepared in I1× kinase reaction buffer consisting of 20 mM Tris, pH 7.5, 5 mM $MgCl_2$, 1 mM EGTA, 5 mM β-glycerophosphate, 5% glycerol (10× stock, KB002A) and 0.2 mM DTT (DS001A). 5 μL of each enzyme were pre-incubated in a Corning (#3574) 384-well, white, non-binding surface microtiter plate (Corning, N.Y.) for 30 min. at 27° C. with a 0.5 μL volume of 50% DMSO and serially diluted compounds prepared in 50% DMSO. Kinase reactions were started with the addition of 45 μL of the ATP/Tyr-Sox peptide substrate mix and monitored every 30-90 seconds for 60 minutes at $\lambda_{ex}360/\lambda_{em}485$ in a Synergy$^4$ plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to ~30 minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).

The EGFR-WT- and EGFR T790M/L858R-modified optimized reagent conditions are:

[EGFR-WT]=5 nM, [ATP]=15 mM, [Y12-Sox]=5 mM (ATP KMapp~12 mM); and

[EGFR-T790M/L858R]=3 nM, [ATP]=50 mM, [Y12-Sox]=5 mM (ATP KMapp~45 mM).

Example 41

Table 7 shows the activity of selected compounds of this invention in the EGFR inhibition assay. The compound numbers correspond to the compound numbers in Table 5. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50} \geq 10,000$ nM.

TABLE 7

EGFR Wild Type and EGFR (mutant C797S) Inhibition Data

| Compound # | EGFR inhibtion | EGFR (T790M/L858R) inhibiton |
|---|---|---|
| I-1 | A | A |
| I-2 | A | A |
| I-3 | A | A |
| I-4 | A | B |
| I-5 | A | A |
| I-6 | B | B |
| I-7 | A | B |
| I-8 | A | D |
| I-9 | A | C |
| I-10 | A | C |
| I-11 | B | E |
| I-12 | B | E |
| I-13 | A | B |
| I-14 | A | B |
| I-15 | A | B |
| I-16 | A | B |
| I-17 | A | B |
| I-18 | A | A |
| I-19 | A | A |
| I-46 | A | A |
| I-47 | A | E |
| I-48 | C | C |
| I-49 | A | A |
| I-50 | A | B |
| I-51 | A | D |
| I-52 | A | A |
| I-53 | B | C |
| I-54 | A | A |
| I-55 | A | A |
| I-56 | A | A |
| I-57 | — | C |
| I-58 | — | C |
| I-59 | A | A |
| I-60 | D | C |
| I-61 | — | A |
| I-63 | A | A |
| I-65 | A | B |
| I-66 | A | C |
| I-67 | A | A |
| I-68 | A | — |
| I-69 | B | — |
| I-70 | A | — |
| I-71 | A | — |
| I-73 | A | — |
| I-75 | A | — |
| I-78 | A | — |
| I-79 | A | — |

TABLE 7-continued

EGFR Wild Type and EGFR (mutant C797S) Inhibition Data

| Compound # | EGFR inhibtion | EGFR (T790M/L858R) inhibiton |
|---|---|---|
| I-80 | C | — |
| I-81 | A | — |
| I-82 | A | — |
| I-83 | B | — |
| I-84 | B | — |
| I-85 | B | — |
| I-86 | B | — |
| I-87 | B | — |
| I-88 | A | — |
| I-89 | A | — |
| I-90 | A | — |
| I-91 | A | — |
| I-92 | A | — |
| I-93 | A | — |
| I-94 | A | A |

Example 42

Cellular Assays for EGFR Activity

Compounds were assayed in A431 human epidermoid carcinoma cells using a method substantially similar to that described in Fry, et al., *Proc. Natl. Acad. Sci. USA* Vol 95, pp 12022-12027, 1998. Specifically, A431 human epidermoid carcinoma cells were grown in 6-well plates to 90% confluence and then incubated in serum-free media for 18 hr. Duplicate sets of cells were treated with 1 µM designated compound for 2, 5, 10, 30, or 60 min. Cells were washed free of the compound with warmed serum-free medium, incubated for 2 hr, washed again, incubated another 2 hr, washed again, and then incubated another 2 hr washed again and incubated for additional 2 hr and then stimulated with 100 ng/ml EGF for 5 min. Extracts were made as described Fry, et al. FIG. 1 depicts the EGFR inhibiting activity of compound I-1.

Compounds were assayed in A431 human epidermoid carcinoma cells using a method substantially similar to that described in Fry, et al. Specifically, A431 human epidermoid carcinoma cells were grown in 6-well plates to 90% confluence and then incubated in serum-free media for 18 hr. Cells were then treated with 10, 1, 0.1, 0.01, or 0.001 µM test compound for 1 hr. Cells were then stimulated with 100 ng/ml EGF for 5 min, and extracts were made as described in Fry, et al. 20 ug total protein from lysates were loaded on gel and blots were probed for either EGFR phosphorylation or p42/p44 Erk phosphorylation.

Figure 3:
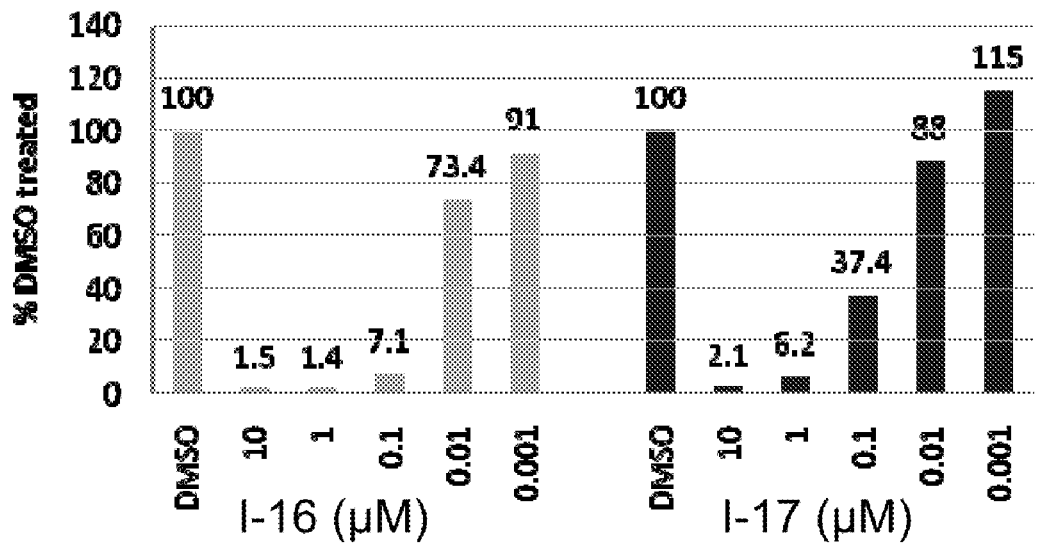
FIG. 3 depicts dose response inhibition of EGFR phosphorylation and p42/p44 Erk phosphorylation with compounds I-16 and I-17 in A431 cells.
Figure 3:
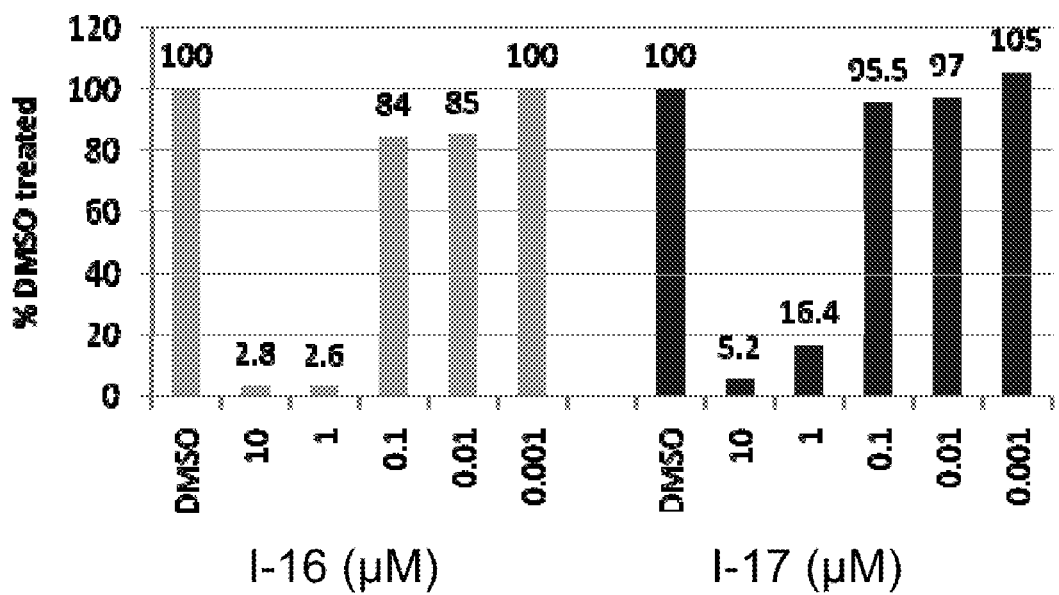
Figure 4:
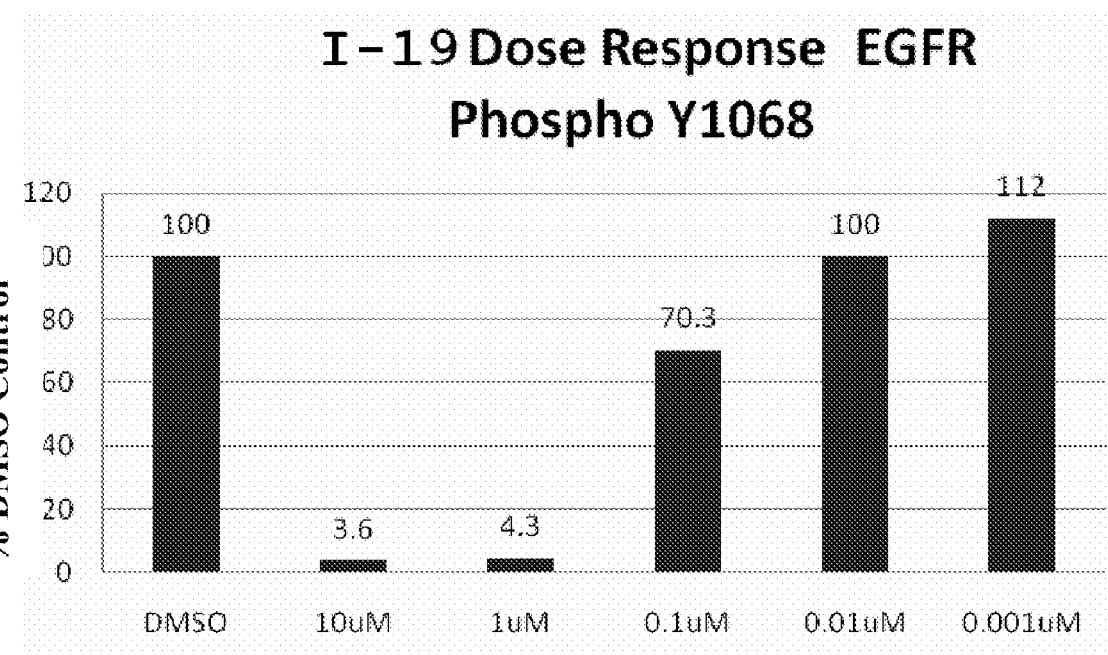
FIG. 4 depicts dose response inhibition of EGFR phosphorylation and p42/p44 Erk phosphorylation with compound I-19 in A431 cells.
Figure 4:
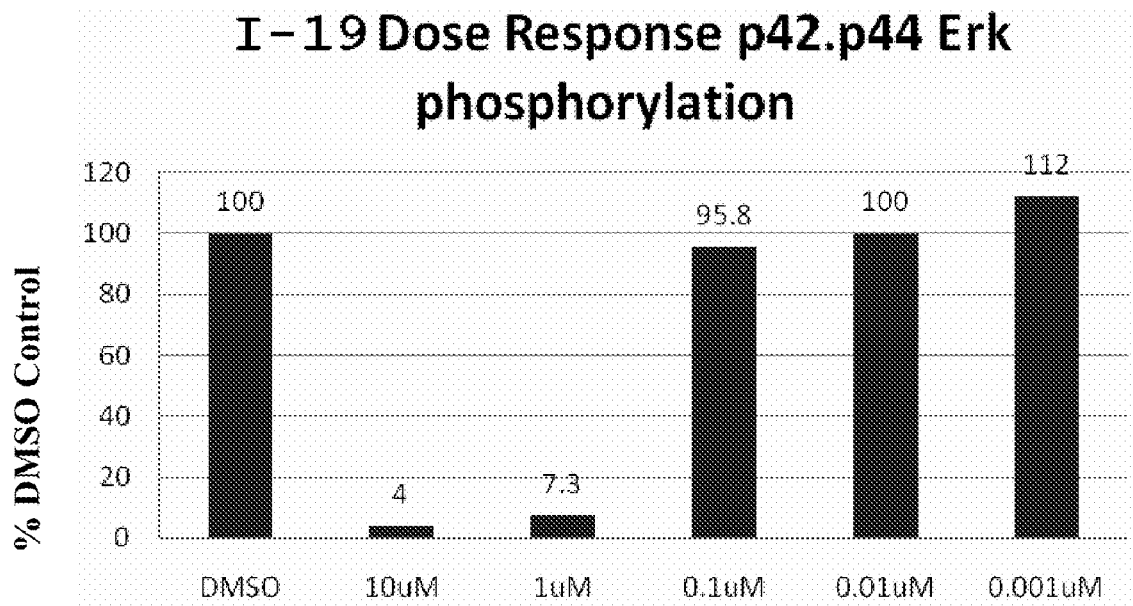
Figure 5:
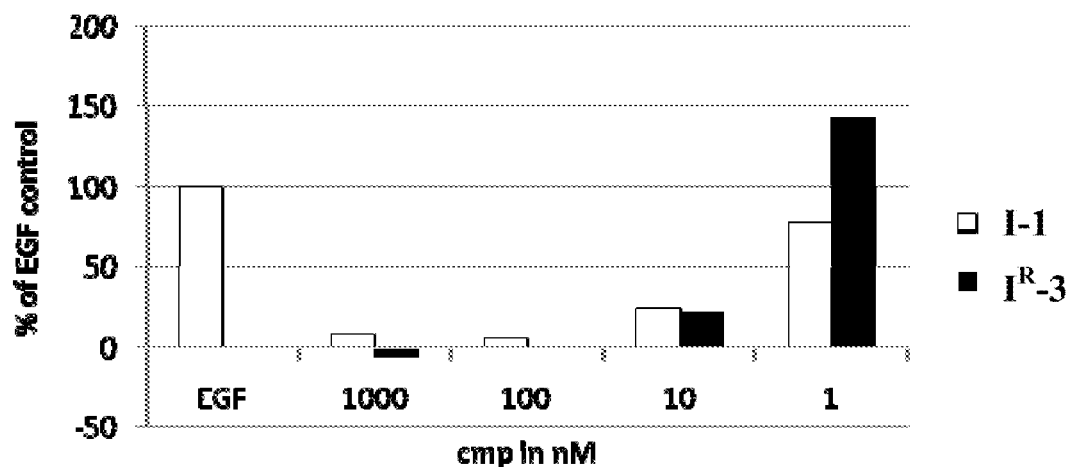
FIG. 5 depicts dose response inhibition of EGFR phosphorylation with compound I-1 in A431 cells as compared with its "reversible control" compound ($I^R$-3).

Dose response inhibition of EGFR phosphorylation and p42/p44 Erk phosphorylation with compound I-16 and I-17 in A431 cells is depicted in FIG. 3. Dose response inhibition of EGFR phosphorylation and p42/p44 Erk phosphorylation with compound I-19 in A431 cells is depicted in FIG. 4. Dose response inhibition of EGFR phosphorylation with compound I-1 in A431 cells, as compared with its "reversible control" compound ($I^R$-3), is depicted in FIG. 5.

Example 43

Washout Experiment for EGFR Activity

Figure 6:
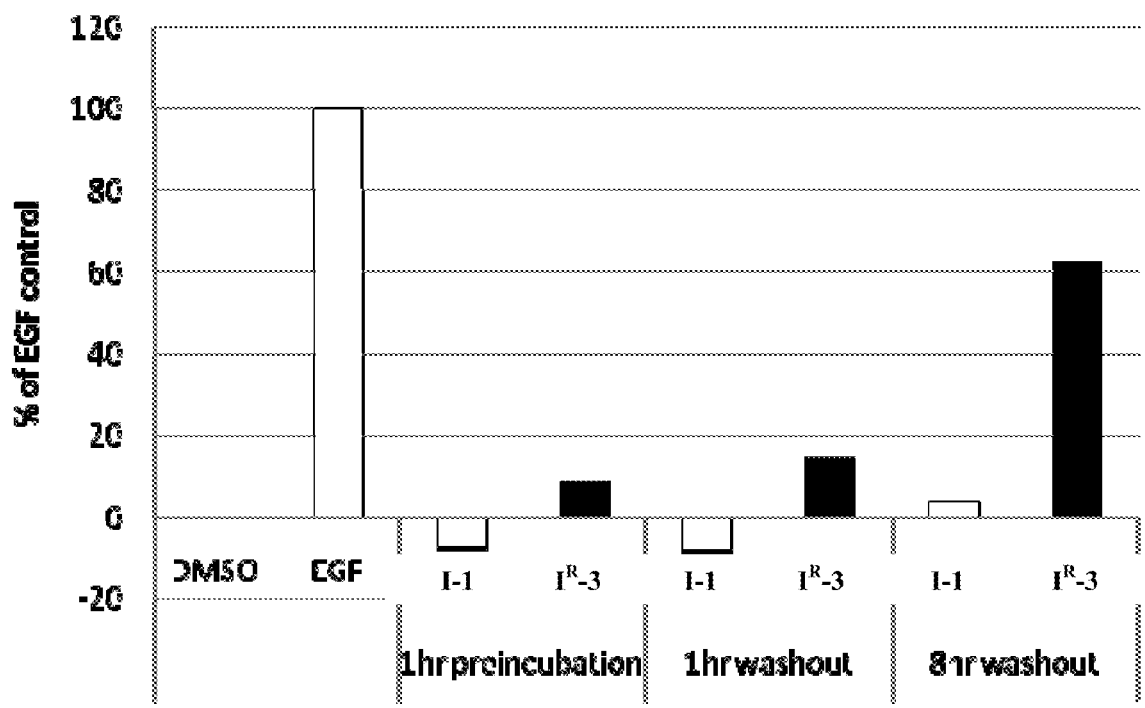
FIG. 6 depicts the results of compound I-1 in a "washout" experiment as compared with its "reversible control" compound ($I^R$-3).

A431 human epidermoid carcinoma cells were grown in 6-well plates to '90% confluence and then incubated in serum-free media for 18 hr. Duplicate sets of cells were treated with 1 µM designated compound for 1 hr. One set of cells was then stimulated with 100 ng/ml EGF for 5 min, and extracts were made as described. The other set of cells was washed free of the compound with warmed compound-free medium, incubated for 2 hr, washed again, incubated another 2 hr, washed again, and then incubated another 2 hr washed again and incubated for additional 2 hr and then stimulated with EGF. The results of this experiment are depicted in FIG. 6 where it is shown that compound I-1 maintains enzyme inhibition after "washout" whereas its "reversible control" compound ($I^R$-3) was washed away in the experiment thereby resulting in reactivated enzyme activity.

Example 44

Mass Spectrometry for ErbB4

ErbB4 kinase domain (Upstate) was incubated with compound for 90 minutes at 10-fold excess of compound I-1 to protein. 1 ul aliquots of the samples (total volume of 4.24 ul) were diluted with 10 ul of 0.1% TFA prior to micro C4 ZipTipping directly onto the MALDI target using Sinapinic acid as the desorption matrix (10 mg/ml in 0.1% TFA:Acetonitrile 50:50). For intact protein mass measurement the instrument was set in Linear mode using a pulsed extraction setting of 16,952 for the myoglobin standard used to calibrate the instrument (Shimadzu Axima $TOF^2$).

Figure 7:
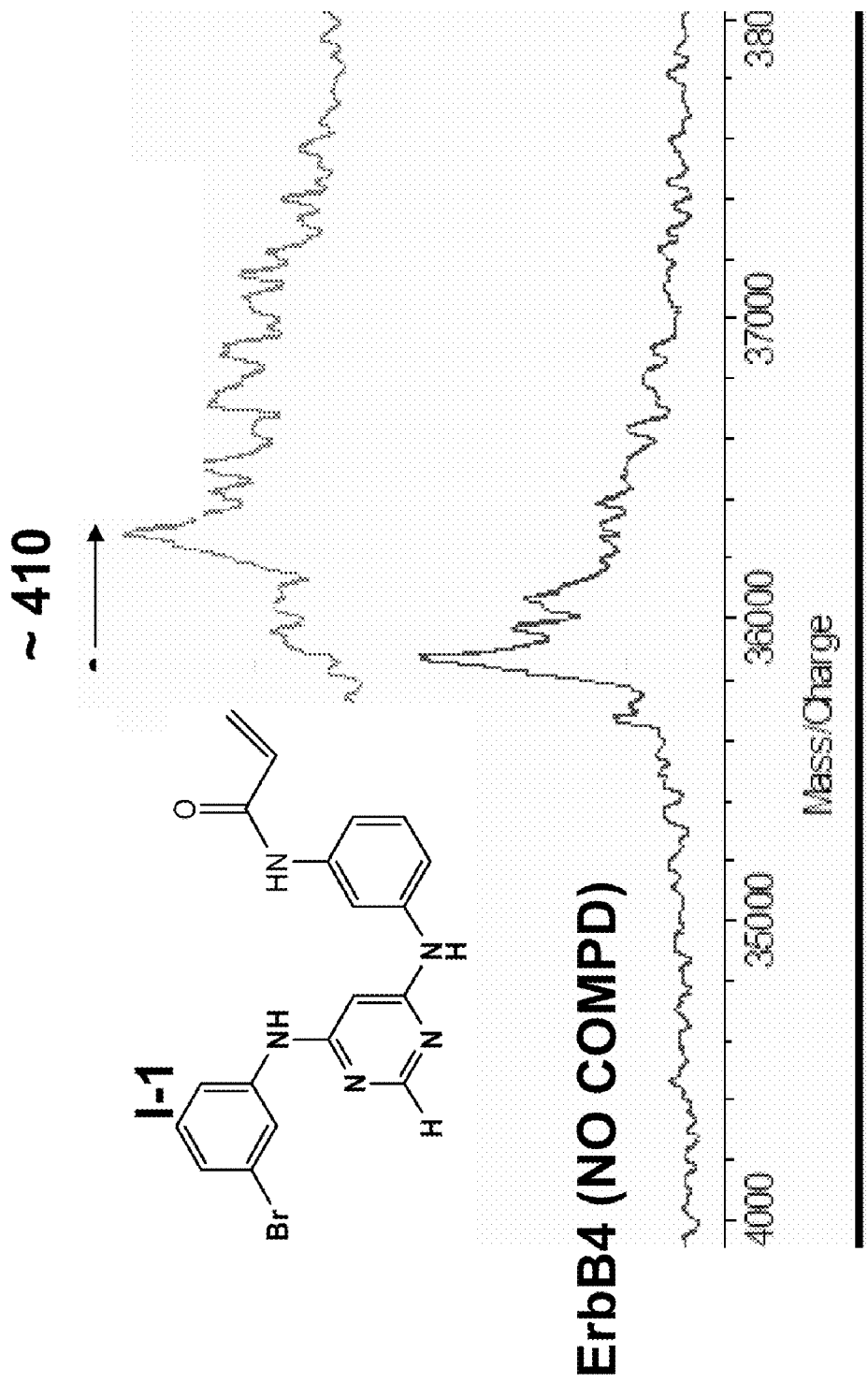
FIG. 7 depicts MS analysis confirming covalent modification of ErbB4 by compound I-1.

Intact ErbB4 protein occurs at MH+ of 35850 with corresponding sinapinic (matrix) adducts occurring about 200 Da higher. A stoichiometric incorporation of the compound I-1 (Mw of 410 Da) produced a new mass peak which is approximately 410 Da higher (MH+ of 36260). This is consistent with covalent modification of ErbB4 with compound I-1 as depicted in FIG. 7.

Example 45

ErbB1, ErbB2 and/or ErbB4 Kinase Inhibition

Compounds of the present invention were assayed as inhibitors of one or more of ErbB1, ErbB2, and/or ErbB4 in a manner substantially similar to the method described by Invitrogen Corp (Invitrogen Corporation, 1600 Faraday Avenue, Carlsbad, Calif., CA; http://www.invitrogen.com/downloads/Z-LYTE_Brochure_1205.pdf) using the Z'-LYTE™ biochemical assay procedure or similar biochemical assay. The Z'-LYTE™ biochemical assay employs a fluorescence-based, coupled-enzyme format and is based on the differential sensitivity of phosphorylated and non-phosphorylated peptides to proteolytic cleavage.

Example 46

Table 8 shows the activity of selected compounds of this invention in the ErbB inhibition assay. The compound numbers correspond to the compound numbers in Table 5.

TABLE 8

ErbB1, ErbB2, and/or ErbB4 Inhibition Data

| Compound # | ErbB1 % Inhibition | ErbB2 % Inhibition | ErbB4 % Inhibition |
|---|---|---|---|
| I-1 | 99% @ 10 nM | 76% @ 1 µM | 86% @ 1 µM |
|  |  | 61% @ 100 nM | 64% @ 100 nM |
| I-2 | 98% @ 100 nM | 96% @ 1 µM | 75% @ 1 µM |
|  | 75% @ 10 nM | 39% @ 100 nM |  |
| I-3 | 96% @ 100 nM | 89% @ 1 µM | 95% @ 1 µM |
|  | 56% @ 10 nM |  |  |
| I-4 | 100% @ 10 nM | 86% @ 1 µM | 78% @ 1 µM |
| I-5 | 100% @ 10 nM | 86% @ 1 µM | 95% @ 1 µM |
| I-6 | 100% @ 100 nM | 84% @ 1 µM | 97% @ 1 µM |
|  | 49% @ 10 nM |  |  |

TABLE 8-continued

ErbB1, ErbB2, and/or ErbB4 Inhibition Data

| Compound # | ErbB1 % Inhibition | ErbB2 % Inhibition | ErbB4 % Inhibition |
| --- | --- | --- | --- |
| I-7 | 100% @ 100 nM 53% @ 10 nM | 89% @ 1 μM | 100% @ 1 μM |
| I-8 | 83% @ 10 nM | — | 57% @ 1 μM |
| I-9 | 100% @ 1 μM | — | 75% @ 1 μM |
| I-10 | 96% @ 1 μM | — | — |
| I-11 | 79% @ 1 μM | — | — |
| I-12 | 82% @ 1 μM | — | — |
| I-13 | 92% @ 1 μM | 98% @ 1 μM | — |
| I-14 | 96% @ 1 μM | — | — |
| I-15 | 98% @ 1 μM | — | — |
| I-16 | 98% @ 1 μM | 87% @ 100 nM 24% @ 10 nM | 93% @ 100 nM 26% @ 10 nM |
| I-17 | 95% @ 1 μM | 89% @ 1 μM | 94% @ 1 μM |
| I-18 | — | 91% @ 1 μM | 94% @ 1 μM |
| I-19 | 96% @ 1 μM | 98% @ 1 μM | 97% @ 1 μM |

Example 47

Mass Spectrometry for TEC Kinase

TEC kinase (45 pmols; Invitrogen) was incubated with (I-13) (450 pmols) for 3 hrs at 10× access prior to tryptic digestion. Iodoacetamide was used as the alkylating agent after compound incubation. A control sample (45 pmols) was also prepared which did not have the addition of (I-13). For tryptic digests a 5 ul aliquot (7.5 pmols) was diluted with 15 ul of 0.1% TFA prior to micro C18 Zip Tipping directly onto the MALDI target using alpha cyano-4-hydroxy cinnamic acid as the matrix (5 mg/ml in 0.1% TFA:Acetonitrile 50:50).

Figure 11:
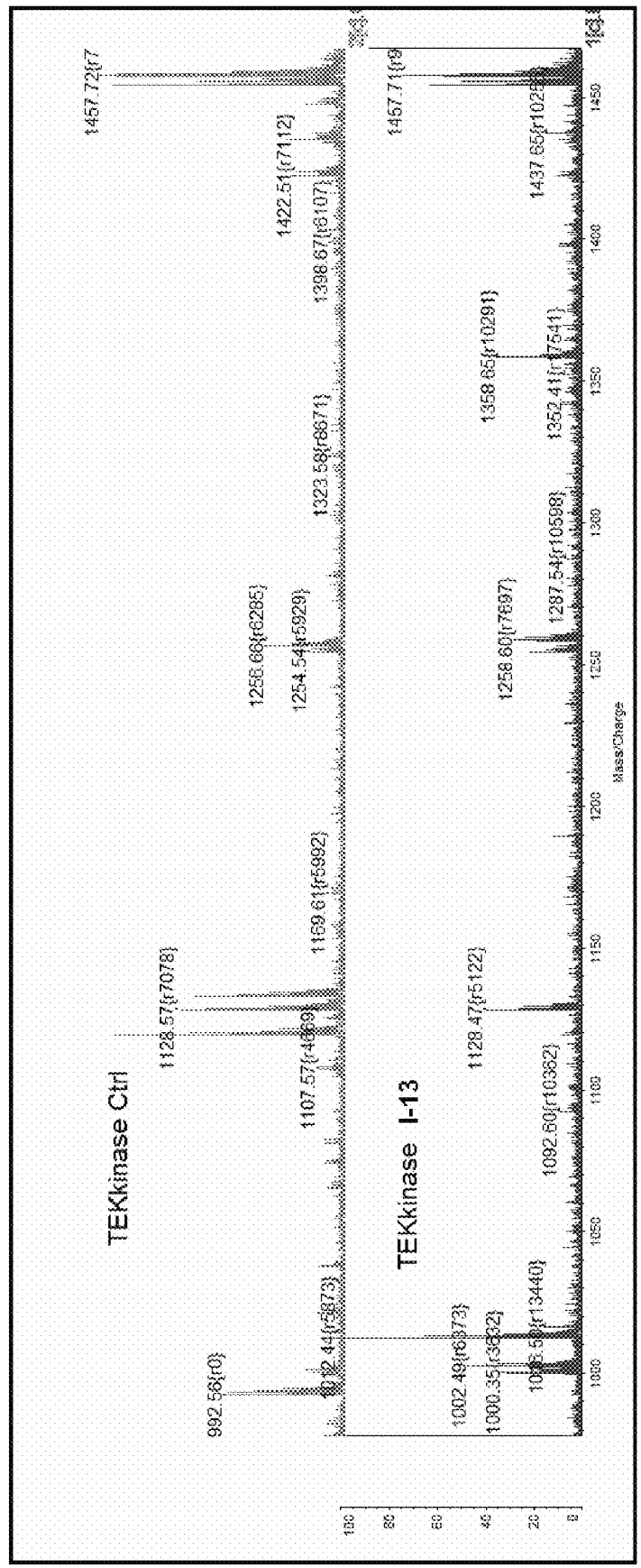
FIG. 11 depicts MS analysis of the tryptic digests confirming covalent modification of TEC kinase by compound I-13.

As depicted in FIG. 11, the expected peptide (G CLLNFLR) to be modified was immediately evident at MH+ of 1358.65. This is the mass to be expected when compound I-13, with an adduct mass of 423.17, is added to the peptide mass of 935.51. The peptide was also quite evident in the control sample as modified by Iodacetamide at MH+ of 992.56. Interestingly the Iodoacetamide modified peptide was not evident in the digest reacted with compound I-13 indicating that the reaction was complete. There was no evidence of any other modified peptides.

Evidence of compound I-13 was observed at MH+ of 424.20 in the low mass range of the spectra. The fragmentation spectra of the 424.20 peak did show many diagnostic fragments that were apparent in the PSD spectra of the modified peptide at 1358.65 (see FIG. 11).

To further verify the presence of the modified peptide with compound I-13, the peptide at MH+ of 1358.65 was subjected to PSD (MS/MS) analysis. A correlational analysis with the homosapien database identified the correct peptide modified by I-13.

Instrumental:

For tryptic digests the instrument was set in Reflectron mode with a pulsed extraction setting of 2200. Calibration was done using the Laser Biolabs Pep Mix standard (1046.54, 1296.69, 1672.92, 2093.09, 2465.20). For CID/PSD analysis the peptide was selected using cursors to set ion gate timing and fragmentation occurred at a laser power about 20% higher and He was used as the collision gas for CID. Calibration for fragments was done using the P14R fragmentation calibration for the Curved field Reflectron.

Example 48

Omnia Assay Protocol for Potency Assessment Against BTK

The Omnia Assay Protocol for potency assessment against BTK is performed in a substantially similar manner as that described in Example 25 above except that the modified BTK-optimized reagent conditions are:

[BTK]=5 nM, [ATP]=40 mM, [Y5–Sox]=10 mM
(ATP KMapp~36 mM).

Example 49

Table 9 shows the activity of selected compounds of this invention in the BTK inhibition assay. The compound numbers correspond to the compound numbers in Table 5. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50} \geq 10,000$ nM.

TABLE 9

BTK Inhibition Data

| Compound # | BTK Inhibition |
| --- | --- |
| I-1 | B |
| I-2 | B |
| I-3 | B |
| I-4 | A |
| I-5 | A |
| I-6 | C |
| I-7 | B |
| I-8 | E |
| I-9 | C |
| I-10 | C |
| I-11 | E |
| I-12 | E |
| I-13 | A |
| I-14 | C |
| I-15 | B |
| I-16 | B |
| I-17 | A |
| I-18 | B |
| I-19 | B |
| I-46 | C |
| I-47 | E |
| I-48 | B |
| I-49 | A |
| I-50 | D |
| I-51 | E |
| I-52 | A |
| I-53 | B |
| I-54 | C |
| I-55 | B |
| I-56 | B |
| I-57 | D |
| I-58 | D |
| I-59 | C |
| I-60 | D |
| I-61 | B |
| I-62 | A |
| I-63 | A |
| I-64 | A |
| I-65 | A |
| I-66 | A |
| I-67 | B |
| I-68 | B |
| I-69 | C |
| I-70 | C |
| I-71 | D |
| I-73 | A |

TABLE 9-continued

BTK Inhibition Data

| Compound # | BTK Inhibition |
|---|---|
| I-75 | A |
| I-78 | A |
| I-79 | A |
| I-80 | D |
| I-81 | A |
| I-82 | A |
| I-83 | B |
| I-84 | D |
| I-85 | B |
| I-86 | B |
| I-87 | E |
| I-88 | A |
| I-89 | A |
| I-90 | A |
| I-91 | A |
| I-92 | B |
| I-93 | D |
| I-94 | A |

Example 50

BTK Ramos Cellular Assay

Figure 9:
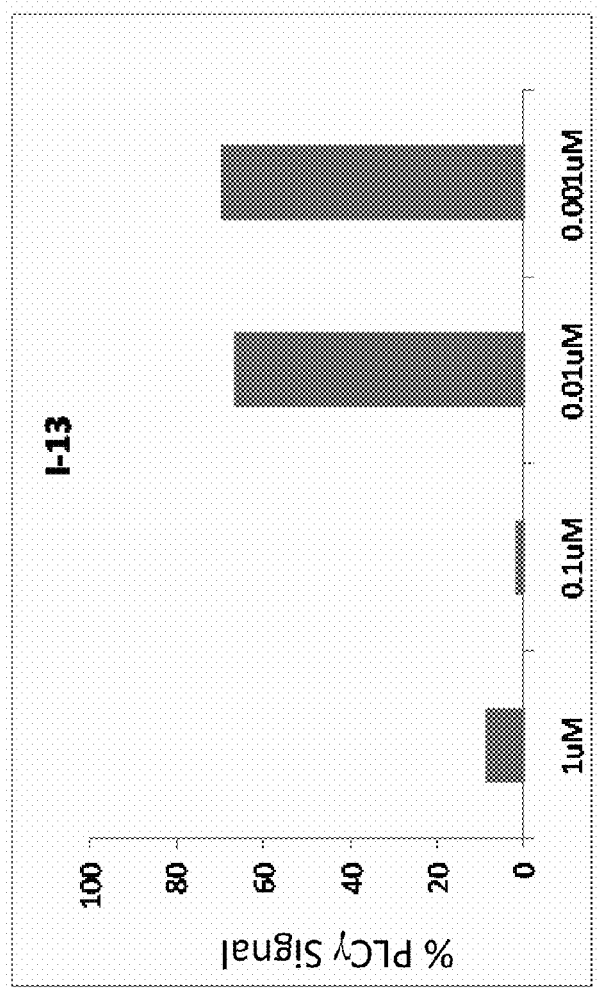
FIG. 9 depicts the inhibition of BTK signaling in Ramos cells by compound I-13.

Compounds I-13 and (I-52) were assayed in Ramos human Burkitt lymphoma cells. Ramos cells were grown in suspension in T225 flasks, spun down, resuspended in 50 mls serum-free media and incubated for 1 hour. Compound was added to Ramos cells in serum free media to a final concentration of 1, 0.1, 0.01, or 0.001 µM. Ramos cells were incubated with compound for 1 hour, washed again and resuspended in 100 ul serum-free media. Cells were then stimulated with 1 µg of goat F(ab')2 Anti-Human IgM and incubated on ice for 10 minutes to activate B cell receptor signaling pathways. After 10 minutes, the cells were washed once with PBS and then lysed on ice with Invitrogen Cell Extraction buffer. 16 µg total protein from lysates was loaded on gels and blots were probed for phosphorylation of the BTK substrate PLCγ2. At 1 µM I-13 showed 85% inhibition and (I-52) showed 50% inhibition of BTK signaling in Ramos cells. Additional dose response inhibition of BTK signaling with I-13 is depicted in FIG. 9.

Table 10 provides inhibition data for selected compounds in Ramos cells. The compound numbers correspond to the compound numbers in Table 5. Compounds having an activity designated as "A" provided an $IC_{50} \leq 10$ nM; compounds having an activity designated as "B" provided an $IC_{50}$ of 10-100 nM; compounds having an activity designated as "C" provided an $IC_{50}$ of 100-1000 nM; compounds having an activity designated as "D" provided an $IC_{50}$ of $\geq 1000$ nM.

TABLE 10

BTK Ramos Cellular Inhibition Data

| Compound # | BTK Inhibition (nM) |
|---|---|
| I-5 | C |
| I-13 | B |
| I-17 | D |
| I-63 | A |
| I-64 | B |
| I-65 | A |
| I-66 | A |
| I-78 | A |
| I-79 | A |
| I-81 | A |
| I-82 | A |

Example 51

Washout Experiment with Ramos Cells for BTK Activity

Figure 10:
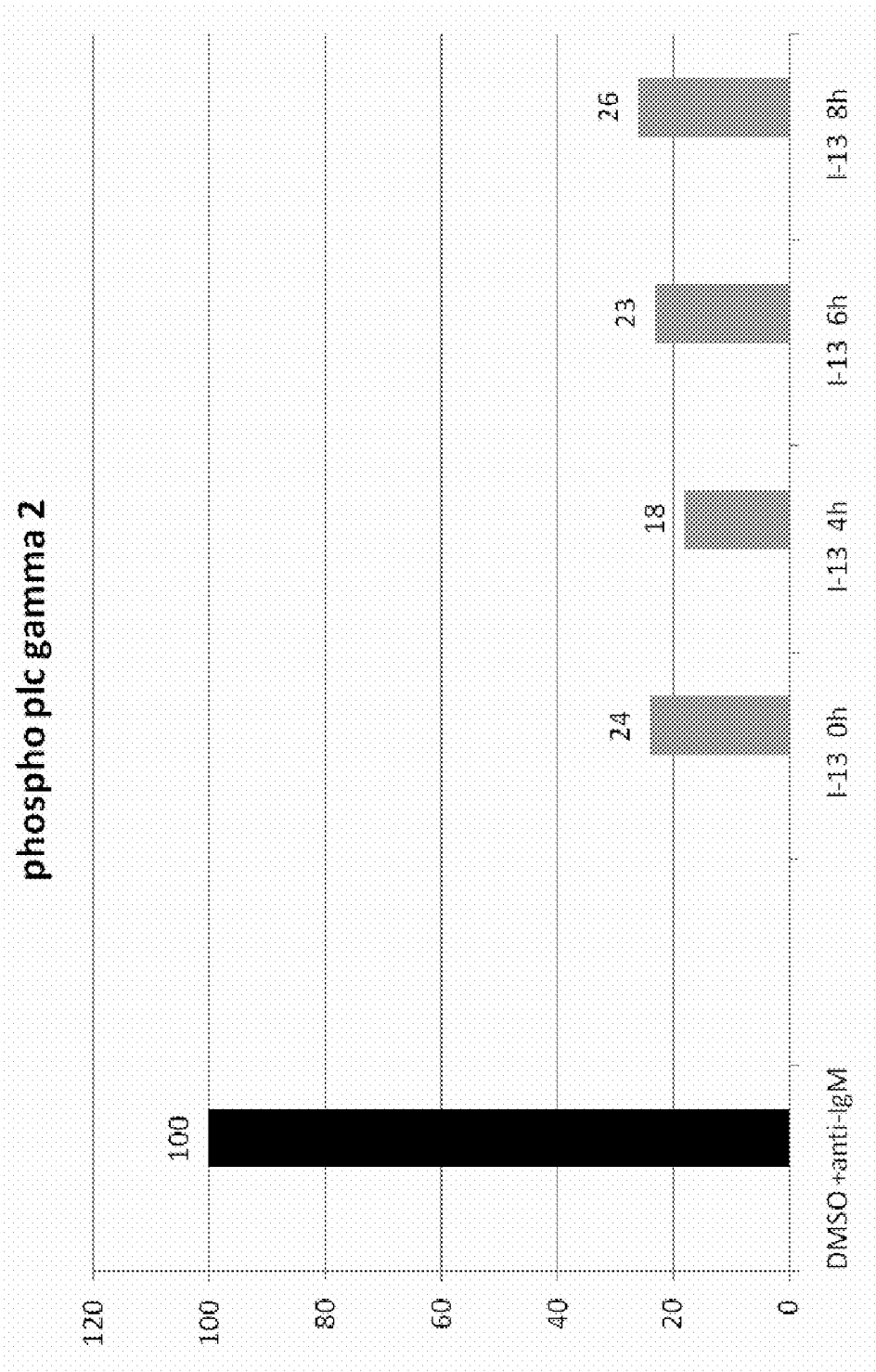
FIG. 10 depicts the results of compound I-13 in a "washout" experiment with BTK in Ramos cells.

Ramos cells were serum starved for one hour in RPMI media +1% glutamine at 37° C. After starvation, Ramos cells were treated with 100 nM compound diluted in serum free RPMI media for 1 hour. After compound treatment, the media was removed and cells were washed with compound-free media. Subsequently, Ramos cells were washed every 2 hours and resuspended in fresh compound-free media. Cells were collected at specified timepoints, treated with 1 ug anti-human IgM (Southern Biotech cat #2022-01) for 10 minutes on ice to induce BCR signaling and then washed in PBS. Ramos cells were then lysed in Cell Extraction Buffer (Invitrogen FNN0011) supplemented with Roche complete protease inhibitor tablets (Roche 11697498001) and phosphatase inhibitors (Roche 04 906 837 001) and 18 ug total protein lysate was loaded in each lane. Inhibition of Btk kinase activity was assayed by measuring its substrate (PLCγ2) phosphorylation by western blot with phospho-specific antibodies from Cell Signaling Technologies cat#3871. FIG. 10 depicts the results of compound I-13 in the washout experiment at 0 hour, 4 hour, 6 hour, and 8 hour time points. As shown in FIG. 10, compound I-13 maintains inhibition of BTK for 8 hours.

Table 11 provides data for selected compounds in the Ramos washout assay.

TABLE 11

BTK Washout Data

| Compound # | BTK Inhibition Type |
|---|---|
| I-13 | irreversible |
| I-63 | irreversible |
| I-64 | irreversible |
| I-65 | reversible |
| I-66 | irreversible |
| I-82 | irreversible |

Example 52

Mass Spectrometry for BTK

Figure 12:
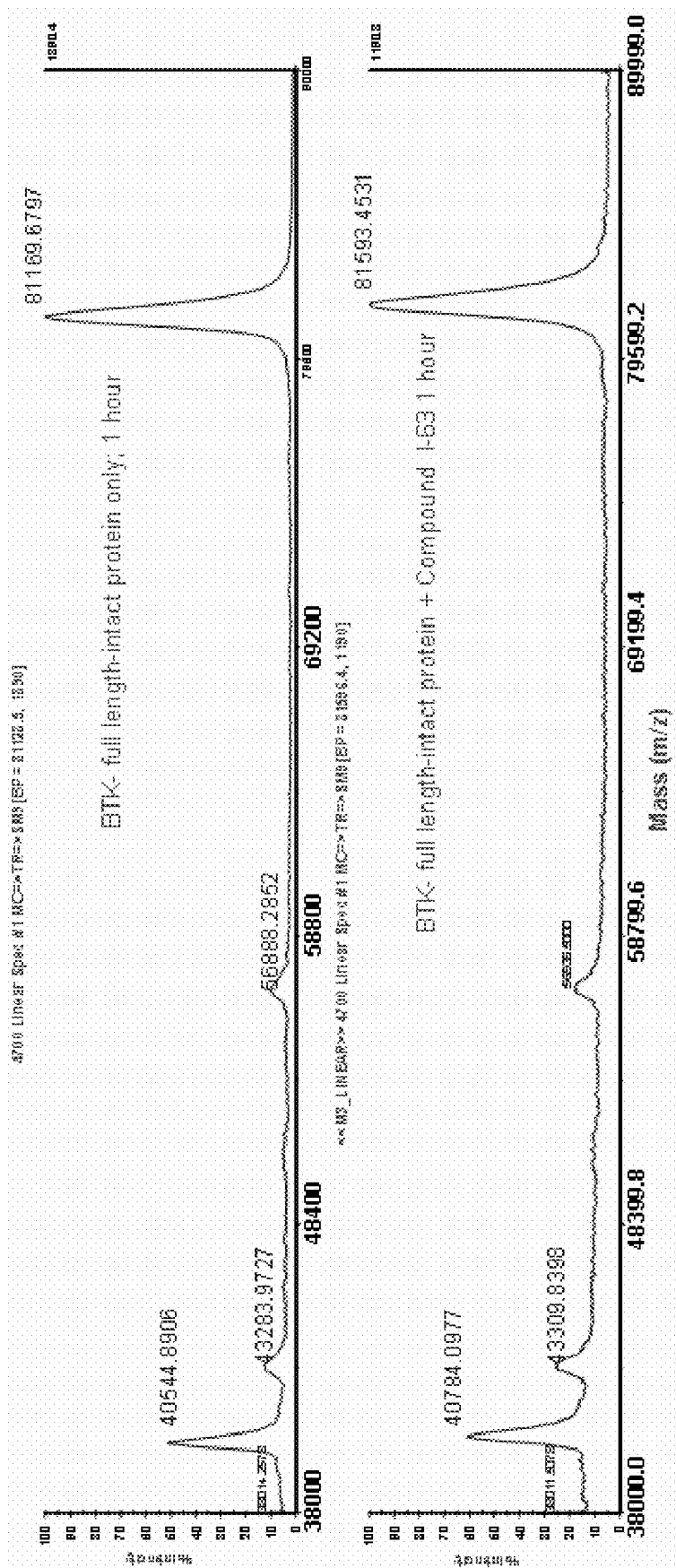
FIG. 12 depicts MS analysis confirming covalent modification of BTK by compound I-63.
Figure 13:
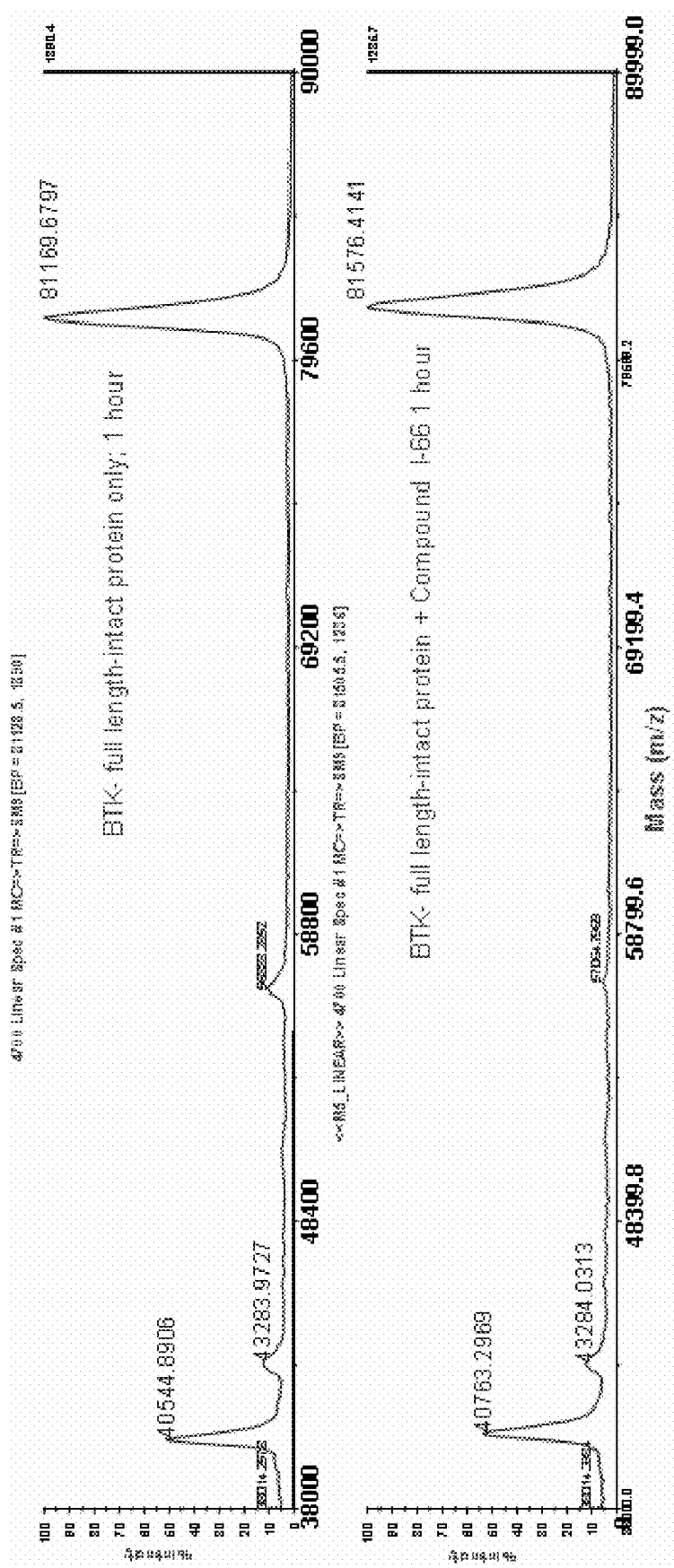
FIG. 13 depicts MS analysis confirming covalent modification of BTK by compound I-66.

Intact BTK was incubated for 1 hr at a 10× fold excess of compound I-63 or I-66 to protein. Aliquots (2 ul) of the samples were diluted with 10 ul of 0.1% TFA prior to micro C4 ZipTipping directly onto the MALDI target using Sinapinic acid as the desorption matrix (10 mg/ml in 0.1% TFA: Acetonitrile 20:80). Mass spectrometry traces are shown in FIG. 12 and FIG. 13. The top panels of FIGS. 12 and 13 show the mass spec trace of the intact BTK protein (m/z 81,169 Da). The bottom panels show the mass spec trace when BTK was incubated with compound I-63 (mw 424.5) or compound I-66 (mw 425.5) in FIGS. 12 and 13, respectively. The centroid mass (m/z 81,593 kDa) in the bottom panel of FIG. 12 shows a positive shift of about 424 Da, indicating complete modification of BTK by compound I-63. The centroid mass (m/z 81,593 kDa) in the bottom panel of FIG. 13 shows a positive shift of about 407 Da, indicating complete modification of BTK by compound I-66.

Example 53

Omnia Assay Protocol for Potency Assessment Against Active Forms of ITK Kinase

This example describes continuous-read kinase assays to measure inherent potency of compound against active forms of ITK enzymes as described in Example 10 above except that the modified ITK-optimized reagent conditions are:

[ITK]=10 nM, [ATP]=25 µM, [Y6–Sox]=10 µM (ATP $K_{Mapp}$=33 µM).

Example 54

Table 12 shows the activity of selected compounds of this invention in the ITK inhibition assay. The compound numbers correspond to the compound numbers in Table 5. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50} \geq 10,000$ nM.

TABLE 12

ITK Inhibition Data

| Compound # | ITK inhibition |
| --- | --- |
| I-10 | E |
| I-13 | D |
| I-14 | D |
| I-15 | D |
| I-63 | D |
| I-64 | B |
| I-65 | B |
| I-66 | D |
| I-78 | B |
| I-79 | A |
| I-81 | B |
| I-88 | B |
| I-89 | C |
| I-90 | C |
| I-94 | B |

Example 55

Omnia Assay Protocol for Potency Assessment Against Active Forms of BMX Kinase

This example describes continuous-read kinase assays to measure inherent potency of compound against active forms of BMX enzymes as described in Example 10 above except that the modified BMX-optimized reagent conditions are:

[BMX]=2.5 nM, [ATP]=100 µM, [Y5–Sox]=7.5 µM (ATP $K_{Mapp}$=107 µM).

Example 56

Table 13 shows the activity of selected compounds of this invention in the BMX inhibition assay. The compound numbers correspond to the compound numbers in Table 5. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50} \geq 10,000$ nM.

TABLE 13

BMX Inhibition Data

| Compound # | BMX inhibition |
| --- | --- |
| I-10 | — |
| I-13 | A |
| I-14 | — |
| I-15 | — |
| I-63 | A |
| I-64 | B |
| I-65 | A |
| I-66 | A |
| I-78 | B |
| I-79 | A |
| I-81 | A |
| I-94 | A |

Example 57

Omnia Assay Protocol for Potency Assessment Against the Active Form of Janus-3 Kinase (JAK3)

The Omnia Assay Protocol for potency assessment against JAK3 is performed in a substantially similar manner as that described in Example 25 above except that the modified JAK3-optimized reagent conditions are:

[JAK3]=5 nM, [ATP]=5 µM, [Y12–Sox]=5 µM (ATP KMapp~5 µM).

Example 58

Table 14 shows the activity of selected compounds of this invention in the JAK3 inhibition assay. The compound numbers correspond to the compound numbers in Table 5. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50}$ of 100-1000 nM; compounds having an activity designated as "D" provided an $IC_{50}$ of 1000-10,000 nM; and compounds having an activity designated as "E" provided an $IC_{50} \geq 10,000$ nM.

TABLE 14

JAK3 Inhibition Data

| Compound # | JAK3 Inhibition |
| --- | --- |
| I-1 | A |
| I-2 | A |
| I-3 | A |
| I-4 | A |
| I-5 | A |
| I-6 | D |
| I-7 | C |
| I-8 | D |
| I-9 | C |
| I-10 | C |
| I-11 | E |
| I-12 | E |
| I-13 | C |
| I-14 | A |
| I-15 | B |
| I-16 | B |
| I-17 | B |
| I-18 | B |
| I-19 | C |
| I-46 | D |
| I-47 | E |
| I-48 | E |
| I-49 | A |
| I-50 | C |

TABLE 14-continued

JAK3 Inhibition Data

| Compound # | JAK3 Inhibition |
|---|---|
| I-51 | E |
| I-52 | A |
| I-53 | C |
| I-54 | D |
| I-55 | B |
| I-56 | B |
| I-57 | E |
| I-58 | C |
| I-59 | D |
| I-60 | D |
| I-61 | B |
| I-62 | C |
| I-63 | B |
| I-64 | A |
| I-65 | A |
| I-66 | C |
| I-67 | A |
| I-68 | A |
| I-69 | C |
| I-70 | C |
| I-71 | D |
| I-73 | A |
| I-75 | C |
| I-78 | A |
| I-79 | A |
| I-80 | E |
| I-81 | A |
| I-82 | B |
| I-83 | B |
| I-84 | E |
| I-85 | D |
| I-86 | E |
| I-92 | B |
| I-93 | E |
| I-94 | A |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

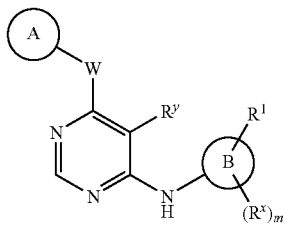

or a pharmaceutically acceptable salt thereof, wherein:

Ring A is an optionally substituted group selected from phenyl, an 8-10 membered bicyclic partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is phenyl, a 5-6 membered heteroaryl ring having 1-3 heteratoms independently selected from N, O or S, a 5-6 membered saturated heterocyclic ring having 1-2 heteroatoms independently selected from N, O or S, or an 8-10 membered bicyclic partially unsaturated or aryl ring having 1-3 heteroatoms independently selected from N, O or S;

$R^1$ is -L-Y, wherein:

L is a bivalent $C_{2-8}$ straight or branched, hydrocarbon chain wherein L has at least one double bond and one or two additional methylene units of L are optionally and independently replaced by —NRC(O)—, —C(O)NR—, —N(R)SO$_2$—, —SO$_2$N(R)—, —S—, —S(O)—, —SO$_2$—, —OC(O)—, —C(O)O—, cyclopropylene, —O—, —N(R)—, or —C(O)—; and Y is hydrogen, $C_{1-6}$ aliphatic optionally substituted with oxo, halogen, NO$_2$, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 $R^e$ groups; and each $R^e$ is independently selected from -Q-Z, oxo, NO$_2$, halogen, CN, or $C_{1-6}$ aliphatic optionally substituted with oxo, halogen, NO$_2$, or CN, or a suitable leaving group selected from alkoxy, sulphonyloxy, optionally substituted alkylsulphonyloxy, optionally substituted alkenylsulfonyloxy, optionally substituted arylsulfonyloxy, acyl, diazonium, Q is a covalent bond or a bivalent $C_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO$_2$—, —N(R)C(O)—, —C(O)N(R)—, —N(R)SO$_2$—, or —SO$_2$N(R)—; and Z is hydrogen or $C_{1-6}$ aliphatic optionally substituted with oxo, halogen, NO$_2$, or CN;

$R^y$ is hydrogen, halogen, CN, lower alkyl, or lower haloalkyl;

W is a bivalent $C_{1-3}$ alkylene chain wherein one methylene unit of W is optionally replaced by —NR$^2$—, —N(R$^2$)C(O)—, —C(O)N(R$^2$)—, —N(R$^2$)SO$_2$—, —SO$_2$N(R$^2$)—, —O—, —C(O)—, —OC(O)—, —C(O)O—, —S—, —SO— or —SO$_2$—;

$R^2$ is hydrogen or optionally substituted $C_{1-6}$ aliphatic;

m is 0-4;

each $R^x$ is independently selected from —R, halogen, —OR, —CN, —NO$_2$, —SO$_2$R, —SOR, —C(O)R, —CO$_2$R, —C(O)N(R)$_2$, —NRC(O)R, —NRC(O)NR$_2$, —NRSO$_2$R, or —N(R)$_2$; or:

$R^x$ and $R^1$ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or $C_{1-6}$ aliphatic; and each R group is independently hydrogen or an optionally substituted group selected from $C_{1-6}$ aliphatic, phenyl, a 4-7 membered heterocylic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

2. The compound according to claim 1, wherein:

L is a bivalent $C_{2-8}$ straight or branched, hydrocarbon chain wherein L has at least one double bond and at least one methylene unit of L is replaced by —C(O)—, —NRC(O)—, —C(O)NR—, —N(R)SO$_2$—, —SO$_2$N(R)—, —S—, —S(O)—, —SO₂—, —OC(O)—, or —C(O)
O—, and one or two additional methylene units of L are
optionally and independently replaced by cyclopropylene, —O—, —N(R)—, or —C(O)—; and Y is hydrogen or C$_{1-6}$ aliphatic optionally substituted with oxo, halogen, NO₂, or CN.

3. The compound according to claim 2, wherein L is a bivalent C$_{2-8}$ straight or branched, hydrocarbon chain wherein L has at least one double bond and at least one methylene unit of L is replaced by —C(O)—, and one or two additional methylene units of L are optionally and independently replaced by cyclopropylene, —O—, —N(R)—, or —C(O)—.

4. The compound according to claim 2, wherein L is a bivalent C$_{2-8}$ straight or branched, hydrocarbon chain wherein L has at least one double bond and at least one methylene unit of L is replaced by —C(O)—.

5. The compound according to claim 2, wherein L is —NRC(O)CH=CH—, —NRC(O)CH=CHCH₂N(CH₃)—, —NRC(O)CH=CHCH₂O—, —CH₂NRC(O)CH=CH—, —NRSO₂CH=CH—, —NRSO₂CH=CHCH₂—, —NRC(O)CH=CHCH₂N(CH₃)—, —NRSO₂CH=CH—, —NRSO₂CH=CHCH₂—, —NRC(O)CH=CHCH₂O—, —NRC(O)C(=CH₂)CH₂—, or —CH₂NRC(O)CH=CH—; wherein R is H or optionally substituted C$_{1-6}$ aliphatic; and Y is hydrogen or C$_{1-6}$ aliphatic optionally substituted with oxo, halogen, NO₂, or CN.

6. The compound according to claim 5, wherein L is —NHC(O)CH=CH—, —NHC(O)CH=CHCH₂N(CH₃)—, —NHC(O)CH=CHCH₂O—, —CH₂NHC(O)CH=CH—, —NHSO₂CH=CH—, —NHSO₂CH=CHCH₂—, —NHC(O)CH=CHCH₂N(CH₃)—, —NHSO₂CH=CH—, —NHSO₂CH=CHCH₂—, —NHC(O)CH=CHCH₂O—, —NHC(O)C(=CH₂)CH₂—, or —CH₂NHC(O)CH=CH—.

7. The compound according to claim 2, wherein L is a bivalent C$_{2-8}$ straight or branched, hydrocarbon chain wherein L has at least one alkylidenyl double bond and at least one methylene unit of L is replaced by —C(O)—, —NRC(O)—, —C(O)NR—, —N(R)SO₂—, —SO₂N(R)—, —S—, —S(O)—, —SO₂—, —OC(O)—, or —C(O)O—, and one or two additional methylene units of L are optionally and independently replaced by cyclopropylene, —O—, —N(R)—, or —C(O)—.

8. A compound of formula I:

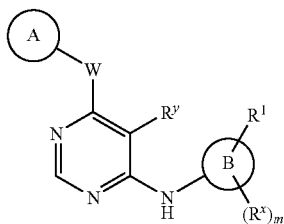

I or a pharmaceutically acceptable salt thereof, wherein:
Ring A is an optionally substituted group selected from phenyl, an 8-10 membered bicyclic partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

Ring B is phenyl, a 5-6 membered heteroaryl ring having 1-3 heteroatoms independently selected from N, O or S, a 5-6 membered saturated heterocyclic ring having 1-2 heteroatoms independently selected from N, O or S, or an 8-10 membered bicyclic partially unsaturated or aryl ring having 1-3 heteroatoms independently selected from N, O or S;

R¹ is -L-Y, wherein:
L is a bivalent C$_{2-8}$ straight or branched, hydrocarbon chain wherein L has at least one triple bond and one or two additional methylene units of L are optionally and independently replaced by —NRC(O)—, —C(O)NR—, —N(R)SO₂—, —SO₂N(R)—, —S—, —S(O)—, —SO₂—, —OC(O)—, or —C(O)O—; and Y is hydrogen, C$_{1-6}$ aliphatic optionally substituted with oxo, halogen, NO₂, or CN, or a 3-10 membered monocyclic or bicyclic, saturated, partially unsaturated, or aryl ring having 0-3 heteroatoms independently selected from nitrogen, oxygen, or sulfur, and wherein said ring is substituted with 1-4 R$^e$ groups; and each R$^e$ is independently selected from -Q-Z, oxo, NO₂, halogen, CN, a suitable leaving group selected from alkoxy, sulphonyloxy, optionally substituted alkylsulphonyloxy, optionally substituted alkenylsulfonyloxy, optionally substituted arylsulfonyloxy, acyl, diazonium, or C$_{1-6}$ aliphatic optionally substituted with oxo, halogen, NO₂, or CN, wherein:

Q is a covalent bond or a bivalent C$_{1-6}$ saturated or unsaturated, straight or branched, hydrocarbon chain, wherein one or two methylene units of Q are optionally and independently replaced by —N(R)—, —S—, —O—, —C(O)—, —OC(O)—, —C(O)O—, —SO—, or —SO₂—, —N(R)C(O)—, —C(O)N(R)—, —N(R)SO₂—, or —SO₂N(R)—; and Z is hydrogen or C$_{1-6}$ aliphatic optionally substituted with oxo, halogen, NO₂, or CN;

R$^y$ is hydrogen, halogen, CN, lower alkyl, or lower haloalkyl;

W is a bivalent C$_{1-3}$ alkylene chain wherein one methylene unit of W is optionally replaced by —NR²—, —N(R²)C(O)—, —C(O)N(R²)—, —N(R²)SO₂—, —SO₂N(R²)—, —O—, —C(O)—, —OC(O)—, —C(O)O—, —S—, —SO— or —SO₂—;

R² is hydrogen or optionally substituted C$_{1-6}$ aliphatic;

m is 0-4;

each R$^x$ is independently selected from —R, halogen, —OR, —CN, —NO₂, —SO₂R, —SOR, —C(O)R, —CO₂R, —C(O)N(R)₂, —NRC(O)R, —NRC(O)NR₂, —NRSO₂R, or —N(R)₂; or:

R$^x$ and R¹ are taken together with their intervening atoms to form a 5-7 membered saturated, partially unsaturated, or aryl ring having 0-3 heteroatoms independently selected from nitrogen, oxygen, or sulfur, wherein said ring is substituted with a warhead group and 0-3 groups independently selected from oxo, halogen, CN, or C$_{1-6}$ aliphatic; and each R group is independently hydrogen or an optionally substituted group selected from C$_{1-6}$ aliphatic, phenyl, a 4-7 membered heterocyclic ring having 1-2 heteroatoms independently selected from nitrogen, oxygen, or sulfur, or a 5-6 membered monocyclic heteroaryl ring having 1-4 heteroatoms independently selected from nitrogen, oxygen, or sulfur.

9. The compound according to claim 8, wherein Y is hydrogen or $C_{1-6}$ aliphatic optionally substituted with oxo, halogen, $NO_2$, or CN.
10. The compound according to claim 9, wherein L is —C≡C—, —C≡CCH₂N(isopropyl)—, —NHC(O)C≡CCH₂CH₂—, —CH₂—C≡C—CH₂—, —C≡CCH₂O—, —CH₂C(O)C≡C—, —C(O)C≡C—, or —CH₂OC(=O)C≡C—.
11. A compound selected from the group consisting of:
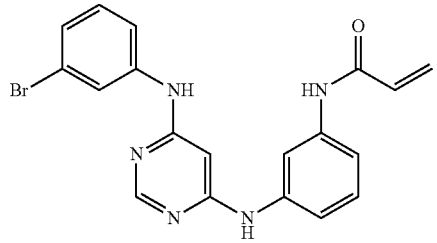
I-1
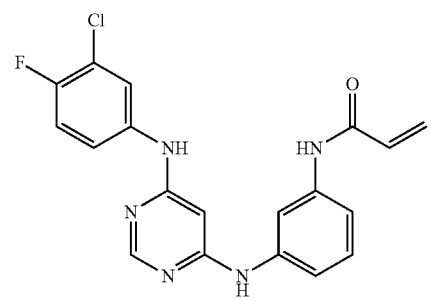
I-2
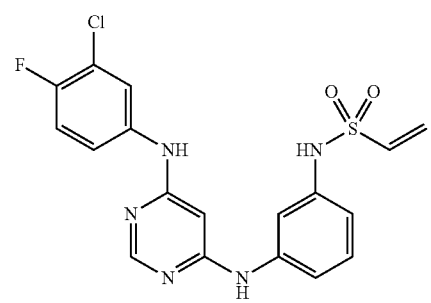
I-3
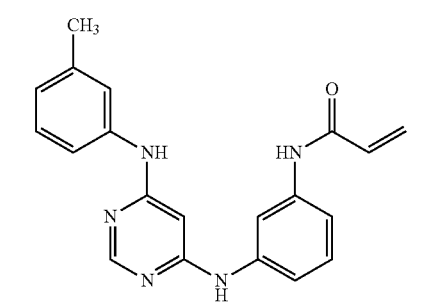
I-4
-continued
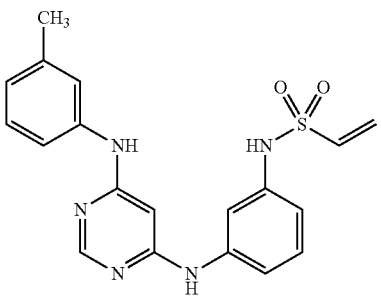
I-5
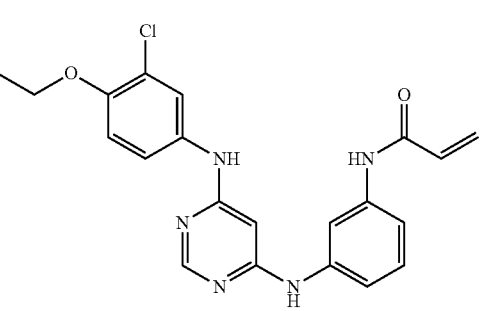
I-6
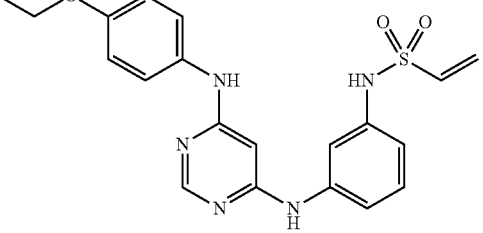
I-7
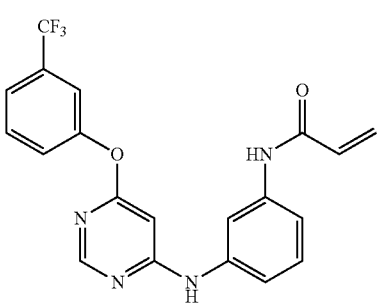
I-8
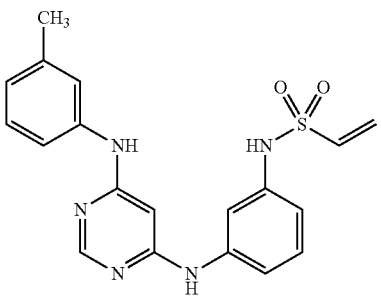
I-9

I-10
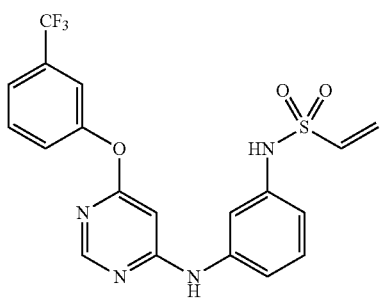
I-11
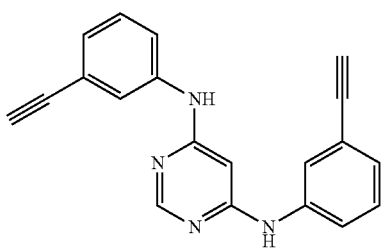
I-12
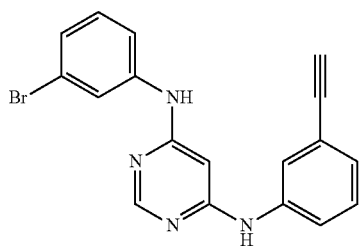
I-13
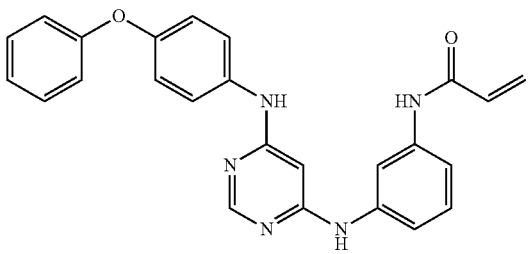
I-15
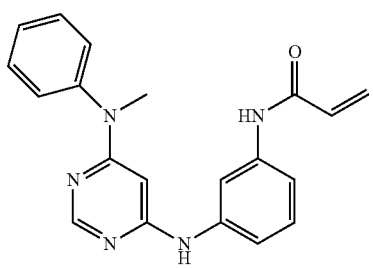
I-16
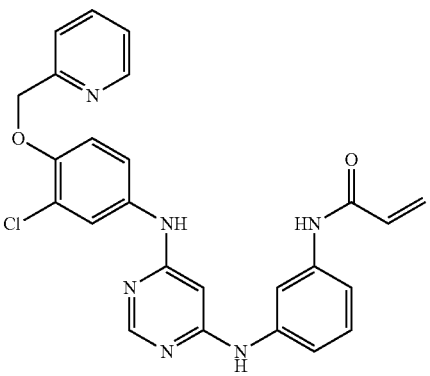
I-17
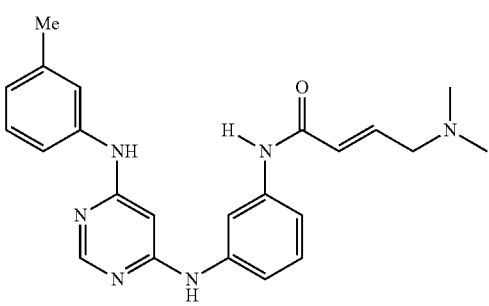
I-18
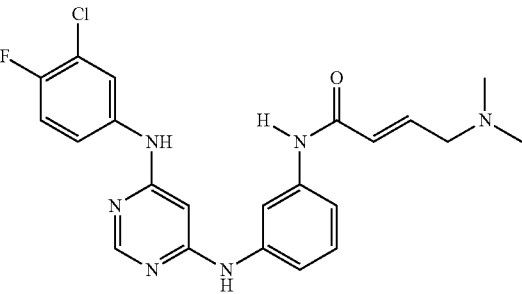
I-19
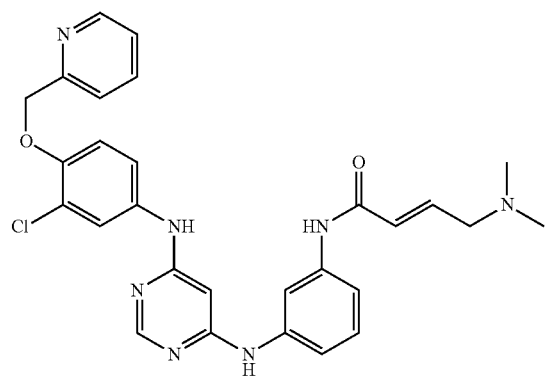

I-20
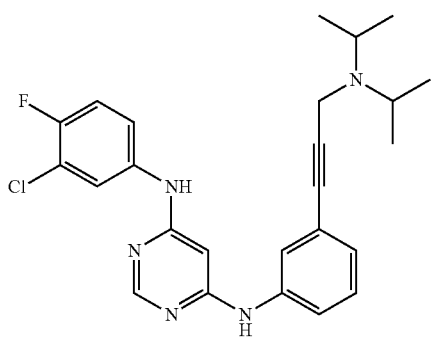
I-24
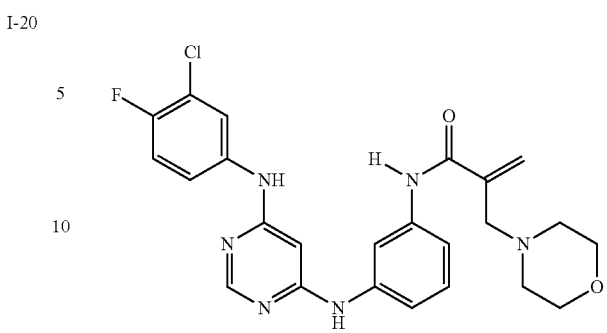
I-21
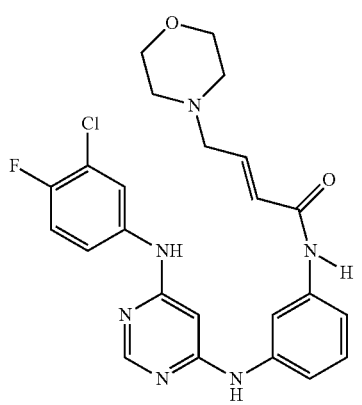
I-25
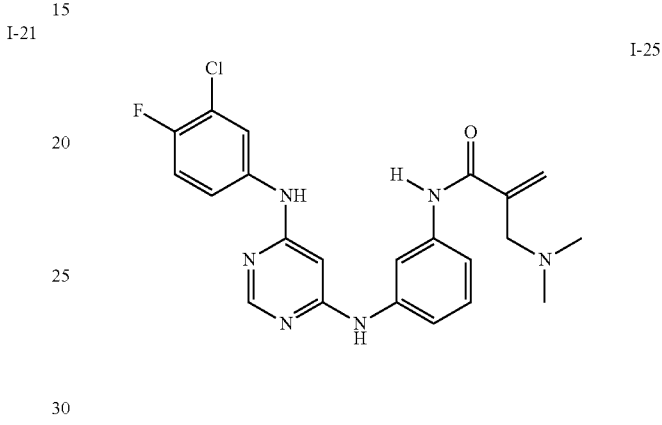
I-22
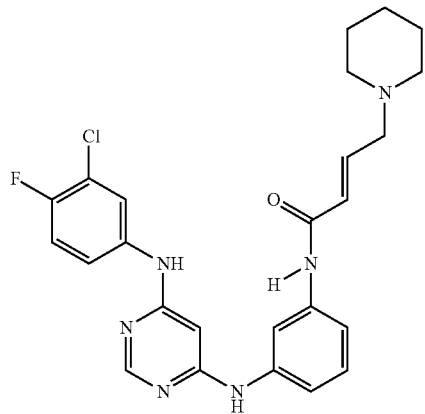
I-26
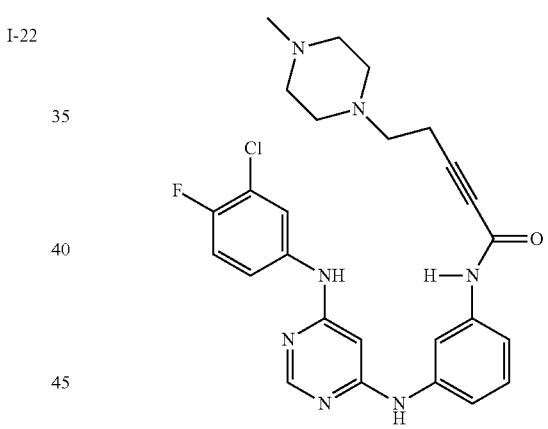
I-23
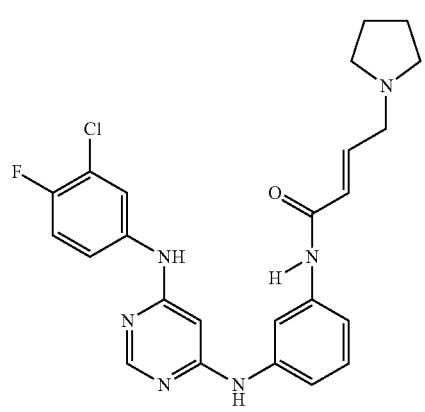
I-27
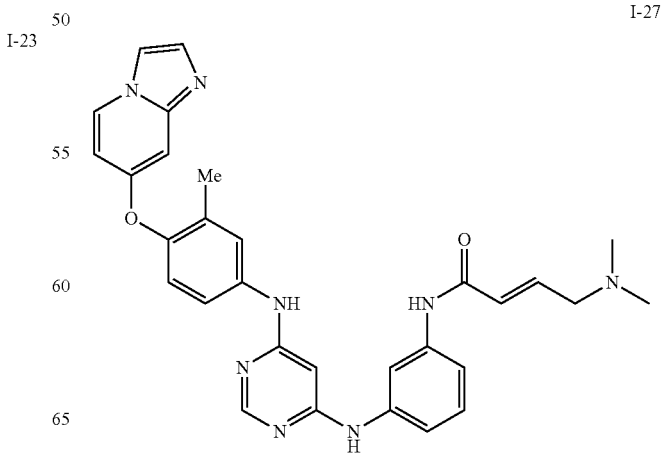

I-28
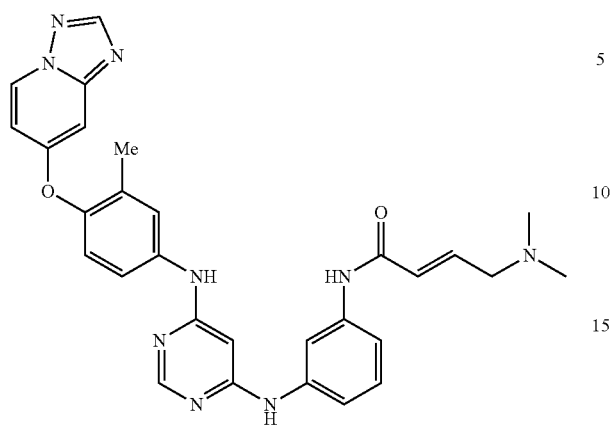
I-32
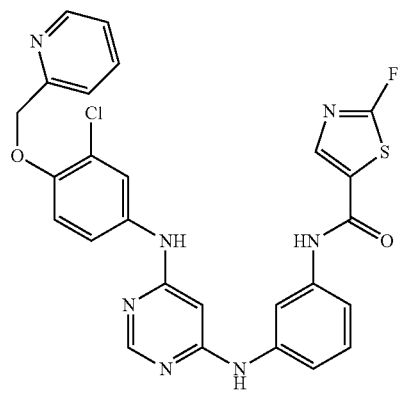
I-29
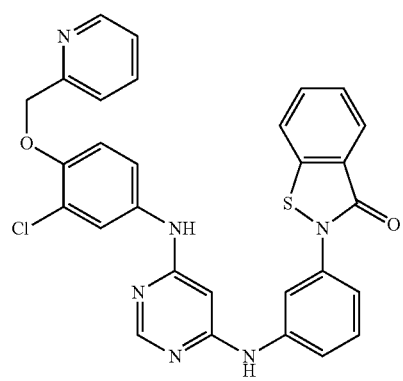
I-33
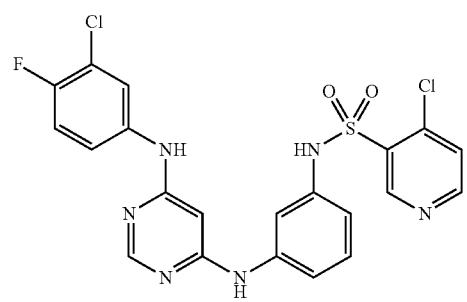
I-30
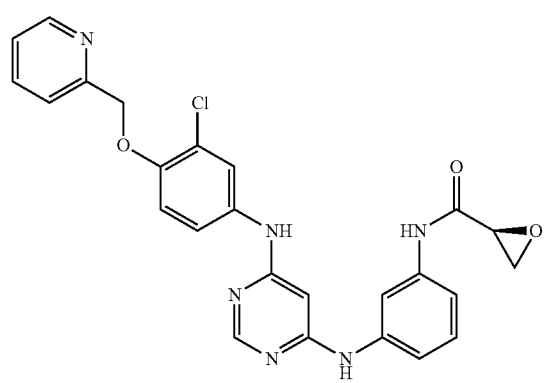
I-34
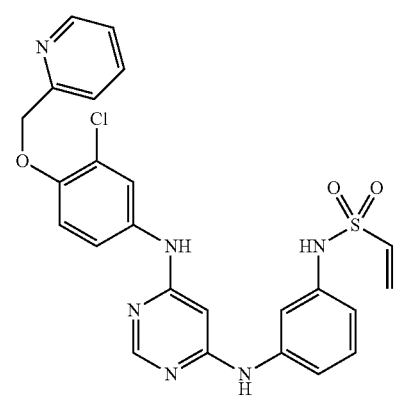
I-31
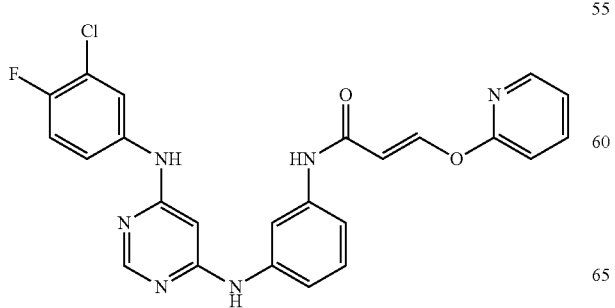
I-35
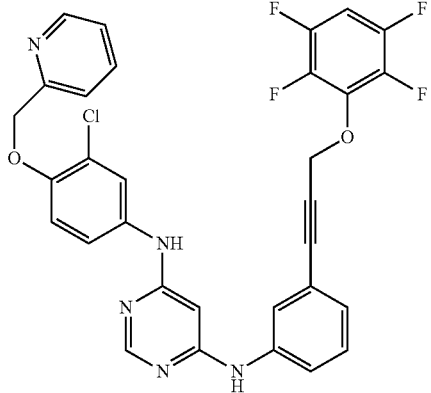

I-36 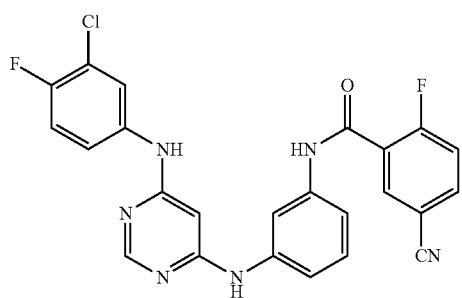
I-41 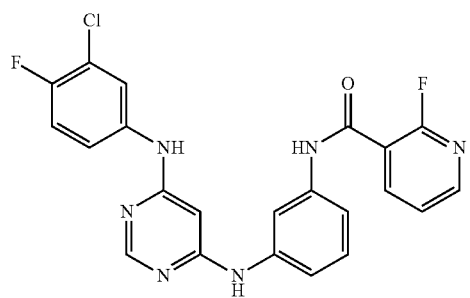
I-37 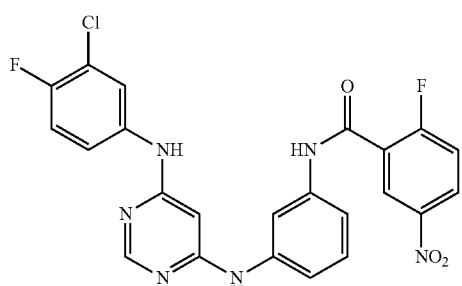
I-42 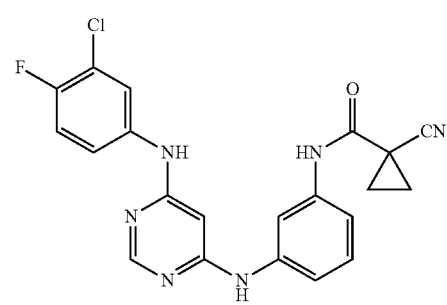
I-38 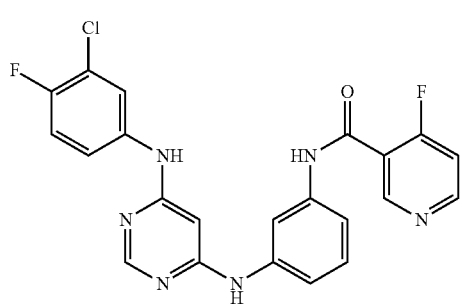
I-43 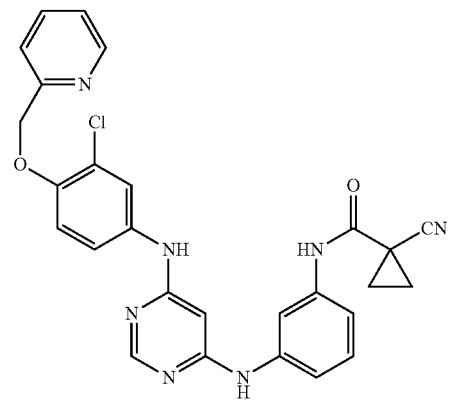
I-39 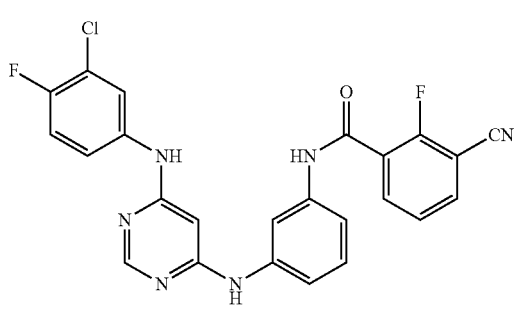
I-40 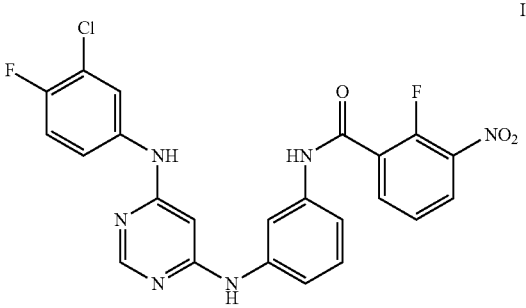
I-44 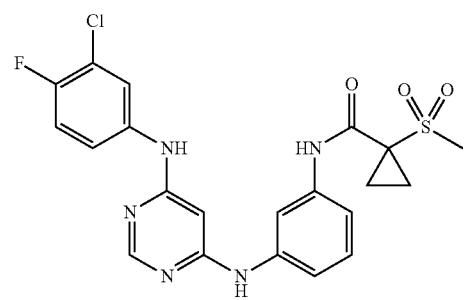

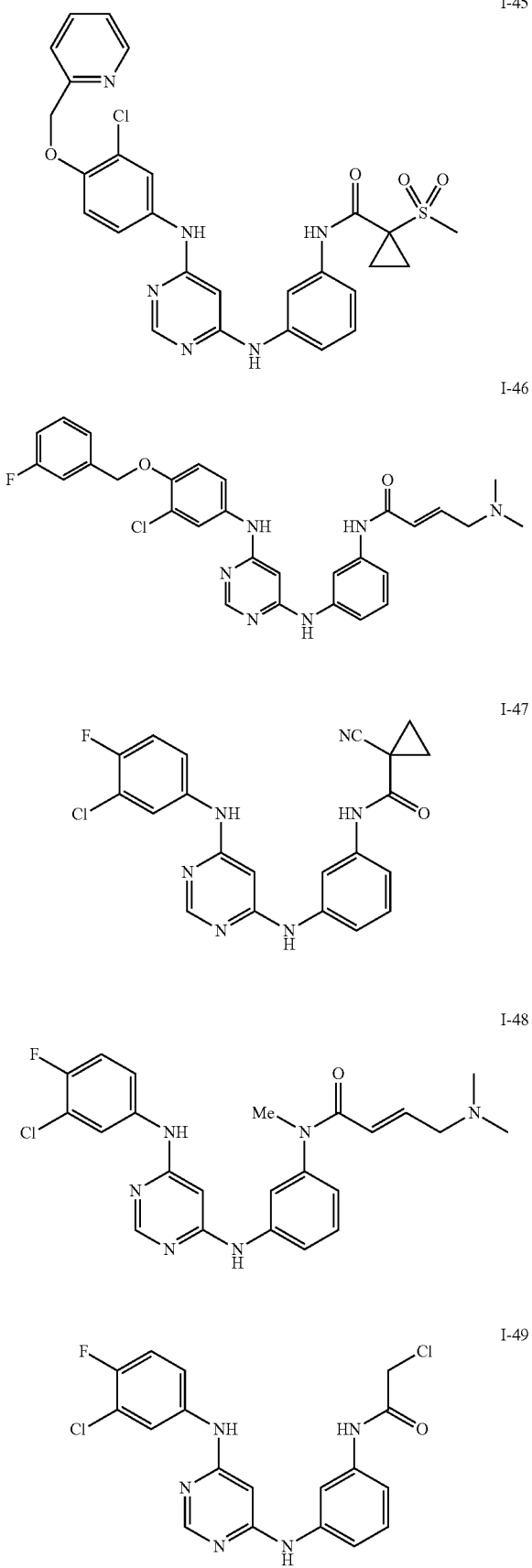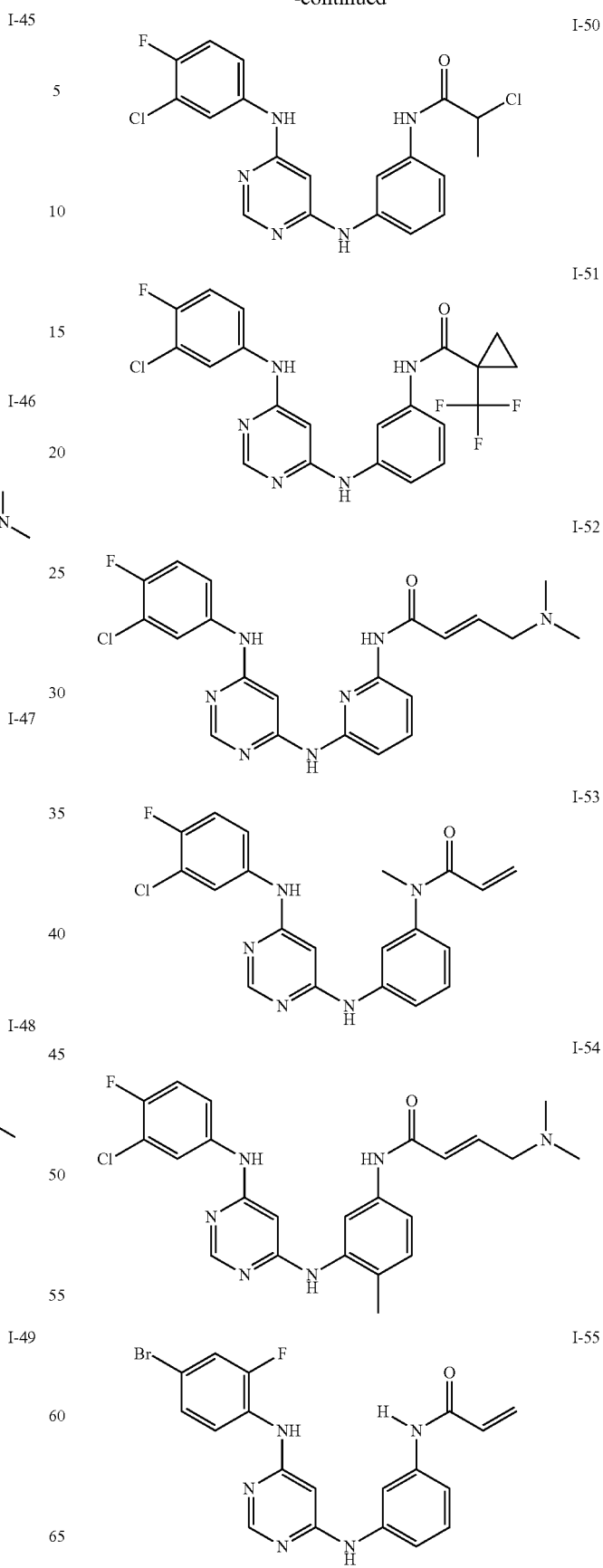

I-56
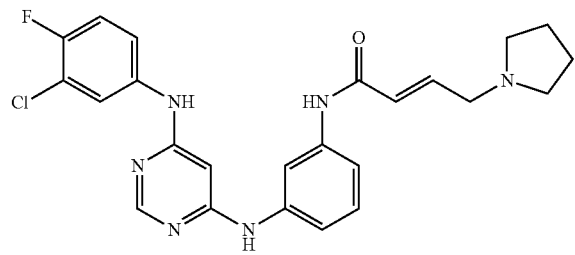
I-57
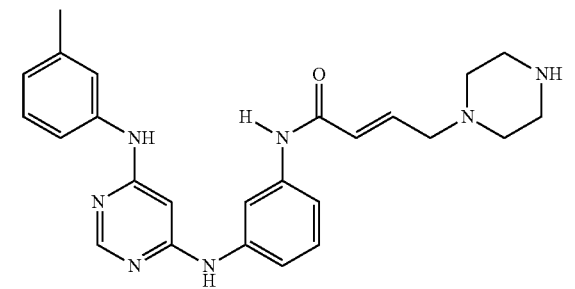
I-58
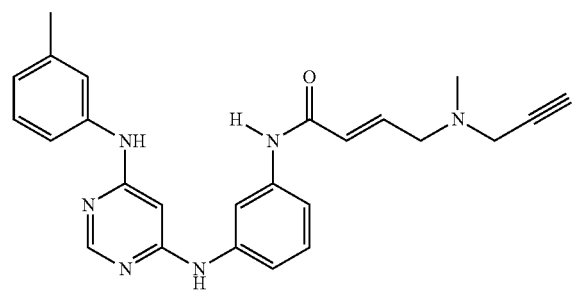
I-59
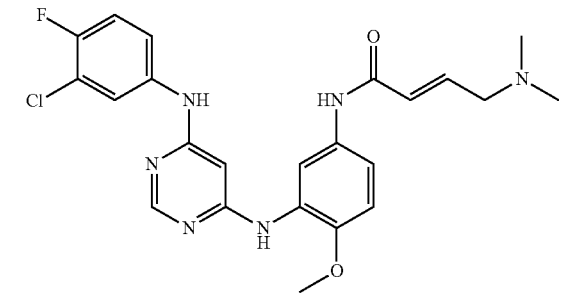
I-60
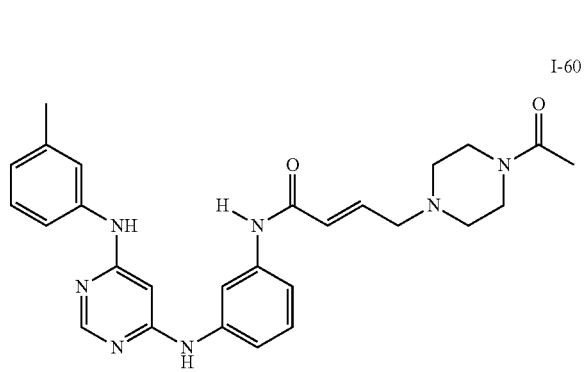
I-61
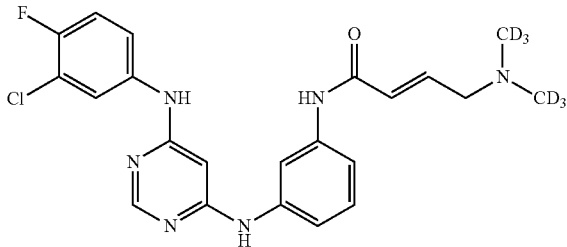
I-62
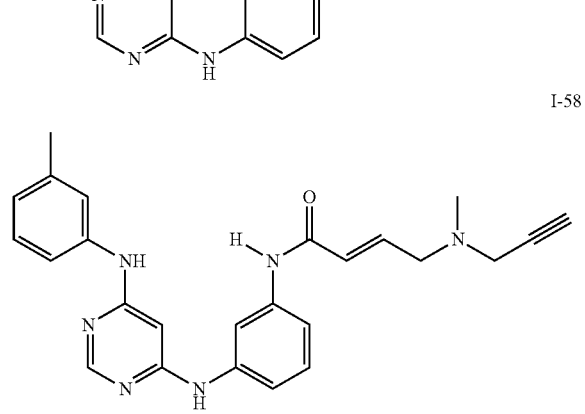
I-63
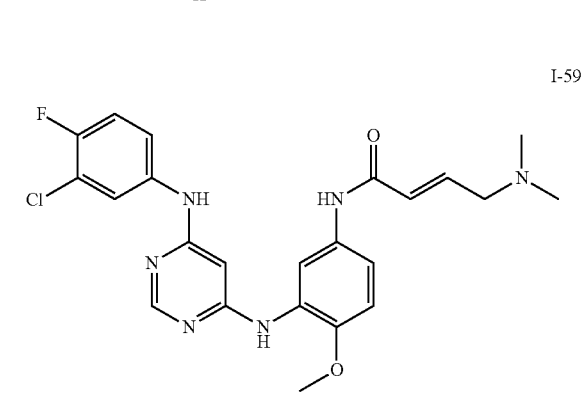
I-64
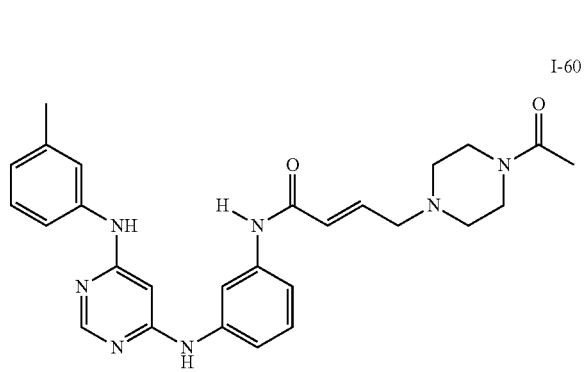

I-65 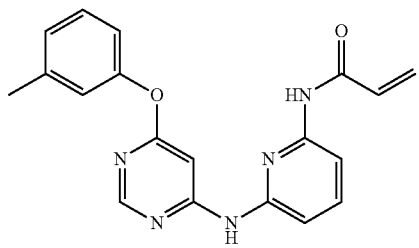
I-66 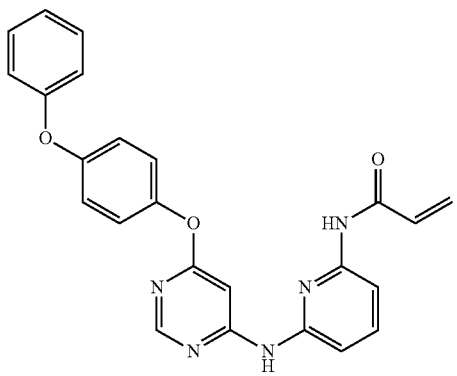
I-67 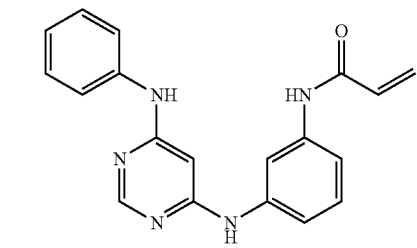
I-68 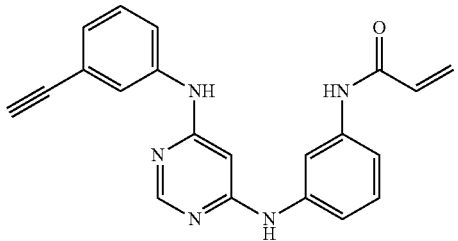
I-69 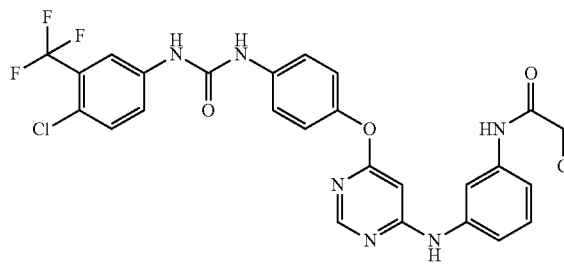
I-70 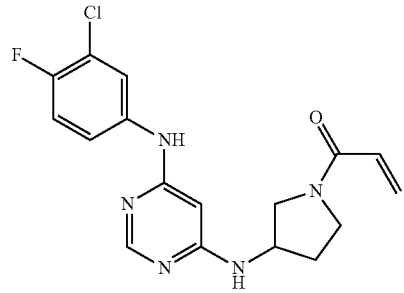
I-71 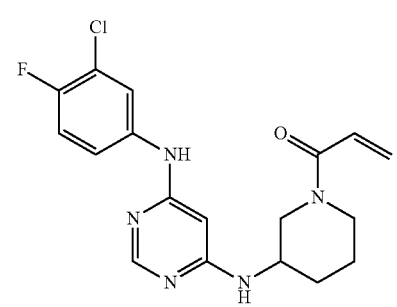
I-72 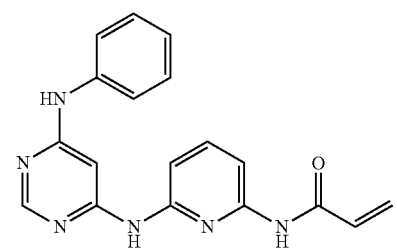
I-73 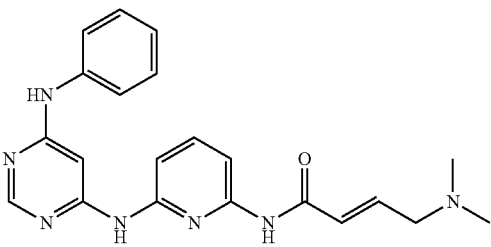
I-74 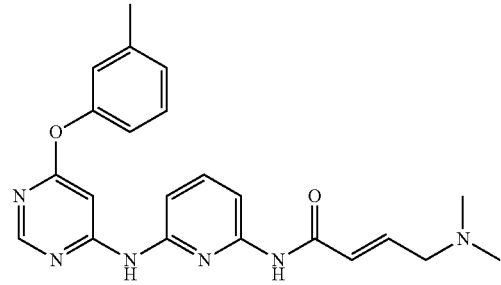

I-75 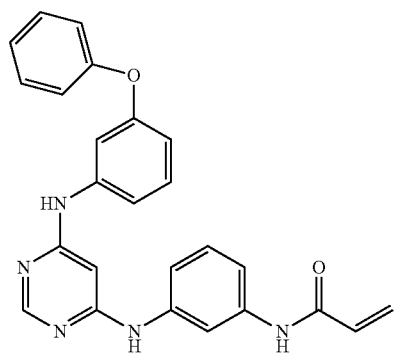
I-76 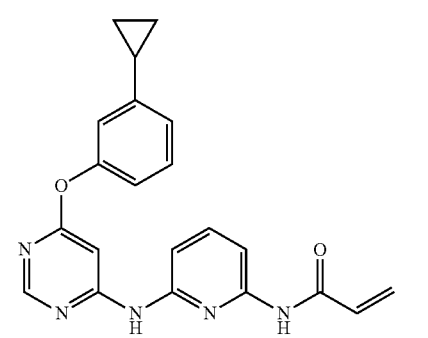
I-77 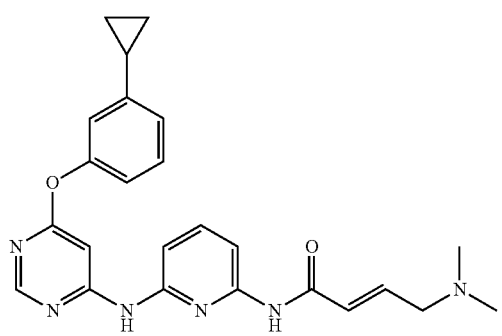
I-78 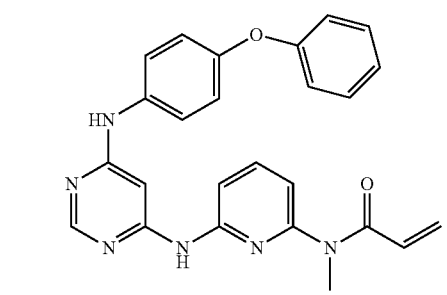
I-79 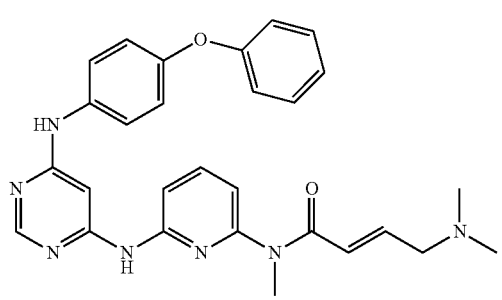
I-80 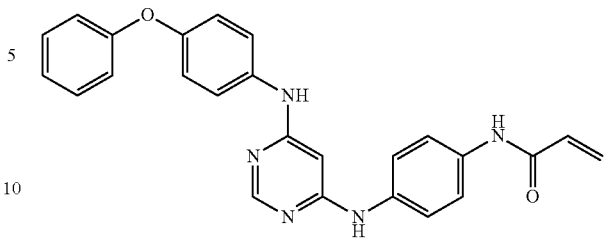
I-81 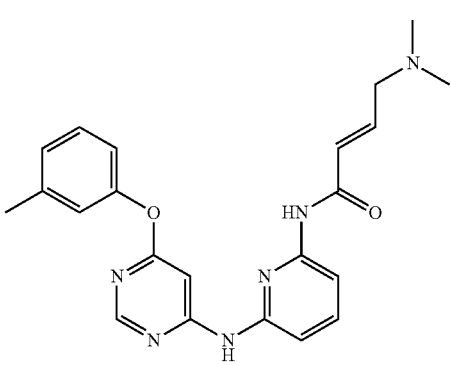
I-82 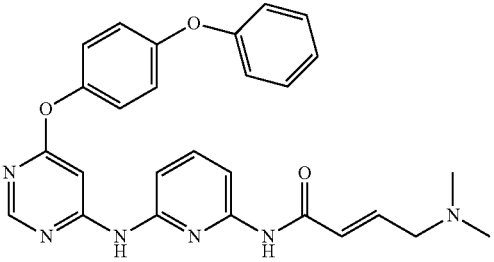
I-83 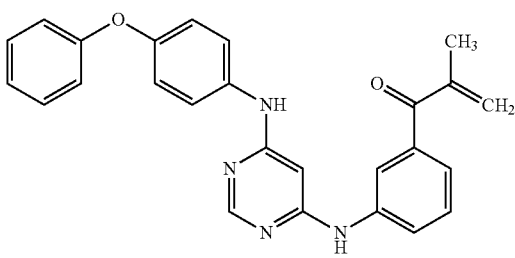
I-84 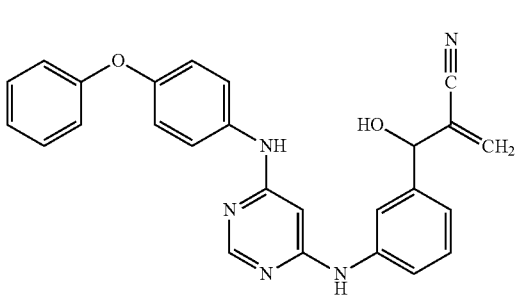

I-85
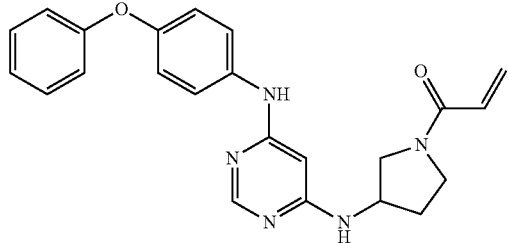
I-86
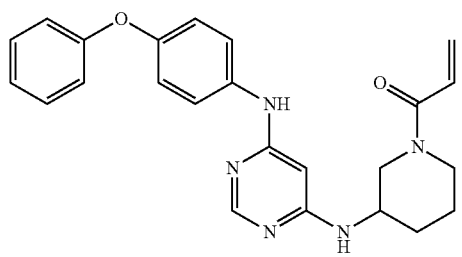
I-87
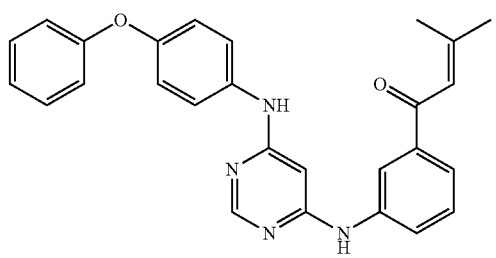
I-88
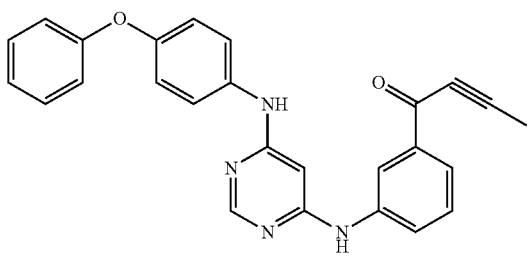
I-89
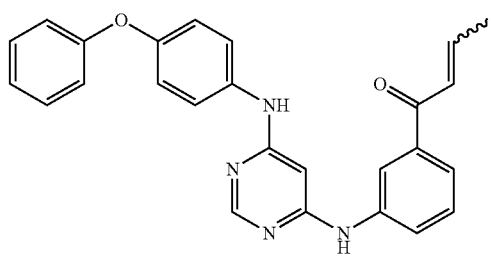
I-90
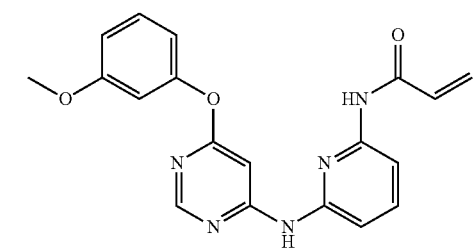
I-91
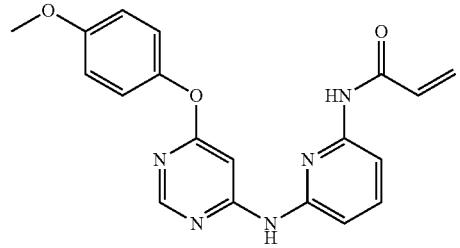
I-92
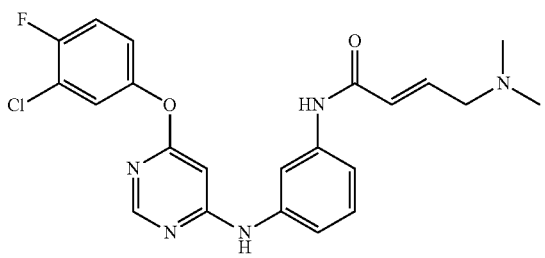
I-93
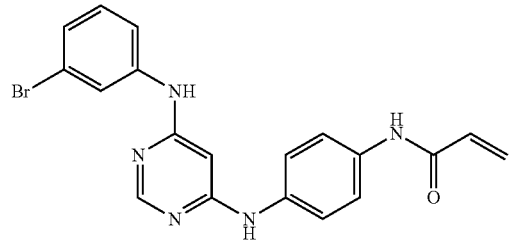
I-94
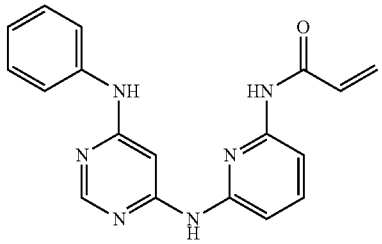
I-95
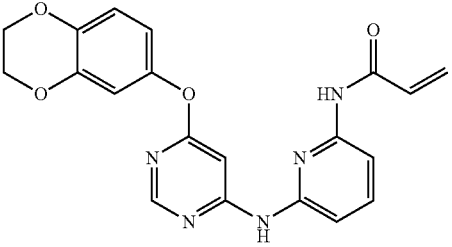
I-96
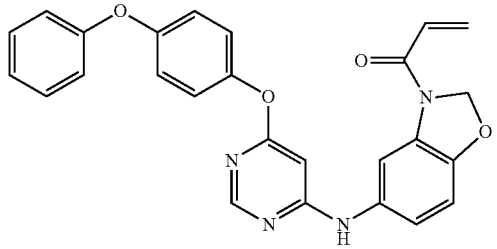
or a pharmaceutically acceptable salt thereof.

12. A compound selected from the group consisting of:
I-16
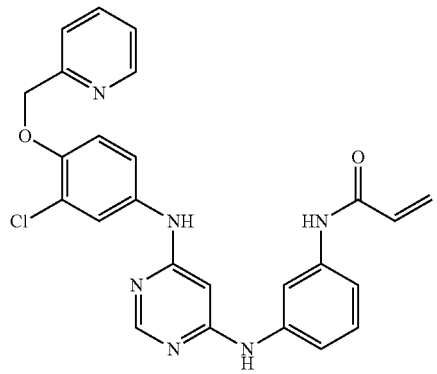
I-17
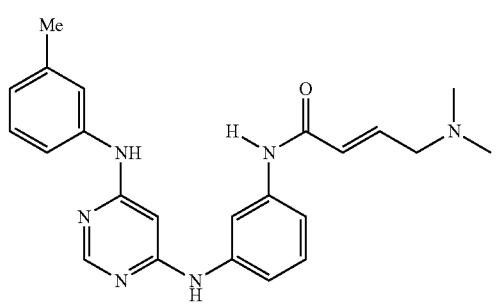
I-18
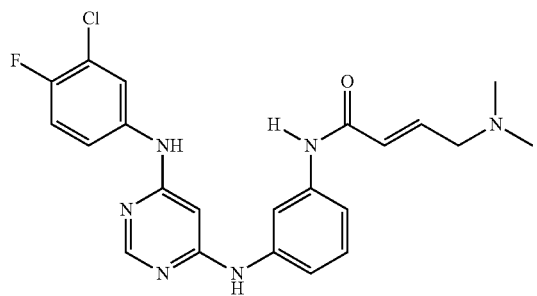
I-19
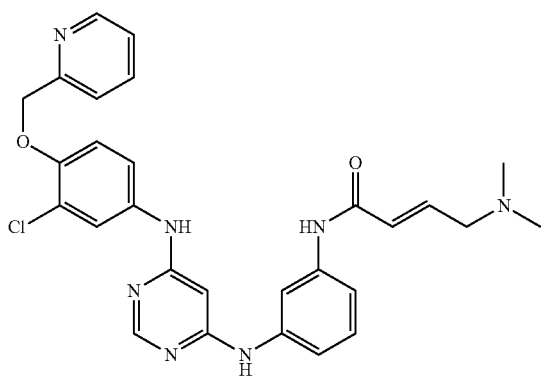
I-6
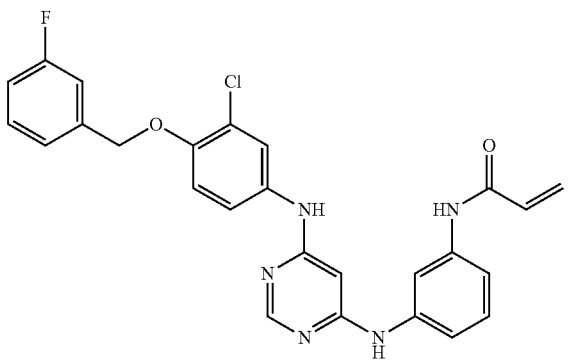
I-66
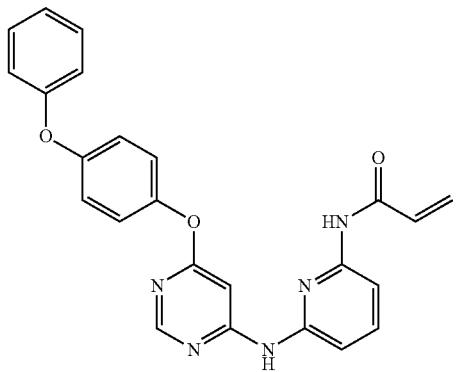
I-82
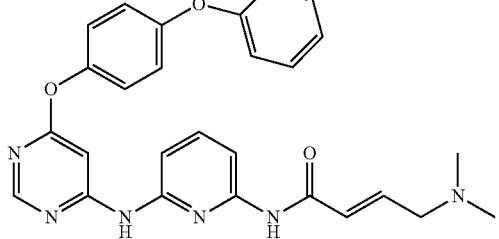
I-89
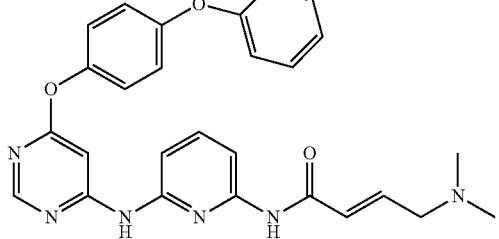
or a pharmaceutically acceptable salt thereof.
* * * * *

SEQUENCE LISTING

<160> NUMBER OF SEQ ID NOS: 9

<210> SEQ ID NO 1
<211> LENGTH: 540
<212> TYPE: PRT
<213> ORGANISM: Homo sapiens

<400> SEQUENCE: 1

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160

Asn Ala Met Gly Cys Gln Ile Leu Glu Asn Arg Asn Gly Ser Leu Lys
                165                 170                 175

Pro Gly Ser Ser His Arg Lys Thr Lys Lys Pro Leu Pro Pro Thr Pro
            180                 185                 190

Glu Glu Asp Gln Ile Leu Lys Lys Pro Leu Pro Pro Glu Pro Ala Ala

```
            195                 200                 205
Ala Pro Val Ser Thr Ser Glu Leu Lys Lys Val Ala Leu Tyr Asp
210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                    245                 250                 255

Lys Asn Gly Gln Glu Gly Tyr Ile Pro Ser Asn Tyr Val Thr Glu Ala
                260                 265                 270

Glu Asp Ser Ile Glu Met Tyr Glu Trp Tyr Ser Lys His Met Thr Arg
            275                 280                 285

Ser Gln Ala Glu Gln Leu Leu Lys Gln Glu Gly Lys Glu Gly Gly Phe
        290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                    325                 330                 335

Cys Ser Thr Pro Gln Ser Gln Tyr Tyr Leu Ala Glu Lys His Leu Phe
                340                 345                 350

Ser Thr Ile Pro Glu Leu Ile Asn Tyr His Gln His Asn Ser Ala Gly
            355                 360                 365

Leu Ile Ser Arg Leu Lys Tyr Pro Val Ser Gln Gln Asn Lys Asn Ala
        370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                    405                 410                 415

Lys Tyr Gly Lys Trp Arg Gly Gln Tyr Asp Val Ala Ile Lys Met Ile
                420                 425                 430

Lys Glu Gly Ser Met Ser Glu Asp Glu Phe Ile Glu Glu Ala Lys Val
            435                 440                 445

Met Met Asn Leu Ser His Glu Lys Leu Val Gln Leu Tyr Gly Val Cys
        450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                    485                 490                 495

Gln Leu Leu Glu Met Cys Lys Asp Val Cys Glu Ala Met Glu Tyr Leu
                500                 505                 510

Glu Ser Lys Gln Phe Leu His Arg Asp Leu Ala Ala Arg Asn Cys Leu
            515                 520                 525

Val Asn Asp Gln Gly Val Val Lys Val Ser Asp Phe
        530                 535                 540

<210> SEQ ID NO 2
<211> LENGTH: 631
<212> TYPE: PRT
<213> ORGANISM: Homo sapiens

<400> SEQUENCE: 2

Met Asn Phe Asn Thr Ile Leu Glu Glu Ile Leu Ile Lys Arg Ser Gln
1               5                   10                  15

Gln Lys Lys Lys Thr Ser Pro Leu Asn Tyr Lys Glu Arg Leu Phe Val
            20                  25                  30

Leu Thr Lys Ser Met Leu Thr Tyr Tyr Glu Gly Arg Ala Glu Lys Lys
```

```
                  35                  40                  45
Tyr Arg Lys Gly Phe Ile Asp Val Ser Lys Ile Lys Cys Val Glu Ile
 50                  55                  60
Val Lys Asn Asp Asp Gly Val Ile Pro Cys Gln Asn Lys Tyr Pro Phe
 65                  70                  75                  80
Gln Val Val His Asp Ala Asn Thr Leu Tyr Ile Phe Ala Pro Ser Pro
                     85                  90                  95
Gln Ser Arg Asp Leu Trp Val Lys Leu Lys Glu Ile Lys Asn
                100                 105                 110
Asn Asn Asn Ile Met Ile Lys Tyr His Pro Lys Phe Trp Thr Asp Gly
            115                 120                 125
Ser Tyr Gln Cys Cys Arg Gln Thr Glu Lys Leu Ala Pro Gly Cys Glu
            130                 135                 140
Lys Tyr Asn Leu Phe Glu Ser Ser Ile Arg Lys Ala Leu Pro Pro Ala
145                 150                 155                 160
Pro Glu Thr Lys Lys Arg Pro Pro Pro Ile Pro Leu Glu Glu
                165                 170                 175
Glu Asp Asn Ser Glu Glu Ile Val Val Ala Met Tyr Asp Phe Gln Ala
            180                 185                 190
Ala Glu Gly His Asp Leu Arg Leu Glu Arg Gly Gln Glu Tyr Leu Ile
            195                 200                 205
Leu Glu Lys Asn Asp Val His Trp Trp Arg Ala Arg Asp Lys Tyr Gly
            210                 215                 220
Asn Glu Gly Tyr Ile Pro Ser Asn Tyr Val Thr Gly Lys Lys Ser Asn
225                 230                 235                 240
Asn Leu Asp Gln Tyr Glu Trp Tyr Cys Arg Asn Met Asn Arg Ser Lys
                245                 250                 255
Ala Glu Gln Leu Leu Arg Ser Glu Asp Lys Glu Gly Gly Phe Met Val
            260                 265                 270
Arg Asp Ser Ser Gln Pro Gly Leu Tyr Thr Val Ser Leu Tyr Thr Lys
            275                 280                 285
Phe Gly Gly Glu Gly Ser Ser Gly Phe Arg His Tyr His Ile Lys Glu
            290                 295                 300
Thr Thr Thr Ser Pro Lys Lys Tyr Tyr Leu Ala Glu Lys His Ala Phe
305                 310                 315                 320
Gly Ser Ile Pro Glu Ile Ile Glu Tyr His Lys His Asn Ala Ala Gly
                325                 330                 335
Leu Val Thr Arg Leu Arg Tyr Pro Val Ser Val Lys Gly Lys Asn Ala
            340                 345                 350
Pro Thr Thr Ala Gly Phe Ser Tyr Glu Lys Trp Glu Ile Asn Pro Ser
            355                 360                 365
Glu Leu Thr Phe Met Arg Glu Leu Gly Ser Gly Leu Phe Gly Val Val
370                 375                 380
Arg Leu Gly Lys Trp Arg Ala Gln Tyr Lys Val Ala Ile Lys Ala Ile
385                 390                 395                 400
Arg Glu Gly Ala Met Cys Glu Glu Asp Phe Ile Glu Glu Ala Lys Val
                405                 410                 415
Met Met Lys Leu Thr His Pro Lys Leu Val Gln Leu Tyr Gly Val Cys
            420                 425                 430
Thr Gln Gln Lys Pro Ile Tyr Ile Val Thr Glu Phe Met Glu Arg Gly
            435                 440                 445
Cys Leu Leu Asn Phe Leu Arg Gln Arg Gln Gly His Phe Ser Arg Asp
            450                 455                 460
```

```
Val Leu Leu Ser Met Cys Gln Asp Val Cys Glu Gly Met Glu Tyr Leu
465                 470                 475                 480

Glu Arg Asn Ser Phe Ile His Arg Asp Leu Ala Ala Arg Asn Cys Leu
                485                 490                 495

Val Ser Glu Ala Gly Val Val Lys Val Ser Asp Phe Gly Met Ala Arg
            500                 505                 510

Tyr Val Leu Asp Asp Gln Tyr Thr Ser Ser Gly Ala Lys Phe Pro
            515                 520                 525

Val Lys Trp Cys Pro Pro Glu Val Phe Asn Tyr Ser Arg Phe Ser Ser
        530                 535                 540

Lys Ser Asp Val Trp Ser Phe Gly Val Leu Met Trp Glu Val Phe Thr
545                 550                 555                 560

Glu Gly Arg Met Pro Phe Glu Lys Tyr Thr Asn Tyr Glu Val Val Thr
                565                 570                 575

Met Val Thr Arg Gly His Arg Leu Tyr Gln Pro Lys Leu Ala Ser Asn
            580                 585                 590

Tyr Val Tyr Glu Val Met Leu Arg Cys Trp Gln Glu Lys Pro Glu Gly
        595                 600                 605

Arg Pro Ser Phe Glu Asp Leu Leu Arg Thr Ile Asp Glu Leu Val Glu
    610                 615                 620

Cys Glu Glu Thr Phe Gly Arg
625                 630

<210> SEQ ID NO 3
<211> LENGTH: 620
<212> TYPE: PRT
<213> ORGANISM: Homo sapiens

<400> SEQUENCE: 3

Met Asn Asn Phe Ile Leu Leu Glu Glu Gln Leu Ile Lys Lys Ser Gln
1               5                   10                  15

Gln Lys Arg Arg Thr Ser Pro Ser Asn Phe Lys Val Arg Phe Phe Val
            20                  25                  30

Leu Thr Lys Ala Ser Leu Ala Tyr Phe Glu Asp Arg His Gly Lys Lys
        35                  40                  45

Arg Thr Leu Lys Gly Ser Ile Glu Leu Ser Arg Ile Lys Cys Val Glu
    50                  55                  60

Ile Val Lys Ser Asp Ile Ser Ile Pro Cys His Tyr Lys Tyr Pro Phe
65                  70                  75                  80

Gln Val Val His Asp Asn Tyr Leu Leu Tyr Val Phe Ala Pro Asp Arg
                85                  90                  95

Glu Ser Arg Gln Arg Trp Val Leu Ala Leu Lys Glu Glu Thr Arg Asn
            100                 105                 110

Asn Asn Ser Leu Val Pro Lys Tyr His Pro Asn Phe Trp Met Asp Gly
        115                 120                 125

Lys Trp Arg Cys Cys Ser Gln Leu Glu Lys Leu Ala Thr Gly Cys Ala
130                 135                 140

Gln Tyr Asp Pro Thr Lys Asn Ala Ser Lys Lys Pro Leu Pro Pro Thr
145                 150                 155                 160

Pro Glu Asp Asn Arg Arg Pro Leu Trp Glu Pro Glu Glu Thr Val Val
                165                 170                 175

Ile Ala Leu Tyr Asp Tyr Gln Thr Asn Asp Pro Gln Glu Leu Ala Leu
            180                 185                 190

Arg Arg Asn Glu Glu Tyr Cys Leu Leu Asp Ser Ser Glu Ile His Trp
        195                 200                 205
```

Trp Arg Val Gln Asp Arg Asn Gly His Glu Gly Tyr Val Pro Ser Ser
210                 215                 220

Tyr Leu Val Glu Lys Ser Pro Asn Asn Leu Glu Thr Tyr Glu Trp Tyr
225                 230                 235                 240

Asn Lys Ser Ile Ser Arg Asp Lys Ala Glu Lys Leu Leu Leu Asp Thr
                245                 250                 255

Gly Lys Glu Gly Ala Phe Met Val Arg Asp Ser Arg Thr Ala Gly Thr
            260                 265                 270

Tyr Thr Val Ser Val Phe Thr Lys Ala Val Val Ser Glu Asn Asn Pro
        275                 280                 285

Cys Ile Lys His Tyr His Ile Lys Glu Thr Asn Asp Asn Pro Lys Arg
290                 295                 300

Tyr Tyr Val Ala Glu Lys Tyr Val Phe Asp Ser Ile Pro Leu Leu Ile
305                 310                 315                 320

Asn Tyr His Gln His Asn Gly Gly Leu Val Thr Arg Leu Arg Tyr
                325                 330                 335

Pro Val Cys Phe Gly Arg Gln Lys Ala Pro Val Thr Ala Gly Leu Arg
                340                 345                 350

Tyr Gly Lys Trp Val Ile Asp Pro Ser Glu Leu Thr Phe Val Gln Glu
            355                 360                 365

Ile Gly Ser Gly Gln Phe Gly Leu Val His Leu Gly Tyr Trp Leu Asn
370                 375                 380

Lys Asp Lys Val Ala Ile Lys Thr Ile Arg Glu Gly Ala Met Ser Glu
385                 390                 395                 400

Glu Asp Phe Ile Glu Ala Glu Val Met Met Lys Leu Ser His Pro
                405                 410                 415

Lys Leu Val Gln Leu Tyr Gly Val Cys Leu Glu Gln Ala Pro Ile Cys
                420                 425                 430

Leu Val Phe Glu Phe Met Glu His Gly Cys Leu Ser Asp Tyr Leu Arg
                435                 440                 445

Thr Gln Arg Gly Leu Phe Ala Ala Glu Thr Leu Leu Gly Met Cys Leu
    450                 455                 460

Asp Val Cys Glu Gly Met Ala Tyr Leu Glu Glu Ala Cys Val Ile His
465                 470                 475                 480

Arg Asp Leu Ala Ala Arg Asn Cys Leu Val Gly Glu Asn Gln Val Ile
                485                 490                 495

Lys Val Ser Asp Phe Gly Met Thr Arg Phe Val Leu Asp Asp Gln Tyr
                500                 505                 510

Thr Ser Ser Thr Gly Thr Lys Phe Pro Val Lys Trp Ala Ser Pro Glu
    515                 520                 525

Val Phe Ser Phe Ser Arg Tyr Ser Ser Lys Ser Asp Val Trp Ser Phe
530                 535                 540

Gly Val Leu Met Trp Glu Val Phe Ser Glu Gly Lys Ile Pro Tyr Glu
545                 550                 555                 560

Asn Arg Ser Asn Ser Glu Val Val Glu Asp Ile Ser Thr Gly Phe Arg
                565                 570                 575

Leu Tyr Lys Pro Arg Leu Ala Ser Thr His Val Tyr Gln Ile Met Asn
                580                 585                 590

His Cys Trp Lys Glu Arg Pro Glu Asp Arg Pro Ala Phe Ser Arg Leu
            595                 600                 605

Leu Arg Gln Leu Ala Glu Ile Ala Glu Ser Gly Leu
    610                 615                 620

<210> SEQ ID NO 4

-continued

```
<211> LENGTH: 675
<212> TYPE: PRT
<213> ORGANISM: Homo sapiens

<400> SEQUENCE: 4

Met Asp Thr Lys Ser Ile Leu Glu Glu Leu Leu Lys Arg Ser Gln
1               5                   10                  15

Gln Lys Lys Lys Met Ser Pro Asn Asn Tyr Lys Glu Arg Leu Phe Val
            20                  25                  30

Leu Thr Lys Thr Asn Leu Ser Tyr Glu Tyr Asp Lys Met Lys Arg
            35                  40                  45

Gly Ser Arg Lys Gly Ser Ile Glu Ile Lys Lys Ile Arg Cys Val Glu
    50                  55                  60

Lys Val Asn Leu Glu Glu Gln Thr Pro Val Glu Arg Gln Tyr Pro Phe
65                  70                  75                  80

Gln Ile Val Tyr Lys Asp Gly Leu Leu Tyr Val Tyr Ala Ser Asn Glu
                85                  90                  95

Glu Ser Arg Ser Gln Trp Leu Lys Ala Leu Gln Lys Glu Ile Arg Gly
            100                 105                 110

Asn Pro His Leu Leu Val Lys Tyr His Ser Gly Phe Phe Val Asp Gly
            115                 120                 125

Lys Phe Leu Cys Cys Gln Gln Ser Cys Lys Ala Ala Pro Gly Cys Thr
130                 135                 140

Leu Trp Glu Ala Tyr Ala Asn Leu His Thr Ala Val Asn Glu Glu Lys
145                 150                 155                 160

His Arg Val Pro Thr Phe Pro Asp Arg Val Leu Lys Ile Pro Arg Ala
                165                 170                 175

Val Pro Val Leu Lys Met Asp Ala Pro Ser Ser Ser Thr Thr Leu Ala
            180                 185                 190

Gln Tyr Asp Asn Glu Ser Lys Lys Asn Tyr Gly Ser Gln Pro Pro Ser
            195                 200                 205

Ser Ser Thr Ser Leu Ala Gln Tyr Asp Ser Asn Ser Lys Lys Ile Tyr
210                 215                 220

Gly Ser Gln Pro Asn Phe Asn Met Gln Tyr Ile Pro Arg Glu Asp Phe
225                 230                 235                 240

Pro Asp Trp Trp Gln Val Arg Lys Leu Lys Ser Ser Ser Ser Glu
                245                 250                 255

Asp Val Ala Ser Ser Asn Gln Lys Glu Arg Asn Val Asn His Thr Thr
            260                 265                 270

Ser Lys Ile Ser Trp Glu Phe Pro Glu Ser Ser Ser Glu Glu Glu
            275                 280                 285

Glu Asn Leu Asp Asp Tyr Asp Trp Phe Ala Gly Asn Ile Ser Arg Ser
    290                 295                 300

Gln Ser Glu Gln Leu Leu Arg Gln Lys Gly Lys Glu Gly Ala Phe Met
305                 310                 315                 320

Val Arg Asn Ser Ser Gln Val Gly Met Tyr Thr Val Ser Leu Phe Ser
                325                 330                 335

Lys Ala Val Asn Asp Lys Lys Gly Thr Val Lys His Tyr His Val His
            340                 345                 350

Thr Asn Ala Glu Asn Lys Leu Tyr Leu Ala Glu Asn Tyr Cys Phe Asp
            355                 360                 365

Ser Ile Pro Lys Leu Ile His Tyr His Gln His Asn Ser Ala Gly Met
370                 375                 380

Ile Thr Arg Leu Arg His Pro Val Ser Thr Lys Ala Asn Lys Val Pro
385                 390                 395                 400
```

Asp Ser Val Ser Leu Gly Asn Gly Ile Trp Glu Leu Lys Arg Glu Glu
            405                 410                 415

Ile Thr Leu Leu Lys Glu Leu Gly Ser Gly Gln Phe Gly Val Val Gln
            420                 425                 430

Leu Gly Lys Trp Lys Gly Gln Tyr Asp Val Ala Val Lys Met Ile Lys
            435                 440                 445

Glu Gly Ser Met Ser Glu Asp Glu Phe Phe Gln Glu Ala Gln Thr Met
        450                 455                 460

Met Lys Leu Ser His Pro Lys Leu Val Lys Phe Tyr Gly Val Cys Ser
465                 470                 475                 480

Lys Glu Tyr Pro Ile Tyr Ile Val Thr Glu Tyr Ile Ser Asn Gly Cys
                485                 490                 495

Leu Leu Asn Tyr Leu Arg Ser His Gly Lys Gly Leu Glu Pro Ser Gln
            500                 505                 510

Leu Leu Glu Met Cys Tyr Asp Val Cys Glu Gly Met Ala Phe Leu Glu
        515                 520                 525

Ser His Gln Phe Ile His Arg Asp Leu Ala Ala Arg Asn Cys Leu Val
        530                 535                 540

Asp Arg Asp Leu Cys Val Lys Val Ser Asp Phe Gly Met Thr Arg Tyr
545                 550                 555                 560

Val Leu Asp Asp Gln Tyr Val Ser Ser Val Gly Thr Lys Phe Pro Val
                565                 570                 575

Lys Trp Ser Ala Pro Glu Val Phe His Tyr Phe Lys Tyr Ser Ser Lys
            580                 585                 590

Ser Asp Val Trp Ala Phe Gly Ile Leu Met Trp Glu Val Phe Ser Leu
        595                 600                 605

Gly Lys Gln Pro Tyr Asp Leu Tyr Asp Asn Ser Gln Val Val Leu Lys
            610                 615                 620

Val Ser Gln Gly His Arg Leu Tyr Arg Pro His Leu Ala Ser Asp Thr
625                 630                 635                 640

Ile Tyr Gln Ile Met Tyr Ser Cys Trp His Glu Leu Pro Glu Lys Arg
                645                 650                 655

Pro Thr Phe Gln Gln Leu Leu Ser Ser Ile Glu Pro Leu Arg Glu Lys
            660                 665                 670

Asp Lys His
        675

<210> SEQ ID NO 5
<211> LENGTH: 1124
<212> TYPE: PRT
<213> ORGANISM: Homo sapiens

<400> SEQUENCE: 5

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
            20                  25                  30

Arg Gly Pro Gly Pro Pro Gln Arg Leu Ser Phe Ser Phe Gly Asp His
        35                  40                  45

Leu Ala Glu Asp Leu Cys Val Gln Ala Ala Lys Ala Ser Gly Ile Leu
    50                  55                  60

Pro Val Tyr His Ser Leu Phe Ala Leu Ala Thr Glu Asp Leu Ser Cys
65                  70                  75                  80

Trp Phe Pro Pro Ser His Ile Phe Ser Val Glu Asp Ala Ser Thr Gln
                85                  90                  95

```
Val Leu Leu Tyr Arg Ile Arg Phe Tyr Phe Pro Asn Trp Phe Gly Leu
            100                 105                 110
Glu Lys Cys His Arg Phe Gly Leu Arg Lys Asp Leu Ala Ser Ala Ile
            115                 120                 125
Leu Asp Leu Pro Val Leu Glu His Leu Phe Ala Gln His Arg Ser Asp
130                 135                 140
Leu Val Ser Gly Arg Leu Pro Val Gly Leu Ser Leu Lys Glu Gln Gly
145                 150                 155                 160
Glu Cys Leu Ser Leu Ala Val Leu Asp Leu Ala Arg Met Ala Arg Glu
                165                 170                 175
Gln Ala Gln Arg Pro Gly Glu Leu Leu Lys Thr Val Ser Tyr Lys Ala
                180                 185                 190
Cys Leu Pro Pro Ser Leu Arg Asp Leu Ile Gln Gly Leu Ser Phe Val
                195                 200                 205
Thr Arg Arg Arg Ile Arg Arg Thr Val Arg Arg Ala Leu Arg Arg Val
            210                 215                 220
Ala Ala Cys Gln Ala Asp Arg His Ser Leu Met Ala Lys Tyr Ile Met
225                 230                 235                 240
Asp Leu Glu Arg Leu Asp Pro Ala Gly Ala Glu Thr Phe His Val
                245                 250                 255
Gly Leu Pro Gly Ala Leu Gly Gly His Asp Gly Leu Gly Leu Leu Arg
            260                 265                 270
Val Ala Gly Asp Gly Gly Ile Ala Trp Thr Gln Gly Glu Gln Glu Val
            275                 280                 285
Leu Gln Pro Phe Cys Asp Phe Pro Glu Ile Val Asp Ile Ser Ile Lys
            290                 295                 300
Gln Ala Pro Arg Val Gly Pro Ala Gly Glu His Arg Leu Val Thr Val
305                 310                 315                 320
Thr Arg Thr Asp Asn Gln Ile Leu Glu Ala Glu Phe Pro Gly Leu Pro
                325                 330                 335
Glu Ala Leu Ser Phe Val Ala Leu Val Asp Gly Tyr Phe Arg Leu Thr
                340                 345                 350
Thr Asp Ser Gln His Phe Phe Cys Lys Glu Val Ala Pro Pro Arg Leu
                355                 360                 365
Leu Glu Glu Val Ala Glu Gln Cys His Gly Pro Ile Thr Leu Asp Phe
            370                 375                 380
Ala Ile Asn Lys Leu Lys Thr Gly Gly Ser Arg Pro Gly Ser Tyr Val
385                 390                 395                 400
Leu Arg Arg Ser Pro Gln Asp Phe Asp Ser Phe Leu Leu Thr Val Cys
                405                 410                 415
Val Gln Asn Pro Leu Gly Pro Asp Tyr Lys Gly Cys Leu Ile Arg Arg
            420                 425                 430
Ser Pro Thr Gly Thr Phe Leu Leu Val Gly Leu Ser Arg Pro His Ser
            435                 440                 445
Ser Leu Arg Glu Leu Leu Ala Thr Cys Trp Asp Gly Gly Leu His Val
            450                 455                 460
Asp Gly Val Ala Val Thr Leu Thr Ser Cys Cys Ile Pro Arg Pro Lys
465                 470                 475                 480
Glu Lys Ser Asn Leu Ile Val Val Gln Arg Gly His Ser Pro Pro Thr
                485                 490                 495
Ser Ser Leu Val Gln Pro Gln Ser Gln Tyr Gln Leu Ser Gln Met Thr
                500                 505                 510
Phe His Lys Ile Pro Ala Asp Ser Leu Glu Trp His Glu Asn Leu Gly
```

-continued

```
            515                 520                 525
His Gly Ser Phe Thr Lys Ile Tyr Arg Gly Cys Arg His Glu Val Val
            530                 535                 540
Asp Gly Glu Ala Arg Lys Thr Glu Val Leu Leu Lys Val Met Asp Ala
545                 550                 555                 560
Lys His Lys Asn Cys Met Glu Ser Phe Leu Glu Ala Ala Ser Leu Met
                565                 570                 575
Ser Gln Val Ser Tyr Arg His Leu Val Leu Leu His Gly Val Cys Met
            580                 585                 590
Ala Gly Asp Ser Thr Met Val Gln Glu Phe Val His Leu Gly Ala Ile
            595                 600                 605
Asp Met Tyr Leu Arg Lys Arg Gly His Leu Val Pro Ala Ser Trp Lys
610                 615                 620
Leu Gln Val Val Lys Gln Leu Ala Tyr Ala Leu Asn Tyr Leu Glu Asp
625                 630                 635                 640
Lys Gly Leu Pro His Gly Asn Val Ser Ala Arg Lys Val Leu Leu Ala
                645                 650                 655
Arg Glu Gly Ala Asp Gly Ser Pro Pro Phe Ile Lys Leu Ser Asp Pro
            660                 665                 670
Gly Val Ser Pro Ala Val Leu Ser Leu Glu Met Leu Thr Asp Arg Ile
            675                 680                 685
Pro Trp Val Ala Pro Glu Cys Leu Arg Glu Ala Gln Thr Leu Ser Leu
            690                 695                 700
Glu Ala Asp Lys Trp Gly Phe Gly Ala Thr Val Trp Glu Val Phe Ser
705                 710                 715                 720
Gly Val Thr Met Pro Ile Ser Ala Leu Asp Pro Ala Lys Lys Leu Gln
                725                 730                 735
Phe Tyr Glu Asp Arg Gln Gln Leu Pro Ala Pro Lys Trp Thr Glu Leu
            740                 745                 750
Ala Leu Leu Ile Gln Gln Cys Met Ala Tyr Glu Pro Val Gln Arg Pro
            755                 760                 765
Ser Phe Arg Ala Val Ile Arg Asp Leu Asn Ser Leu Ile Ser Ser Asp
            770                 775                 780
Tyr Glu Leu Leu Ser Asp Pro Thr Pro Gly Ala Leu Ala Pro Arg Asp
785                 790                 795                 800
Gly Leu Trp Asn Gly Ala Gln Leu Tyr Ala Cys Gln Asp Pro Thr Ile
                805                 810                 815
Phe Glu Glu Arg His Leu Lys Tyr Ile Ser Gln Leu Gly Lys Gly Asn
            820                 825                 830
Phe Gly Ser Val Glu Leu Cys Arg Tyr Asp Pro Leu Gly Asp Asn Thr
            835                 840                 845
Gly Ala Leu Val Ala Val Lys Gln Leu Gln His Ser Gly Pro Asp Gln
            850                 855                 860
Gln Arg Asp Phe Gln Arg Glu Ile Gln Ile Leu Lys Ala Leu His Ser
865                 870                 875                 880
Asp Phe Ile Val Lys Tyr Arg Gly Val Ser Tyr Gly Pro Gly Arg Gln
                885                 890                 895
Ser Leu Arg Leu Val Met Glu Tyr Leu Pro Ser Gly Cys Leu Arg Asp
            900                 905                 910
Phe Leu Gln Arg His Arg Ala Arg Leu Asp Ala Ser Arg Leu Leu Leu
            915                 920                 925
Tyr Ser Ser Gln Ile Cys Lys Gly Met Glu Tyr Leu Gly Ser Arg Arg
            930                 935                 940
```

```
Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
        995                 1000                1005

Asp Val Trp Ser Phe Gly Val Val Leu Tyr Glu Leu Phe Thr Tyr
    1010                1015                1020

Cys Asp Lys Ser Cys Ser Pro Ser Ala Glu Phe Leu Arg Met Met
    1025                1030                1035

Gly Cys Glu Arg Asp Val Pro Ala Leu Cys Arg Leu Leu Glu Leu
    1040                1045                1050

Leu Glu Glu Gly Gln Arg Leu Pro Ala Pro Pro Ala Cys Pro Ala
    1055                1060                1065

Glu Val His Glu Leu Met Lys Leu Cys Trp Ala Pro Ser Pro Gln
    1070                1075                1080

Asp Arg Pro Ser Phe Ser Ala Leu Gly Pro Gln Leu Asp Met Leu
    1085                1090                1095

Trp Ser Gly Ser Arg Gly Cys Glu Thr His Ala Phe Thr Ala His
    1100                1105                1110

Pro Glu Gly Lys His His Ser Leu Ser Phe Ser
    1115                1120

<210> SEQ ID NO 6
<211> LENGTH: 527
<212> TYPE: PRT
<213> ORGANISM: Homo sapiens

<400> SEQUENCE: 6

Met Ile Leu Ser Ser Tyr Asn Thr Ile Gln Ser Val Phe Cys Cys Cys
1               5                   10                  15

Cys Cys Cys Ser Val Gln Lys Arg Gln Met Arg Thr Gln Ile Ser Leu
            20                  25                  30

Ser Thr Asp Glu Glu Leu Pro Glu Lys Tyr Thr Gln Arg Arg Arg Pro
        35                  40                  45

Trp Leu Ser Gln Leu Ser Asn Lys Lys Gln Ser Asn Thr Gly Arg Val
    50                  55                  60

Gln Pro Ser Lys Arg Lys Pro Leu Pro Pro Leu Pro Pro Ser Glu Val
65                  70                  75                  80

Ala Glu Glu Lys Ile Gln Val Lys Ala Leu Tyr Asp Phe Leu Pro Arg
                85                  90                  95

Glu Pro Cys Asn Leu Ala Leu Arg Arg Ala Glu Glu Tyr Leu Ile Leu
            100                 105                 110

Glu Lys Tyr Asn Pro His Trp Trp Lys Ala Arg Asp Arg Leu Gly Asn
        115                 120                 125

Glu Gly Leu Ile Pro Ser Asn Tyr Val Thr Glu Asn Lys Ile Thr Asn
    130                 135                 140

Leu Glu Ile Tyr Glu Trp Tyr His Arg Asn Ile Thr Arg Asn Gln Ala
145                 150                 155                 160

Glu His Leu Leu Arg Gln Glu Ser Lys Glu Gly Ala Phe Ile Val Arg
                165                 170                 175

Asp Ser Arg His Leu Gly Ser Tyr Thr Ile Ser Val Phe Met Gly Ala
            180                 185                 190
```

```
Arg Arg Ser Thr Glu Ala Ala Ile Lys His Tyr Gln Ile Lys Lys Asn
        195                 200                 205

Asp Ser Gly Gln Trp Tyr Val Ala Glu Arg His Ala Phe Gln Ser Ile
    210                 215                 220

Pro Glu Leu Ile Trp Tyr His Gln His Asn Ala Ala Gly Leu Met Thr
225                 230                 235                 240

Arg Leu Arg Tyr Pro Val Gly Leu Met Gly Ser Cys Leu Pro Ala Thr
                245                 250                 255

Ala Gly Phe Ser Tyr Glu Lys Trp Glu Ile Asp Pro Ser Glu Leu Ala
            260                 265                 270

Phe Ile Lys Glu Ile Gly Ser Gly Gln Phe Gly Val Val His Leu Gly
        275                 280                 285

Glu Trp Arg Ser His Ile Gln Val Ala Ile Lys Ala Ile Asn Glu Gly
    290                 295                 300

Ser Met Ser Glu Glu Asp Phe Ile Glu Ala Lys Val Met Met Lys
305                 310                 315                 320

Leu Ser His Ser Lys Leu Val Gln Leu Tyr Gly Val Cys Ile Gln Arg
                325                 330                 335

Lys Pro Leu Tyr Ile Val Thr Glu Phe Met Glu Asn Gly Cys Leu Leu
            340                 345                 350

Asn Tyr Leu Arg Glu Asn Lys Gly Lys Leu Arg Lys Glu Met Leu Leu
        355                 360                 365

Ser Val Cys Gln Asp Ile Cys Glu Gly Met Glu Tyr Leu Glu Arg Asn
    370                 375                 380

Gly Tyr Ile His Arg Asp Leu Ala Ala Arg Asn Cys Leu Val Ser Ser
385                 390                 395                 400

Thr Cys Ile Val Lys Ile Ser Asp Phe Gly Met Thr Arg Tyr Val Leu
                405                 410                 415

Asp Asp Glu Tyr Val Ser Ser Phe Gly Ala Lys Phe Pro Ile Lys Trp
            420                 425                 430

Ser Pro Pro Glu Val Phe Leu Phe Asn Lys Tyr Ser Ser Lys Ser Asp
        435                 440                 445

Val Trp Ser Phe Gly Val Leu Met Trp Glu Val Phe Thr Glu Gly Lys
    450                 455                 460

Met Pro Phe Glu Asn Lys Ser Asn Leu Gln Val Glu Ala Ile Ser
465                 470                 475                 480

Glu Gly Phe Arg Leu Tyr Arg Pro His Leu Ala Pro Met Ser Ile Tyr
                485                 490                 495

Glu Val Met Tyr Ser Cys Trp His Glu Lys Pro Glu Gly Arg Pro Thr
            500                 505                 510

Phe Ala Glu Leu Leu Arg Ala Val Thr Glu Ile Ala Glu Thr Trp
        515                 520                 525

<210> SEQ ID NO 7
<211> LENGTH: 17
<212> TYPE: PRT
<213> ORGANISM: Homo sapiens

<400> SEQUENCE: 7

Ile Thr Gln Leu Met Pro Phe Gly Cys Leu Leu Asp Tyr Val Arg Glu
1               5                   10                  15

His

<210> SEQ ID NO 8
<211> LENGTH: 17
<212> TYPE: PRT
```

```
<213> ORGANISM: Homo sapiens

<400> SEQUENCE: 8

Val Thr Gln Leu Met Pro Tyr Gly Cys Leu Leu Asp His Val Arg Glu
1               5                   10                  15

Asn

<210> SEQ ID NO 9
<211> LENGTH: 17
<212> TYPE: PRT
<213> ORGANISM: Homo sapiens

<400> SEQUENCE: 9

Val Thr Gln Leu Met Pro His Gly Cys Leu Leu Glu Tyr Val His Glu
1               5                   10                  15

His
```